US011408008B2

(12) United States Patent
Marks et al.

(10) Patent No.: US 11,408,008 B2
(45) Date of Patent: Aug. 9, 2022

(54) PLANTS HAVING INCREASED OIL QUALITY

(71) Applicant: Regents of the University of Minnesota, Minneapolis, MN (US)

(72) Inventors: Michael David Marks, Roseville, MN (US); Ratan Chopra, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 16/831,145

(22) Filed: Mar. 26, 2020

(65) Prior Publication Data
US 2020/0308596 A1 Oct. 1, 2020

Related U.S. Application Data

(60) Provisional application No. 62/825,283, filed on Mar. 28, 2019.

(51) Int. Cl.
*C12N 15/82* (2006.01)
*C07K 14/415* (2006.01)
*A01H 5/10* (2018.01)
*A01H 1/06* (2006.01)

(52) U.S. Cl.
CPC ........... *C12N 15/8247* (2013.01); *A01H 1/06* (2013.01); *A01H 5/10* (2013.01); *C07K 14/415* (2013.01)

(58) Field of Classification Search
None
See application file for complete search history.

(56) References Cited

U.S. PATENT DOCUMENTS

| 2008/0160530 A1 | 7/2008 | Li |
| 2015/0143573 A1 | 5/2015 | Denolf et al. |
| 2017/0051299 A1 | 2/2017 | Fabijanski et al. |
| 2019/0053457 A1 | 2/2019 | Marks et al. |
| 2019/0053458 A1 | 2/2019 | Marks et al. |
| 2020/0131523 A1 | 4/2020 | Marks et al. |
| 2020/0370062 A1 | 11/2020 | Marks et al. |

FOREIGN PATENT DOCUMENTS

| WO | WO-0036114 A1 * | 6/2000 | ......... C12N 15/8247 |
| WO | WO-2006052912 A2 * | 5/2006 | ............ C12P 7/6463 |
| WO | WO 2013/112578 | 8/2013 | |
| WO | WO 2017/004375 | 1/2017 | |
| WO | WO 2017/117633 | 7/2017 | |
| WO | WO 2018/140782 | 8/2018 | |

OTHER PUBLICATIONS

Xi et al. (Molecular Plant., 6(6):1975-1983; Published Nov. 2013).*
Sedbrook et al. (Plant Science, 227:122-132, 2014).*
Blande et al. (GenBank Sequence Accession No. GEVK01020461.1, Published Nov. 4, 2016).*
Claver et al. (GenBank Sequence Accession No. GenBank KT223025.1, Published Nov. 29, 2015).*
Blacklock et al., "Substrate specificity of Arabidopsis 3-ketoacyl-CoA synthases," Biochem. Biohpys. Res. Communications, Jun. 5, 2006, 346(2):583-590.
Joubes et al., "The VLCFA elongase gene family in Arabidopsis thaliana: phylogenetic analysis, 3D modelling and expression profiling," Plant Mol. Biology, May 9, 2008, 67(5):547-566.
Millar et al., "Very-long-chain fatty acid biosynthesis is controlled through the expression and specificity of the condensing enzyme," Plant Journal, Jul. 1997, 12(1):121-131.
Morineau et al., "Dual Fatty Acid Elongase Complex Interactions in Arabidopsis," PLoS One, Sep. 1, 2016, 11(9):e0160631, 20 pages.
Wang et al., "A functional genomics resource for Brassica napus: development of an EMS mutagenized population and discovery of FAE1 point mutations by TILLING," New Phytologist, Dec. 2008, 180(4):751-765.
U.S. Appl. No. 16/104,318, filed Aug. 17, 2018, Michael David Marks, Published.
U.S. Appl. No. 16/104,478, filed Aug. 17, 2018, Michael David Marks, Published.
U.S. Appl. No. 16/480,881, filed Jul. 25, 2019, Michael David Marks, Published.
U.S. Appl. No. 16/969,434, filed Aug. 12, 2020, Michael David Marks, Published.
GenBank Accession No. KT223025.1, "Thlaspi arvense cultivar French 3-ketoacyl-CoA synthase (FAE1) mRNA, complete cds," Nov. 29, 2015, 2 pages.
Xie et al., "RNA-Guided Genome Editing in Plants Using a CRISPR-Cas System," Molecular Plant, Nov. 2013, 6(6):1975-1983.
Bai et al., "The Biochemistry of Headgroup Exchange During Triacylglycerol Synthesis in Canola," The Plant Journal, 103(1):83-94, Jan. 2020.
Baud et al., "Physiological and developmental regulation of seed oil production," Prog Lipid Res., 49(3):235-49, Jul. 2010.
Belide et al., "Modification of seed oil composition in Arabidopsis by artificial microRNA-mediated gene silencing," Frontiers in plant science, 3:168, Jul. 2012.
Bell, "Factors affecting the nutritional value of canola meal: a review," Canadian Journal of Animal Science, 73(4):679-697, Dec. 1993.

(Continued)

Primary Examiner — Vinod Kumar
(74) Attorney, Agent, or Firm — Fish & Richardson P.C.

(57) ABSTRACT

This document provides oilseed plants (e.g., pennycress plants) having increased levels of one or more saturated fatty acids, increased levels of one or more polyunsaturated fatty acids (PUFAs), altered (e.g., increased or decreased) levels of oleic acid, and/or altered (e.g., increased or decreased) levels of erucic acid. For example, oilseed plants having reduced polypeptide levels and/or reduced polypeptide activity of one or more polypeptides involved in triglyceride synthesis (e.g., diacylglycerol O-acyltransferase 1 (TAG1) can have increased levels of stearic acid, increased levels of one or more PUFAs, altered levels of oleic acid, and/or altered levels of erucic acid. Also provided herein are methods and materials for making and using oilseed plants having increased levels of one or more saturated fatty acids, increased levels of one or more PUFAs, altered levels of oleic acid, and/or altered levels of erucic acid.

5 Claims, 24 Drawing Sheets
Specification includes a Sequence Listing.

(56) References Cited

OTHER PUBLICATIONS

Bligh et al., "A rapid method of total lipid extraction and purification," Canadian Journal of Biochemistry and Physiology, 37(8):911-917, Aug. 1959.

Boateng et al., "Producing stable pyrolysis liquids from the oil-seed presscakes of mustard family plants: Pennycress (*Thlaspi arvense* L.) and Camelina (*Camelina sativa*)," Energy & Fuels, 24(12):6624-6632, Nov. 2010.

Britt, "From stinkweed to oilseed," Nat. Food, 1:24-25, Jan. 2020.

Chopra et al., "Identification and stacking of crucial traits required for the domestication of pennycress," Nat. Food, 1:84-91, Jan. 2020.

Chopra et al., "The adaptable use of *Brassica* NIRS calibration equations to identify pennycress variants to facilitate the rapid domestication of a new winter oilseed crop," Industrial Crops and Products, 128:55-61, Feb. 2019.

Chopra et al., "Transcriptome profiling and validation of gene based single nucleotide polymorphisms (SNPs) in sorghum genotypes with contrasting responses to cold stress," BMC Genomics, 16(1):1040, Dec. 2015.

Chopra et al., "Translational genomics using *Arabidopsis* as a model enables the characterization of pennycress genes through forward and reverse genetics," The Plant Journal, 96(6):1093-1105, Dec. 2018.

Claver et al., "Identification of target genes and processes involved in erucic acid accumulation during seed development in the biodiesel feedstock Pennycress (*Thlaspi arvense* L.)," Journal of plant physiology, 208:7-16, Jan. 2017.

Crevillén et al., "Epigenetic reprogramming that prevents transgenerational inheritance of the vernalized state," Nature, 515(7528):587-90, Nov. 2014.

Dorn et al., "De novo assembly of the pennycress (*Thlaspi arvense*) transcriptome provides tools for the development of a winter cover crop and biodiesel feedstock," The Plant Journal, 75(6):1028-38, Sep. 2013.

Downey and Craig, "Genetic control of fatty acid biosynthesis in rapeseed (*Brassica napus* L.)," Journal of the American Oil Chemists' Society, Jul.;41(7):475-8, Jul. 1964.

Fauser et al., "Both CRISPR/C as-based nucleases and nickases can be used efficiently for genome engineering in *A rabidopsis thaliana*," Plant J., 79(2):348-359, Jul. 2014.

Ferrándiz et al., "Negative regulation of the SHATTERPROOF genes by FRUITFULL during *Arabidopsis* fruit development," Science, 289(5478):436-438, Jul. 2000.

Fourmann et al., "The two genes homologous to *Arabidopsis* FAE1 co-segregate with the two loci governing erucic acid content in *Brassica napus*," Theor. Appl. Genet., 96(6-7):852-8, May 1998.

Girin et al., "Brassicaceae INDEHISCENT genes specify valve margin cell fate and repress replum formation," Plant J., 63(2):329-338, Jul. 2010.

Golebiowski et al., "Near infrared reflectance spectroscopy of oil in intact canola seed (*Brassica napus* L.). II. Association between principal components and oil content," Journal of near Infrared Spectroscopy, 13(5):255-264, Oct. 2005.

Han et al., "Functional characterization of beta-ketoacyl-CoA synthase genes from *Brassica napus* L," Plant molecular biology, 46(2):229-39, May 2001.

James et al., "Directed Tagging of the *Arabidopsis* Fatty Acid Elongation1 (FAE1) Gene with the Maize Transposon Activator," The Plant Cell, 7:309-319, Mar. 1995.

Javidfar and Cheng, "Single locus, multiallelic inheritance of erucic acid content and linkage mapping of FAE1 gene in yellow mustard," Crop Science, 53(3):825-32, May 2013.

Kano-Murakami et al., "A rice homeotic gene, OSH1, causes unusual phenotypes in transgenic tobacco," FEBS letters, 334(3):365-8, Nov. 1993.

Katavic et al., "Alteration of Seed Fatty Acid Composition by an Ethyl Methanesulfonate-induced Mutation in *Arabidopsis thaliana* Affecting Diacylglycerol Acyltransferase Activity," Plant Physiology, May 1995, 108(1):399-409.

Kim et al., "Toward production of jet fuel functionality in oilseeds: identification of FatB acyl-acyl carrier protein thioesterases and evaluation of combinatorial expression strategies in Camelina seeds," Journal of Experimental Botany, 66(14):4251-4265, May 2015.

Liljegren et al., "SHATTERPROOF MADS-box genes control seed dispersal in *Arabidopsis*," Nature, 404(6779):766-770, Apr. 2000.

Lu et al., "*Arabidopsis* Mutants Deficient in Diacylglycerol Acyltransferase Display Increased Sensitivity to Abscisic Acid, Sugars, and Osmotic Stress During Germination and Seedling Development," Plant Physiology, Jul. 2002, 129(3):1352-1358.

Lu et al., "Expression pattern of diacylglycerol acyltransferase-1, an enzyme involved in triacylglycerol biosynthesis, in *Arabidopsis thaliana*," Plant Mol. Biology, May 2003, 52(1):31-41.

McGinn et al., "Molecular tools enabling pennycress (*Thlaspi arvense*) as a modelplant and oilseed cash cover crop," Plant Biotechnology Journal, 17(4):776-788, Apr. 2019.

Montero de Espinosa et al., "Plant oils: The perfect renewable resource for polymer science?!" European Polymer Journal, 47(5):837-852, May 2011.

Moser et al., "Composition and physical properties of cress (*Lepidium sativum* L.) and field pennycress (*Thlaspi arvense* L.) oils," Industrial Crops and Products, 30(2):199-205, Sep. 2009.

Moser et al., "Production and evaluation of biodiesel from field pennycress (*Thlaspi arvense* L.) oil," Energy & Fuels, 23(8):4149-4155, Jul. 2009.

Phippen et al., "Soybean seed yield and quality as a response to field pennycress residue," Crop Science, 52(6):2767-2773, Nov. 2012.

Riu et al., "[Detection of erucic acid and glucosinolate in intact rapeseed by near-infrared diffuse reflectance spectroscopy]," Spectroscopy and Spectral Analysis, Dec. 2006, 26(12):2190-2192, (with English abstract).

Roeder et al., "The role of the REPLUMLESS homeodomain protein in patterning the *Arabidopsis* fruit," Curr. Biol., 13(18):1630-1635, Sep. 2003.

Rosas et al., "One-step, codominant detection of imidazolinone resistance mutations in weedy rice (*Oryza sativa* L.)," Electron. J. Biotechnol., 17:95-101, Mar. 2014.

Roscoe et al., "Mutations in the fatty acid elongation 1 gene are associated with a loss of β-ketoacyl-CoA synthase activity in low erucic acid rapeseed," FEBS letters, 492(1-2):107-11, Mar. 2001.

Routaboul et al., "The TAG1 locus of *Arabidopsis* encodes for a diacylglycerol acyltransferase," Plant Physiol Biochemistry, Nov. 1999, 37(11):831-840.

Sanyal et al., "Stearic sunflower oil as a sustainable and healthy alternative to palm oil. A review," Agron. Sustain. Development, May 17, 2017, 37:18, 11 pages.

Sedbrook et al., "New approaches to facilitate rapid domestication of a wild plant to an oilseed crop: example pennycress (*Thlaspi arvense* L.)," Plant Sci., 227:122-32, Oct. 2014.

Sidhu et al., "Diode Array Near Infrared Spectrometer Calibrations for Composition Analysis of Single Plant Canola (*Brassica napus*) Seed," Applied Engineering in Agriculture, 30(1):69-76, Jan. 2014.

Steinert et al., "Highly efficient heritable plant genome engineering using Cas9 orthologues from *Streptococcus thermophilus* and *Staphylococcus aureus*," Plant J., 84:1295-305, Dec. 2015.

Van Gelderen et al, "An INDEHISCENT-Controlled Auxin Response Specifies the Separation Layer in Early *Arabidopsis* Fruit," Molecular Plant, Jun. 2016, 9:857-869.

Vogel et al., "Expression of the *Arabidopsis* Wrinkled 1 transcription factor leads to higher accumulation of palmitate in soybean seed," Plant Biotechnol. Journal, Jan. 17, 2019, 17(7):1369-1379.

Warwick et al., "The biology of Canadian weeds. 9. Thlaspi arvense L.(updated)," Canadian Journal of Plant Science, 82(4):803-823, Oct. 2002.

Wu et al., "Zero erucic acid trait of rapeseed (*Brassica napus* L.) results from a deletion of four base pairs in the fatty acid elongase 1 gene," Theoretical and applied genetics, 116(4):491-9, Feb. 2008.

Xin et al., "Mid-infrared spectral characteristics of lipid molecular structures in *Brassica carinata* seeds: relationship to oil content, fatty acid and glucosinolate profiles, polyphenols, and condensed tannins," J. Agric. Food Chem., 62(32):7977-7988, Aug. 2014.

(56) References Cited

OTHER PUBLICATIONS

Yu et al., "Modulation of brassinosteroid-regulated gene expression by Jumonji domain-containing proteins ELF6 and REF6 in *Arabidopsis*," Proceedings of the National Academy of Sciences, 105(21):7618-23, May 2008.

Zarhloul et al., "Breeding high-stearic oilseed rape (*Brassica napus*) with high- and low-erucic background using optimised promoter-gene constructs," Mol. Breeding, Sep. 2006, 18(3):241-251.

Zou et al., "The *Arabidopsis thaliana* TAG1 mutant has a mutation in a diacylglycerol acyltransferase gene.," The Plant Journal, Sep. 1999, 19(6):645-653.

Batsale et al., "Biosynthesis and Functions of Very-Long-Chain Fatty Acids in the Responses of Plants to Abiotic and Biotic Stresses," Cells, May 21, 2021, 10:1284, 26 pages.

Claver et al., "Functional analysis of β-ketoacyl-CoA synthase from biofuel feedstock Thlaspi arvense reveals differences in the triacylglycerol biosynthetic pathway among Brassicaceae," Plant Mol. Biology, 104(3):283-296, Aug. 1, 2020.

Dorn et al., "A draft genome of field pennycress (*Thlaspi arvense*) provides tools for the domestication of a new winter biofuel crop," DNA Research, Apr. 2015, 22(2):121-131.

ENA Accession No. PRJEB46635, "Chromosome-level Thlaspi arvense genome provides new tools for translational research and for a newly domesticated cash cover crop of the cooler climates," dated Aug. 2, 2021, 2 pages.

GenBank Accession No. AAC49186.1, "beta-ketoacyl-CoA synthase [Simmondsia chinensis]," dated Oct. 31, 1995, 2 pages.

GenBank Accession No. AZNP01000000.1, "Thlaspi arvense cultivar MN106, whole genome shotgun sequencing project," dated Mar. 19, 2015, 1 page.

GenBank Accession No. NP_195178.1, "3-ketoacyl-CoA synthase 18 [*Arabidopsis thaliana*]," dated Jan. 22, 2014, 2 pages.

Geng et al., "Genomic analysis of field pennycress (*Thlaspi arvense*) provides insights into mechanisms of adaptation to high elevation," BMC Biology, Jul. 22, 2021, 19:143, 14 pages.

Gigolashvili et al., "The R2R3-MYB transcription factor HAG1/MYB28 is a regulator of methionine-derived glucosinolate biosynthesis in *Arabidopsis thaliana*," Plant Journal, 51(2):247-261, Jul. 2007.

Haslam et al., "Extending the story of very-long-chain fatty acid elongation," Plant Science, 210:93-107, Sep. 2013.

Kafri et al., "The regulatory utilization of genetic redundancy through responsive backup circuits," Proc. Nat. Acad. Sci. USA, 103(31):11653-11658, Aug. 2006.

Lassner et al., "A jojoba beta-Ketoacyl-CoA synthase cDNA complements the canola fatty acid elongation mutation in transgenic plants," Plant Cell, 8(2):281-292, Feb. 1996.

Nunn et al., "Chromosome-level Thlaspi arvense genome provides new tools for translational research and for a newly domesticated cash cover crop of the cooler climates," bioRxiv, Aug. 1, 2021, 48 pages.

Shen et al., "Resistance gene candidates identified by PCR with degenerate oligonucleotide primers map to clusters of resistance genes in lettuce," Mol. Plant Microbe Interactions, 11(8):815-823, Aug. 1998.

Tresch et al., "Inhibition of saturated very-long-chain fatty acid biosynthesis by mefluidide and perfluidone, selective inhibitors of 3-ketoacyl-CoA synthases," Phytochemistry, Apr. 2012, 76:162-171.

Yang et al., "Comprehensive analysis of KCS gene family in Citrinae reveals the involvement of CsKCS2 and CsKCS11 in fruit cuticular wax synthesis at ripening," Plant Science, Sep. 2021, 310:110972, 11 pages.

Zeng et al. (Plant cell, 26:2648-2659, Jun. 2014).

* cited by examiner

```
At_TAG1    MAILDSAGVTTVTENGGGEFVDLDRLRRRKSRSDSSNGLL-LSGSDNNSPSDDVGAPADV  59
Ta_TAG1    MAILDSGGVTMPTENGGGEFADLDTLRRRKSRSDSNEPLSDSAPGTDAFPSDDVGAPSDA  60
Ta_tag1-1  MAILDSGGVTMPTENGGGEFADLDTLRRRKSRSDSNEPLSDSAPGTDAFPSDDVGAPSDA  60
Ta_tag1-2  MAILDSGGVTMPTENGGGEFADLDTLRRRKSRSDSNEPLSDSAPGTDAFPSDDVGAPSDA  60
Ta_tag1-3  MAILDSGGVTMPTENGGGEFADLDTLRRRKSRSDSNEPLSDSAPGTDAFPSDDVGAPSDA  60
Gm_TAG1    MAISDEPETVA---------TALNHSSLRRRPTAAG-----L--------FNSPE---TTTDSSG  40
Os_TAG1    ------------------------------------M--------APPPS---LAPDR--G  12
Sl_TAG1    ----------------------------------------------------MDGSG   5

At_TAG1    RDRIDSVVNDDAQGTANLAGDNNGGGDNN---GGGRGGGEGRGNADATFTYRPSVPAHRRA  117
Ta_TAG1    RDRIDSAV-DDAQGTANLAGDNGGDTEIRETGGGGGGGEARGDADTRYTYRPSVPAHRRA  119
Ta_tag1-1  RDRIDSAV-DDAQGTANLAGDNGGDTEIRETGGGGGGGEARGDADTRYTYRPSVPAHRRA  119
Ta_tag1-2  RDRIDSAV-DDAQGTANLAGDNGGDTEIRETGGGGGGGEARGDADTRYTYRPSVPAHRRA  119
Ta_tag1-3  RDRIDSAV-DDAQGTANLAGDNGGDTEIRETGGGGGGGEARGDADTRYTYRPSVPAHRRA  119
Gm_TAG1    DD------LAKDS-GSDDSISSDAANSQ------------PQQKQDTDFSVLKFAYRPSVPAHRKV   87
Os_TAG1    GGEPDDALRLR-APAAAAAGDAPAPQ-------QQQEQRHQEQQQQLLWYRASAPAHRRV   64
Sl_TAG1    NGGLDRVSEAV-STTIGKISDGDGIQ--------EEQRKANETTPLKYVYRASAPAHRRN   56

At_TAG1    RESPLSSDAIFKQSHAGLFNLCVVVLIAVNSRLIIENLMKYGWLIRTDFWFSSPSLRDWP  177
Ta_TAG1    RESPLSSDAIFKQSHAGLFNLCVVVLIAVNSRLIIENLMKYGWLIRTDFWFSSTSLRDWP  179
Ta_tag1-1  RESPLSSDAIFKQSHAGLFNLCVVVLIAVNSRLIIENLMKYGWLIKTDFWFSSTSLRDWP  179
Ta_tag1-2  RESPLSSDAIFKQSHAGLFNLCVVVLIAVNSRLIIENLMKYGWLIRTDFWFSSTSLRDWP  179
Ta_tag1-3  RESPLSSDAIFKQSHAGLFNLCVVVLIAVNSRLIIENLMKYGWLIRTDFWFSSTSLRDWP  179
Gm_TAG1    KESPLSSDTIFRQSHAGLFNLCIVVLVAVNSRLIIENLMKYGWLIKSGFWFSSKSLRDWP  147
Os_TAG1    RESPLSSDAIFRQSHAGLLNLCIVVLVAVNSRLIIENLMKYGLLIRAGFWFSGTSLADWP  124
Sl_TAG1    KESPLSSAAIFKQSHAGLLNLCIVVLIAVNSRLIIENLMKYGLLIGSGFWSSTSVRDWP  116

At_TAG1    LFMCCISLSIFPLAAFTVEKLVLQKYISEPVVIFLHIIITMTE------------------  220
Ta_TAG1    LFI--ISLSIFPLAAFTVEKLVLQKCISEPVNKFVVSWRTYKFLSDNIKGCHHSSYYNHN  237
Ta_tag1-1  LFI---ISLSIFPLAAFTVEKLVLQKCISEPVNKFVVSWRTYKFLSDNIKGCHHSSYYNHN  237
Ta_tag1-2  LFI---ISLSIFPLAAFTVEKLVLQKCISEPVNKFVVSWRTYKFLSDNIKGCHHSSYYNHN  237
Ta_tag1-3  LFI---ISLSIFPLAAFTVEKLVLQKCISEPVNKFVVSWRTYKFLSDNIKGCHHSSYYNHN  237
Gm_TAG1    LFMCCLSLVVFPFAAFIVEKLAQQKCIPEPVVVVLHIIITSAS-----------------  190
Os_TAG1    LLMCCLTLPTFPLAALMVEKLAQRKLISKHVVILLHIVITTSV----------------  167
Sl_TAG1    LLMCCLSLPIFPLAAFLVEKMAQKKYMTEHVVVTLHIIITTAS-----------------  159

At_TAG1    ---------------VLYPVYVTLRCDSAFLSGVTLMLLTCIVWLKLVSYAHTSYDIRSLAN  267
Ta_TAG1    DRGLVSSLRHPKLTNSMILKMDRCDSAFLSGVTLMLLTCIVWLKLVSYAHTSYDIRTLAN  297
Ta_tag1-1  DRGLVSSLRHPKLTNSMILKMDRCDSAFLSGVTLMLLTCIVWLKLVSYAHTSYDIRTLAN  297
Ta_tag1-2  DRGLVSSLRHPKLTNSMILKMDRCDSAFLSGVTLMLLTYIVWLKLVSYAHTSYDIRTLAN  297
Ta_tag1-3  DRGLVSSLRHPKLTNSMILKMDRCDSAFLSGVTLMLLTCIVWLKLVSYAHTSYDIRTLAN  297
Gm_TAG1    ---------------LFYPVLVILRCDSAFLSGVTLMLFACVVWLKLVSYAHTNYDMRALTK  237
Os_TAG1    ---------------LVYPVVVILKCDSAVLSGFVLMFLASIIWLKLVSFAHTNYDIRMLSK  214
Sl_TAG1    ---------------ILYPVLVILRCDSAFLSGVTLMMFACIVWMKLVSYAHTNYDMRQLAK  206
```

FIG. 1

```
At_TAG1     AADK-------ANPEVSYYVSLKSLAYFMVAPTLCYQPSYPRSACIRKGWVARQFAKLVI  320
Ta_TAG1     SADK-------ANPEVSYYVSLKSLAYFMVAPTLCYQLSYPRSPCIRKGWVARQFAKLVI  350
Ta_tag1-1   SADK-------ANPEVSYYVSLKSLAYFMVAPTLCYQLSYPRSPCIRKGWVARQFAKLVI  350
Ta_tag1-2   SADK-------ANPEVSYYVSLKSLAYFMVAPTLCYQLSYPRSPCIRKGWVARQFAKLVI  350
Ta_tag1-3   SADK-------ANPEVSYYVSLKSLAYFMVAPTLCYQLSYPRSPCIRKGWVARQFAKLVI  350
Gm_TAG1     SVEKGEALPDTLNMDYPYNVSFKSLAYFLVAPTLCYQPSYPRTPYIRKGWLFRQLVKLII  297
Os_TAG1     SIEKGVTHDISIDPENIKWPTFKRLSYFMLAPTLCYQPSYPRTTYIRKGWVVRQLIKCLV  274
Sl_TAG1     SVNEGEN----SEINYSYNVSFESLAYFMVAPTLCYQLSYPRSASIRKGWLARQLIKLVI  262

At_TAG1     FTGFMGFIIEQYINPIVRNSKHPLKGDLLYAIERVLKLSVPNLYVWLCMFYCFFHLWLNI  380
Ta_TAG1     FTGFMGFIIEQYINPIVRNSKHPLKGDLLYAIERVLKLSVPNLYVWLCMFYCFFHLWLNI  410
Ta_tag1-1   FTGFMGFIIEQYINPIVRNSKHPLKGDLLYAIERVLKLSVPNLYVWLCMFYCFFHLWLNI  410
Ta_tag1-2   FTGFMGFIIEQYINPIVRNSKHPLKGDLLYAIERVLKLSVPNLYVWLCMFYCFFHLWLNI  410
Ta_tag1-3   FTGFMGFIIEQYINPIVRNSKHPLKGDLLYAIERVLKLSVPNLYVWLCMFYCFFHLWLNI  410
Gm_TAG1     FTGVMGFIIEQYINPIVQNSQHPLKGNLLYAIERVLKLSVPNLYVWLCMFYCFFHLWLNI  357
Os_TAG1     FTGLMGFIIEQYINPIVKNSKHPLKGNFLNAIERVLKLSVPTLYVWLCMFYCFFHLWLNI  334
Sl_TAG1     FTGLMGFIIEQYINPIVRSSRHPFEGNLLYAIERVLKLSVPILYVWLCMFYSLFHLWLNI  322

At_TAG1     LAELLCFGDREFYKDWWNAKSVGDYWRMWNMPVHKWMVRHIYFPCLRSKIPKT-------  433
Ta_TAG1     LAELLCFGDREFYKDWWNAKSVGDYWRMWNMPVHKWMVRHIYFPCLRSKIPKVSNMYDSD  470
Ta_tag1-1   LAELLCFGDREFYKDWWNAKSVGDYWRMWNMPVHKWMVRHIYFPCLRSKIPKVSNMYDSD  470
Ta_tag1-2   LAELLCFGDREFYKDWWNAKSVGDYWRMWNMPVHKWMVRHIYFPCLRSKIPKVSNMYDSD  470
Ta_tag1-3   LAELLCFGDREFYKD*--------------------------------------------  425
Gm_TAG1     LAELLRFGDREFYQDWWNAKTVEDYWRMWNMPVHKWMIRHLYFPCLRHGIPKA-------  410
Os_TAG1     LAELLCFGDREFYKDWWNAKTVEEYWRMWNMPVHKWVIRHIYFPCIRNGFSKG-------  387
Sl_TAG1     LAEVLRFGDREFYKDWWNAKTIDEYWRLWNMPVHKWMVRHIYFPCLRNGIPKG-------  375

At_TAG1     ------------LAIIIAFLVSAVFHELCIAVPCRLFKLWAFLGIMFQVPLVFITNYLQERFG  484
Ta_TAG1     LRWPRLYSVPAIIIAFLVSAVFHELCIAVPCRLFNLWAFMGIMFQVPLVFITNYLQERFG  530
Ta_tag1-1   LRWPRLYSVPAIIIAFLVSAVFHELCIAVPCRLFNLWAFMGIMFQVPLVFITNYLQERFG  530
Ta_tag1-2   LRWPRLYSVPAIIIAFLVSAVFHELCIAVPCRLFNLWAFMGIMFQVPLVFITNYLQERFG  530
Ta_tag1-3   ------------------------------------------------------------  425
Gm_TAG1     ----------VALLIAFLVSALFHELCIAVPCHIFKLWAFGGIMFQVPLVFITNYLQNKFR  461
Os_TAG1     ----------VAILISFLVSAAFHELCVAVPCHIFKFWAFIGIMFQIPLVFLTKYLQDKFN  438
Sl_TAG1     ----------VAMVISFFISAVFHELCIAVPCRLFKFWAFLGIMFQIPLVILTNFLQNKFK  426

At_TAG1     -STVGNMIFWFIFCIFGQPMCVLLYYHDLMNRKGSMS*--    520
Ta_TAG1     -SMVGNMVFWFIFCIFGQPMCVLLYYHDLMNRKGSMA---    566
Ta_tag1-1   -SMVGNMVFWFIFCIFGQPMCVLLYYHDLMNRKGSMA---    566
Ta_tag1-2   -SMVGNMVFWFIFCIFGQPMCVLLYYHDLMNRKGSMA---    566
Ta_tag1-3   ----------------------------------------  425
Gm_TAG1     NSMVGNMIFWFIFSILGQPMCVLLYYHDLMNRKGKLD*--    498
Os_TAG1     NTMVGNMIFWFFFSILGQPMCVLLYYHDVMNRQQAQTNR*   477
Sl_TAG1     NSNVGNMTFWCFFCIVGQPMCVLLYYHDVMNRNGSSS*--   463
```

FIG. 1 (continued)

| Genotype | Palmatic | Stearic | Oleic | Linoleic | Linolenic | Eicosenoic | Erucic | Nervonic |
|---|---|---|---|---|---|---|---|---|
| wild-type | 3.78 | 4.94 | 9.69 | 18.46 | 12.98 | 8.58 | 37.70 | 2.87 |
| fae1 | 8.49 | 7.20 | 37.40 | 30.48 | 16.27 | 0.15 | 0.00 | 0.00 |
| fad2 | 3.09 | 7.92 | 28.59 | 0.00 | 2.14 | 9.72 | 44.79 | 3.75 |
| rod1 | 3.60 | 5.74 | 16.81 | 8.58 | 10.69 | 9.64 | 41.05 | 3.89 |
| tag1 | 7.47 | 17.04 | 8.76 | 18.40 | 30.29 | 1.63 | 14.61 | 1.05 |
| tag1/fad2 | 17.74 | 53.80 | 0.00 | 12.32 | 13.04 | 0.00 | 3.09 | 0.00 |
| fae1/tag1 | 7.67 | 7.22 | 21.04 | 40.83 | 22.67 | 0.00 | 0.00 | 0.00 |
| fae1/fad2 | 4.03 | 8.20 | 83.02 | 1.01 | 2.40 | 1.34 | 0.00 | 0.00 |
| tag1/rod1 | 8.38 | 16.36 | 13.29 | 15.28 | 26.81 | 2.23 | 16.19 | 1.08 |
| fae1/rod1 | 4.42 | 5.86 | 60.27 | 15.70 | 12.71 | 1.04 | 0.00 | 0.00 |
| fae1/tag1/fad2 | 7.06 | 7.58 | 52.00 | 17.40 | 14.63 | 0.25 | 0.00 | 0.13 |

SEQ ID NO:17

TTGTCTAAATTTGATAAAATATATGATGACGACAATTCCGGTGGATCACAgtttgcttcatttggcttttttgtgtgtttgtc
aagttgctattcaataagaatttgtgattttgattggtctcctcaaaattctgtgaaattttagtaacaaggaagaaattaaca
aatcacaacaagaaagagatgtgagctgtcgtatcaaatcttattcgttttctcaacgcaatcgttttagttttttttaactta
acgccacttctctgctccatacactccttttgtccacgtacttttcatttgtggtaatccatttcttcactttggatctttca
tctgaacaacaatttcttgactcaatcaattaccacccgttcttgtgcttttgtatagattcataatcttgtgtgtttcagctt
ctcattgctttggttcttgttttttttctgcagAAACATGGGTGCAGGTGGAAGAATGACGGTTCCTACTTCTTCCAAGAAGT
CTGAAACCAATGCCTTAAAGCGTGTGCCGTGCGAGAAACCGCCGTTCACGCTCGGAGAACTGAAGAAAGCAATCCCACAGCATT
GTTTCAATCGCTCAATCCCTCGCTCTTTCTCCTACCTTATCTGGGACATCATCATAGCCTCTTGCTTCTACTACGTTGCCACCA
CTTACTTCTCTCTCCTCCCTCAGCCTCTCTCTTACTTGGCTTGGCCTCTCTATTGGGTCTGTCAAGGCTGTGTCTTAACCGGAG
TCTGGGTCATAGCTCACGAATGCGGCCACCACGCCTTCAGCGACTACCAATGGCTTGACGACACAGTCGGTCTGATCTTCCATT
CTTTCCTCCTCGTCCCTTACTTCTCCTGGAAATACAGCCACCGCCGTCACCATTCCAACACCGGATCACTTGAAAAGGACGAAG
TGTTTGTCCCTAAACAGAAATCCGCCATCAAATGGTACGGCAAGTACCTCAACAACCCTCTGGGACGCACCGTGATGTTAACCG
TCCAGTTCACCCTTGGCTGGCCCTTGTACTTAGCCTTCAACGTCTCGGGGAGACCCTACGACGGGTTCGCTTGCCACTTCCACC
CAAACGCTCCCATCTACAACGACCGTGAACGCCTCCAGATATACATCTCGGATGCTGGTATCCTCGCCGTCTGTTACGGTCTCT
ACCGTTACGCTGCTGCACAAGGAGTGGCCTCGATGATCTGCGTCTACGGAGTTCCGCTTCTGATAGTCAACGGGTTCCTCGTCT
TGATCACATACTTGCAGCACACCCATCCCTCGTTGCCTCACTACGATTCATCCGAGTGGGATTGGTTCAGGGGAGCTTTGGCTA
CCGTAGACAGAGACTATGGAATCCTGAACAAGGTCTTCCACAACATCACGGACACGCACGTGGCTCACCACCTGTTCTCGACGA
TGCCGCATTACCATGCGATGGAGGCCACGAAGGCGATAAAGCCGATACTCGGGGACTATTACCAGTTTGATGGAACACCGGTCT
TCAAGGCGATGTGGAGGGAGGCGAAGGAGTGTGTCTATGTAGAACCGGACAGGAAAGGTGAGAAGAAAGtgtgttctggtaca
acaacaagttgtgaggatgatcaggtgaaagaagaaggaagaaaaatcgtcggcctttctcttgtctggttatctttgtttaa
gaagatatatgtttgtttcaataatcttattgtccattttgttgtgttctgacattgtggcttaaattattatgtgatgttagt
gtccaattgttctgcgtctgtattgttcttctcatcgctgtttgttgggatcgtagaaatgtgactttcggacaattaaactc
ttgtactcaagctatcactctgttggcagcatcaaaagtgttttcatagtttcggtcttttggtctctgtttgtttgatactgt
tggtgagaatggctcttcaagtgttggaatctacctaaggtgaacacattgtaggatttttctttatttaattgccattgtat
accacactgcagtgaaccgcaactatgttgaccatgtcgatgaatgtaagtgaaccatgaaactaatctttctgtacaatttac
ttacttctgagtcattgtgatgtttggttggcaggtcacctttatttctcacactccctccactcatgtgatgtggttgggatt
ttcttttcataagtagcttttgtaaagaactcagtctttctctttcaaatcatggaaaccttttcaacaaaagccaaatccat
gttacataagcaaaatatctgctttcttcatctttcctttctttcatatttgagAGGGAACAAAAGAAGAGGAAGAAAATGAAG
CAAAGTAA

SEQ ID NO:18

ATGTCTAAATTTGATAAAATATATGATGACGACAATTCCGGTGGATCACAAAACATGGGTGCAGGTGGAAGAATGACGGTTCCT
ACTTCTTCCAAGAAGTCTGAAACCAATGCCTTAAAGCGTGTGCCGTGCGAGAAACCGCCGTTCACGCTCGGAGAACTGAAGAAA
GCAATCCCACAGCATTGTTTCAATCGCTCAATCCCTCGCTCTTTCTCCTACCTTATCTGGGACATCATCATAGCCTCTTGCTTC
TACTACGTTGCCACCACTTACTTCTCTCTCCTCCCTCAGCCTCTCTCTTACTTGGCTTGGCCTCTCTATTGGGTCTGTCAAGGC
TGTGTCTTAACCGGAGTCTGGGTCATAGCTCACGAATGCGGCCACCACGCCTTCAGCGACTACCAATGGCTTGACGACACAGTC
GGTCTGATCTTCCATTCTTTCCTCCTCGTCCCTTACTTCTCCTGGAAATACAGCCACCGCCGTCACCATTCCAACACCGGATCA
CTTGAAAAGGACGAAGTGTTTGTCCCTAAACAGAAATCCGCCATCAAATGGTACGGCAAGTACCTCAACAACCCTCTGGGACGC
ACCGTGATGTTAACCGTCCAGTTCACCCTTGGCTGGCCCTTGTACTTAGCCTTCAACGTCTCGGGGAGACCCTACGACGGGTTC
GCTTGCCACTTCCACCCAAACGCTCCCATCTACAACGACCGTGAACGCCTCCAGATATACATCTCGGATGCTGGTATCCTCGCC
GTCTGTTACGGTCTCTACCGTTACGCTGCTGCACAAGGAGTGGCCTCGATGATCTGCGTCTACGGAGTTCCGCTTCTGATAGTC
AACGGGTTCCTCGTCTTGATCACATACTTGCAGCACACCCATCCCTCGTTGCCTCACTACGATTCATCCGAGTGGGATTGGTTC
AGGGGAGCTTTGGCTACCGTAGACAGAGACTATGGAATCCTGAACAAGGTCTTCCACAACATCACGGACACGCACGTGGCTCAC
CACCTGTTCTCGACGATGCCGCATTACCATGCGATGGAGGCCACGAAGGCGATAAAGCCGATACTCGGGGACTATTACCAGTTT
GATGGAACACCGGTCTTCAAGGCGATGTGGAGGGAGGCGAAGGAGTGTGTCTATGTAGAACCGGACAGGAAAGGTGAGAAGAAA
GAGGGAACAAAAGAAGAGGAAGAAAATGAAGCAAAGTAA

FIG. 3A

SEQ ID NO:19

ATGTCTAAATTTGATAAAATATATGATGACGACAATTCCGGTGGATCACAgtttgcttcatttggcttttttgtgtgtttgtc
aagttgctattcaataagaatttgtgattttgattggtctcctcaaaattctgtgaaattttagtaacaaggaagaaattaaca
aatcacaacaagaaagagatgtgagctgtcgtatcaaatcttattcgttttctcaacgcaatcgttttagttttttttaactta
acgccacttctctgctccatacactccttttgtccacgtacttttcatttgtggtaatccatttcttcactttggatctttca
tctgaacaacaatttcttgactcaatcaattaccacccgttcttgtgctttgtatagattcataatcttgtgtgtttcagctt
ctcattgctttggttcttgtttttttttctgcagAAACATGGGTGCAGGTGGAAGAATGACGGTTCCTACTTCTTCCAAGAAGT
CTGAAACCGATGCCTTAAAGCGTGTGCCGTGCGAGAAACCGCCGTTCACGCTCGGAGAACTGAAGAAAGCAATCCCACAGCATT
GTTTCAATCGCTCAATCCCTCGCTCTTTCTCCTACCTTATCTGGGACATCATCATAGCCTCTTGCTTCTACTACGTTGCCACCA
CTTACTTCTCTCTCCTCCCTCAGCCTCTCTCTTACTTGGCTTGGCCTCTCTATTGGGTCTGTCAAGGCTGTGTCTTAACCGGAG
TCTGGGTCATAGCTCACGAATGCGGCCACCACGCCTTCAGCGACTACCAATGGCTTGACACACAGTCGATCTGATCTTCCATT
CTTTCCTCCTCGTCCCTTACTTCTCCTGGAAATACAGCCACCGCCGTCACCATTCCAACACCGGATCACTTGAAAAGGACGAAG
TGTTTGTCCCTAAACAGAAATCCGCCATCAAATGGTACGGCAAGTACCTCAACAACCCTCTGGGACGCACCGTGATGTTAACCG
TCCAGTTCACCCTTGGCTGGCCCTTGTACTTAGCCTTCAACGTCTCGGGGAGACCCTACGACGGGTTCGCTTGCCACTTCCACC
CAAACGCTCCCATCTACAACGACCGTGAACGCCTCCAGATATACATCTCGGATGCTGGTATCCTCGCCGTCTGTTACGGTCTCT
ACCGTTACGCTGCTGCACAAGGAGTGGCCTCGATGATCTGCGTCTACGGAGTTCCGCTTCTGATAGTCAACGGGTTCCTCGTCT
TGATCACATACTTGCAGCACACCCATCCCTCGTTGCCTCACTACGATTCATCCGAGTGGGATTGGTTCAGGGGAGCTTTGGCTA
CCGTAGACAGAGACTATGGAATCCTGAACAAGGTCTTCCACAACATCACGGACACGCACGTGGCTCACCACCTGTTCTCGACGA
TGCCGCATTACCATGCGATGGAGGCCACGAAGGCGATAAAGCCGATACTCGGGGACTATTACCAGTTTGATGGAACACCGGTCT
TCAAGGCGATGTGGAGGGAGGCGAAGGAGTGTGTCTATGTAGAACCGGACAGGAAAGGTGAGAAGAAAGtgtgttctggtaca
acaacaagttgtgaggatgatcaggtgaaagaagaaggaagaaaaatcgtcggcctttctcttgtctggttatctttgtttaa
gaagatatatgtttgtttcaataatcttattgtccatttgttgtgttctgacattgtggcttaaattattatgtgatgttagt
gtccaattgttctgcgtctgtattgttcttctcatcgctgttttgttgggatcgtagaaatgtgactttcggacaattaaactc
ttgtactcaagctatcactctgttggcagcatcaaaagtgttttcatagtttcggtcttttggtctctgtttgtttgatactgt
tggtgagaatggctcttcaagtgttggaatctacctaaggtgaacacattgtaggattttttcttttatttaattgccattgtat
accacactgcagtgaacgcaactatgttgaccatgtcgatgaatgtaagtgaaccatgaaactaatctttctgtacaatttac
ttacttctgagtcattgtgatgtttggttggcaggtcacctttatttctcacactccctccactcatgtgatgtggttgggatt
ttcttttcataagtagcttttgtaaagaactcagtcttctctttcaaatcatggaaaccttttcaacaaaagccaaatccat
gttacataagcaaaatatctgctttcttcatctttcctttctttcatatttgagAGGGAACAAAGAAGAGGAAGAAAATGAAG
CAAAGTAA

SEQ ID NO:20

ATGTCTAAATTTGATAAAATATATGATGACGACAATTCCGGTGGATCACAAAACATGGGTGCAGGTGGAAGAATGACGGTTCCT
ACTTCTTCCAAGAAGTCTGAAACCGATGCCTTAAAGCGTGTGCCGTGCGAGAAACCGCCGTTCACGCTCGGAGAACTGAAGAAA
GCAATCCCACAGCATTGTTTCAATCGCTCAATCCCTCGCTCTTTCTCCTACCTTATCTGGGACATCATCATAGCCTCTTGCTTC
TACTACGTTGCCACCACTTACTTCTCTCTCCTCCCTCAGCCTCTCTCTTACTTGGCTTGGCCTCTCTATTGGGTCTGTCAAGGC
TGTGTCTTAACCGGAGTCTGGGTCATAGCTCACGAATGCGGCCACCACGCCTTCAGCGACTACCAATGGCTTGACACACAGTC
GATCTGATCTTCCATTCTTTCCTCCTCGTCCCTTACTTCTCCTGGAAATACAGCCACCGCCGTCACCATTCCAACACCGGATCA
CTTGAAAAGGACGAAGTGTTTGTCCCTAAACAGAAATCCGCCATCAAATGGTACGGCAAGTACCTCAACAACCCTCTGGGACGC
ACCGTGATGTTAACCGTCCAGTTCACCCTTGGCTGGCCCTTGTACTTAGCCTTCAACGTCTCGGGGAGACCCTACGACGGGTTC
GCTTGCCACTTCCACCCAAACGCTCCCATCTACAACGACCGTGAACGCCTCCAGATATACATCTCGGATGCTGGTATCCTCGCC
GTCTGTTACGGTCTCTACCGTTACGCTGCTGCACAAGGAGTGGCCTCGATGATCTGCGTCTACGGAGTTCCGCTTCTGATAGTC
AACGGGTTCCTCGTCTTGATCACATACTTGCAGCACACCCATCCCTCGTTGCCTCACTACGATTCATCCGAGTGGGATTGGTTC
AGGGGAGCTTTGGCTACCGTAGACAGAGACTATGGAATCCTGAACAAGGTCTTCCACAACATCACGGACACGCACGTGGCTCAC
CACCTGTTCTCGACGATGCCGCATTACCATGCGATGGAGGCCACGAAGGCGATAAAGCCGATACTCGGGGACTATTACCAGTTT
GATGGAACACCGGTCTTCAAGGCGATGTGGAGGGAGGCGAAGGAGTGTGTCTATGTAGAACCGGACAGGAAAGGTGAGAAGAAA
GAGGGAACAAAGAAGAGGAAGAAAATGAAGCAAAGTAA

FIG. 3B

SEQ ID NO:21

ATGTCTAAATTTGATAAAATATATGATGACGACAATTCCGGTGGATCACAgtttgcttcatttggcttttttgtgtgtttgtc
aagttgctattcaataagaatttgtgattttgattggtctcctcaaaattctgtgaaattttagtaacaaggaagaaattaaca
aatcacaacaagaaagagatgtgagctgtcgtatcaaatcttattcgttttctcaacgcaatcgttttagttttttttaactta
acgccacttctctgctccatacactccttttgtccacgtacttttcatttgtggtaatccatttcttcactttggatctttca
tctgaacaacaatttcttgactcaatcaattaccaccegttcttgtgctttgtatagattcataatcttgtgtgtttcagctt
ctcattgctttggttcttgtttttttttctgcagAAACATGGGTGCAGGTGGAAGAATGACGGTTCCTACTTCTTCCAAGAAGT
CTGAAACCGATGCCTTAAAGCGTGTGCCGTGCGAGAAACCGCCGTTCACGCTCGGAGAACTGAAGAAAGCAATCCCACAGCATT
GTTTCAATCGCTCAATCCCTCGCTCTTTCTCCTACCTTATCTGGGACATCATCATAGCCTCTTGCTTCTACTACGTTGCCACCA
CTTACTTCTCTCTCCTCCCTCAGCCTCTCTCTTACTTGGCTTGGCCTCTCTATTGGGTCTGTCAAGGCTGTGTCTTAACCGGAG
TCTGGGTCATAGCTCACGAATGCGGCCACCACGCCTTCAGCGACTACCAATGGCTTGACGACACAGTCGGTCTGATCTTCCATT
CTTTCCTCCTCGTCCCTTACTTCTCCTGGAAATACAGCCACCGCCGTCACCATTCCAACACCGGATCACTTGAAAAGGACGAAG
TGTTTGTCCCTAAACAGAAATCCGCCATCAAATGGTACGGCAAGTACCTCAACAACCCTCTGGGACGCACCGTGATGTTAACCG
TCCAGTTCACCCTTGGCTGGCCCTTGTACTTAGCCTTCAACGTCTCGGGGAGACCCTACGACGGGTTCGCTTGCCACTTCCACC
CAAACGCTCCCATCTACAACGACCGTGAACGCCTCCAGATATACATCTCGGATGCTGGTATCCTCGCCGTCTGTTACGGTCTCT
ACCGTTACGCTGCTGCACAAGGAGTGGCCTCGATGATCTGCGTCTACGGAGTTCCGCTTCTGATAGTCAACGGGTTCCTCGTCT
TGATCACATACTTGCAGCACACCCATCCCTCGTTGCCTTACTACGATTCATCCGAGTGGGATTGGTTCAGGGGAGCTTTGGCTA
CCGTAGACAGAGACTATGGAATCCTGAACAAGGTCTTCCACAACATCACGGACACGCACGTGGCTCACCACCTGTTCTCGACGA
TGCCGCATTACCATGCGATGGAGGCCACGAAGGCGATAAAGCCGATACTCGGGGACTATTACCAGTTTGATGGAACACCGGTCT
TCAAGGCGATGTGGAGGGAGGCGAAGGAGTGTGTCTATGTAGAACCGGACAGGAAAGGTGAGAAGAAAGtgtgttctggtaca
acaacaagttgtgaggatgatcaggtgaaagaagaaggaagaaaaatcgtcggccttttctcttgtctggttatctttgttttaa
gaagatatatgtttgtttcaataatcttattgtccatttttgttgtgttctgacattgtggcttaaattattatgtgatgttagt
gtccaattgttctgcgtctgtattgttcttctcatcgctgttttgttgggatcgtagaaatgtgactttcggacaattaaactc
ttgtactcaagctatcactctgttggcagcatcaaaagtgttttcatagtttcggtcttttggtctctgtttgtttgatactgt
tggtgagaatggctcttcaagtgttggaatctacctaaggtgaacacattgtaggattttttcttttatttaattgccattgtat
accacactgcagtgaaccgcaactatgttgaccatgtcgatgaatgtaagtgaaccatgaaactaatctttctgtacaatttac
ttacttctgagtcattgtgatgtttggttggcaggtcacctttatttctcacactccctccactcatgtgatgtggttgggatt
ttcttttcataagtagcttttgtaaagaactcagtctttctctttcaaatcatggaaaccttttcaacaaaagccaaatccat
gttacataagcaaaatatctgctttcttcatctttccttttctttcatatttgagAGGGAACAAAAGAAGAGGAAGAAAATGAAG
CAAAGTAA

SEQ ID NO:22

ATGTCTAAATTTGATAAAATATATGATGACGACAATTCCGGTGGATCACAAAACATGGGTGCAGGTGGAAGAATGACGGTTCCT
ACTTCTTCCAAGAAGTCTGAAACCGATGCCTTAAAGCGTGTGCCGTGCGAGAAACCGCCGTTCACGCTCGGAGAACTGAAGAAA
GCAATCCCACAGCATTGTTTCAATCGCTCAATCCCTCGCTCTTTCTCCTACCTTATCTGGGACATCATCATAGCCTCTTGCTTC
TACTACGTTGCCACCACTTACTTCTCTCTCCTCCCTCAGCCTCTCTCTTACTTGGCTTGGCCTCTCTATTGGGTCTGTCAAGGC
TGTGTCTTAACCGGAGTCTGGGTCATAGCTCACGAATGCGGCCACCACGCCTTCAGCGACTACCAATGGCTTGACGACACAGTC
GGTCTGATCTTCCATTCTTTCCTCCTCGTCCCTTACTTCTCCTGGAAATACAGCCACCGCCGTCACCATTCCAACACCGGATCA
CTTGAAAAGGACGAAGTGTTTGTCCCTAAACAGAAATCCGCCATCAAATGGTACGGCAAGTACCTCAACAACCCTCTGGGACGC
ACCGTGATGTTAACCGTCCAGTTCACCCTTGGCTGGCCCTTGTACTTAGCCTTCAACGTCTCGGGGAGACCCTACGACGGGTTC
GCTTGCCACTTCCACCCAAACGCTCCCATCTACAACGACCGTGAACGCCTCCAGATATACATCTCGGATGCTGGTATCCTCGCC
GTCTGTTACGGTCTCTACCGTTACGCTGCTGCACAAGGAGTGGCCTCGATGATCTGCGTCTACGGAGTTCCGCTTCTGATAGTC
AACGGGTTCCTCGTCTTGATCACATACTTGCAGCACACCCATCCCTCGTTGCCTTACTACGATTCATCCGAGTGGGATTGGTTC
AGGGGAGCTTTGGCTACCGTAGACAGAGACTATGGAATCCTGAACAAGGTCTTCCACAACATCACGGACACGCACGTGGCTCAC
CACCTGTTCTCGACGATGCCGCATTACCATGCGATGGAGGCCACGAAGGCGATAAAGCCGATACTCGGGGACTATTACCAGTTT
GATGGAACACCGGTCTTCAAGGCGATGTGGAGGGAGGCGAAGGAGTGTGTCTATGTAGAACCGGACAGGAAAGGTGAGAAGAAA
GAGGGAACAAAAGAAGAGGAAGAAAATGAAGCAAAGTAA

FIG. 3C

```
At_FAD2      ------------------MGAGGRMPVPTSS-------KKSETDTTKRVPCEKPPFSVGD  35
Ta_FAD2      MSKFDKIYDDDNSGGSQNMGAGGRMTVPTSS-------KKSETDALKRVPCEKPPFTLGE  53
Ta-fad2-1    MSKFDKIYDDDNSGGSQNMGAGGRMTVPTSS-------KKSETNALKRVPCEKPPFTLGE  53
Ta-fad2-2    MSKFDKIYDDDNSGGSQNMGAGGRMTVPTSS-------KKSETDALKRVPCEKPPFTLGE  53
Ta-fad2-3    MSKFDKIYDDDNSGGSQNMGAGGRMTVPTSS-------KKSETDALKRVPCEKPPFTLGE  53
Os_FAD2      --------------MGAGGRMTEKEREEQQKLLGRAGNGAAVQRSPTDKPPFTLGQ     42
Gm_FAD2      ------------------MGAGGRTDVPPAN--------RKSEVDPLKRVPFEKPQFSLSQ 35
Sl_FAD2      ------------------MGAGGRMSAPNGG--------TEVKKNPLQKVPTSKPPFTVGD 35

At_FAD2      LKKAIPPHCFKRSIPRSFSYLISDIIIASCFYYVATNYFSLLPQPLSYLAWPLYWACQGC  95
Ta_FAD2      LKKAIPQHCFNRSIPRSFSYLIWDIIIASCFYYVATTYFSLLPQPLSYLAWPLYWVCQGC 113
Ta-fad2-1    LKKAIPQHCFNRSIPRSFSYLIWDIIIASCFYYVATTYFSLLPQPLSYLAWPLYWVCQGC 113
Ta-fad2-2    LKKAIPQHCFNRSIPRSFSYLIWDIIIASCFYYVATTYFSLLPQPLSYLAWPLYWVCQGC 113
Ta-fad2-3    LKKAIPQHCFNRSIPRSFSYLIWDIIIASCFYYVATTYFSLLPQPLSYLAWPLYWVCQGC 113
Os_FAD2      IKKAIPPHCFQRSVIKSFSYVVVHDLVIVAALLYFALVMIPVLPSGMEFAAWPLYWIAQGC 102
Gm_FAD2      IKKAIPPHCFQRSVLRSFSYVVVYDLTIAFCLYYVATHYFHLLPGPLSFRGMAIYWAVQGC 95
Sl_FAD2      IKKAIPPHCFQRSLIRSFSYVVVYDLILVSIMYYVANTYFHLIPSPYCYIAWPIYWICQGC 95

At_FAD2      VLTGIWVIAHECGHHAFSDYQWLDDTVGLIFHSFLLVPYFSWKYSHRRHHSNTGSLERDE 155
Ta_FAD2      VLTGVWVIAHECGHHAFSDYQWLDDTVGLIFHSFLLVPYFSWKYSHRRHHSNTGSLEKDE 173
Ta-fad2-1    VLTGVWVIAHECGHHAFSDYQWLDDTVGLIFHSFLLVPYFSWKYSHRRHHSNTGSLEKDE 173
Ta-fad2-2    VLTGVWVIAHECGHHAFSDYQWLDDTVDLIFHSFLLVPYFSWKYSHRRHHSNTGSLEKDE 173
Ta-fad2-3    VLTGVWVIAHECGHHAFSDYQWLDDTVGLIFHSFLLVPYFSWKYSHRRHHSNTGSLEKDE 173
Os_FAD2      VLTGVWVIAHECGHHAFSDYSVLDDIVGLVHSSLLVPYFSWKYSHRRHHSNTGSLERDE  162
Gm_FAD2      ILTGVWVIAHECGHHAFSDYQLLDDIVGLILHSALLVPYFSWKYSHRRHHSNTGSLERDE 155
Sl_FAD2      VCTGIWVNAHECGHHAFSDYQLVDDTVGLILHSALLVPYFSWKYSHRRHHSNTGSLERDE 155

At_FAD2      VFVPKQKSAIKWYGKYL-NNPLGRIMMLTVQFVLGWPLYLAFNVSGRPYDGFACHFFPNA 214
Ta_FAD2      VFVPKQKSAIKWYGKYL-NNPLGRTVMLTVQFTLGWPLYLAFNVSGRPYDGFACHFHPNA 232
Ta-fad2-1    VFVPKQKSAIKWYGKYL-NNPLGRTVMLTVQFTLGWPLYLAFNVSGRPYDGFACHFHPNA 232
Ta-fad2-2    VFVPKQKSAIKWYGKYL-NNPLGRTVMLTVQFTLGWPLYLAFNVSGRPYDGFACHFHPNA 232
Ta-fad2-3    VFVPKQKSAIKWYGKYL-NNPLGRTVMLTVQFTLGWPLYLAFNVSGRPYDGFACHFHPNA 232
Os_FAD2      VFVPKQKSAMAWYTPYVYHNPIGRLVHIFVQLTLGWPLYLAFNVSGRPYPRFACHFDPYG 222
Gm_FAD2      VFVPKQKSCIKWYSKYL-NNPPGRVLTLAVTLTLGWPLYLALNVSGRPYDRFACHYDPYG 214
Sl_FAD2      VFVPKSKSQLGWYSKYL-NNPLGRVITLTVTLTLGWPLYLAFNVSGRPYDRFACHYDPYG
```

FIG. 4

```
At_FAD2     PIYNDRERLQIYLSDAGILAVCFGLYRYAAAQGMASMICLYGVPLLIVNAFLVLITYLQH  274
Ta_FAD2     PIYNDRERLQIYISDAGILAVCYGLYRYAAAQGVASMICVYGVPLLIVNGFLVLITYLQH  292
Ta-fad2-1   PIYNDRERLQIYISDAGILAVCYGLYRYAAAQGVASMICVYGVPLLIVNGFLVLITYLQH  292
Ta-fad2-2   PIYNDRERLQIYISDAGILAVCYGLYRYAAAQGVASMICVYGVPLLIVNGFLVLITYLQH  292
Ta-fad2-3   PIYNDRERLQIYISDAGILAVCYGLYRYAAAQGVASMICVYGVPLLIVNGFLVLITYLQH  292
Os_FAD2     PIYNDRERVQIFISDVGVVSAGLALFKLSSAFGFWWVVRVYGVPLLIVNAWLVLITYLQH  282
Gm_FAD2     PIYSDRERLQIYISDAGVLAVVYGLFRLAMAKGLAWVVCVYGVPLLVVNGFLVLITFLQH  274
Sl_FAD2     PIYNNRERLQIFLSDAGVLGACYLLYRVALVKGLAWLVCIYGVPLLVVNGFLVLITYLQH  274

At_FAD2     THPSLPHYDSSEWDWLRGALATVDRDYGILNKVFHNITDTHVAHHLFSTMPHYNAMEATK  334
Ta_FAD2     THPSLPHYDSSEWDWFRGALATVDRDYGILNKVFHNITDTHVAHHLFSTMPHYHAMEATK  352
Ta-fad2-1   THPSLPHYDSSEWDWFRGALATVDRDYGILNKVFHNITDTHVAHHLFSTMPHYHAMEATK  352
Ta-fad2-2   THPSLPHYDSSEWDWFRGALATVDRDYGILNKVFHNITDTHVAHHLFSTMPHYHAMEATK  352
Ta-fad2-3   THPSLPYYDSSEWDWFRGALATVDRDYGILNKVFHNITDTHVAHHLFSTMPHYHAMEATK  352
Os_FAD2     THPALPHYDSSEWDWLRGALATVDRDYGILNKVFHNITDTHVAHHLFSTMPHYHAMEATK  342
Gm_FAD2     THPALPHYTSSEWDWLRGALATVDRDYGILNKVFHNITDTHVAHHLFSTMPHYHAMEATK  334
Sl_FAD2     THPSLPHYDSTEWDWLRGALATCDRDYGVLNKVFHNITDTHVVHHLFSAMPHYNAMEATK  334

At_FAD2     AIKPILGDYYQFDGTPWYVAMYREAKECIYVPDREGDKKGVYWYNNKL----         383
Ta_FAD2     AIKPILGDYYQFDGTPVFKAMWREAKECVYVEPDRKGEKKEGTKEEEENEAK          404
Ta-fad2-1   AIKPILGDYYQFDGTPVFKAMWREAKECVYVEPDRKGEKKEGTKEEEENEAK          404
Ta-fad2-2   AIKPILGDYYQFDGTPVFKAMWREAKECVYVEPDRKGEKKEGTKEEEENEAK          404
Ta-fad2-3   AIKPILGDYYQFDGTPVFKAMWREAKECVYVEPDRKGEKKEGTKEEEENEAK          404
Os_FAD2     AIRPILGEYYQFDPTPVAKATWREAKECIYVEPE---DNKGVFWYNNKF---          388
Gm_FAD2     AIKPILGEYYRFDETPFVKAMWREARECIYVEPDQSTESKGVFWYNNKL---          383
Sl_FAD2     AVKPLLGDYYQFDGTPIFKAMWREAKECLYVEKDESSQGKGVFWYKNKL*--          383
```

FIG. 4 (continued)

SEQ ID NO:31

TTGTCTAAATTTGATAAAATATATGATGACGACAATTCCGGTGGATCACAgtttgcttcatttggcttttttgtgtgtttgtc
aagttgctattcaataagaatttgtgattttgattggtctcctcaaaattctgtgaaattttagtaacaaggaagaaattaaca
aatcacaacaagaaagagatgtgagctgtcgtatcaaatcttattcgttttctcaacgcaatcgttttagttttttttaactta
acgccacttctctgctccatacactccttttgtccacgtacttttcatttgtggtaatccatttcttcactttggatctttca
tctgaacaacaatttcttgactcaatcaattaccacccgttcttgtgcttttgtatagattcataatcttgtgtgtttcagctt
ctcattgctttggttcttgtttttttttctgcagAAACATGGGTGCAGGTGGAAGAATGACGGTTCCTACTTCTTCCAAGAAGT
CTGAAACCAATGCCTTAAAGCGTGTGCCGTGCGAGAAACCGCCGTTCACGCTCGGAGAACTGAAGAAAGCAATCCCACAGCATT
GTTTCAATCGCTCAATCCCTCGCTCTTTCTCCTACCTTATCTGGGACATCATCATAGCCTCTTGCTTCTACTACGTTGCCACCA
CTTACTTCTCTCTCCTCCCTCAGCCTCTCTCTTACTTGGCTTGGCCTCTCTATTGGGTCTGTCAAGGCTGTGTCTTAACCGGAG
TCTGGGTCATAGCTCACGAATGCGGCCACCACGCCTTCAGCGACTACCAATGGCTTGACGACACAGTCGGTCTGATCTTCCATT
CTTTCCTCCTCGTCCCTTACTTCTCCTGGAAATACAGCCACCGCCGTCACCATTCCAACACCGGATCACTTGAAAAGGACGAAG
TGTTTGTCCCTAAACAGAAATCCGCCATCAAATGGTACGGCAAGTACCTCAACAACCCTCTGGGACGCACCGTGATGTTAACCG
TCCAGTTCACCCTTGGCTGGCCCTTGTACTTAGCCTTCAACGTCTCGGGGAGACCCTACGACGGGTTCGCTTGCCACTTCCACC
ATGACGTCCGTTAACGTTAAGCTCCTTTACCATTACGTCATCACCAACTTTTTCAACCTTTGCTTCTTCCCGTTAGCGGCGATC
GTTGCCGGAAAAGCCTCTCGGCTTACCACAAACGATCTTCACCACTTCTACTATTCCTATCTCCAACACAACCTAATAACCATA
TCTCTACTCTTTGCCTTCACCGTTTTCGGTTTGGCTCTCTACATCGTAACCCGGCCCAAACCGGTTTACCTCGTTGACCATTCC
TGCTACCTTCCACCATCGCATCTTAGAAGCAGTATCTCTAAGGTCATGGATATCTTCTATCAAGTAAGATTAGCCGATCCTTTA
CGGAACGCGGCAAGCGATGATTCGTCCTGGCTTGATTTCTTGAGGAAGATTCAGGAGCGGTCTGGTCTAGGCGATGAAACCCAC
GGCCCCGAGGGACTGCTTCAGGTCCCTCCACGAAGACTTTTGCCGCGGCGCGTGAAGAAACAGAGCAAGTGATCATCGGTGCG
CTCGAAAAACTATTCGAGAACACCAAAGTTAACCCTAAAGAGATTGGTATACTTGTGGTGAACTCAAGCATGTTTAATCCGACT
CCTTCGCTCTCGGCGATGGTTGTTAATACTTTCAAGCTCCGAAGCAACATCAGAAGCTTTAATCTTGGAGGAATGGGTTGTAGT
GCCGGCGTTATAGCCATTGATCTGGCTAAGGACTTGTTGCATGTCCATAAAAACACTTATGCTCTTGTGGTGAGCACAGAGAAC
ATCACTTACAACATTTATGCTGGTGATAACAGATCCATGATGGTTTCGAATTGCTTGTTCCGTGTTGGTGGGGCCGCGATTTTG
CTCTCCAACAAGCCGAGGGACCGGAGACGGTCCAAGTACCAGCTACTTCACACGGTTCGGACGCATACCGGAGCTGACGACAAG
TCTTTCCGATGTGTGCAACAAGAAGACGACGAGAGCGGTAAAACCGGGGTGTGTTTGTCCAAGGACATAACCGGTGTTGCCGGG
AGAACTGTTTAGAAAAACATAACAACATTGGGTCCGTTGGTTCTTCCTTTTAGCGAGAAATTTCTTTTTTTCGTTACCTTCATC
GCCAAGAAACTCTTTAAAGACAAGATCAAACATTACTACGTCCCGGATTTCAAGCTTGCTATCGACCATTTTGTATTCATGCC
GGAGGCAGAGCCGTGATCGATGTGCTACAGAAGAACTTAGGTCTATTGCCGATCGATGTGGAGGCATCTAGGTCAACGTTACAT
AGATTTGGGAACACTTCGTCTAGCTCAATTTGGTATGAATTGGCGTACATAGAGGCAAAAGGAAGGATGAAGAGAGGGAACAAA
GTTTGGCAGATTGCTTTAGGGTCAGGGTTTAAGTGTAATAGTGCGGTTTGGGTGGCTCTACGCAATGTCAAGGCTTCGACAAAT
AGTCCTTGGGAACATTGCATTGATAGATATCCAGATGCAATTGATTCTGATTCGGGTAAGTCAGAGACTCGTGTCCAAAACGGT
CGGTCCTAA

FIG. 5A

SEQ ID NO:32

```
ATGACGTCCGTTAACGTTAAGCTCCTTTACCATTACGTCATCACCAACTTTTTCAACCTTTGCTTCTTCCCGTTAGCGGCGATC
GTTGCCGGAAAAGCCTCTCGGCTTACCACAAACGATCTTCACCACTTCTACTATTCCTATCTCCAACACAACCTAATAACCATA
TCTCTACTCTTTGCCTTCACCGTTTTCGGTTTGGCTCTCTACATCGTAACCCGGCCCAAACCGGTTTACCTCGTTGACCATTCC
TGCTACCTTCCACCATCGCATCTTAGAAGCAGTATCTCTAAGGTCATGGATATCTTCTATCAAGTAAGATTAGCCGATCCTTTA
CGGAACGCGGCAAGCGATGATTCGTCCTGGCTTGATTTCTTGAGGAAGATTCAGGAGCGGTCTGGTCTAGGCGATGAAACCCAC
GGCCCCGAGGGACTGCTTCAGGTCCCTCCACGGAAGACTTTTGCCGCGGCGCGTGAAGAAACAGAGCAAGTGATCATCGGTGCG
CTCGAAAAACTATTCGAGAACACCAAAGTTAACCCTAAAGAGATTGGTATACTTGTGGTGAACTCAAGCATGTTTAATCCGACT
CCTTCGCTCTCGGCGATGGTTGTTAATACTTTCAAGCTCCGAAGCAACATCAGAAGCTTTAATCTTGGAGGAATGGGTTGTAGT
GCCGGCGTTATAGCCATTGATCTGGCTAAGGACTTGTTGCATGTCCATAAAAACACTTATGCTCTTGTGGTGAGCACAGAGAAC
ATCACTTACAACATTTATGCTGGTGATAACAGATCCATGATGGTTTCGAATTGCTTGTTCCGTGTTGGTGGGGCCGCGATTTTG
CTCTCCAACAAGCCGAGGGACCGGAGACGGTCCAAGTACCAGCTACTTCACACGGTTCGGACGCATACCGGAGCTGACGACAAG
TCTTTCCGATGTGTGCAACAAGAAGACGACGAGAGCGGTAAAACCGGGGTGTGTTTGTCCAAGGACATAACCGGTGTTGCCGGG
AGAACTGTTTAGAAAAACATAACAACATTGGGTCCGTTGGTTCTTCCTTTTAGCGAGAAATTTCTTTTTTTCGTTACCTTCATC
GCCAAGAAACTCTTTAAAGACAAGATCAAACATTACTACGTCCCGGATTTCAAGCTTGCTATCGACCATTTTGTATTCATGCC
GGAGGCAGAGCCGTGATCGATGTGCTACAGAAGAACTTAGGTCTATTGCCGATCGATGTGGAGGCATCTAGGTCAACGTTACAT
AGATTTGGGAACACTTCGTCTAGCTCAATTTGGTATGAATTGGCGTACATAGAGGCAAAAGGAAGGATGAAGAGAGGGAACAAA
GTTTAGCAGATTGCTTTAGGGTCAGGGTTTAAGTGTAATAGTGCGGTTTGGGTGGCTCTACGCAATGTCAAGGCTTCGACAAAT
AGTCCTTGGGAACATTGCATTGATAGATATCCAGATGCAATTGATTCTGATTCGGGTAAGTCAGAGACTCGTGTCCAAAACGGT
CGGTCCTAA
```

FIG. 5B

```
At_FAE1    ----------------------------------MTS----VNVKLLYRYVLTNFFNLCL    22
Ta-FAE1    ----------------------------------MTS---VNVKLLYHYVITNFFNLCF    22
Ta-fae1-1  ----------------------------------MTS---VNVKLLYHYVITNFFNLCF    22
Ta-fae1-2  ----------------------------------MTS----VNVKLLYHYVITNFFNLCF   22
Os_FAE1    --------------MNGGDAAAA----AATPSHRRLPDFLQSVNLKYVKLGYHYLITHLLTPLL    46
Gm_FAE1    --------MTVTMSGEEEAAVGVQIQQKSRMVLPDFLQSVNLKYVKLGYHYLISNLVTLFL    53
Sl_FAE1    MNGATGTQVNTANGGGGEPVGVQIQQSR--RLPDFLQSVNLKYVKLGYHYLISHLLTLCL    58

At_FAE1    FPLTAFLAGKASRLTINDLHNF-LSYLQHNLITVTLLFAFTVFGLVLYIVTRPNPVYLVD    81
Ta-FAE1    FPLAAIVAGKASRLTTNDLHHFYYSYLQHNLITISLLFAFTVFGLALYIVTRPKPVYLVD    82
Ta-fae1-1  FPLAAIVAGKASRLTTNDLHHFYYSYLQHNLITISLLFAFTVFGLALYIVTRPKPVYLVD    82
Ta-fae1-2  FPLAAIVAGKASRLTTNDLHHFYYSYLQHNLITISLLFAFTVFGLALYIVTRPKPVYLVD    82
Os_FAE1    LPLMAVIVLEAGRTDPDDLRQLWL-HLQYNLVSVLVLSAVLVFGATVYVLTRPRPVYLVD   105
Gm_FAE1    VPLILVTLIQVSQ--TTDLRHLWL-HLQYNLLTILTCSAVLVFGLTLYAVTCPRFVYLLD   110
Sl_FAE1    IPVMAVILIEASQMNPDDIRQLWL-HLQYNLVSVIICSAVLVFGSTVYIMTRPRPVYLID   117

At_FAE1    YSCYLPPPHLKVSVSKVMDIFYQIRKADTSSRNVACDDPSSLDFLRKIQERSGLGDETYS   141
Ta-FAE1    HSCYLPPSHLRSSISKVMDIFYQVRLADP-LRNAASDDSSWLDFLRKIQERSGLGDETHG   141
Ta-fae1-1  HSCYLPPSHLRSSISKVMDIFYQVRLADP-LRNAASDDSSWLDFLRKIQERSGLGDETHG   141
Ta-fae1-2  HSCYLPPSHLRSSISKVMDIFYQVRLADP-LRNAASDDSSWLDFLRKIQERSGLGDETHG   141
Os_FAE1    FACYKPPDKLKVRFDEFLHH----------SKLCG-FSDDCLEFQRKILERSGLSEETYV   154
Gm_FAE1    SACFRPADHLKAPFRSFMDH----------SRLTGDFEESSLEFQRKILERSGLGEETYV   160
Sl_FAE1    YSCYKAPEHLKAPYERFMQH----------SRLTGDFDESSLEFQRKILERSGLGDETYV   167

At_FAE1    PEGLIHVPPRKTFAASPEETEKVIIGALENLFENTKVNPREIGILVVNSSMFNPTPSLSA   201
Ta-FAE1    PEGLLQVPPRKTFAAAREETEQVIIGALEKLFENTKVNPKEIGILVVNSSMFNPTPSLSA   201
Ta-fae1-1  PEGLLQVPPRKTFAAAREETEQVIIGALEKLFENTKVNPKEIGILVVNSSMFNPTPSLSA   201
Ta-fae1-2  PEGLLQVPPRKTFAAAREETEQVIIGALEKLFENTKVNPKEIGILVVNSSMFNPTPSLSA   201
Os_FAE1    PEAMHLIPPEPTMANARAEAESVMFGALDKLFKFTGVKPKDVGVLVVNCSLFNPTPSLSA   214
Gm_FAE1    PDAMHSIPPQPSMAAARAEAEQVMFGALDNLFQSTNIKPKDIGILIVNCSLFNPTPSLSS   220
Sl_FAE1    PEAMHQLPPQPSMQAAPEEAEQVMFGALDKLFANTSVKPKKIGVLVVNCSLFNPTPSLSA   227

At_FAE1    MVVNTFKLRSNIKSFNLGGMGCSAGVIAIDLAKDLLHVHKNTYALVVSTENITQGIYAGE   261
Ta-FAE1    MVVNTFKLRSNIRSFNLGGMGCSAGVIAIDLAKDLLHVHKNTYALVVSTENITYNIYAGD   261
Ta-fae1-1  MVVNTFKLRSNIRSFNLGGMGCSAGVIAIDLAKDLLHVHKNTYALVVSTENITYNIYAGD   261
Ta-fae1-2  MVVNTFKLRSNIRSFNLGGMGCSAGVIAIDLAKDLLHVHKNTYALVVSTENITYNIYAGD   261
Os_FAE1    MIVNKYKLRGNIKSFNLGGMGCSAGVIAVDLARDMLQVHRNTYAVVVSTENITQNWYFGN   274
Gm_FAE1    MIVNKYKLRGNIRSFNLGGMGCSAGVIAVDLAKDLLQVHRNTYAVVVSTENITQNWYFGN   280
Sl_FAE1    MIVNKYKLRGNIRSFNLGGMGCSAGVIAVDLAKDMLQVHRNTYAVVVSTENITQNWYFGN   287
```

FIG. 6

```
At_FAE1      NRSMMVSNCLFRVGGAAILLSNKSGDRRRSKYKLVHTVRTHTGADDKSFRCVQQEDDESG    321
Ta-FAE1      NRSMMVSNCLFRVGGAAILLSNKPRDRRRSKYQLLHTVRTHTGADDKSFRCVQQEDDESG    321
Ta-fae1-1    NRSMMVSNCLFRVGGAAILLSNKPRDRRRSKYQLLHTVRTHTGADDKSFRCVQQEDDESG    321
Ta-fae1-2    NRSMMVSNCLFRVGGAAILLSNKPRDRRRSKYQLLHTVRTHTGADDKSFRCVQQEDDESG    321
Os_FAE1      RKSMLIPNCLFRVGGAAVLLSNRGADRRRAKYALKHVVRTHKGADNKAFNCVYQEQDDEG    334
Gm_FAE1      KKSMLIPNCLFRVGCSVLLLSNKPADRRRAKYRLVHVVRTHRGADDKAFRCVYQEQDDAG    340
Sl_FAE1      KKSMLIPNCLFRVGGSAVLLSNKSVDRRRAKYKLVHVVRTHRGADDKAFRCVYQEQDDAG    347

At_FAE1      KIGVCLSKDITNVAGTTLTKNIATLGPLILPLSEKFLFFATFVAKKLLKDKIKHYYVPDF    381
Ta-FAE1      KTGVCLSKDITGVAGRTVQKNITTLGPLVLPFSEKFLFFVTFIAKKLFKDKIKHYYVPDF    381
Ta-fae1-1    KTGVCLSKDITGVAGRTV*-----------------------------------------    339
Ta-fae1-2    KTGVCLSKDITGVAGRTVQKNITTLGPLVLPFSEKFLFFVTFIAKKLFKDKIKHYYVPDF    381
Os_FAE1      KTGVSLSKDLMAIAGGALKTNITTLGPLVLPFSEQLLFFATLVAKKLFNAKIKP-YIPDF    393
Gm_FAE1      KTGVSLSKDLMAIAGGALKTNITTLGPLVLPISEQLLFFVTLLMKKLFKADVKP-YIPDF    399
Sl_FAE1      KTGVSLSKDLMAIAGGALKTNITTLGPLVLPISEQLLFFGSLIIKKIFNKHIKP-YIPDF    406

At_FAE1      KLAVDHFCIHAGGRAVIDELEKNLGLSPIDVEASRSTLHRFGNTSSSSIWYELAYIEAKG    441
Ta-FAE1      KLAIDHFCIHAGGRAVIDVLQKNLGLLPIDVEASRSTLHRFGNTSSSSIWYELAYIEAKG    441
Ta-fae1-1    ------------------------------------------------------------    339
Ta-fae1-2    KLAIDHFCIHAGGRAVIDVLQKNLGLLPIDVEASRSTLHRFGNTSSSSIWYELAYIEAKG    441
Os_FAE1      KLAFEHFCIHAGGRAVIDELEKNLQLQPVHVEASRMTLHRFGNTSSSSIWYELAYMEAKG    453
Gm_FAE1      KLAFDHFCIHAGGRAVIDELEKNLQLLPEHVEASRMTLHRFGNTSSSSIWYELAYIEAKG    459
Sl_FAE1      KLAFDHFCIHAGGRAVIDELEKNLQLTQVHVEASRMTLHRFGNTSSSSIWYELAYIEAKG    466

At_FAE1      PMKKGNKAWQIALGSGFKCNSAVWVALRNVKASANSPWQHCIDRYPVKIDSDLSKSKTHV    501
Ta-FAE1      RMKRGNKVWQIALGSGFKCNSAVWVALRNVKASTNSPWEHCIDRYPDAIDSDSGKSETRV    501
Ta-fae1-1    ------------------------------------------------------------    339
Ta-fae1-2    RMKRGNKV*---------------------------------------------------    449
Os_FAE1      RVPRGHRIWQIAFGSGFKCNSAVWHALRNVNPSPESPWEDCIDRYPVELVDGFATHNNTQ    513
Gm_FAE1      RIKKGNRIWQIAFGSGFKCNSAVWQALRNVRPSPNGPWEDCIDKYPVEIVS---------    510
Sl_FAE1      RMKKGNKVWQIAFGSGFKCNSAVWQALRNVKPSPDGPWEDCIDRYPVKVVS*--------    517

At_FAE1      QNGRS-     506
Ta-FAE1      QNGRS*     506
Ta-fae1-1    ------     339
Ta-fae1-2    ------     449
Os_FAE1      Q*----     514
Gm_FAE1      ------     510
Sl_FAE1      ------     517
```

FIG. 6 (continued)

SEQ ID NO:40

ATGTCAACTAAAACCGTCGTCCCTCTCCGTCGCAGATCTAAGCCCCTTAACGGAAATCACACTAACGGCGTCGCCATTGACGGA
AGCCTCGACGACGACCACAACCGTCGCATCGGATCAGTAAATAGCCAAATGGATAACATTGCTAAGAAAACGGACGACGGCTAC
GCAAACGGCGGAGGAGGAGGAGGAGGAGGAAAAGCAAGGCGTCGTTTATGACGTGGACGGCGCGTGACGTTGTGTACGTGGCG
AGGTACCATTGGATACCGTGTTTGTTCGCGGTCGGGGTTCTGTTCTTCACGGGCGTGGAGTACACGCTCCAGATGATTCCCGCG
AGGTCTGAGCCGTTCGATATTGGGTTTGTGGCCACGCGCTCTCTGAATCGCGTCTTGGCAAATTCACCGGATCTTAACACCGTC
TTAGCCGCTCTAAACACGgtaatttcgtactaattaatttagggtaaaaaatatagtatttaataatgactatcctcaattcct
ttcatgcttcacctaatattttgtttttttttcgttgtcattaaaatcgtaataatatattgagttagtcaaatgaaaaaaacaa
gtggcgtagtgattggaaacaaatctcagatcttttatctgtttaataaggtatttaattatccagctggaattatgctgtca
agtgtcaacacagtagtagtaacatgcaatggaatttctcaatagaaaaaggtcttaattagtatagataattagtggacaaaa
atgtagttaatgtaatctctttgctaagtagttatcataatcatcttttttaacaactgccattttgtctgtgtgtttgttttac
aacgaagtagtagtagaatagatcgcttttagcttttgaaagtttcgaacccaaggaaaagggacacatgggttatgagttgg
agacacgatcacatgcaaacagagagattggttaaattatcgacttttttgtagtacttttaaaaaaaactatttatataaaa
aacatggtggatggtggggacagGTGTTCGTAGGGATGCAAACGACGTATATTGTATGGACATGGTTAATGGAAGGACGACCAC
GAGCCACCATCTCGGCTTGCTTCATGTTTACTTGTCGAGGCATTCTTGGTTACTCTACTCAGCTCCCTCTTCCTCAGgttccaa
tcaacacttttcttctatctcttttcttaattaaaataattaccaattaactaaatgctaatcagtcgatatatcatagttcca
acgttttggacgtgtgatttccattggccactaccatataaaacaacagagtctctttattcattattcaatatatatttgagt
attgatattattcatagggaggtttcatttgtactatcaataaaatttctacaactcttggatttttctgctacattttgtag
ttattttttttaattacttttaaaaacttgtgaataggagagactaatagtagtacgtaatatgattgtatcaaatgctttaaca
tgtgggggtttgggttaactatcatcatttcatagatcactattttgttttcgtttgttacctaactttttgttatctttgaaaa
ataatgttccacgagttgattgactggacataaaaatcagattctctcactcatttacgttctacggttctagccactcgtttt
tttcttttttctttctgtggtgtaacacgtagataatggatttctatgtgtgtcgtcttgctcaagaataataaatgtggttaa
aggttaaatatagctctggaaattaattatctcctctttttttattaaccagGATTTTCTAGGATCAGGTGTCGATTTTCCGGT
GGGAAACGTCTCGTTCTTCCTCTTCTACTCGGGTCACGTCGCCGGTTCGATGATCGCATCTTTGGACATAAGGAGAATGCAGAG
GATGAGACTAGCGATGCTTTTTGACATCCTCAATGTATTACAATCGATCAGGCTGCTCGGGACGAGAGGACACTACACGATTGA
TCTCGCTGTCGGAGTTGGCGCTGGGATTCTCTTTGATTCATTCGCCGGCAAGTACGAAGAGATGATAAGCAAGAGACACAATTT
AGTCAATGGTTTTGGTTTGATTTCGAAAGACTCGCTAGTCAATTAA

SEQ ID NO:41

ATGTCAACTAAAACCGTCGTCCCTCTCCGTCGCAGATCTAAGCCCCTTAACGGAAATCACACTAACGGCGTCGCCATTGACGGA
AGCCTCGACGACGACCACAACCGTCGCATCGGATCAGTAAATAGCCAAATGGATAACATTGCTAAGAAAACGGACGACGGCTAC
GCAAACGGCGGAGGAGGAGGAGGAGGAGGAAAAGCAAGGCGTCGTTTATGACGTGGACGGCGCGTGACGTTGTGTACGTGGCG
AGGTACCATTGGATACCGTGTTTGTTCGCGGTCGGGGTTCTGTTCTTCACGGGCGTGGAGTACACGCTCCAGATGATTCCCGCG
AGGTCTGAGCCGTTCGATATTGGGTTTGTGGCCACGCGCTCTCTGAATCGCGTCTTGGCAAATTCACCGGATCTTAACACCGTC
TTAGCCGCTCTAAACACGGTGTTCGTAGGGATGCAAACGACGTATATTGTATGGACATGGTTAATGGAAGGACGACCACGAGCC
ACCATCTCGGCTTGCTTCATGTTTACTTGTCGAGGCATTCTTGGTTACTCTACTCAGCTCCCTCTTCCTCAGGATTTTCTAGGA
TCAGGTGTCGATTTTCCGGTGGGAAACGTCTCGTTCTTCCTCTTCTACTCGGGTCACGTCGCCGGTTCGATGATCGCATCTTTG
GACATAAGGAGAATGCAGAGGATGAGACTAGCGATGCTTTTTGACATCCTCAATGTATTACAATCGATCAGGCTGCTCGGGACG
AGAGGACACTACACGATTGATCTCGCTGTCGGAGTTGGCGCTGGGATTCTCTTTGATTCATTCGCCGGCAAGTACGAAGAGATG
ATAAGCAAGAGACACAATTTAGTCAATGGTTTTGGTTTGATTTCGAAAGACTCGCTAGTCAATTAA

FIG. 7A

SEQ ID NO:42

ATGTCAACTAAAACCGTCGTCCCTCTCCGTCGCAGATCTAAGCCCCTTAACGGAAATCACACTAACGGCGTCGCCATTGACGGA
AGCCTCGACGACGACCACAACCGTCGCATCGGATCAGTAAATAGCCAAATGGATAACATTGCTAAGAAAACGGACGACGGCTAC
GCAAACGGCGGAGGAGGAGGAGGAGGAGGGAAAAGCAAGGCGTCGTTTATGACGTGGACGGCGCGTGACGTTGTGTACGTGGCG
AGGTACCATTGGATACCGTGTTTGTTCGCGGTCGGGGTTCTGTTCTTCACGGGCGTGGAGTACACGCTCCAGATGATTCCCGCG
AGGTCTGAGCCGTTCGATATTGGGTTTGTGGCCACGCGCTCTCTGAATCGCGTCTTGGCAAATTCACCGGATCTTAACACCGTC
TTAGCCGCTCTAAACACGgtaatttcgtactaattaatttagggtaaaaaatatagtatttaataatgactatcctcaattcct
ttcatgcttcacctaatattttgttttttttcgttgtcattaaaatcgtaataatatattgagttagtcaaatgaaaaaaacaa
gtggcggtagtgattggaaacaaatctcagatcttttatctgtttaataaggtatttaattatccagctggaattatgctgtca
agtgtcaacacagtagtagtaacatgcaatggaatttctcaatagaaaaggtcttaattagtatagataattagtggacaaaa
atgtagttaatgtaatctctttgctaagtagttatcataatcatcttttaacaactgccattttgtctgtgtgtttgttttac
aacgaagtagtagtagaatagatcgcttttagcttttgaaagtttcgaacccaaggaaaagggacacatgggttatgagttgg
agacacgatcacatgcaaacagagagattggttaaattatcgacttttgtagtacttttaaaaaaaaactatttatataaaa
aacatggtggatggtggggacagGTGTTCGTAGGGATGCAAACGACGTATATTGTATGGACATGGTTAATGGAAGGACGACCAC
GAGCCACCATCTCGGCTTGCTTCATGTTTACTTGTCGAGGCATTCTTGGTTACTCTACTCAGCTCCCTCTTCCTCAGgttccaa
tcaacacttttcttctatctcttttcttaattaaaataattaccaattaactaaatgctaatcagtcgatatatcatagttcca
acgttttggacgtgtgatttccattggccactaccatataaaacaacagagtctctttattcattattcaatatatatttgagt
attgatattattcatagggagtttcatttgtactatcaataaaatttctacaactcttggatttttctgctacattttgtag
ttatttttttaattacttttaaaaacttgtgaataggagagactaatagtagtacgtaatatgattgtatcaaatgctttaaca
tgtggggtttgggttaactatcatcatttcatagatcactattttgttttcgtttgttacctaacttttgttatctttgaaaa
ataatgttccacgagttgattgactggacataaaaatcagattctctcactcatttacgttctacggttctagccactcgtttt
tttcttttcttctgtggtgtaacacgtagataatggattttctatgtgtgtcgtcttgctcaagaataataaatgtggttaa
aggttaaatatagctctggaaattaattatctcctcttttttattaaccagGATTTTCTAGGATCAGGTGTCGATTTTCCGGT
GGGAAACGTCTCGTTCTTCCTCTTCTACTCGGGTCACGTCGCCGGTTCGATGATCGCATCTTTGGACATGAGGAGAATGCAGAG
GATGAGACTAGCGATGCTTTTTGACATCCTCAATGTATTACAATCGATCAAGCTGCTCGGGACGAGAGGACACTACACGATTGA
TCTCGCTGTCGGAGTTGGCGCTGGGATTCTCTTTGATTCATTCGCCGGCAAGTACAAGAGATGATAAGCAAGAGACACAATTT
AGTCAATGGTTTTGGTTTGATTTCGAAAGACTCGCTAGTCAATTAA

SEQ ID NO:43

ATGTCAACTAAAACCGTCGTCCCTCTCCGTCGCAGATCTAAGCCCCTTAACGGAAATCACACTAACGGCGTCGCCATTGACGGA
AGCCTCGACGACGACCACAACCGTCGCATCGGATCAGTAAATAGCCAAATGGATAACATTGCTAAGAAAACGGACGACGGCTAC
GCAAACGGCGGAGGAGGAGGAGGAGGAGGGAAAAGCAAGGCGTCGTTTATGACGTGGACGGCGCGTGACGTTGTGTACGTGGCG
AGGTACCATTGGATACCGTGTTTGTTCGCGGTCGGGGTTCTGTTCTTCACGGGCGTGGAGTACACGCTCCAGATGATTCCCGCG
AGGTCTGAGCCGTTCGATATTGGGTTTGTGGCCACGCGCTCTCTGAATCGCGTCTTGGCAAATTCACCGGATCTTAACACCGTC
TTAGCCGCTCTAAACACGGTGTTCGTAGGGATGCAAACGACGTATATTGTATGGACATGGTTAATGGAAGGACGACCACGAGCC
ACCATCTCGGCTTGCTTCATGTTTACTTGTCGAGGCATTCTTGGTTACTCTACTCAGCTCCCTCTTCCTCAGGATTTTCTAGGA
TCAGGTGTCGATTTTCCGGTGGGAAACGTCTCGTTCTTCCTCTTCTACTCGGGTCACGTCGCCGGTTCGATGATCGCATCTTTG
GACATGAGGAGAATGCAGAGGATGAGACTAGCGATGCTTTTTGACATCCTCAATGTATTACAATCGATCAAGCTGCTCGGGACG
AGAGGACACTACACGATTGATCTCGCTGTCGGAGTTGGCGCTGGGATTCTCTTTGATTCATTCGCCGGCAAGTACAAGAGATG
ATAAGCAAGAGACACAATTTAGTCAATGGTTTTGGTTTGATTTCGAAAGACTCGCTAGTCAATTAA

FIG. 7B

```
At_ROD1     MSAAAAETDVSLRRRSNSLNGNHTNGV--AIDGTLDN---NNRRVGDTNTHMDISAKKTD    55
Ta_ROD1     ----MSTKTVVPLRRRSKPLNGNHTNGV--AIDGSLDDD--HNRRIGSVNSQMDNIAKKTD    53
Ta-rod1-1   ---MSTKTVVPLRRRSKPLNGNHTNGV--AIDGSLDDD--HNRRIGSVNSQMDNIAKKTD    53
Ta-rod1-2   ---MSTKTVVPLRRRSKPLNGNHTNGV--AIDGSLDDD--HNRRIGSVNSQMDNIAKKTD    53
Os_ROD1     ----MPFPPPPFSLTANTASSMGNAEAVVVLFANG-------GARRRADKVVHPAFMPDRAA    50
Gm_ROD1     ------------------------MNGGAEASVNHRRRHQAASAN----G--VKIA      26
Sl_ROD1     -----------------MNGDTFHSR--NSSSSTL----SKRNTTERKVDVTEMKKKSA    36

At_ROD1     NGYANGV---------GGG--GWRSKASFTTW-TARDIVYVVRYHWIPCMFAAGLLFFMGVEY    106
Ta_ROD1     DGYANGG---------GGGGGGKSKASFMTW-TARDVVYVARYHWIPCLFAVGVLFFTGVEY    105
Ta-rod1-1   DGYANGG---------GGGGGGKSKASFMTW-TARDVVYVARYHWIPCLFAVGVLFFTGVEY    105
Ta-rod1-2   DGYANGG---------GGGGGGKSKASFMTW-TARDVVYVARYHWIPCLFAVGVLFFTGVEY    105
Os_ROD1     GGAMEREGGGVGGGGEVGGWRRF------EWCSAAGVGAGVLRRHPAAAAFGCGLLLFMAVEY    106
Gm_ROD1     NGAM--A--------KFSSTLCYDASFMKW-TVADAVHVATHHWMPCLFALGLLFFMAVEY    76
Sl_ROD1     SATGTEV--------GGYGWWLGNAYFMKW-RMEDVFGVVKYHPIPCIFAASLLFFMGVEY    88

At_ROD1     TLQMIPARSEPFDLGFVVTRSLNRVLASSPDLNTVLAALNTVFVGMQTTYIVWTWLVEGR    166
Ta_ROD1     TLQMIPARSEPFDIGFVATRSLNRVLANSPDLNTVLAALNTVFVGMQTTYIVWTWLMEGR    165
Ta-rod1-1   TLQMIPARSEPFDIGFVATRSLNRVLANSPDLNTVLAALNTVFVGMQTTYIVWTWLMEGR    165
Ta-rod1-2   TLQMIPARSEPFDIGFVATRSLNRVLANSPDLNTVLAALNTVFVGMQTTYIVWTWLMEGR    165
Os_ROD1     TIPMVPPAAPPVDLGFAATAALHAGIAARPWLNSLLAALNTVFVAMQAAYILWAILGEGR    166
Gm_ROD1     TLLMVPPSSPPFDLGFIATRSLHALLESSPNLNTLFAGLNTVFVGMQTSYILWTWLIEGR    136
Sl_ROD1     TLHMIPASAPPFDLGFIVTVPLNRLLAAKPALNTLFAGLNTVFVAMQTAYILGTFLIEGR    148
```

FIG. 8

```
At_ROD1      APATIAALFMFTCRGILGYSTQLPLPQDFLGSGVDFPVGNVSFFLFFSGHVAGSMIASLD    226
Ta_ROD1      PRATISACFMFTCRGILGYSTQLPLPQDFLGSGVDFPVGNVSFFLFYSGHVAGSMIASLD    225
Ta-rod1-1    PRATISACFMFTCRGILGYSTQLPLPQDFLGSGVDFPVGNVSFFLFYSGHVAGSMIASLD    225
Ta-rod1-2    PRATISACFMFTCRGILGYSTQLPLPQDFLGSGVDFPVGNVSFFLFYSGHVAGSMIASLD    225
Os_ROD1      PRAAVAAMMMFTCRGALGCATQLPLPAEFLGSGMDFPVGNVSFFLFFSGHVAGAVIAAED    226
Gm_ROD1      PRATISALFMFTCRGILGYSTQLPLPQGFLGSGVDFPVGNVSFFLFFSGHVAGSVIASLD    196
Sl_ROD1      PRATISALFMFTFRGILGYATQLPLPEDFLGSGVDFPVGNVSFFLFYSGHVAASVIASLD    208

At_ROD1      MRRMQRLRLAMVFDILNVLQSIRLLGTRGHYTIDLAVGVGAGILFDSLAGKYEEMMSKRH    286
Ta_ROD1      MRRMQRMRLAMLFDILNVLQSIRLLGTRGHYTIDLAVGVGAGILFDSFAGKYEEMISKRH    285
Ta-rod1-1    IRRMQRMRLAMLFDILNVLQSIRLLGTRGHYTIDLAVGVGAGILFDSFAGKYEEMISKRH    285
Ta-rod1-2    MRRMQRMRLAMLFDILNVLQSIKLLGTRGHYTIDLAVGVGAGILFDSFAGKYEEMISKRH    285
Os_ROD1      MRRAGRRGMARLYDALNLLQGVRLLACRGHYTIDLAVGVGAGLLFDMLAGRYLDGKNTVD    286
Gm_ROD1      MRRMQRWELAWTFDVLNVLQAVRLLGTRGHYTIDLAVGVGAGILFDSLAGKYEDSKRNAA    256
Sl_ROD1      MKRMQRWEMARVFDALNVLQVVRLLSTRGHYTIDLAVGIGAGILFDSMAGNYVETRTKLS    268

At_ROD1      -LG----TGFSLISKDSLVN---------    301
Ta_ROD1      NLV---NGFGLISKDSLVN*--------    301
Ta-rod1-1    NLV---NGFGLISKDSLVN*--------    301
Ta-rod1-2    NLV---NGFGLISKDSLVN*--------    301
Os_ROD1      GGAAVAPGSRCCSCHKALLSQ--------    307
Gm_ROD1      LSTTHRAQFDCVNNVDIAKKINK----    279
Sl_ROD1      ATNGIGVEYS--PKHENGVKYQSVSSD    293
```

FIG. 8 (continued)

| Line | C-16:0 | C-18:0 | C-18:1 | C-18:2 | C-18:3 | C-20:1 | C-22:1 | Number | Sample type |
|---|---|---|---|---|---|---|---|---|---|
| MN106 | 2.82 | 0.46 | 8.56 | 18.43 | 14.09 | 8.65 | 47.00 | 2 | |
| fae1-1 | 3.76 | 1.07 | 40.88 | 34.33 | 18.38 | 1.00 | 0.24 | 2 | |
| tag1-3 | 3.90 | 0.79 | 10.72 | 20.37 | 25.38 | 4.32 | 34.50 | 2 | |
| rod1-1 | 2.62 | 0.46 | 19.32 | 8.67 | 10.40 | 9.41 | 49.12 | 2 | Bulk sample |
| fae1/tag1 | 3.75 | 0.71 | 31.01 | 41.20 | 22.87 | 0.46 | 0.00 | 2 | |
| tag1/rod1 | 3.41 | 0.73 | 23.64 | 17.81 | 24.78 | 3.83 | 25.80 | 2 | |
| fae1/rod1 | 3.83 | 1.85 | 61.56 | 13.69 | 18.68 | 0.39 | 0.00 | 2 | |
| Line | C-16:0 | C-18:0 | C-18:1 | C-18:2 | C-18:3 | C-20:1 | C-22:1 | Number | Sample type |
| Wild-type | 7.67 | 4.52 | 12.43 | 16.86 | 10.82 | 7.11 | 40.61 | 2 | |
| tag1-3 | 7.83 | 4.28 | 10.49 | 25.19 | 27.67 | 1.99 | 22.54 | 2 | Single seed |
| fad2-2 | 6.22 | 3.88 | 33.92 | 0.28 | 2.37 | 9.71 | 43.62 | 2 | |
| tag1-3/fad2-2 | 25.54 | 19.23 | 28.06 | 0.00 | 4.59 | 0.00 | 22.58 | 2 | |

FIG. 11

SEQUENCE LISTING

<160> NUMBER OF SEQ ID NOS: 50

<210> SEQ ID NO 1
<211> LENGTH: 773
<212> TYPE: PRT
<213> ORGANISM: Arabidopsis thaliana

<400> SEQUENCE: 1

```
Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Gly Arg Gly Gly Gly Glu
                85                  90                  95

Gly Arg Gly Asn Ala Asp Ala Thr Phe Thr Tyr Arg Pro Ser Val Pro
            100                 105                 110
```

```
Ala His Arg Arg Ala Arg Glu Ser Pro Leu Ser Ser Asp Ala Ile Phe
            115                 120                 125

Lys Gln Ser His Ala Gly Leu Phe Asn Leu Cys Val Val Leu Ile
130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Ser Arg Ser Leu Arg Asp Trp
                165                 170                 175

Pro Leu Phe Met Cys Cys Ile Ser Leu Ser Ile Phe Pro Leu Ala Ala
                180                 185                 190

Phe Thr Val Glu Lys Leu Val Leu Gln Lys Tyr Ile Ser Glu Pro Val
            195                 200                 205

Val Ile Phe Leu His Ile Ile Ile Thr Met Thr Glu Val Leu Tyr Pro
            210                 215                 220

Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
                245                 250                 255

His Thr Ser Tyr Asp Ile Arg Ser Leu Ala Asn Ala Ala Asp Lys Ala
                260                 265                 270

Asn Pro Glu Val Ser Tyr Tyr Val Ser Leu Lys Ser Leu Ala Tyr Phe
            275                 280                 285

Met Val Ala Pro Thr Leu Cys Tyr Gln Pro Ser Tyr Pro Arg Ser Ala
            290                 295                 300

Cys Ile Arg Lys Gly Trp Val Ala Arg Gln Phe Ala Lys Leu Val Ile
305                 310                 315                 320

Phe Thr Gly Phe Met Gly Phe Ile Ile Glu Gln Tyr Ile Asn Pro Ile
                325                 330                 335

Val Arg Asn Ser Lys His Pro Leu Lys Gly Asp Leu Leu Tyr Ala Ile
                340                 345                 350

Glu Arg Val Leu Lys Leu Ser Val Pro Asn Leu Tyr Val Trp Leu Cys
            355                 360                 365

Met Phe Tyr Cys Phe Phe His Leu Trp Leu Asn Ile Leu Ala Glu Leu
            370                 375                 380

Leu Cys Phe Gly Asp Arg Glu Phe Tyr Lys Asp Trp Trp Asn Ala Lys
385                 390                 395                 400

Ser Val Gly Asp Tyr Trp Arg Met Trp Asn Met Pro Val His Lys Trp
                405                 410                 415

Met Val Arg His Ile Tyr Phe Pro Cys Leu Arg Ser Lys Ile Pro Lys
                420                 425                 430

Thr Leu Ala Ile Ile Ile Ala Phe Leu Val Ser Ala Val Phe His Glu
            435                 440                 445

Leu Cys Ile Ala Val Pro Cys Arg Leu Phe Lys Leu Trp Ala Phe Leu
            450                 455                 460

Gly Ile Met Phe Gln Val Pro Leu Val Phe Ile Thr Asn Tyr Leu Gln
465                 470                 475                 480

Glu Arg Phe Gly Ser Thr Val Gly Asn Met Ile Phe Trp Phe Ile Phe
                485                 490                 495

Cys Ile Phe Gly Gln Pro Met Cys Val Leu Leu Tyr Tyr His Asp Leu
            500                 505                 510

Met Asn Arg Lys Gly Ser Met Ser Ala Ala Asp Lys Ala Asn Pro Glu
            515                 520                 525
```

```
Val Ser Tyr Tyr Val Ser Leu Lys Ser Leu Ala Tyr Phe Met Val Ala
    530                 535                 540

Pro Thr Leu Cys Tyr Gln Pro Ser Tyr Pro Arg Ser Ala Cys Ile Arg
545                 550                 555                 560

Lys Gly Trp Val Ala Arg Gln Phe Ala Lys Leu Val Ile Phe Thr Gly
                565                 570                 575

Phe Met Gly Phe Ile Ile Glu Gln Tyr Ile Asn Pro Ile Val Arg Asn
            580                 585                 590

Ser Lys His Pro Leu Lys Gly Asp Leu Leu Tyr Ala Ile Glu Arg Val
        595                 600                 605

Leu Lys Leu Ser Val Pro Asn Leu Tyr Val Trp Leu Cys Met Phe Tyr
    610                 615                 620

Cys Phe Phe His Leu Trp Leu Asn Ile Leu Ala Glu Leu Leu Cys Phe
625                 630                 635                 640

Gly Asp Arg Glu Phe Tyr Lys Asp Trp Trp Asn Ala Lys Ser Val Gly
                645                 650                 655

Asp Tyr Trp Arg Met Trp Asn Met Pro Val His Lys Trp Met Val Arg
            660                 665                 670

His Ile Tyr Phe Pro Cys Leu Arg Ser Lys Ile Pro Lys Thr Leu Ala
        675                 680                 685

Ile Ile Ile Ala Phe Leu Val Ser Ala Val Phe His Glu Leu Cys Ile
    690                 695                 700

Ala Val Pro Cys Arg Leu Phe Lys Leu Trp Ala Phe Leu Gly Ile Met
705                 710                 715                 720

Phe Gln Val Pro Leu Val Phe Ile Thr Asn Tyr Leu Gln Glu Arg Phe
                725                 730                 735

Gly Ser Thr Val Gly Asn Met Ile Phe Trp Phe Ile Phe Cys Ile Phe
            740                 745                 750

Gly Gln Pro Met Cys Val Leu Leu Tyr Tyr His Asp Leu Met Asn Arg
        755                 760                 765

Lys Gly Ser Met Ser
    770

<210> SEQ ID NO 2
<211> LENGTH: 566
<212> TYPE: PRT
<213> ORGANISM: Thlaspi arvense

<400> SEQUENCE: 2

Met Ala Ile Leu Asp Ser Gly Gly Val Thr Met Pro Thr Glu Asn Gly
1               5                   10                  15

Gly Gly Glu Phe Ala Asp Leu Asp Thr Leu Arg Arg Lys Ser Arg
            20                  25                  30

Ser Asp Ser Asn Glu Pro Leu Ser Asp Ser Ala Pro Gly Thr Asp Ala
        35                  40                  45

Phe Pro Ser Asp Asp Val Gly Ala Pro Ser Ala Arg Asp Arg Ile
    50                  55                  60

Asp Ser Ala Val Asp Asp Ala Gln Gly Thr Ala Asn Leu Ala Gly Asp
65                  70                  75                  80

Asn Gly Gly Asp Thr Glu Ile Arg Glu Thr Gly Gly Gly Gly Gly
                85                  90                  95

Gly Glu Ala Arg Gly Asp Ala Asp Thr Arg Tyr Thr Tyr Arg Pro Ser
            100                 105                 110
```

```
Val Pro Ala His Arg Arg Ala Arg Glu Ser Pro Leu Ser Ser Asp Ala
            115                 120                 125
Ile Phe Lys Gln Ser His Ala Gly Leu Phe Asn Leu Cys Val Val Val
    130                 135                 140
Leu Ile Ala Val Asn Ser Arg Leu Ile Ile Glu Asn Leu Met Lys Tyr
145                 150                 155                 160
Gly Trp Leu Ile Arg Thr Asp Phe Trp Phe Ser Ser Thr Ser Leu Arg
                165                 170                 175
Asp Trp Pro Leu Phe Ile Ile Ser Leu Ser Ile Phe Pro Leu Ala Ala
            180                 185                 190
Phe Thr Val Glu Lys Leu Val Leu Gln Lys Cys Ile Ser Glu Pro Val
        195                 200                 205
Asn Lys Phe Val Val Ser Trp Arg Thr Tyr Lys Phe Leu Ser Asp Asn
    210                 215                 220
Ile Lys Gly Cys His His Ser Ser Tyr Tyr Asn His Asn Asp Arg Gly
225                 230                 235                 240
Leu Val Ser Ser Leu Arg His Pro Lys Leu Thr Asn Ser Met Ile Leu
                245                 250                 255
Lys Met Asp Arg Cys Asp Ser Ala Phe Leu Ser Gly Val Thr Leu Met
            260                 265                 270
Leu Leu Thr Cys Ile Val Trp Leu Lys Leu Val Ser Tyr Ala His Thr
        275                 280                 285
Ser Tyr Asp Ile Arg Thr Leu Ala Asn Ser Ala Asp Lys Ala Asn Pro
    290                 295                 300
Glu Val Ser Tyr Tyr Val Ser Leu Lys Ser Leu Ala Tyr Phe Met Val
305                 310                 315                 320
Ala Pro Thr Leu Cys Tyr Gln Leu Ser Tyr Pro Arg Ser Pro Cys Ile
                325                 330                 335
Arg Lys Gly Trp Val Ala Arg Gln Phe Ala Lys Leu Val Ile Phe Thr
            340                 345                 350
Gly Phe Met Gly Phe Ile Ile Glu Gln Tyr Ile Asn Pro Ile Val Arg
        355                 360                 365
Asn Ser Lys His Pro Leu Lys Gly Asp Leu Leu Tyr Ala Ile Glu Arg
    370                 375                 380
Val Leu Lys Leu Ser Val Pro Asn Leu Tyr Val Trp Leu Cys Met Phe
385                 390                 395                 400
Tyr Cys Phe Phe His Leu Trp Leu Asn Ile Leu Ala Glu Leu Leu Cys
                405                 410                 415
Phe Gly Asp Arg Glu Phe Tyr Lys Asp Trp Trp Asn Ala Lys Ser Val
            420                 425                 430
Gly Asp Tyr Trp Arg Met Trp Asn Met Pro Val His Lys Trp Met Val
        435                 440                 445
Arg His Ile Tyr Phe Pro Cys Leu Arg Ser Lys Ile Pro Lys Val Ser
    450                 455                 460
Asn Met Tyr Asp Ser Asp Leu Arg Trp Pro Arg Leu Tyr Ser Val Pro
465                 470                 475                 480
Ala Ile Ile Ile Ala Phe Leu Val Ser Ala Val Phe His Glu Leu Cys
                485                 490                 495
Ile Ala Val Pro Cys Arg Leu Phe Asn Leu Trp Ala Phe Met Gly Ile
            500                 505                 510
Met Phe Gln Val Pro Leu Val Phe Ile Thr Asn Tyr Leu Gln Glu Arg
        515                 520                 525
```

```
Phe Gly Ser Met Val Gly Asn Met Val Phe Trp Phe Ile Phe Cys Ile
            530                 535                 540

Phe Gly Gln Pro Met Cys Val Leu Leu Tyr Tyr His Asp Leu Met Asn
545                 550                 555                 560

Arg Lys Gly Ser Met Ala
                565

<210> SEQ ID NO 3
<211> LENGTH: 566
<212> TYPE: PRT
<213> ORGANISM: Artificial Sequence
<220> FEATURE:
<223> OTHER INFORMATION: modified TAG1 polypeptide

<400> SEQUENCE: 3

Met Ala Ile Leu Asp Ser Gly Gly Val Thr Met Pro Thr Glu Asn Gly
1               5                   10                  15

Gly Gly Glu Phe Ala Asp Leu Asp Thr Leu Arg Arg Arg Lys Ser Arg
            20                  25                  30

Ser Asp Ser Asn Glu Pro Leu Ser Asp Ser Ala Pro Gly Thr Asp Ala
        35                  40                  45

Phe Pro Ser Asp Asp Val Gly Ala Pro Ser Asp Ala Arg Asp Arg Ile
    50                  55                  60

Asp Ser Ala Val Asp Asp Ala Gln Gly Thr Ala Asn Leu Ala Gly Asp
65                  70                  75                  80

Asn Gly Gly Asp Thr Glu Ile Arg Glu Thr Gly Gly Gly Gly Gly Gly
                85                  90                  95

Gly Glu Ala Arg Gly Asp Ala Asp Thr Arg Tyr Thr Tyr Arg Pro Ser
            100                 105                 110

Val Pro Ala His Arg Arg Ala Arg Glu Ser Pro Leu Ser Ser Asp Ala
        115                 120                 125

Ile Phe Lys Gln Ser His Ala Gly Leu Phe Asn Leu Cys Val Val Val
    130                 135                 140

Leu Ile Ala Val Asn Ser Arg Leu Ile Ile Glu Asn Leu Met Lys Tyr
145                 150                 155                 160

Gly Trp Leu Ile Lys Thr Asp Phe Trp Phe Ser Ser Thr Ser Leu Arg
                165                 170                 175

Asp Trp Pro Leu Phe Ile Ile Ser Leu Ser Ile Phe Pro Leu Ala Ala
            180                 185                 190

Phe Thr Val Glu Lys Leu Val Leu Gln Lys Cys Ile Ser Glu Pro Val
        195                 200                 205

Asn Lys Phe Val Val Ser Trp Arg Thr Tyr Lys Phe Leu Ser Asp Asn
    210                 215                 220

Ile Lys Gly Cys His His Ser Ser Tyr Tyr Asn His Asn Asp Arg Gly
225                 230                 235                 240

Leu Val Ser Ser Leu Arg His Pro Lys Leu Thr Asn Ser Met Ile Leu
                245                 250                 255

Lys Met Asp Arg Cys Asp Ser Ala Phe Leu Ser Gly Val Thr Leu Met
            260                 265                 270

Leu Leu Thr Cys Ile Val Trp Leu Lys Leu Val Ser Tyr Ala His Thr
        275                 280                 285

Ser Tyr Asp Ile Arg Thr Leu Ala Asn Ser Ala Asp Lys Ala Asn Pro
    290                 295                 300

Glu Val Ser Tyr Tyr Val Ser Leu Lys Ser Leu Ala Tyr Phe Met Val
305                 310                 315                 320
```

```
Ala Pro Thr Leu Cys Tyr Gln Leu Ser Tyr Pro Arg Ser Pro Cys Ile
            325                 330                 335

Arg Lys Gly Trp Val Ala Arg Gln Phe Ala Lys Leu Val Ile Phe Thr
            340                 345                 350

Gly Phe Met Gly Phe Ile Ile Glu Gln Tyr Ile Asn Pro Ile Val Arg
            355                 360                 365

Asn Ser Lys His Pro Leu Lys Gly Asp Leu Leu Tyr Ala Ile Glu Arg
        370                 375                 380

Val Leu Lys Leu Ser Val Pro Asn Leu Tyr Val Trp Leu Cys Met Phe
385                 390                 395                 400

Tyr Cys Phe Phe His Leu Trp Leu Asn Ile Leu Ala Glu Leu Leu Cys
                405                 410                 415

Phe Gly Asp Arg Glu Phe Tyr Lys Asp Trp Trp Asn Ala Lys Ser Val
            420                 425                 430

Gly Asp Tyr Trp Arg Met Trp Asn Met Pro Val His Lys Trp Met Val
            435                 440                 445

Arg His Ile Tyr Phe Pro Cys Leu Arg Ser Lys Ile Pro Lys Val Ser
        450                 455                 460

Asn Met Tyr Asp Ser Asp Leu Arg Trp Pro Arg Leu Tyr Ser Val Pro
465                 470                 475                 480

Ala Ile Ile Ile Ala Phe Leu Val Ser Ala Val Phe His Glu Leu Cys
                485                 490                 495

Ile Ala Val Pro Cys Arg Leu Phe Asn Leu Trp Ala Phe Met Gly Ile
            500                 505                 510

Met Phe Gln Val Pro Leu Val Phe Ile Thr Asn Tyr Leu Gln Glu Arg
            515                 520                 525

Phe Gly Ser Met Val Gly Asn Met Val Phe Trp Phe Ile Phe Cys Ile
        530                 535                 540

Phe Gly Gln Pro Met Cys Val Leu Leu Tyr Tyr His Asp Leu Met Asn
545                 550                 555                 560

Arg Lys Gly Ser Met Ala
                565

<210> SEQ ID NO 4
<211> LENGTH: 566
<212> TYPE: PRT
<213> ORGANISM: Artificial Sequence
<220> FEATURE:
<223> OTHER INFORMATION: modified TAG1 polypeptide

<400> SEQUENCE: 4

Met Ala Ile Leu Asp Ser Gly Gly Val Thr Met Pro Thr Glu Asn Gly
1               5                   10                  15

Gly Gly Glu Phe Ala Asp Leu Asp Thr Leu Arg Arg Arg Lys Ser Arg
            20                  25                  30

Ser Asp Ser Asn Glu Pro Leu Ser Asp Ser Ala Pro Gly Thr Asp Ala
        35                  40                  45

Phe Pro Ser Asp Asp Val Gly Ala Pro Ser Asp Arg Ala Arg Asp Arg Ile
    50                  55                  60

Asp Ser Ala Val Asp Asp Ala Gln Gly Thr Ala Asn Leu Ala Gly Asp
65                  70                  75                  80

Asn Gly Gly Asp Thr Glu Ile Arg Glu Thr Gly Gly Gly Gly Gly Gly
                85                  90                  95

Gly Glu Ala Arg Gly Asp Ala Asp Thr Arg Tyr Thr Tyr Arg Pro Ser
            100                 105                 110
```

-continued

```
Val Pro Ala His Arg Arg Ala Arg Glu Ser Pro Leu Ser Ser Asp Ala
            115                 120                 125

Ile Phe Lys Gln Ser His Ala Gly Leu Phe Asn Leu Cys Val Val
130                 135                 140

Leu Ile Ala Val Asn Ser Arg Leu Ile Ile Glu Asn Leu Met Lys Tyr
145                 150                 155                 160

Gly Trp Leu Ile Arg Thr Asp Phe Trp Phe Ser Ser Thr Ser Leu Arg
                165                 170                 175

Asp Trp Pro Leu Phe Ile Ile Ser Leu Ser Ile Phe Pro Leu Ala Ala
            180                 185                 190

Phe Thr Val Glu Lys Leu Val Leu Gln Lys Cys Ile Ser Glu Pro Val
        195                 200                 205

Asn Lys Phe Val Val Ser Trp Arg Thr Tyr Lys Phe Leu Ser Asp Asn
210                 215                 220

Ile Lys Gly Cys His His Ser Ser Tyr Tyr Asn His Asn Asp Arg Gly
225                 230                 235                 240

Leu Val Ser Ser Leu Arg His Pro Lys Leu Thr Asn Ser Met Ile Leu
                245                 250                 255

Lys Met Asp Arg Cys Asp Ser Ala Phe Leu Ser Gly Val Thr Leu Met
            260                 265                 270

Leu Leu Thr Tyr Ile Val Trp Leu Lys Leu Val Ser Tyr Ala His Thr
        275                 280                 285

Ser Tyr Asp Ile Arg Thr Leu Ala Asn Ser Ala Asp Lys Ala Asn Pro
    290                 295                 300

Glu Val Ser Tyr Val Ser Leu Lys Ser Leu Ala Tyr Phe Met Val
305                 310                 315                 320

Ala Pro Thr Leu Cys Tyr Gln Leu Ser Tyr Pro Arg Ser Pro Cys Ile
                325                 330                 335

Arg Lys Gly Trp Val Ala Arg Gln Phe Ala Lys Leu Val Ile Phe Thr
            340                 345                 350

Gly Phe Met Gly Phe Ile Ile Glu Gln Tyr Ile Asn Pro Ile Val Arg
        355                 360                 365

Asn Ser Lys His Pro Leu Lys Gly Asp Leu Leu Tyr Ala Ile Glu Arg
    370                 375                 380

Val Leu Lys Leu Ser Val Pro Asn Leu Tyr Val Trp Leu Cys Met Phe
385                 390                 395                 400

Tyr Cys Phe Phe His Leu Trp Leu Asn Ile Leu Ala Glu Leu Leu Cys
                405                 410                 415

Phe Gly Asp Arg Glu Phe Tyr Lys Asp Trp Asn Ala Lys Ser Val
            420                 425                 430

Gly Asp Tyr Trp Arg Met Trp Asn Met Pro Val His Lys Trp Met Val
        435                 440                 445

Arg His Ile Tyr Phe Pro Cys Leu Arg Ser Lys Ile Pro Lys Val Ser
    450                 455                 460

Asn Met Tyr Asp Ser Asp Leu Arg Trp Pro Arg Leu Tyr Ser Val Pro
465                 470                 475                 480

Ala Ile Ile Ile Ala Phe Leu Val Ser Ala Val Phe His Glu Leu Cys
                485                 490                 495

Ile Ala Val Pro Cys Arg Leu Phe Asn Leu Trp Ala Phe Met Gly Ile
            500                 505                 510

Met Phe Gln Val Pro Leu Val Phe Ile Thr Asn Tyr Leu Gln Glu Arg
        515                 520                 525
```

```
Phe Gly Ser Met Val Gly Asn Met Val Phe Trp Phe Ile Phe Cys Ile
            530                 535                 540

Phe Gly Gln Pro Met Cys Val Leu Leu Tyr Tyr His Asp Leu Met Asn
545                 550                 555                 560

Arg Lys Gly Ser Met Ala
                565

<210> SEQ ID NO 5
<211> LENGTH: 425
<212> TYPE: PRT
<213> ORGANISM: Artificial Sequence
<220> FEATURE:
<223> OTHER INFORMATION: modified TAG1 polypeptide

<400> SEQUENCE: 5

Met Ala Ile Leu Asp Ser Gly Gly Val Thr Met Pro Thr Glu Asn Gly
1               5                   10                  15

Gly Gly Glu Phe Ala Asp Leu Asp Thr Leu Arg Arg Arg Lys Ser Arg
                20                  25                  30

Ser Asp Ser Asn Glu Pro Leu Ser Asp Ser Ala Pro Gly Thr Asp Ala
            35                  40                  45

Phe Pro Ser Asp Asp Val Gly Ala Pro Ser Asp Ala Arg Asp Arg Ile
    50                  55                  60

Asp Ser Ala Val Asp Asp Ala Gln Gly Thr Ala Asn Leu Ala Gly Asp
65                  70                  75                  80

Asn Gly Gly Asp Thr Glu Ile Arg Glu Thr Gly Gly Gly Gly Gly Gly
                85                  90                  95

Gly Glu Ala Arg Gly Asp Ala Asp Thr Arg Tyr Thr Tyr Arg Pro Ser
            100                 105                 110

Val Pro Ala His Arg Arg Ala Arg Glu Ser Pro Leu Ser Ser Asp Ala
        115                 120                 125

Ile Phe Lys Gln Ser His Ala Gly Leu Phe Asn Leu Cys Val Val Val
    130                 135                 140

Leu Ile Ala Val Asn Ser Arg Leu Ile Ile Glu Asn Leu Met Lys Tyr
145                 150                 155                 160

Gly Trp Leu Ile Arg Thr Asp Phe Trp Phe Ser Ser Thr Ser Leu Arg
                165                 170                 175

Asp Trp Pro Leu Phe Ile Ile Ser Leu Ser Ile Phe Pro Leu Ala Ala
            180                 185                 190

Phe Thr Val Glu Lys Leu Val Leu Gln Lys Cys Ile Ser Glu Pro Val
        195                 200                 205

Asn Lys Phe Val Val Ser Trp Arg Thr Tyr Lys Phe Leu Ser Asp Asn
    210                 215                 220

Ile Lys Gly Cys His His Ser Ser Tyr Tyr Asn His Asn Asp Arg Gly
225                 230                 235                 240

Leu Val Ser Ser Leu Arg His Pro Lys Leu Thr Asn Ser Met Ile Leu
                245                 250                 255

Lys Met Asp Arg Cys Asp Ser Ala Phe Leu Ser Gly Val Thr Leu Met
            260                 265                 270

Leu Leu Thr Cys Ile Val Trp Leu Lys Leu Val Ser Tyr Ala His Thr
        275                 280                 285

Ser Tyr Asp Ile Arg Thr Leu Ala Asn Ser Ala Asp Lys Ala Asn Pro
    290                 295                 300

Glu Val Ser Tyr Tyr Val Ser Leu Lys Ser Leu Ala Tyr Phe Met Val
305                 310                 315                 320
```

```
Ala Pro Thr Leu Cys Tyr Gln Leu Ser Tyr Pro Arg Ser Pro Cys Ile
            325                 330                 335

Arg Lys Gly Trp Val Ala Arg Gln Phe Ala Lys Leu Val Ile Phe Thr
            340                 345                 350

Gly Phe Met Gly Phe Ile Ile Glu Gln Tyr Ile Asn Pro Ile Val Arg
            355                 360                 365

Asn Ser Lys His Pro Leu Lys Gly Asp Leu Leu Tyr Ala Ile Glu Arg
            370                 375                 380

Val Leu Lys Leu Ser Val Pro Asn Leu Tyr Val Trp Leu Cys Met Phe
385                 390                 395                 400

Tyr Cys Phe Phe His Leu Trp Leu Asn Ile Leu Ala Glu Leu Leu Cys
                405                 410                 415

Phe Gly Asp Arg Glu Phe Tyr Lys Asp
            420                 425

<210> SEQ ID NO 6
<211> LENGTH: 498
<212> TYPE: PRT
<213> ORGANISM: Glycine max

<400> SEQUENCE: 6

Met Ala Ile Ser Asp Glu Pro Glu Thr Val Ala Thr Ala Leu Asn His
1               5                   10                  15

Ser Ser Leu Arg Arg Arg Pro Thr Ala Ala Gly Leu Phe Asn Ser Pro
            20                  25                  30

Glu Thr Thr Thr Asp Ser Ser Gly Asp Asp Leu Ala Lys Asp Ser Gly
        35                  40                  45

Ser Asp Asp Ser Ile Ser Ser Asp Ala Ala Asn Ser Gln Pro Gln Gln
    50                  55                  60

Lys Gln Asp Thr Asp Phe Ser Val Leu Lys Phe Ala Tyr Arg Pro Ser
65                  70                  75                  80

Val Pro Ala His Arg Lys Val Lys Glu Ser Pro Leu Ser Ser Asp Thr
                85                  90                  95

Ile Phe Arg Gln Ser His Ala Gly Leu Phe Asn Leu Cys Ile Val Val
            100                 105                 110

Leu Val Ala Val Asn Ser Arg Leu Ile Ile Glu Asn Leu Met Lys Tyr
            115                 120                 125

Gly Trp Leu Ile Lys Ser Gly Phe Trp Phe Ser Ser Lys Ser Leu Arg
        130                 135                 140

Asp Trp Pro Leu Phe Met Cys Cys Leu Ser Leu Val Val Phe Pro Phe
145                 150                 155                 160

Ala Ala Phe Ile Val Glu Lys Leu Ala Gln Gln Lys Cys Ile Pro Glu
                165                 170                 175

Pro Val Val Val Leu His Ile Ile Ile Thr Ser Ala Ser Leu Phe
            180                 185                 190

Tyr Pro Val Leu Val Ile Leu Arg Cys Asp Ser Ala Phe Leu Ser Gly
            195                 200                 205

Val Thr Leu Met Leu Phe Ala Cys Val Val Trp Leu Lys Leu Val Ser
        210                 215                 220

Tyr Ala His Thr Asn Tyr Asp Met Arg Ala Leu Thr Lys Ser Val Glu
225                 230                 235                 240

Lys Gly Glu Ala Leu Pro Asp Thr Leu Asn Met Asp Tyr Pro Tyr Asn
                245                 250                 255
```

Val Ser Phe Lys Ser Leu Ala Tyr Phe Leu Val Ala Pro Thr Leu Cys
                260                 265                 270

Tyr Gln Pro Ser Tyr Pro Arg Thr Pro Tyr Ile Arg Lys Gly Trp Leu
            275                 280                 285

Phe Arg Gln Leu Val Lys Leu Ile Ile Phe Thr Gly Val Met Gly Phe
290                 295                 300

Ile Ile Glu Gln Tyr Ile Asn Pro Ile Val Gln Asn Ser Gln His Pro
305                 310                 315                 320

Leu Lys Gly Asn Leu Leu Tyr Ala Ile Glu Arg Val Leu Lys Leu Ser
                325                 330                 335

Val Pro Asn Leu Tyr Val Trp Leu Cys Met Phe Tyr Cys Phe His
                340                 345                 350

Leu Trp Leu Asn Ile Leu Ala Glu Leu Leu Arg Phe Gly Asp Arg Glu
            355                 360                 365

Phe Tyr Gln Asp Trp Trp Asn Ala Lys Thr Val Glu Asp Tyr Trp Arg
370                 375                 380

Met Trp Asn Met Pro Val His Lys Trp Met Ile Arg His Leu Tyr Phe
385                 390                 395                 400

Pro Cys Leu Arg His Gly Ile Pro Lys Ala Val Ala Leu Leu Ile Ala
                405                 410                 415

Phe Leu Val Ser Ala Leu Phe His Glu Leu Cys Ile Ala Val Pro Cys
            420                 425                 430

His Ile Phe Lys Leu Trp Ala Phe Gly Gly Ile Met Phe Gln Val Pro
435                 440                 445

Leu Val Phe Ile Thr Asn Tyr Leu Gln Asn Lys Phe Arg Asn Ser Met
450                 455                 460

Val Gly Asn Met Ile Phe Trp Phe Ile Phe Ser Ile Leu Gly Gln Pro
465                 470                 475                 480

Met Cys Val Leu Leu Tyr Tyr His Asp Leu Met Asn Arg Lys Gly Lys
                485                 490                 495

Leu Asp

<210> SEQ ID NO 7
<211> LENGTH: 477
<212> TYPE: PRT
<213> ORGANISM: Oryza sativa

<400> SEQUENCE: 7

Met Ala Pro Pro Pro Ser Leu Ala Pro Asp Arg Gly Gly Gly Glu Pro
1               5                   10                  15

Asp Asp Ala Leu Arg Leu Arg Ala Arg Ala Ala Ala Ala Ala Gly Asp
            20                  25                  30

Ala Pro Ala Pro Gln Gln Gln Glu Gln Arg His Gln Glu Gln Gln
        35                  40                  45

Gln Gln Leu Leu Trp Tyr Arg Ala Ser Ala Pro Ala His Arg Arg Val
    50                  55                  60

Arg Glu Ser Pro Leu Ser Ser Asp Ala Ile Phe Arg Gln Ser His Ala
65                  70                  75                  80

Gly Leu Leu Asn Leu Cys Ile Val Val Leu Val Ala Val Asn Ser Arg
                85                  90                  95

Leu Ile Ile Glu Asn Leu Met Lys Tyr Gly Leu Leu Ile Arg Ala Gly
            100                 105                 110

Phe Trp Phe Ser Gly Thr Ser Leu Ala Asp Trp Pro Leu Leu Met Cys
        115                 120                 125

Cys Leu Thr Leu Pro Thr Phe Pro Leu Ala Ala Leu Met Val Glu Lys
            130                 135                 140

Leu Ala Gln Arg Lys Leu Ile Ser Lys His Val Val Ile Leu Leu His
145                 150                 155                 160

Ile Val Ile Thr Thr Ser Val Leu Val Tyr Pro Val Val Ile Leu
                165                 170                 175

Lys Cys Asp Ser Ala Val Leu Ser Gly Phe Val Leu Met Phe Leu Ala
            180                 185                 190

Ser Ile Ile Trp Leu Lys Leu Val Ser Phe Ala His Thr Asn Tyr Asp
        195                 200                 205

Ile Arg Met Leu Ser Lys Ser Ile Glu Lys Gly Val Thr His Asp Ile
210                 215                 220

Ser Ile Asp Pro Glu Asn Ile Lys Trp Pro Thr Phe Lys Arg Leu Ser
225                 230                 235                 240

Tyr Phe Met Leu Ala Pro Thr Leu Cys Tyr Gln Pro Ser Tyr Pro Arg
                245                 250                 255

Thr Thr Tyr Ile Arg Lys Gly Trp Val Val Arg Gln Leu Ile Lys Cys
            260                 265                 270

Leu Val Phe Thr Gly Leu Met Gly Phe Ile Ile Glu Gln Tyr Ile Asn
        275                 280                 285

Pro Ile Val Lys Asn Ser Lys His Pro Leu Lys Gly Asn Phe Leu Asn
290                 295                 300

Ala Ile Glu Arg Val Leu Lys Leu Ser Val Pro Thr Leu Tyr Val Trp
305                 310                 315                 320

Leu Cys Met Phe Tyr Cys Phe His Leu Trp Leu Asn Ile Leu Ala
                325                 330                 335

Glu Leu Leu Cys Phe Gly Asp Arg Glu Phe Tyr Lys Asp Trp Trp Asn
            340                 345                 350

Ala Lys Thr Val Glu Glu Tyr Trp Arg Met Trp Asn Met Pro Val His
        355                 360                 365

Lys Trp Val Ile Arg His Ile Tyr Phe Pro Cys Ile Arg Asn Gly Phe
370                 375                 380

Ser Lys Gly Val Ala Ile Leu Ile Ser Phe Leu Val Ser Ala Ala Phe
385                 390                 395                 400

His Glu Leu Cys Val Ala Val Pro Cys His Ile Phe Lys Phe Trp Ala
                405                 410                 415

Phe Ile Gly Ile Met Phe Gln Ile Pro Leu Val Phe Leu Thr Lys Tyr
            420                 425                 430

Leu Gln Asp Lys Phe Asn Asn Thr Met Val Gly Asn Met Ile Phe Trp
        435                 440                 445

Phe Phe Phe Ser Ile Leu Gly Gln Pro Met Cys Val Leu Leu Tyr Tyr
450                 455                 460

His Asp Val Met Asn Arg Gln Gln Ala Gln Thr Asn Arg
465                 470                 475

<210> SEQ ID NO 8
<211> LENGTH: 463
<212> TYPE: PRT
<213> ORGANISM: Solanum lycopersicum

<400> SEQUENCE: 8

Met Asp Gly Ser Gly Asn Gly Gly Leu Asp Arg Val Ser Glu Ala Val
1               5                   10                  15

```
Ser Thr Thr Ile Gly Lys Ile Ser Asp Gly Asp Gly Ile Gln Glu Glu
            20                  25                  30

Gln Arg Lys Ala Asn Glu Thr Thr Pro Leu Lys Tyr Val Tyr Arg Ala
        35                  40                  45

Ser Ala Pro Ala His Arg Arg Asn Lys Glu Ser Pro Leu Ser Ser Ala
    50                  55                  60

Ala Ile Phe Lys Gln Ser His Ala Gly Leu Leu Asn Leu Cys Ile Val
65                  70                  75                  80

Val Leu Ile Ala Val Asn Ser Arg Leu Ile Ile Glu Asn Leu Met Lys
                85                  90                  95

Tyr Gly Leu Leu Ile Gly Ser Gly Phe Trp Ser Ser Thr Ser Val
            100                 105                 110

Arg Asp Trp Pro Leu Leu Met Cys Cys Leu Ser Leu Pro Ile Phe Pro
        115                 120                 125

Leu Ala Ala Phe Leu Val Glu Lys Met Ala Gln Lys Lys Tyr Met Thr
    130                 135                 140

Glu His Val Val Val Thr Leu His Ile Ile Ile Thr Thr Ala Ser Ile
145                 150                 155                 160

Leu Tyr Pro Val Leu Val Ile Leu Arg Cys Asp Ser Ala Phe Leu Ser
                165                 170                 175

Gly Val Thr Leu Met Met Phe Ala Cys Ile Val Trp Met Lys Leu Val
            180                 185                 190

Ser Tyr Ala His Thr Asn Tyr Asp Met Arg Gln Leu Ala Lys Ser Val
        195                 200                 205

Asn Glu Gly Glu Asn Ser Glu Ile Asn Tyr Ser Tyr Asn Val Ser Phe
    210                 215                 220

Glu Ser Leu Ala Tyr Phe Met Val Ala Pro Thr Leu Cys Tyr Gln Leu
225                 230                 235                 240

Ser Tyr Pro Arg Ser Ala Ser Ile Arg Lys Gly Trp Leu Ala Arg Gln
                245                 250                 255

Leu Ile Lys Leu Val Ile Phe Thr Gly Leu Met Gly Phe Ile Ile Glu
            260                 265                 270

Gln Tyr Ile Asn Pro Ile Val Arg Ser Ser Arg His Pro Phe Glu Gly
        275                 280                 285

Asn Leu Leu Tyr Ala Ile Glu Arg Val Leu Lys Leu Ser Val Pro Ile
    290                 295                 300

Leu Tyr Val Trp Leu Cys Met Phe Tyr Ser Leu Phe His Leu Trp Leu
305                 310                 315                 320

Asn Ile Leu Ala Glu Val Leu Arg Phe Gly Asp Arg Glu Phe Tyr Lys
                325                 330                 335

Asp Trp Trp Asn Ala Lys Thr Ile Asp Glu Tyr Trp Arg Leu Trp Asn
            340                 345                 350

Met Pro Val His Lys Trp Met Val Arg His Ile Tyr Phe Pro Cys Leu
        355                 360                 365

Arg Asn Gly Ile Pro Lys Gly Val Ala Met Val Ile Ser Phe Phe Ile
    370                 375                 380

Ser Ala Val Phe His Glu Leu Cys Ile Ala Val Pro Cys Arg Leu Phe
385                 390                 395                 400

Lys Phe Trp Ala Phe Leu Gly Ile Met Phe Gln Ile Pro Leu Val Ile
                405                 410                 415

Leu Thr Asn Phe Leu Gln Asn Lys Phe Lys Asn Ser Asn Val Gly Asn
            420                 425                 430
```

```
Met Thr Phe Trp Cys Phe Phe Cys Ile Val Gly Gln Pro Met Cys Val
                435                 440                 445

Leu Leu Tyr Tyr His Asp Val Met Asn Arg Asn Gly Ser Ser Ser
    450                 455                 460

<210> SEQ ID NO 9
<211> LENGTH: 3117
<212> TYPE: DNA
<213> ORGANISM: Thlaspi arvense

<400> SEQUENCE: 9
```

| | | | | | |
|---|---|---|---|---|---|
| atggcgattt | tggattctgg | aggcgtcact | atgccgacgg | agaacggtgg cggagagttt | 60 |
| gcggatctcg | atactcttcg | tcgacggaaa | tcacgatcgg | attccaacga acctctttcc | 120 |
| gattccgcac | ccgtaccga | tgctttccca | tcagatgatg | ttggagctcc gtccgacgcg | 180 |
| agggatcgga | ttgattcagc | tgtcgacgac | gctcagggaa | cagcgaattt ggcaggagat | 240 |
| aacggcggag | ataccgaaat | tagggaaact | ggtggaggag | gaggcggcgg tgaagcaaga | 300 |
| ggagacgccg | atacaaggta | tacgtatcgt | ccgtcggttc | cagctcatcg gagggctagg | 360 |
| gaaagtccac | tcagctccga | cgcaatcttc | aaacaggtaa | atctcagatt ctacgctgga | 420 |
| caatctccga | atttggtgct | tgatactgtc | taatgttaga | ggagaatttc aaactgagtt | 480 |
| tcatgttaac | ttttagagag | gacaatttct | tcatttcatt | tgactcgagt ttgtgttgtc | 540 |
| ttccatggca | gagccatgcc | ggattattca | acctgtgtgt | agtagttctt attgctgtaa | 600 |
| acagtagact | catcatcgag | aacttgatga | aggttagtta | ctttttttct cctatggctt | 660 |
| gaaaattgaa | ttaggtttgt | tcttgagctg | agaactttat | caagaccttacctttgttgt | 720 |
| tgccttcatt | cctgtagtac | ggttggttga | tcagaacaga | tttctggttt agttcaacat | 780 |
| cgctgcgaga | ttggccgctt | tcatgtgtt | ggtaatatat | aattttttt tctttcgtaa | 840 |
| tgttacattc | ttattcatat | aatgatgtgt | ttagagattc | agatatttct ataaattctt | 900 |
| ctgttgcagt | atctctcttt | cgatctttcc | tctggctgcc | tttaccgtcg agaaactggt | 960 |
| acttcagaaa | tgcatatctg | aacctgtgag | taaactactg | actatatagc tattactgga | 1020 |
| ttgtttactg | aagacaagtt | tgttgtatcc | tggagaactt | ataagtttct ttctgataat | 1080 |
| attaaaggtt | gtcatcattc | ttcatattat | aatcacaatg | acagaggtct tgtatccagt | 1140 |
| ttacgtcacc | ctaaggtgtg | aattaagcta | aggtgtttct | gatctcagct tgtgatactc | 1200 |
| tcttttttaa | ttctagttga | ctaactcgat | gatcttgaaa | atggacaggt gtgattccgc | 1260 |
| cttcttgtca | ggtgtcacat | tgatgctcct | cacttgcatt | gtgtggctaa agttggtttc | 1320 |
| ttatgctcat | actagctacg | acataagaac | cctagccaat | tcagctgata aggtaaaaga | 1380 |
| atcaaaagaa | atatatacta | gtcactagcc | ttgtgttact | atttaaccca gatactgtta | 1440 |
| tgaactaaag | gccaatcctg | aagtctccta | ctatgttagc | ttgaagagct ggcatatttt | 1500 |
| catggttgct | cccacattgt | gttatcaggt | aatgagatgc | gtcttttttt aatagcatca | 1560 |
| aacattctta | aacttacaaa | agcttcttgt | ctaaaccttg | cgtctttgct tttttcccagc | 1620 |
| tgagctatcc | acgttctcct | tgtatccgga | agggttgggt | ggctcgtcaa tttgcaaaac | 1680 |
| tggtcatatt | cactgggattc | atgggattta | taatagagca | agtgcgttct caacatcttg | 1740 |
| cttttttattt | ttccttgtga | aaatcatcat | ctctgcatcg | tcaatcgctt gacttctgtt | 1800 |
| ttttttttgt | tacttttttt | ggcagtatat | aaatcctatt | gttaggaact caaagcatcc | 1860 |
| tttgaaaggg | gatcttctat | acgctattga | aagagtcttg | aagctttcag ttccaaattt | 1920 |
| atacgtgtgg | ctctgcatgt | tctactgctt | cttccaccct | tggtatgtcg tgatcccttc | 1980 |

| | | | |
|---|---|---|---|
| tctttcgatg | tagtttccag | agacgaacaa | cagaaataag ctgtctcgtc aagaaattga | 2040 |
| taatttatag | ccagggatgt | aatttcagtt | actgaacaca aatctctttg cgttgttctt | 2100 |
| gtccccaggt | taaacatatt | ggcagagctc | ctctgcttcg gggatcgtga attctacaaa | 2160 |
| gattggtgga | atgcaaaaag | tgtgggagac | gtgagttgtt attacatacg tcttactcaa | 2220 |
| aaagcatatg | atttttatat | gctatcgttg | ttttgaggtc acttaactaa ccaaaattca | 2280 |
| tgtttccatc | acttgtcttc | ctttatcagt | attggagaat gtggaatatg gtaaggttct | 2340 |
| tttcctaaaa | catcgccttc | ttttctatac | aaaacataag aagagaggta atacagatct | 2400 |
| tgttttctct | aacagcctgt | tcataaatgg | atggttcgac atatatactt tccgtgtctg | 2460 |
| cgcagcaaga | taccaaaagt | gagtaatatg | tatgatagtg atttgcgatg gccgagatta | 2520 |
| tattccgttt | tttttctaa | aactacaatc | atccactcat tttcttgttc tcaggtacct | 2580 |
| gccattatca | ttgctttctt | agtctctgca | gtctttcatg aggtatatat atcctctgca | 2640 |
| ttgcactgtc | tctaatattc | aaagcattgt | tgttacgcac attctcatgt ttacaaattt | 2700 |
| ccttgcagtt | atgcatcgct | gttccttgcc | gtctcttcaa cctatgggct ttcatgggga | 2760 |
| ttatgtttca | ggtataaaaa | aattgacaaa | acaatctgga agttttgtca tttctaatct | 2820 |
| cattttctta | ccaccaccaa | atgtgttttg | agtaggtgcc tttggtcttt atcacaaact | 2880 |
| atctacaaga | aaggtttggc | tccatggtat | gctctctaaa ggccgaataa cacttttctg | 2940 |
| atcatagcca | cttaaatatt | taatttttt | gatggaaact aaaaagattg actgttttgg | 3000 |
| aatgtgatca | tttaggtggg | caacatggtt | ttctggttca tcttctgcat tttcggtcaa | 3060 |
| cccatgtgtg | tgcttcttta | ttaccacgat | ctgatgaacc gcaaaggatc catggcc | 3117 |

<210> SEQ ID NO 10
<211> LENGTH: 1698
<212> TYPE: DNA
<213> ORGANISM: Artificial Sequence
<220> FEATURE:
<223> OTHER INFORMATION: nucleic acid that can encode a TAG1 polypeptide

<400> SEQUENCE: 10

| | | | |
|---|---|---|---|
| atggcgattt | tggattctgg | aggcgtcact | atgccgacgg agaacggtgg cggagagttt | 60 |
| gcggatctcg | atactcttcg | tcgacggaaa | tcacgatcgg attccaacga acctctttcc | 120 |
| gattccgcac | ccgtaccga | tgctttccca | tcagatgatg ttggagctcc gtccgacgcg | 180 |
| agggatcgga | ttgattcagc | tgtcgacgac | gctcagggaa cagcgaattt ggcaggagat | 240 |
| aacggcggag | ataccgaaat | tagggaaact | ggtggaggag gaggcggcgg tgaagcaaga | 300 |
| ggagacgccg | atacaaggta | tacgtatcgt | ccgtcggttc cagctcatcg gagggctagg | 360 |
| gaaagtccac | tcagctccga | cgcaatcttc | aaacagagcc atgccggatt attcaacctg | 420 |
| tgtgtagtag | ttcttattgc | tgtaaacagt | agactcatca tcgagaactt gatgaagtac | 480 |
| ggttggttga | tcagaacaga | tttctggttt | agttcaacat cgctgcgaga ttggccgctt | 540 |
| ttcattatct | ctctttcgat | cttttcctctg | gctgccttta ccgtcgagaa actggtactt | 600 |
| cagaaatgca | tatctgaacc | tgtgaacaag | tttgttgtat cctggagaac ttataagttt | 660 |
| ctttctgata | atattaaagg | ttgtcatcat | tcttcatatt ataatcacaa tgacagaggt | 720 |
| cttgtatcca | gtttacgtca | ccctaagttg | actaactcga tgatcttgaa aatggacagg | 780 |
| tgtgattccg | ccttccttgtc | aggtgtcaca | ttgatgctcc tcacttgcat tgtgtggcta | 840 |
| aagttggttt | cttatgctca | tactagctac | gacataagaa ccctagccaa ttcagctgat | 900 |

```
aaggccaatc ctgaagtctc ctactatgtt agcttgaaga gcttggcata tttcatggtt      960
gctcccacat tgtgttatca gctgagctat ccacgttctc cttgtatccg gaagggttgg     1020
gtggctcgtc aatttgcaaa actggtcata ttcactggat tcatgggatt tataatagag     1080
caatatataa atcctattgt taggaactca aagcatcctt tgaaagggga tcttctatac     1140
gctattgaaa gagtcttgaa gctttcagtt ccaaatttat acgtgtggct ctgcatgttc     1200
tactgcttct tccacctttg gttaaacata ttggcagagc tcctctgctt cggggatcgt     1260
gaattctaca aagattggtg aatgcaaaa agtgtgggag actattggag aatgtggaat      1320
atgcctgttc ataaatggat ggttcgacat atatacttc cgtgtctgcg cagcaagata      1380
ccaaaagtga gtaatatgta tgatagtgat ttgcgatggc cgagattata ttccgtacct     1440
gccattatca ttgctttctt agtctctgca gtctttcatg agttatgcat cgctgttcct     1500
tgccgtctct tcaacctatg gctttcatg gggattatgt ttcaggtgcc tttggtcttt      1560
atcacaaact atctacaaga aaggtttggc tccatggtgg gcaacatggt tttctggttc     1620
atcttctgca ttttcggtca acccatgtgt gtgcttcttt attaccacga tctgatgaac     1680
cgcaaaggat ccatggcc                                                   1698
```

<210> SEQ ID NO 11
<211> LENGTH: 3117
<212> TYPE: DNA
<213> ORGANISM: Artificial Sequence
<220> FEATURE:
<223> OTHER INFORMATION: modified nucleic acid that can encode a
      modified TAG1 polypeptide

<400> SEQUENCE: 11

```
atggcgattt tggattctgg aggcgtcact atgccgacgg agaacggtgg cggagagttt       60
gcggatctcg atactcttcg tcgacggaaa tcacgatcgg attccaacga acctctttcc      120
gattccgcac ccgtaccga tgctttccca tcagatgatg ttggagctcc gtccgacgcg       180
agggatcgga ttgattcagc tgtcgacgac gctcagggaa cagcgaattt ggcaggagat      240
aacggcggag ataccgaaat tagggaaact ggtggaggag gaggcggcgg tgaagcaaga      300
ggagacgccg atacaaggta tacgtatcgt ccgtcggttc cagctcatcg gagggctagg      360
gaaagtccac tcagctccga cgcaatcttc aaacaggtaa atctcagatt ctacgctgga      420
caatctccga atttggtgct tgatactgtc taatgttaga ggagaatttc aaactgagtt      480
tcatgttaac ttttagagag gacaatttct tcatttcatt tgactcgagt ttgtgttgtc      540
ttccatggca gagccatgcc ggattattca acctgtgtgt agtagttctt attgctgtaa      600
acagtagact catcatcgag aacttgatga aggttagtta ctttttttct cctatggctt      660
gaaaattgaa ttaggtttgt tcttgagctg agaactttat caagaccttt cctttgttgt      720
tgccttcatt cctgtagtac ggttggttga tcaaaacaga tttctggttt agttcaacat      780
cgctgcgaga ttgccgcgtt tcatgtgttt ggtaatatat aattttttt tctttcgtaa       840 tgttacattc ttattcatat aatgatgtgt ttagagattc agatatttct ataaattctt      900
ctgttgcagt atctctcttt cgatcttttcc tctggctgcc tttaccgtcg agaaactggt     960
acttcagaaa tgcatatctg aacctgtgag taaactactg actatatagc tattactgga    1020
ttgtttactg aagacaagtt tgttgtatcc tggagaactt ataagtttct ttctgataat    1080
attaaaggtt gtcatcattc ttcatattat aatcacaatg acagaggtct tgtatccagt    1140
ttacgtcacc ctaaggtgtg aattaagcta aggtgtttct gatctcagct tgtgatactc    1200
```

```
tcttttttaa ttctagttga ctaactcgat gatcttgaaa atggacaggt gtgattccgc   1260
cttcttgtca ggtgtcacat tgatgctcct cacttgcatt gtgtggctaa agttggtttc   1320
ttatgctcat actagctacg acataagaac cctagccaat tcagctgata aggtaaaaga   1380
atcaaaagaa atatatacta gtcactagcc ttgtgttact atttttaacca gatactgtta   1440 tgaactaaag gccaatcctg aagtctccta ctatgttagc ttgaagagct tggcatattt   1500
catggttgct cccacattgt gttatcaggt aatgagatgc gtctttttt aatagcatca    1560 aacattctta aacttacaaa agcttcttgt ctaaaccttg cgtctttgct ttttcccagc   1620
tgagctatcc acgttctcct tgtatccgga agggttgggt ggctcgtcaa tttgcaaaac   1680
tggtcatatt cactggattc atgggattta aatagagca agtgcgttct caacatcttg    1740 cttttattt ttccttgtga aaatcatcat ctctgcatcg tcaatcgctt gacttctgtt     1800
ttttttttgt tactttttt ggcagtatat aaatcctatt gttaggaact caaagcatcc    1860
tttgaaaggg gatcttctat acgctattga aagagtcttg aagctttcag ttccaaattt   1920
atacgtgtgg ctctgcatgt tctactgctt cttccaccct tggtatgtcg tgatcccttc   1980
tctttcgatg tagtttccag agacgaacaa cagaaataag ctgtctcgtc aagaaattga   2040
taatttatag ccagggatgt aatttcagtt actgaacaca atctctttg cgttgttctt    2100 gtccccaggt taaacatatt ggcagagctc ctctgcttcg gggatcgtga attctacaaa   2160
gattggtgga atgcaaaaag tgtgggagac gtgagttgtt attacatacg tcttactcaa   2220
aaagcatatg attttatat gctatcgttg ttttgaggtc acttaactaa ccaaaattca    2280
tgtttccatc acttgtcttc ctttatcagt attggagaat gtggaatatg gtaaggttct   2340
tttcctaaaa catcgccttc ttttctatac aaaacataag aagagaggta atacagatct   2400
tgttttctct aacagcctgt tcataaatgg atggttcgac atatatactt ccgtgtctg    2460 cgcagcaaga taccaaaagt gagtaatatg tatgatagtg atttgcgatg gccgagatta   2520
tattccgttt tttttctaa aactacaatc atccactcat tttcttgttc tcaggtacct    2580
gccattatca ttgctttctt agtctctgca gtctttcatg aggtatatat atcctctgca   2640
ttgcactgtc tctaatattc aaagcattgt tgttacgcac attctcatgt ttacaaattt   2700
ccttgcagtt atgcatcgct gttccttgcc gtctcttcaa cctatgggct tcatgggga    2760 ttatgtttca ggtataaaaa aattgacaaa acaatctgga agttttgtca tttctaatct   2820
cattttctta ccaccaccaa atgtgttttg agtaggtgcc tttggtcttt atcacaaact   2880
atctacaaga aaggtttggc tccatggtat gctctctaaa ggccgaataa cacttttctg   2940
atcatagcca cttaaatatt taattttttt gatggaaact aaaaagattg actgttttgg   3000
aatgtgatca tttaggtggg caacatggtt ttctggttca tcttctgcat tttcggtcaa   3060
cccatgtgtg tgcttctta ttaccacgat ctgatgaacc gcaaaggatc catggcc      3117
```

<210> SEQ ID NO 12
<211> LENGTH: 1698
<212> TYPE: DNA
<213> ORGANISM: Artificial Sequence
<220> FEATURE:
<223> OTHER INFORMATION: modified nucleic acid that can encode a
    modified TAG1 polypeptide

<400> SEQUENCE: 12

```
atggcgattt tggattctgg aggcgtcact atgccgacgg agaacggtgg cggagagttt    60
gcggatctcg atactcttcg tcgacggaaa tcacgatcgg attccaacga acctctttcc   120
```

```
gattccgcac ccggtaccga tgctttccca tcagatgatg ttggagctcc gtccgacgcg      180
agggatcgga ttgattcagc tgtcgacgac gctcagggaa cagcgaattt ggcaggagat      240
aacggcggag ataccgaaat tagggaaact ggtggaggag gaggcggcgg tgaagcaaga      300
ggagacgccg atacaaggta tacgtatcgt ccgtcggttc cagctcatcg agggctagg       360 gaaagtccac tcagctccga cgcaatcttc aaacagagcc atgccggatt attcaacctg      420
tgtgtagtag ttcttattgc tgtaaacagt agactcatca tcgagaactt gatgaagtac      480
ggttggttga tcaaaacaga tttctggttt agttcaacat cgctgcgaga ttggccgctt      540
ttcattatct ctctttcgat cttcctctg gctgccttta ccgtcgagaa actggtactt       600
cagaaatgca tatctgaacc tgtgaacaag tttgttgtat cctggagaac ttataagttt      660
ctttctgata atattaaagg ttgtcatcat tcttcatatt ataatcacaa tgacagaggt      720
cttgtatcca gtttacgtca ccctaagttg actaactcga tgatcttgaa aatggacagg      780
tgtgattccg ccttcttgtc aggtgtcaca ttgatgctcc tcacttgcat tgtgtggcta      840
aagttggttt cttatgctca tactagctac gacataagaa ccctagccaa tcagctgat       900 aaggccaatc ctgaagtctc ctactatgtt agcttgaaga gcttggcata tttcatggtt      960
gctcccacat tgtgttatca gctgagctat ccacgttctc cttgtatccg gaagggttgg     1020
gtggctcgtc aatttgcaaa actggtcata ttcactggat tcatgggatt tataatagag     1080
caatatataa atcctattgt taggaactca agcatcctt  tgaaagggga tcttctatac     1140
gctattgaaa gagtcttgaa gctttcagtt ccaaatttat acgtgtggct ctgcatgttc     1200
tactgcttct tccacctttg gttaaacata ttggcagagc tcctctgctt cggggatcgt     1260
gaattctaca agattggtg gaatgcaaaa agtgtgggag actattggag aatgtggaat      1320
atgcctgttc ataatggat ggttcgacat atatactttc cgtgtctgcg cagcaagata      1380
ccaaaagtga gtaatatgta tgatagtgat ttgcgatggc cgagattata ttccgtacct     1440
gccattatca ttgctttctt agtctctgca gtctttcatg agttatgcat cgctgttcct     1500
tgccgtctct tcaacctatg gctttcatg gggattatgt ttcaggtgcc tttggtcttt      1560
atcacaaact atctacaaga aaggtttggc tccatggtgg gcaacatggt tttctggttc     1620
atcttctgca ttttcggtca acccatgtgt gtgcttcttt attaccacga tctgatgaac     1680
cgcaaaggat ccatggcc                                                   1698

<210> SEQ ID NO 13
<211> LENGTH: 3117
<212> TYPE: DNA
<213> ORGANISM: Artificial Sequence
<220> FEATURE:
<223> OTHER INFORMATION: modified nucleic acid that can encode a
      modified TAG1 polypeptide

<400> SEQUENCE: 13
atggcgattt tggattctgg aggcgtcact atgccgacgg agaacggtgg cggagagttt       60
gcggatctcg atactcttcg tcgacggaaa tcacgatcgg attccaacga acctctttcc      120
gattccgcac ccggtaccga tgctttccca tcagatgatg ttggagctcc gtccgacgcg      180
agggatcgga ttgattcagc tgtcgacgac gctcagggaa cagcgaattt ggcaggagat      240
aacggcggag ataccgaaat tagggaaact ggtggaggag gaggcggcgg tgaagcaaga      300
ggagacgccg atacaaggta tacgtatcgt ccgtcggttc cagctcatcg agggctagg       360 gaaagtccac tcagctccga cgcaatcttc aaacaggtaa atctcagatt ctacgctgga      420
```

```
caatctccga atttggtgct tgatactgtc taatgttaga ggagaatttc aaactgagtt    480
tcatgttaac ttttagagag gacaatttct tcatttcatt tgactcgagt ttgtgttgtc    540
ttccatggca gagccatgcc ggattattca acctgtgtgt agtagttctt attgctgtaa    600
acagtagact catcatcgag aacttgatga aggttagtta ctttttttct cctatggctt    660
gaaaattgaa ttaggtttgt tcttgagctg agaactttat caagacctta cctttgttgt    720
tgccttcatt cctgtagtac ggttggttga tcagaacaga tttctggttt agttcaacat    780
cgctgcgaga ttggccgctt tcatgtgtt ggtaatatat aattttttt tctttcgtaa     840 tgttacattc ttattcatat aatgatgtgt ttagagattc agatatttct ataaattctt    900
ctgttgcagt atctctcttt cgatctttcc tctggctgcc tttaccgtcg agaaactggt    960
acttcagaaa tgcatatctg aacctgtgag taaactactg actatatagc tattactgga   1020
ttgtttactg aagacaagtt tgttgtatcc tggagaactt ataagtttct ttctgataat   1080
attaaaggtt gtcatcattc ttcatattat aatcacaatg acagaggtct tgtatccagt   1140
ttacgtcacc ctaaggtgtg aattaagcta aggtgtttct gatctcagct tgtgatactc   1200
tcttttttaa ttctagttga ctaactcgat gatcttgaaa atggacaggt gtgattccgc   1260
cttcttgtca ggtgtcacat tgatgctcct cacttacatt gtgtggctaa agttggtttc   1320
ttatgctcat actagctacg acataagaac cctagccaat tcagctgata aggtaaaaga   1380
atcaaaagaa atatatacta gtcactagcc ttgtgttact attttaacca gatactgtta   1440
tgaactaaag gccaatcctg aagtctccta ctatgttagc ttgaagagct tggcatattt   1500
catggttgct cccacattgt gttatcaggt aatgagatgc gtctttttt aatagcatca    1560 aacattctta aacttacaaa agcttcttgt ctaaaccttg cgtctttgct ttttcccagc   1620
tgagctatcc acgttctcct tgtatccgga agggttgggt ggctcgtcaa tttgcaaaac   1680
tggtcatatt cactggattc atgggattta taatagagca agtgcgttct caacatcttg   1740 cttttatt ttccttgtga aaatcatcat ctctgcatcg tcaatcgctt gacttctgtt      1800 ttttttgt tacttttttt ggcagtatat aaatcctatt gttaggaact caaagcatcc     1860
tttgaaaggg gatcttctat acgctattga aagagtcttg aagctttcag ttccaaattt   1920
atacgtgtgg ctctgcatgt tctactgctt cttccacctt tggtatgtcg tgatcccttc   1980
tctttcgatg tagtttccag agacgaacaa cagaaataag ctgtctcgtc aagaaattga   2040
taatttatag ccagggatgt aatttcagtt actgaacaca atctctttg cgttgttctt    2100 gtccccaggt taaacatatt ggcagagctc ctctgcttcg gggatcgtga attctacaaa   2160
gattggtgga atgcaaaaag tgtgggagac gtgagttgtt attacatacg tcttactcaa   2220
aaagcatatg attttatat gctatcgttg ttttgaggtc acttaactaa ccaaaattca    2280
tgtttccatc acttgtcttc ctttatcagt attggagaat gtggaatatg gtaaggttct   2340
tttcctaaaa catcgccttc ttttctatac aaaacataag aagagaggta atacagatct   2400
tgttttctct aacagcctgt tcataaatgg atggttcgac atatatactt tccgtgtctg   2460
cgcagcaaga taccaaaagt gagtaatatg tatgatagtg atttgcgatg gccgagatta   2520
tattccgttt tttttctaa aactacaatc atccactcat tttcttgttc tcaggtacct    2580
gccattatca ttgctttctt agtctctgca gtctttcatg aggtatatat atcctctgca   2640
ttgcactgtc tctaatattc aaagcattgt tgttacgcac attctcatgt ttacaaattt   2700
ccttgcagtt atgcatcgct gttccttgcc gtctcttcaa cctatgggct tcatggggaa   2760
ttatgtttca ggtataaaaa aattgacaaa acaatctgga agttttgtca tttctaatct   2820
```

```
cattttctta ccaccaccaa atgtgttttg agtaggtgcc tttggtcttt atcacaaact    2880
atctacaaga aaggtttggc tccatggtat gctctctaaa ggccgaataa cacttttctg    2940
atcatagcca cttaaatatt taattttttt gatggaaact aaaaagattg actgttttgg    3000
aatgtgatca tttaggtggg caacatggtt ttctggttca tcttctgcat tttcggtcaa    3060
cccatgtgtg tgcttcttta ttaccacgat ctgatgaacc gcaaaggatc catggcc       3117
```

<210> SEQ ID NO 14
<211> LENGTH: 1698
<212> TYPE: DNA
<213> ORGANISM: Artificial Sequence
<220> FEATURE:
<223> OTHER INFORMATION: modified nucleic acid that can encode a
     modified TAG1 polypeptide

<400> SEQUENCE: 14

```
atggcgattt tggattctgg aggcgtcact atgccgacgg agaacggtgg cggagagttt      60
gcggatctcg atactcttcg tcgacggaaa tcacgatcgg attccaacga acctctttcc     120
gattccgcac ccgtaccgga tgctttccca tcagatgatg ttggagctcc gtccgacgcg     180
agggatcgga ttgattcagc tgtcgacgac gctcagggaa cagcgaattt ggcaggagat     240
aacggcggag ataccgaaat tagggaaact ggtggaggag gaggcggcgg tgaagcaaga     300
ggagacgccg ataccaggta tacgtatcgt ccgtcggttc cagctcatcg gagggctagg     360
gaaagtccac tcagctccga cgcaatcttc aaacagagcc atgccggatt attcaacctg     420
tgtgtagtag ttcttattgc tgtaaacagt agactcatca tcgagaactt gatgaagtac     480
ggttggttga tcagaacaga tttctggttt agttcaacat cgctgcgaga ttggccgctt     540
ttcattatct ctctttcgat cttccctctg gctgccttta ccgtcgagaa actggtactt     600
cagaaatgca tatctgaacc tgtgaacaag tttgttgtat cctggagaac ttataagttt     660
ctttctgata atattaaagg ttgtcatcat tcttcatatt ataatcacaa tgacagaggt     720
cttgtatcca gtttacgtca ccctaagttg actaactcga tgatcttgaa aatggacagg     780
tgtgattccg ccttcttgtc aggtgtcaca ttgatgctcc tcacttacat tgtgtggcta     840
aagttggttt cttatgctca tactagctac gacataagaa ccctagccaa ttcagctgat     900
aaggccaatc ctgaagtctc ctactatgtt agcttgaaga gcttggcata tttcatggtt     960
gctcccacat tgtgttatca gctgagctat ccacgttctc cttgtatccg gaagggttgg    1020
gtggctcgtc aatttgcaaa actggtcata ttcactggat tcatgggatt tataatagag    1080
caatatataa atcctattgt taggaactca aagcatcctt tgaaagggga tcttctatac    1140
gctattgaaa gagtcttgaa gctttcagtt ccaaatttat acgtgtggct ctgcatgttc    1200
tactgcttct tccacctttg gttaaacata ttggcagagc tcctctgctt cggggatcgt    1260
gaattctaca agattggtga atgcaaaa agtgtgggag actattggag aatgtggaat     1320
atgcctgttc ataaatggat ggttcgacat atatactttc cgtgtctgcg cagcaagata    1380
ccaaaagtga gtaatatgta tgatagtgat ttgcgatggc cgagattata ttccgtacct    1440
gccattatca ttgctttctt agtctctgca gtctttcatg agttatgcat cgctgttcct    1500
tgccgtctct tcaacctatg ggctttcatg gggattatgt ttcaggtgcc tttggtcttt    1560
atcacaaact atctacaaga aaggtttggc tccatggtgg caacatggtt tttctggttc    1620
atcttctgca ttttcggtca acccatgtgt gtgcttcttt attaccacga tctgatgaac    1680
cgcaaaggat ccatggcc                                                    1698
```

<210> SEQ ID NO 15
<211> LENGTH: 3117
<212> TYPE: DNA
<213> ORGANISM: Artificial Sequence
<220> FEATURE:
<223> OTHER INFORMATION: modified nucleic acid that can encode a
      modified TAG1 polypeptide

<400> SEQUENCE: 15

| | | | | | |
|---|---|---|---|---|---|
| atggcgattt | tggattctgg | aggcgtcact | atgccgacgg | agaacggtgg | cggagagttt | 60 |
| gcggatctcg | atactcttcg | tcgacggaaa | tcacgatcgg | attccaacga | acctcttttcc | 120 |
| gattccgcac | ccggtaccga | tgctttccca | tcagatgatg | ttggagctcc | gtccgacgcg | 180 |
| agggatcgga | ttgattcagc | tgtcgacgac | gctcagggaa | cagcgaattt | ggcaggagat | 240 |
| aacggcggag | ataccgaaat | tagggaaact | ggtggaggag | gaggcggcgg | tgaagcaaga | 300 |
| ggagacgccg | atacaaggta | tacgtatcgt | ccgtcggttc | cagctcatcg | gagggctagg | 360 |
| gaaagtccac | tcagctccga | cgcaatcttc | aaacaggtaa | atctcagatt | ctacgctgga | 420 |
| caatctccga | atttggtgct | tgatactgtc | taatgttaga | ggagaatttc | aaactgagtt | 480 |
| tcatgttaac | ttttagagag | acaatttcct | tcatttcatt | tgactcgagt | ttgtgttgtc | 540 |
| ttccatggca | gagccatgcc | ggattattca | acctgtgtgt | agtagttctt | attgctgtaa | 600 |
| acagtagact | catcatcgag | aacttgatga | aggttagtta | cttttttttct | cctatggctt | 660 |
| gaaaattgaa | ttaggtttgt | tcttgagctg | agaactttat | caagacctta | cctttgttgt | 720 |
| tgccttcatt | cctgtagtac | ggttggttga | tcagaacaga | tttctggttt | agttcaacat | 780 |
| cgctgcgaga | ttggccgctt | ttcatgtgtt | ggtaatatat | aatttttttt | tctttcgtaa | 840 |
| tgttacattc | ttattcatat | aatgatgtgt | ttagagattc | agatatttct | ataaattctt | 900 |
| ctgttgcagt | atctctcttt | cgatctttcc | tctggctgcc | tttaccgtcg | agaaactggt | 960 |
| acttcagaaa | tgcatatctg | aacctgtgag | taaaactactg | actatatagc | tattactgga | 1020 |
| ttgtttactg | aagacaagtt | tgttgtatcc | tggagaactt | ataagtttct | ttctgataat | 1080 |
| attaaaggtt | gtcatcattc | ttcatattat | aatcacaatg | acagaggtct | tgtatccagt | 1140 |
| ttacgtcacc | ctaaggtgtg | aattaagcta | aggtgtttct | gatctcagct | tgtgatactc | 1200 |
| tctttttttaa | ttctagttga | ctaactcgat | gatcttgaaa | atggacaggt | gtgattccgc | 1260 |
| cttcttgtca | ggtgtcacat | tgatgctcct | cacttgcatt | gtgtggctaa | agttggtttc | 1320 |
| ttatgctcat | actagctacg | acataagaac | cctagccaat | tcagctgata | aggtaaaaga | 1380 |
| atcaaaagaa | atatatacta | gtcactagcc | ttgtgttact | attttaacca | gatactgtta | 1440 |
| tgaactaaag | gccaatcctg | aagtctccta | ctatgttagc | ttgaagagct | tggcatattt | 1500 |
| catggttgct | cccacattgt | gttatcaggt | aatgagatgc | gtctttttt | aatagcatca | 1560 |
| aacattctta | aacttacaaa | agcttcttgt | ctaaaccttg | cgtctttgct | ttttcccagc | 1620 |
| tgagctatcc | acgttctcct | tgtatccgga | agggttgggg | ggctcgtcaa | tttgcaaaac | 1680 |
| tggtcatatt | cactggattc | atgggattta | taatagagca | agtgcgttct | caacatcttg | 1740 |
| cttttttattt | ttccttgtga | aaatcatcat | ctctgcatcg | tcaatcgctt | gacttctgtt | 1800 |
| ttttttttgt | tactttttttt | ggcagtatat | aaatcctatt | gttaggaact | caaagcatcc | 1860 |
| tttgaaaggg | gatcttctat | acgctattga | aagagtcttg | aagctttcag | ttccaaattt | 1920 |
| atacgtgtgg | ctctgcatgt | tctactgctt | cttccaccct | tggtatgtcg | tgatcccttc | 1980 |
| tctttcgatg | tagtttccag | agacgaacaa | cagaaataag | ctgtctcgtc | aagaaattga | 2040 |

```
taatttatag ccagggatgt aatttcagtt actgaacaca aatctctttg cgttgttctt      2100
gtccccaggt taaacatatt ggcagagctc ctctgcttcg gggatcgtga attctacaaa      2160
gattgatgga atgcaaaaag tgtgggagac gtgagttgtt attacatacg tcttactcaa      2220
aaagcatatg attttatat gctatcgttg ttttgaggtc acttaactaa ccaaaattca       2280
tgtttccatc acttgtcttc ctttatcagt attggagaat gtggaatatg gtaaggttct      2340
tttcctaaaa catcgccttc ttttctatac aaaacataag aagagaggta atacagatct      2400
tgttttctct aacagcctgt tcataaatgg atggttcgac atatatactt ccgtgtctg       2460 cgcagcaaga taccaaaagt gagtaatatg tatgatagtg atttgcgatg ccgagatta       2520 tattccgttt tttttctaa aactacaatc atccactcat tttcttgttc tcaggtacct       2580
gccattatca ttgcttctt agtctctgca gtctttcatg aggtatatat atcctctgca       2640
ttgcactgtc tctaatattc aaagcattgt tgttacgcac attctcatgt ttacaaattt      2700
ccttgcagtt atgcatcgct gttccttgcc gtctcttcaa cctatgggct ttcatgggga     2760
ttatgtttca ggtataaaaa aattgacaaa acaatctgga agttttgtca tttctaatct      2820
cattttctta ccaccaccaa atgtgttttg agtaggtgcc tttggtcttt atcacaaact      2880
atctacaaga aaggtttggc tccatggtat gctctctaaa ggccgaataa cacttttctg      2940
atcatagcca cttaaatatt taatttttt gatggaaact aaaaagattg actgttttgg       3000
aatgtgatca tttaggtggg caacatggtt ttctggttca tcttctgcat tttcggtcaa      3060
cccatgtgtg tgcttcttta ttaccacgat ctgatgaacc gcaaaggatc catggcc        3117
```

<210> SEQ ID NO 16  
<211> LENGTH: 1698  
<212> TYPE: DNA  
<213> ORGANISM: Artificial Sequence  
<220> FEATURE:  
<223> OTHER INFORMATION: modified nucleic acid that can encode a modified TAG1 polypeptide
<400> SEQUENCE: 16

```
atggcgattt tggattctgg aggcgtcact atgccgacgg agaacggtgg cggagagttt        60
gcggatctcg atactcttcg tcgacggaaa tcacgatcgg attccaacga acctctttcc       120
gattccgcac ccgtaccga tgctttccca tcagatgatg ttggagctcc gtccgacgcg        180
agggatcgga ttgattcagc tgtcgacgac gctcagggaa cagcgaattt ggcaggagat       240
aacggcggag ataccgaaat tagggaaact ggtggaggag gaggcggcgg tgaagcaaga       300
ggagacgccg ataccaggta tacgtatcgt ccgtcggttc cagctcatcg gagggctagg       360
gaaagtccac tcagctccga cgcaatcttc aaacagagcc atgccggatt attcaacctg       420
tgtgtagtag ttcttattgc tgtaaacagt agactcatca tcgagaactt gatgaagtac       480
ggttggttga tcagaacaga tttctggttt agttcaacat cgctgcgaga ttggccgctt       540
ttcattatct ctctttcgat cttttcctctg gctgcctta ccgtcgagaa actggtactt       600
cagaaatgca tatctgaacc tgtgaacaag tttgttgtat cctggagaac ttataagttt       660
ctttctgata atattaaagg ttgtcatcat tcttcatatt ataatcacaa tgacagaggt       720
cttgtatcca gtttacgtca ccctaagttg actaactcga tgatcttgaa aatggacagg       780
tgtgattccg ccttcttgtc aggtgtcaca ttgatgctcc tcacttgcat tgtgtggcta       840
aagttggttt cttatgctca tactagctac gacataagaa ccctagccaa tcagctgat      900 aaggccaatc ctgaagtctc ctactatgtt agcttgaaga gcttggcata tttcatggtt      960
```

```
gctcccacat tgtgttatca gctgagctat ccacgttctc cttgtatccg aagggttgg      1020 gtggctcgtc aatttgcaaa actggtcata ttcactggat tcatgggatt tataatagag     1080
caatatataa atcctattgt taggaactca aagcatcctt tgaaagggga tcttctatac     1140
gctattgaaa gagtcttgaa gctttcagtt ccaaatttat acgtgtggct ctgcatgttc     1200
tactgcttct tccacctttg gttaaacata ttggcagagc tcctctgctt cggggatcgt    1260
gaattctaca aagattgatg gaatgcaaaa agtgtgggag actattggag aatgtggaat     1320
atgcctgttc ataaatggat ggttcgacat atatactttc cgtgtctgcg cagcaagata     1380
ccaaaagtga gtaatatgta tgatagtgat ttgcgatggc cgagattata ttccgtacct     1440
gccattatca ttgctttctt agtctctgca gtctttcatg agttatgcat cgctgttcct     1500
tgccgtctct tcaacctatg gctttcatg gggattatgt ttcaggtgcc tttggtctttt    1560 atcacaaact atctacaaga aaggtttggc tccatggtgg gcaacatggt tttctggttc    1620
atcttctgca ttttcggtca acccatgtgt gtgcttcttt attaccacga tctgatgaac    1680
cgcaaaggat ccatggcc                                                  1698

<210> SEQ ID NO 17
<211> LENGTH: 2360
<212> TYPE: DNA
<213> ORGANISM: Artificial Sequence
<220> FEATURE:
<223> OTHER INFORMATION: modified nucleic acid that can encode a
      modified FAD2 polypeptide

<400> SEQUENCE: 17
ttgtctaaat ttgataaaat atatgatgac gacaattccg gtggatcaca gtttgcttca      60
tttggctttt tttgtgtgtt tgtcaagttg ctattcaata agaatttgtg attttgattg     120
gtctcctcaa aattctgtga aattttagta acaaggaaga aattaacaaa tcacaacaag    180
aaagagatgt gagctgtcgt atcaaatctt attcgttttc tcaacgcaat cgttttagtt   240 tttttaact taacgccact ctctgctcc atacactcct ttttgtccac gtacttttca     300
tttgtggtaa tccatttctt cactttggat ctttcatctg aacaacaatt tcttgactca    360
atcaattacc acccgttctt gtgcttttgt atagattcat aatcttgtgt gtttcagctt    420
ctcattgctt tggttcttgt ttttttttct gcagaaacat gggtgcaggt ggaagaatga    480
cggttcctac ttcttccaag aagtctgaaa ccaatgcctt aaagcgtgtg ccgtgcgaga    540
aaccgccgtt cacgctcgga gaactgaaga aagcaatccc acagcattgt ttcaatcgct    600
caatccctcg ctctttctcc taccttatct gggacatcat catagcctct tgcttctact    660
acgttgccac cacttacttc tctctcctcc ctcagcctct ctcttacttg gcttggcctc    720
tctattgggt ctgtcaaggc tgtgtcttaa ccggagtctg ggtcatagct cacgaatgcg    780
gccaccacgc cttcagcgac taccaatggc ttgacgacac agtcggtctg atcttccatt    840
ctttcctcct cgtcccttac ttctcctgga atacagcca ccgccgtcac cattccaaca    900
ccggatcact tgaaaaggac gaagtgtttg tccctaaaca gaaatccgcc atcaaatggt   960
acggcaagta cctcaacaac cctctgggac gcaccgtgat gttaaccgtc cagttcaccc    1020
ttggctggcc cttgtactta gccttcaacg tctcggggag accctacgac gggttcgctt   1080
gccacttcca cccaaacgct cccatctaca acgaccgtga acgcctccag atatacatct   1140
cggatgctgg tatcctcgcc gtctgttacg gtctctaccg ttacgctgct gcacaaggag    1200
tggcctcgat gatctgcgtc tacggagttc cgcttctgat agtcaacggg ttcctcgtct    1260
```

```
tgatcacata cttgcagcac acccatccct cgttgcctca ctacgattca tccgagtggg    1320
attggttcag gggagctttg gctaccgtag acagagacta tggaatcctg aacaaggtct    1380
tccacaacat cacggacacg cacgtggctc accacctgtt ctcgacgatg ccgcattacc    1440
atgcgatgga ggccacgaag gcgataaagc cgatactcgg ggactattac cagtttgatg    1500
gaacaccggt cttcaaggcg atgtggaggg aggcgaagga gtgtgtctat gtagaaccgg    1560
acaggaaagg tgagaagaaa ggtgtgttct ggtacaacaa caagttgtga ggatgatcag    1620 gtgaagaag aaggaagaaa atcgtcggc ctttctcttg tctggttatc tttgttttaa    1680
gaagatatat gtttgtttca ataatcttat tgtccatttt gttgtgttct gacattgtgg    1740
cttaaattat tatgtgatgt tagtgtccaa ttgttctgcg tctgtattgt tcttctcatc    1800
gctgttttgt tgggatcgta gaaatgtgac tttcggacaa ttaaactctt gtactcaagc    1860
tatcactctg ttggcagcat caaaagtgtt ttcatagttt cggtcttttg gtctctgttt    1920
gtttgatact gttggtgaga atggctcttc aagtgttgga atctacctaa ggtgaacaca    1980
ttgtaggatt tttctttta ttaattgcca ttgtatacca cactgcagtg aaccgcaact    2040
atgttgacca tgtcgatgaa tgtaagtgaa ccatgaaact aatctttctg tacaatttac    2100
ttacttctga gtcattgtga tgtttggttg gcaggtcacc tttatttctc acactccctc    2160
cactcatgtg atgtggttgg gattttcttt tcataagtag ctttttgtaa agaactcagt    2220
ctttctcttt caaatcatgg aaaccttttc aacaaaagcc aaatccatgt tacataagca    2280
aaatatctgc tttcttcatc tttcctttct ttcatatttg agagggaaca aaagaagagg    2340
aagaaaatga agcaaagtaa                                                 2360

<210> SEQ ID NO 18
<211> LENGTH: 1215
<212> TYPE: DNA
<213> ORGANISM: Artificial Sequence
<220> FEATURE:
<223> OTHER INFORMATION: modified nucleic acid that can encode a
      modified FAD2 polypeptide

<400> SEQUENCE: 18
atgtctaaat ttgataaaat atatgatgac gacaattccg gtggatcaca aaacatgggt     60
gcaggtggaa gaatgacggt tcctacttct tccaagaagt ctgaaaccaa tgccttaaag   120
cgtgtgccgt gcgagaaacc gccgttcacg ctcggagaac tgaagaaagc aatcccacag   180
cattgtttca atcgctcaat ccctcgctct ttctcctacc ttatctggga catcatcata   240
gcctcttgct tctactacgt tgccaccact tacttctctc tcctccctca gcctctctct   300
tacttggctt ggcctctcta ttgggtctgt caaggctgtg tcttaaccgg agtctgggtc   360
atagctcacg aatgcggcca ccacgccttc agcgactacc aatggcttga cgacacagtc   420
ggtctgatct tccattcttt cctcctcgtc ccttacttct cctggaaata cagccaccgc   480
cgtcaccatt ccaacaccgg atcacttgaa aaggacgaag tgtttgtccc taaacagaaa   540
tccgccatca atggtacgg caagtacctc aacaaccctc tgggacgcac cgtgatgtta   600
accgtccagt tcacccttgg ctggcccttg tacttagcct tcaacgtctc ggggagaccc   660
tacgacgggt tcgcttgcca cttccaccca aacgctccca tctacaacga ccgtgaacgc   720
ctccagatat acatctcgga tgctggtatc ctgccgtct gttacggtct ctaccgttac   780
gctgctgcac aaggagtggc ctcgatgatc tgcgtctacg agttccgct tctgatagtc   840 aacgggttcc tcgtcttgat cacatacttg cagcacaccc atcctcgtt gcctcactac   900
```

| | | |
|---|---|---|
| gattcatccg agtgggattg gttcagggga gctttggcta ccgtagacag agactatgga | 960 | |
| atcctgaaca aggtcttcca caacatcacg gacacgcacg tggctcacca cctgttctcg | 1020 | |
| acgatgccgc attaccatgc gatggaggcc acgaaggcga taaagccgat actcggggac | 1080 | |
| tattaccagt ttgatggaac accggtcttc aaggcgatgt ggagggaggc gaaggagtgt | 1140 | |
| gtctatgtag aaccggacag gaaaggtgag aagaaagagg gaacaaaaga gaggaagaa | 1200 | |
| aatgaagcaa agtaa | 1215 | |

<210> SEQ ID NO 19
<211> LENGTH: 2360
<212> TYPE: DNA
<213> ORGANISM: Artificial Sequence
<220> FEATURE:
<223> OTHER INFORMATION: modified nucleic acid that can encode a
      modified FAD2 polypeptide

<400> SEQUENCE: 19

| | | |
|---|---|---|
| atgtctaaat ttgataaaat atatgatgac gacaattccg gtggatcaca gtttgcttca | 60 | |
| tttggctttt tttgtgtgtt tgtcaagttg ctattcaata agaatttgtg attttgattg | 120 | |
| gtctcctcaa aattctgtga aatttttagta acaaggaaga aattaacaaa tcacaacaag | 180 | |
| aaagagatgt gagctgtcgt atcaaatctt attcgttttc tcaacgcaat cgttttagtt | 240 | |
| ttttttaact taacgccact tctctgctcc atacactcct ttttgtccac gtactttttca | 300 | |
| tttgtggtaa tccatttctt cactttggat cttcatctg aacaacaatt tcttgactca | 360 | |
| atcaattacc cccgttctt gtgcttttgt atagattcat aatcttgtgt gtttcagctt | 420 | |
| ctcattgctt tggttcttgt tttttttct gcagaaacat gggtgcaggt ggaagaatga | 480 | |
| cggttcctac ttcttccaag aagtctgaaa ccgatgcctt aaagcgtgtg ccgtgcgaga | 540 | |
| aaccgccgtt cacgctcgga gaactgaaga agcaatccc acagcattgt tcaatcgct | 600 | |
| caatccctcg ctctttctcc taccttatct gggacatcat catagcctct tgcttctact | 660 | |
| acgttgccac cacttacttc tctctcctcc ctcagcctct ctcttacttg gcttggcctc | 720 | |
| tctattgggt ctgtcaaggc tgtgtcttaa ccggagtctg ggtcatagct cacgaatgcg | 780 | |
| gccaccacgc cttcagcgac taccaatggc ttgacgacac agtcgatctg atcttccatt | 840 | |
| ctttcctcct cgtcccttac ttctcctgga atacagccca ccgccgtcac cattccaaca | 900 | |
| ccggatcact tgaaaaggac gaagtgtttg tccctaaaca gaaatccgcc atcaaatggt | 960 | |
| acggcaagta cctcaacaac cctctgggac gcaccgtgat gttaaccgtc cagttcaccc | 1020 | |
| ttggctggcc cttgtactta gccttcaacg tctcggggag accctacgac gggttcgctt | 1080 | |
| gccacttcca cccaaacgct cccatcctaca acgaccgtga acgcctccag atatacatct | 1140 | |
| cggatgctgg tatcctcgcc gtctgttacg gtctctaccg ttacgctgct gcacaaggag | 1200 | |
| tggcctcgat gatctgcgtc tacgagttcg cgcttctgat agtcaacggg ttcctcgtct | 1260 | |
| tgatcacata cttgcagcac acccatcct cgttgcctca ctacgattca tccgagtggg | 1320 | |
| attggttcag gggagctttg gctaccgtag acagagacta tggaatcctg aacaaggtct | 1380 | |
| tccacaacat cacggacacg cacgtggctc accacctgtt ctcgacgatg ccgcattacc | 1440 | |
| atgcgatgga ggccacgaag gcgataaagc cgatactcgg ggactattac agtttgatg | 1500 | |
| gaacaccggt cttcaaggcg atgtggaggg aggcgaagga gtgtgtctat gtagaaccgg | 1560 | |
| acaggaaagg tgagaagaaa ggtgtgttct ggtacaacaa caagttgtga ggatgatcag | 1620 | |
| gtgaaagaag aaggaagaaa aatcgtcggc ctttctcttg tctggttatc tttgtttaa | 1680 | |

```
gaagatatat gtttgtttca ataatcttat tgtccatttt gttgtgttct gacattgtgg      1740
cttaaattat tatgtgatgt tagtgtccaa ttgttctgcg tctgtattgt tcttctcatc      1800
gctgttttgt tgggatcgta gaaatgtgac tttcggacaa ttaaactctt gtactcaagc      1860
tatcactctg ttggcagcat caaaagtgtt ttcatagttt cggtcttttg gtctctgttt      1920
gtttgatact gttggtgaga atggctcttc aagtgttgga atctacctaa ggtgaacaca      1980
ttgtaggatt tttcttttat ttaattgcca ttgtatacca cactgcagtg aaccgcaact      2040
atgttgacca tgtcgatgaa tgtaagtgaa ccatgaaact aatctttctg tacaatttac      2100
ttacttctga gtcattgtga tgtttggttg gcaggtcacc tttatttctc acactccctc      2160
cactcatgtg atgtggttgg gattttcttt tcataagtag cttttgtaa agaactcagt       2220 cttttctcttt caaatcatgg aaaccttttc aacaaaagcc aaatccatgt tacataagca     2280
aaatatctgc tttcttcatc tttcctttct ttcatatttg agagggaaca aaagaagagg      2340
aagaaaatga agcaaagtaa                                                  2360

<210> SEQ ID NO 20
<211> LENGTH: 1215
<212> TYPE: DNA
<213> ORGANISM: Artificial Sequence
<220> FEATURE:
<223> OTHER INFORMATION: modified nucleic acid that can encode a
      modified FAD2 polypeptide

<400> SEQUENCE: 20
atgtctaaat ttgataaaat atatgatgac gacaattccg gtggatcaca aaacatgggt        60
gcaggtggaa gaatgacggt tcctacttct tccaagaagt ctgaaaccga tgccttaaag       120
cgtgtgccgt gcgagaaacc gccgttcacg ctcggagaac tgaagaaagc aatcccacag       180
cattgtttca atcgctcaat ccctcgctct ttctcctacc ttatctggga catcatcata       240
gcctcttgct tctactacgt tgccaccact tacttctctc tcctcccctca gcctctctct      300 tacttggctt ggcctctcta ttgggtctgt caaggctgtg tcttaaccgg agtctgggtc       360
atagctcacg aatgcggcca ccacgccttc agcgactacc aatggcttga cgacacagtc       420
gatctgatct tccattcttt cctcctcgtc ccttacttct cctgaaaata cagccaccgc       480
cgtcaccatt ccaacaccgg atcacttgaa aaggacgaag tgtttgtccc taaacagaaa       540
tccgccatca aatggtacgg caagtacctc aacaaccctc tgggacgcac cgtgatgtta       600
accgtccagt tcacccttgg ctggcccttg tacttagcct tcaacgtctc ggggagaccc       660
tacgacgggt tcgcttgcca cttccaccca aacgctccca tctacaacga ccgtgaacgc       720
ctccagatat acatctcgga tgctggtatc ctcgccgtct gttacggtct ctaccgttac       780
gctgctgcac aaggagtggc ctcgatgatc tgcgtctacg gagttccgct tctgatagtc       840
aacgggttcc tcgtcttgat cacatacttg cagcacaccc atccctcgtt gcctcactac       900
gattcatccg agtgggattg gttcaggggA gctttggcta ccgtagacag agactatgga       960
atcctgaaca aggtcttcca caacatcacg gacacgcacg tggctcacca cctgttctcg      1020
acgatgccgc attaccatgc gatggaggcc acgaaggcga taaagccgat actcgggac      1080 tattaccagt ttgatggaac accggtcttc aaggcgatgt ggagggaggc gaaggagtgt      1140
gtctatgtag aaccggacag gaaaggtgag aagaaagagg gaacaaaaga gaggaagaa      1200 aatgaagcaa agtaa                                                      1215
```

<210> SEQ ID NO 21
<211> LENGTH: 2360
<212> TYPE: DNA
<213> ORGANISM: Artificial Sequence
<220> FEATURE:
<223> OTHER INFORMATION: modified nucleic acid that can encode a
     modified FAD2 polypeptide

<400> SEQUENCE: 21

| | | | | | |
|---|---|---|---|---|---|
| atgtctaaat | tgataaaat | atatgatgac | gacaattccg | gtggatcaca | gtttgcttca | 60 |
| tttggctttt | tttgtgtgtt | tgtcaagttg | ctattcaata | agaatttgtg | attttgattg | 120 |
| gtctcctcaa | aattctgtga | aattttagta | acaaggaaga | aattaacaaa | tcacaacaag | 180 |
| aaagagatgt | gagctgtcgt | atcaaatctt | attcgttttc | tcaacgcaat | cgttttagtt | 240 |
| tttttttaact | taacgccact | tctctgctcc | atacactcct | ttttgtccac | gtacttttca | 300 |
| tttgtggtaa | tccatttctt | cactttggat | ctttcatctg | aacaacaatt | tcttgactca | 360 |
| atcaattacc | acccgttctt | gtgcttttgt | atagattcat | aatcttgtgt | gtttcagctt | 420 |
| ctcattgctt | tggttcttgt | ttttttttct | gcagaaacat | gggtgcaggt | ggaagaatga | 480 |
| cggttcctac | ttcttccaag | aagtctgaaa | ccgatgcctt | aaagcgtgtg | ccgtgcgaga | 540 |
| aaccgccgtt | cacgctcgga | gaactgaaga | agcaatcccc | acagcattgt | tcaatcgct | 600 |
| caatccctcg | ctcttctcc | taccttatct | gggacatcat | catagcctct | tgcttctact | 660 |
| acgttgccac | cacttacttc | tctctcctcc | ctcagcctct | ctcttacttg | gcttggcctc | 720 |
| tctattgggt | ctgtcaaggc | tgtgtcttaa | ccggagtctg | ggtcatagct | cacgaatgcg | 780 |
| gccaccacgc | cttcagcgac | taccaatggc | ttgacgacac | agtcggtctg | atcttccatt | 840 |
| ctttcctcct | cgtcccttac | ttctcctgga | aatacagcca | ccgccgtcac | cattccaaca | 900 |
| ccggatcact | tgaaaaggac | gaagtgtttg | tccctaaaca | gaaatccgcc | atcaaatggt | 960 |
| acggcaagta | cctcaacaac | cctctgggac | gcaccgtgat | gttaaccgtc | cagttcaccc | 1020 |
| ttggctggcc | cttgtactta | gccttcaacg | tctcggggag | accctacgac | gggttcgctt | 1080 |
| gccacttcca | cccaaacgct | cccatctaca | acgaccgtga | acgcctccag | atatacatct | 1140 |
| cggatgctgg | tatcctcgcc | gtctgttacg | gtctctaccg | ttacgctgct | gcacaaggag | 1200 |
| tggcctcgat | gatctgcgtc | tacggagttc | cgcttctgat | agtcaacggg | ttcctcgtct | 1260 |
| tgatcacata | cttgcagcac | acccatcct | cgttgccta | ctacgattca | tccgagtggg | 1320 |
| attggttcag | gggagctttg | gctaccgtag | acagagacta | tggaatcctg | aacaaggtct | 1380 |
| tccacaacat | cacggacacg | cacgtggctc | accacctgtt | ctcgacgatg | ccgcattacc | 1440 |
| atgcgatgga | ggccacgaag | gcgataaagc | cgatactcgg | ggactattac | cagtttgatg | 1500 |
| gaaccaccggt | cttcaaggcg | atgtggaggg | aggcgaagga | gtgtgtctat | gtagaaccgg | 1560 |
| acaggaaagg | tgagaagaaa | ggtgtgttct | ggtacaacaa | caagttgtga | ggatgatcag | 1620 |
| gtgaaagaag | aaggaagaaa | aatcgtcggc | ctttctcttg | tctggttatc | tttgttttaa | 1680 |
| gaagatatat | gtttgtttca | ataatcttat | tgtccatttt | gttgtgttct | gacattgtgg | 1740 |
| cttaaattat | tatgtgatgt | tagtgtccaa | ttgttctgcg | tctgtattgt | tcttctcatc | 1800 |
| gctgttttgt | tgggatcgta | gaaatgtgac | tttcggacaa | ttaaactctt | gtactcaagc | 1860 |
| tatcactctg | ttggcagcat | caaaagtgtt | ttcatagttt | cggtcttttg | gtctctgttt | 1920 |
| gtttgatact | gttggtgaga | atggctcttc | aagtgtggga | atctacctaa | ggtgaacaca | 1980 |
| ttgtaggatt | tttcttttat | ttaattgcca | tttgtatacca | cactgcagtg | aaccgcaact | 2040 |
| atgttgacca | tgtcgatgaa | tgtaagtgaa | ccatgaaact | aatctttctg | tacaatttac | 2100 |

```
ttacttctga gtcattgtga tgtttggttg gcaggtcacc tttatttctc acactccctc    2160
cactcatgtg atgtggttgg gattttcttt tcataagtag ctttttgtaa agaactcagt    2220
ctttctcttt caaatcatgg aaaccttttc aacaaaagcc aaatccatgt tacataagca    2280
aaatatctgc tttcttcatc tttcctttct ttcatatttg agagggaaca aaagaagagg    2340
aagaaaatga agcaaagtaa                                                2360
```

<210> SEQ ID NO 22
<211> LENGTH: 1215
<212> TYPE: DNA
<213> ORGANISM: Artificial Sequence
<220> FEATURE:
<223> OTHER INFORMATION: modified nucleic acid that can encode a
      modified FAD2 polypeptide

<400> SEQUENCE: 22

```
atgtctaaat tgataaaat atatgatgac gacaattccg gtggatcaca aaacatgggt      60
gcaggtggaa gaatgacggt tcctacttct tccaagaagt ctgaaaccga tgccttaaag    120
cgtgtgccgt gcgagaaacc gccgttcacg ctcggagaac tgaagaaagc aatcccacag    180
cattgtttca atcgctcaat ccctcgctct ttctcctacc ttatctggga catcatcata    240
gcctcttgct tctactacgt tgccaccact tacttctctc cctcccctca gcctctctct    300
tacttggctt ggcctctcta ttgggtctgt caaggctgtg tcttaaccgg agtctgggtc    360
atagctcacg aatgcggcca ccacgccttc agcgactacc aatggcttga cgacacagtc    420
ggtctgatct tccattcttt cctcctcgtc ccttacttct cctggaaata cagccaccgc    480
cgtcaccatt ccaacaccgg atcacttgaa aaggacgaag tgtttgtccc taaacagaaa    540
tccgccatca aatggtacgg caagtacctc aacaaccctc tgggacgcac cgtgatgtta    600
accgtccagt tcacccttgg ctggcccttg tacttagcct tcaacgtctc ggggagaccc    660
tacgacgggt tcgcttgcca cttccaccca aacgctccca tctacaacga ccgtgaacgc    720
ctccagatat acatctcgga tgctggtatc ctcgccgtct gttacggtct ctaccgttac    780
gctgctgcac aaggagtggc ctcgatgatc tgcgtctacg agttccgct tctgatagtc    840 aacgggttcc tcgtcttgat cacatacttg cagcacaccc atccctcgtt gccttactac    900
gattcatccg agtgggattg gttcagggga gctttggcta ccgtagacag agactatgga    960
atcctgaaca aggtcttcca caacatcacg gacacgcacg tggctcacca cctgttctcg   1020
acgatgccgc attaccatgc gatggaggcc acgaaggcga taaagccgat actcggggac   1080
tattaccagt ttgatggaac accggtcttc aaggcgatgt ggagggaggc gaaggagtgt   1140
gtctatgtag aaccggacag gaaaggtgag aagaaagagg aacaaaaga agaggaagaa   1200 aatgaagcaa agtaa                                                    1215
```

<210> SEQ ID NO 23
<211> LENGTH: 383
<212> TYPE: PRT
<213> ORGANISM: Arabidopsis thaliana

<400> SEQUENCE: 23

Met Gly Ala Gly Gly Arg Met Pro Val Pro Thr Ser Ser Lys Lys Ser
1               5                   10                  15

Glu Thr Asp Thr Thr Lys Arg Val Pro Cys Glu Lys Pro Pro Phe Ser
            20                  25                  30

```
Val Gly Asp Leu Lys Lys Ala Ile Pro Pro His Cys Phe Lys Arg Ser
         35                  40                  45

Ile Pro Arg Ser Phe Ser Tyr Leu Ile Ser Asp Ile Ile Ala Ser
     50                  55                  60

Cys Phe Tyr Tyr Val Ala Thr Asn Tyr Phe Ser Leu Leu Pro Gln Pro
 65                  70                  75                  80

Leu Ser Tyr Leu Ala Trp Pro Leu Tyr Trp Ala Cys Gln Gly Cys Val
                 85                  90                  95

Leu Thr Gly Ile Trp Val Ile Ala His Glu Cys Gly His His Ala Phe
             100                 105                 110

Ser Asp Tyr Gln Trp Leu Asp Asp Thr Val Gly Leu Ile Phe His Ser
             115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Gln Lys Ser Ala Ile Lys Trp Tyr Gly Lys Tyr Leu Asn Asn Pro Leu
                 165                 170                 175

Gly Arg Ile Met Met Leu Thr Val Gln Phe Val Leu Gly Trp Pro Leu
             180                 185                 190

Tyr Leu Ala Phe Asn Val Ser Gly Arg Pro Tyr Asp Gly Phe Ala Cys
             195                 200                 205

His Phe Phe Pro Asn Ala Pro Ile Tyr Asn Asp Arg Glu Arg Leu Gln
             210                 215                 220

Ile Tyr Leu Ser Asp Ala Gly Ile Leu Ala Val Cys Phe Gly Leu Tyr
225                 230                 235                 240

Arg Tyr Ala Ala Ala Gln Gly Met Ala Ser Met Ile Cys Leu Tyr Gly
                 245                 250                 255

Val Pro Leu Leu Ile Val Asn Ala Phe Leu Val Leu Ile Thr Tyr Leu
             260                 265                 270

Gln His Thr His Pro Ser Leu Pro His Tyr Asp Ser Ser Glu Trp Asp
             275                 280                 285

Trp Leu Arg Gly Ala Leu Ala Thr Val Asp Arg Asp Tyr Gly Ile Leu
             290                 295                 300

Asn Lys Val Phe His Asn Ile Thr Asp Thr His Val Ala His His Leu
305                 310                 315                 320

Phe Ser Thr Met Pro His Tyr Asn Ala Met Glu Ala Thr Lys Ala Ile
                 325                 330                 335

Lys Pro Ile Leu Gly Asp Tyr Tyr Gln Phe Asp Gly Thr Pro Trp Tyr
             340                 345                 350

Val Ala Met Tyr Arg Glu Ala Lys Glu Cys Ile Tyr Val Glu Pro Asp
             355                 360                 365

Arg Glu Gly Asp Lys Lys Gly Val Tyr Trp Tyr Asn Asn Lys Leu
370                 375                 380

<210> SEQ ID NO 24
<211> LENGTH: 404
<212> TYPE: PRT
<213> ORGANISM: Thlaspi arvense

<400> SEQUENCE: 24

Met Ser Lys Phe Asp Lys Ile Tyr Asp Asp Asn Ser Gly Gly Ser
 1               5                  10                  15
```

Gln Asn Met Gly Ala Gly Arg Met Thr Val Pro Thr Ser Ser Lys
              20                  25                  30

Lys Ser Glu Thr Asp Ala Leu Lys Arg Val Pro Cys Glu Lys Pro Pro
         35                  40                  45

Phe Thr Leu Gly Glu Leu Lys Lys Ala Ile Pro Gln His Cys Phe Asn
 50                  55                  60

Arg Ser Ile Pro Arg Ser Phe Ser Tyr Leu Ile Trp Asp Ile Ile Ile
 65                  70                  75                  80

Ala Ser Cys Phe Tyr Tyr Val Ala Thr Thr Tyr Phe Ser Leu Leu Pro
                 85                  90                  95

Gln Pro Leu Ser Tyr Leu Ala Trp Pro Leu Tyr Trp Val Cys Gln Gly
             100                 105                 110

Cys Val Leu Thr Gly Val Trp Val Ile Ala His Glu Cys Gly His His
             115                 120                 125

Ala Phe Ser Asp Tyr Gln Trp Leu Asp Asp Thr Val Gly Leu Ile Phe
130                 135                 140

His Ser Phe Leu Leu Val Pro Tyr Phe Ser Trp Lys Tyr Ser His Arg
145                 150                 155                 160

Arg His His Ser Asn Thr Gly Ser Leu Glu Lys Asp Glu Val Phe Val
                165                 170                 175

Pro Lys Gln Lys Ser Ala Ile Lys Trp Tyr Gly Lys Tyr Leu Asn Asn
            180                 185                 190

Pro Leu Gly Arg Thr Val Met Leu Thr Val Gln Phe Thr Leu Gly Trp
            195                 200                 205

Pro Leu Tyr Leu Ala Phe Asn Val Ser Gly Arg Pro Tyr Asp Gly Phe
210                 215                 220

Ala Cys His Phe His Pro Asn Ala Pro Ile Tyr Asn Asp Arg Glu Arg
225                 230                 235                 240

Leu Gln Ile Tyr Ile Ser Asp Ala Gly Ile Leu Ala Val Cys Tyr Gly
                245                 250                 255

Leu Tyr Arg Tyr Ala Ala Ala Gln Gly Val Ala Ser Met Ile Cys Val
            260                 265                 270

Tyr Gly Val Pro Leu Leu Ile Val Asn Gly Phe Leu Val Leu Ile Thr
            275                 280                 285

Tyr Leu Gln His Thr His Pro Ser Leu Pro His Tyr Asp Ser Ser Glu
290                 295                 300

Trp Asp Trp Phe Arg Gly Ala Leu Ala Thr Val Asp Arg Asp Tyr Gly
305                 310                 315                 320

Ile Leu Asn Lys Val Phe His Asn Ile Thr Asp Thr His Val Ala His
                325                 330                 335

His Leu Phe Ser Thr Met Pro His Tyr His Ala Met Glu Ala Thr Lys
            340                 345                 350

Ala Ile Lys Pro Ile Leu Gly Asp Tyr Tyr Gln Phe Asp Gly Thr Pro
            355                 360                 365

Val Phe Lys Ala Met Trp Arg Glu Ala Lys Glu Cys Val Tyr Val Glu
370                 375                 380

Pro Asp Arg Lys Gly Glu Lys Lys Glu Gly Thr Lys Glu Glu Glu Glu
385                 390                 395                 400

Asn Glu Ala Lys

<210> SEQ ID NO 25
<211> LENGTH: 404
<212> TYPE: PRT

<213> ORGANISM: Artificial Sequence
<220> FEATURE:
<223> OTHER INFORMATION: modified FAD2 polypeptide

<400> SEQUENCE: 25

```
Met Ser Lys Phe Asp Lys Ile Tyr Asp Asp Asn Ser Gly Gly Ser
1               5                   10                  15

Gln Asn Met Gly Ala Gly Gly Arg Met Thr Val Pro Thr Ser Ser Lys
            20                  25                  30

Lys Ser Glu Thr Asn Ala Leu Lys Arg Val Pro Cys Glu Lys Pro Pro
            35                  40                  45

Phe Thr Leu Gly Glu Leu Lys Lys Ala Ile Pro Gln His Cys Phe Asn
50                  55                  60

Arg Ser Ile Pro Arg Ser Phe Ser Tyr Leu Ile Trp Asp Ile Ile Ile
65                  70                  75                  80

Ala Ser Cys Phe Tyr Tyr Val Ala Thr Thr Tyr Phe Ser Leu Leu Pro
                85                  90                  95

Gln Pro Leu Ser Tyr Leu Ala Trp Pro Leu Tyr Trp Val Cys Gln Gly
                100                 105                 110

Cys Val Leu Thr Gly Val Trp Val Ile Ala His Glu Cys Gly His His
            115                 120                 125

Ala Phe Ser Asp Tyr Gln Trp Leu Asp Asp Thr Val Gly Leu Ile Phe
130                 135                 140

His Ser Phe Leu Leu Val Pro Tyr Phe Ser Trp Lys Tyr Ser His Arg
145                 150                 155                 160

Arg His His Ser Asn Thr Gly Ser Leu Glu Lys Asp Glu Val Phe Val
                165                 170                 175

Pro Lys Gln Lys Ser Ala Ile Lys Trp Tyr Gly Lys Tyr Leu Asn Asn
            180                 185                 190

Pro Leu Gly Arg Thr Val Met Leu Thr Val Gln Phe Thr Leu Gly Trp
            195                 200                 205

Pro Leu Tyr Leu Ala Phe Asn Val Ser Gly Arg Pro Tyr Asp Gly Phe
210                 215                 220

Ala Cys His Phe His Pro Asn Ala Pro Ile Tyr Asn Asp Arg Glu Arg
225                 230                 235                 240

Leu Gln Ile Tyr Ile Ser Asp Ala Gly Ile Leu Ala Val Cys Tyr Gly
                245                 250                 255

Leu Tyr Arg Tyr Ala Ala Ala Gln Gly Val Ala Ser Met Ile Cys Val
            260                 265                 270

Tyr Gly Val Pro Leu Leu Ile Val Asn Gly Phe Leu Val Leu Ile Thr
            275                 280                 285

Tyr Leu Gln His Thr His Pro Ser Leu Pro His Tyr Asp Ser Ser Glu
290                 295                 300

Trp Asp Trp Phe Arg Gly Ala Leu Ala Thr Val Asp Arg Asp Tyr Gly
305                 310                 315                 320

Ile Leu Asn Lys Val Phe His Asn Ile Thr Asp Thr His Val Ala His
                325                 330                 335

His Leu Phe Ser Thr Met Pro His Tyr His Ala Met Glu Ala Thr Lys
            340                 345                 350

Ala Ile Lys Pro Ile Leu Gly Asp Tyr Tyr Gln Phe Asp Gly Thr Pro
            355                 360                 365

Val Phe Lys Ala Met Trp Arg Glu Ala Lys Glu Cys Val Tyr Val Glu
            370                 375                 380
```

```
Pro Asp Arg Lys Gly Glu Lys Lys Glu Gly Thr Lys Glu Glu Glu Glu
385                 390                 395                 400

Asn Glu Ala Lys

<210> SEQ ID NO 26
<211> LENGTH: 404
<212> TYPE: PRT
<213> ORGANISM: Artificial Sequence
<220> FEATURE:
<223> OTHER INFORMATION: modified FAD2 polypeptide

<400> SEQUENCE: 26

Met Ser Lys Phe Asp Lys Ile Tyr Asp Asp Asn Ser Gly Gly Ser
1               5                   10                  15

Gln Asn Met Gly Ala Gly Gly Arg Met Thr Val Pro Thr Ser Ser Lys
                20                  25                  30

Lys Ser Glu Thr Asp Ala Leu Lys Arg Val Pro Cys Glu Lys Pro Pro
                35                  40                  45

Phe Thr Leu Gly Glu Leu Lys Lys Ala Ile Pro Gln His Cys Phe Asn
                50                  55                  60

Arg Ser Ile Pro Arg Ser Phe Ser Tyr Leu Ile Trp Asp Ile Ile Ile
65              70                  75                  80

Ala Ser Cys Phe Tyr Tyr Val Ala Thr Thr Tyr Phe Ser Leu Leu Pro
                85                  90                  95

Gln Pro Leu Ser Tyr Leu Ala Trp Pro Leu Tyr Trp Val Cys Gln Gly
                100                 105                 110

Cys Val Leu Thr Gly Val Trp Val Ile Ala His Glu Cys Gly His His
                115                 120                 125

Ala Phe Ser Asp Tyr Gln Trp Leu Asp Asp Thr Val Asp Leu Ile Phe
130                 135                 140

His Ser Phe Leu Leu Val Pro Tyr Phe Ser Trp Lys Tyr Ser His Arg
145                 150                 155                 160

Arg His His Ser Asn Thr Gly Ser Leu Glu Lys Asp Glu Val Phe Val
                165                 170                 175

Pro Lys Gln Lys Ser Ala Ile Lys Trp Tyr Gly Lys Tyr Leu Asn Asn
                180                 185                 190

Pro Leu Gly Arg Thr Val Met Leu Thr Val Gln Phe Thr Leu Gly Trp
                195                 200                 205

Pro Leu Tyr Leu Ala Phe Asn Val Ser Gly Arg Pro Tyr Asp Gly Phe
210                 215                 220

Ala Cys His Phe His Pro Asn Ala Pro Ile Tyr Asn Asp Arg Glu Arg
225                 230                 235                 240

Leu Gln Ile Tyr Ile Ser Asp Ala Gly Ile Leu Ala Val Cys Tyr Gly
                245                 250                 255

Leu Tyr Arg Tyr Ala Ala Ala Gln Gly Val Ala Ser Met Ile Cys Val
                260                 265                 270

Tyr Gly Val Pro Leu Leu Ile Val Asn Gly Phe Leu Val Leu Ile Thr
                275                 280                 285

Tyr Leu Gln His Thr His Pro Ser Leu Pro His Tyr Asp Ser Ser Glu
                290                 295                 300

Trp Asp Trp Phe Arg Gly Ala Leu Ala Thr Val Asp Arg Asp Tyr Gly
305                 310                 315                 320

Ile Leu Asn Lys Val Phe His Asn Ile Thr Asp Thr His Val Ala His
                325                 330                 335
```

```
His Leu Phe Ser Thr Met Pro His Tyr His Ala Met Glu Ala Thr Lys
                340                 345                 350

Ala Ile Lys Pro Ile Leu Gly Asp Tyr Gln Phe Asp Gly Thr Pro
            355                 360                 365

Val Phe Lys Ala Met Trp Arg Glu Ala Lys Glu Cys Val Tyr Val Glu
    370                 375                 380

Pro Asp Arg Lys Gly Glu Lys Lys Glu Gly Thr Lys Glu Glu Glu Glu
385                 390                 395                 400

Asn Glu Ala Lys

<210> SEQ ID NO 27
<211> LENGTH: 404
<212> TYPE: PRT
<213> ORGANISM: Artificial Sequence
<220> FEATURE:
<223> OTHER INFORMATION: modified FAD2 polypeptide

<400> SEQUENCE: 27

Met Ser Lys Phe Asp Lys Ile Tyr Asp Asp Asn Ser Gly Gly Ser
1               5                   10                  15

Gln Asn Met Gly Ala Gly Gly Arg Met Thr Val Pro Thr Ser Ser Lys
            20                  25                  30

Lys Ser Glu Thr Asp Ala Leu Lys Arg Val Pro Cys Glu Lys Pro Pro
            35                  40                  45

Phe Thr Leu Gly Glu Leu Lys Lys Ala Ile Pro Gln His Cys Phe Asn
        50                  55                  60

Arg Ser Ile Pro Arg Ser Phe Ser Tyr Leu Ile Trp Asp Ile Ile Ile
65                  70                  75                  80

Ala Ser Cys Phe Tyr Tyr Val Ala Thr Thr Tyr Phe Ser Leu Leu Pro
                85                  90                  95

Gln Pro Leu Ser Tyr Leu Ala Trp Pro Leu Tyr Trp Val Cys Gln Gly
            100                 105                 110

Cys Val Leu Thr Gly Val Trp Val Ile Ala His Glu Cys Gly His His
            115                 120                 125

Ala Phe Ser Asp Tyr Gln Trp Leu Asp Asp Thr Val Gly Leu Ile Phe
        130                 135                 140

His Ser Phe Leu Leu Val Pro Tyr Phe Ser Trp Lys Tyr Ser His Arg
145                 150                 155                 160

Arg His His Ser Asn Thr Gly Ser Leu Glu Lys Asp Glu Val Phe Val
                165                 170                 175

Pro Lys Gln Lys Ser Ala Ile Lys Trp Tyr Gly Lys Tyr Leu Asn Asn
            180                 185                 190

Pro Leu Gly Arg Thr Val Met Leu Thr Val Gln Phe Thr Leu Gly Trp
        195                 200                 205

Pro Leu Tyr Leu Ala Phe Asn Val Ser Gly Arg Pro Tyr Asp Gly Phe
    210                 215                 220

Ala Cys His Phe His Pro Asn Ala Pro Ile Tyr Asn Asp Arg Glu Arg
225                 230                 235                 240

Leu Gln Ile Tyr Ile Ser Asp Ala Gly Ile Leu Ala Val Cys Tyr Gly
                245                 250                 255

Leu Tyr Arg Tyr Ala Ala Ala Gln Gly Val Ala Ser Met Ile Cys Val
            260                 265                 270

Tyr Gly Val Pro Leu Leu Ile Val Asn Gly Phe Leu Val Leu Ile Thr
        275                 280                 285
```

```
Tyr Leu Gln His Thr His Pro Ser Leu Pro Tyr Tyr Asp Ser Ser Glu
        290                 295                 300

Trp Asp Trp Phe Arg Gly Ala Leu Ala Thr Val Asp Arg Asp Tyr Gly
305                 310                 315                 320

Ile Leu Asn Lys Val Phe His Asn Ile Thr Asp Thr His Val Ala His
                325                 330                 335

His Leu Phe Ser Thr Met Pro His Tyr His Ala Met Glu Ala Thr Lys
            340                 345                 350

Ala Ile Lys Pro Ile Leu Gly Asp Tyr Tyr Gln Phe Asp Gly Thr Pro
        355                 360                 365

Val Phe Lys Ala Met Trp Arg Glu Ala Lys Glu Cys Val Tyr Val Glu
    370                 375                 380

Pro Asp Arg Lys Gly Glu Lys Lys Glu Gly Thr Lys Glu Glu Glu
385                 390                 395                 400

Asn Glu Ala Lys

<210> SEQ ID NO 28
<211> LENGTH: 388
<212> TYPE: PRT
<213> ORGANISM: Oryza sativa

<400> SEQUENCE: 28

Met Gly Ala Gly Gly Arg Met Thr Glu Lys Glu Arg Glu Glu Gln Gln
1               5                   10                  15

Lys Leu Leu Gly Arg Ala Gly Asn Gly Ala Ala Val Gln Arg Ser Pro
            20                  25                  30

Thr Asp Lys Pro Pro Phe Thr Leu Gly Gln Ile Lys Lys Ala Ile Pro
        35                  40                  45

Pro His Cys Phe Gln Arg Ser Val Ile Lys Ser Phe Ser Tyr Val Val
    50                  55                  60

His Asp Leu Val Ile Val Ala Ala Leu Leu Tyr Phe Ala Leu Val Met
65                  70                  75                  80

Ile Pro Val Leu Pro Ser Gly Met Glu Phe Ala Ala Trp Pro Leu Tyr
                85                  90                  95

Trp Ile Ala Gln Gly Cys Val Leu Thr Gly Val Trp Val Ile Ala His
            100                 105                 110

Glu Cys Gly His His Ala Phe Ser Asp Tyr Ser Val Leu Asp Asp Ile
        115                 120                 125

Val Gly Leu Val Leu His Ser Ser Leu Leu Val Pro Tyr Phe Ser Trp
    130                 135                 140

Lys Tyr Ser His Arg Arg His His Ser Asn Thr Gly Ser Leu Glu Arg
145                 150                 155                 160

Asp Glu Val Phe Val Pro Lys Gln Lys Ser Ala Met Ala Trp Tyr Thr
                165                 170                 175

Pro Tyr Val Tyr His Asn Pro Ile Gly Arg Leu Val His Ile Phe Val
            180                 185                 190

Gln Leu Thr Leu Gly Trp Pro Leu Tyr Leu Ala Phe Asn Val Ser Gly
        195                 200                 205

Arg Pro Tyr Pro Arg Phe Ala Cys His Phe Asp Pro Tyr Gly Pro Ile
    210                 215                 220

Tyr Asn Asp Arg Glu Arg Val Gln Ile Phe Ile Ser Asp Val Gly Val
225                 230                 235                 240

Val Ser Ala Gly Leu Ala Leu Phe Lys Leu Ser Ser Ala Phe Gly Phe
                245                 250                 255
```

```
Trp Trp Val Val Arg Val Tyr Gly Val Pro Leu Leu Ile Val Asn Ala
        260                 265                 270

Trp Leu Val Leu Ile Thr Tyr Leu Gln His Thr His Pro Ala Leu Pro
        275                 280                 285

His Tyr Asp Ser Ser Glu Trp Asp Trp Leu Arg Gly Ala Leu Ala Thr
290                 295                 300

Val Asp Arg Asp Tyr Gly Ile Leu Asn Lys Val Phe His Asn Ile Thr
305                 310                 315                 320

Asp Thr His Val Ala His His Leu Phe Ser Thr Met Pro His Tyr His
            325                 330                 335

Ala Met Glu Ala Thr Lys Ala Ile Arg Pro Ile Leu Gly Glu Tyr Tyr
        340                 345                 350

Gln Phe Asp Pro Thr Pro Val Ala Lys Ala Thr Trp Arg Glu Ala Lys
        355                 360                 365

Glu Cys Ile Tyr Val Glu Pro Glu Asp Asn Lys Gly Val Phe Trp Tyr
        370                 375                 380

Asn Asn Lys Phe
385

<210> SEQ ID NO 29
<211> LENGTH: 383
<212> TYPE: PRT
<213> ORGANISM: Glycine max

<400> SEQUENCE: 29

Met Gly Ala Gly Gly Arg Thr Asp Val Pro Pro Ala Asn Arg Lys Ser
1               5                   10                  15

Glu Val Asp Pro Leu Lys Arg Val Pro Phe Glu Lys Pro Gln Phe Ser
            20                  25                  30

Leu Ser Gln Ile Lys Lys Ala Ile Pro Pro His Cys Phe Gln Arg Ser
        35                  40                  45

Val Leu Arg Ser Phe Ser Tyr Val Val Tyr Asp Leu Thr Ile Ala Phe
    50                  55                  60

Cys Leu Tyr Tyr Val Ala Thr His Tyr Phe His Leu Leu Pro Gly Pro
65                  70                  75                  80

Leu Ser Phe Arg Gly Met Ala Ile Tyr Trp Ala Val Gln Gly Cys Ile
                85                  90                  95

Leu Thr Gly Val Trp Val Ile Ala His Glu Cys Gly His His Ala Phe
            100                 105                 110

Ser Asp Tyr Gln Leu Leu Asp Asp Ile Val Gly Leu Ile Leu His Ser
        115                 120                 125

Ala Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Gln Lys Ser Cys Ile Lys Trp Tyr Ser Lys Tyr Leu Asn Asn Pro Pro
                165                 170                 175

Gly Arg Val Leu Thr Leu Ala Val Thr Leu Thr Leu Gly Trp Pro Leu
            180                 185                 190

Tyr Leu Ala Leu Asn Val Ser Gly Arg Pro Tyr Asp Arg Phe Ala Cys
        195                 200                 205

His Tyr Asp Pro Tyr Gly Pro Ile Tyr Ser Asp Arg Glu Arg Leu Gln
    210                 215                 220
```

```
Ile Tyr Ile Ser Asp Ala Gly Val Leu Ala Val Val Tyr Gly Leu Phe
225                 230                 235                 240

Arg Leu Ala Met Ala Lys Gly Leu Ala Trp Val Val Cys Val Tyr Gly
                245                 250                 255

Val Pro Leu Leu Val Val Asn Gly Phe Leu Val Leu Ile Thr Phe Leu
                260                 265                 270

Gln His Thr His Pro Ala Leu Pro His Tyr Thr Ser Glu Trp Asp
                275                 280                 285

Trp Leu Arg Gly Ala Leu Ala Thr Val Asp Arg Asp Tyr Gly Ile Leu
290                 295                 300

Asn Lys Val Phe His Asn Ile Thr Asp Thr His Val Ala His His Leu
305                 310                 315                 320

Phe Ser Thr Met Pro His Tyr His Ala Met Glu Ala Thr Lys Ala Ile
                325                 330                 335

Lys Pro Ile Leu Gly Glu Tyr Tyr Arg Phe Asp Glu Thr Pro Phe Val
                340                 345                 350

Lys Ala Met Trp Arg Glu Ala Arg Glu Cys Ile Tyr Val Glu Pro Asp
                355                 360                 365

Gln Ser Thr Glu Ser Lys Gly Val Phe Trp Tyr Asn Asn Lys Leu
                370                 375                 380

<210> SEQ ID NO 30
<211> LENGTH: 383
<212> TYPE: PRT
<213> ORGANISM: Solanum lycopersicum

<400> SEQUENCE: 30

Met Gly Ala Gly Gly Arg Met Ser Ala Pro Asn Gly Gly Thr Glu Val
1               5                   10                  15

Lys Lys Asn Pro Leu Gln Lys Val Pro Thr Ser Lys Pro Pro Phe Thr
                20                  25                  30

Val Gly Asp Ile Lys Lys Ala Ile Pro Pro His Cys Phe Gln Arg Ser
                35                  40                  45

Leu Ile Arg Ser Phe Ser Tyr Val Val Tyr Asp Leu Ile Leu Val Ser
            50                  55                  60

Ile Met Tyr Tyr Val Ala Asn Thr Tyr Phe His Leu Ile Pro Ser Pro
65              70                  75                  80

Tyr Cys Tyr Ile Ala Trp Pro Ile Tyr Trp Ile Cys Gln Gly Cys Val
                85                  90                  95

Cys Thr Gly Ile Trp Val Asn Ala His Glu Cys Gly His His Ala Phe
                100                 105                 110

Ser Asp Tyr Gln Leu Val Asp Asp Thr Val Gly Leu Ile Leu His Ser
                115                 120                 125

Ala Leu Leu Val Pro Tyr Phe Ser Trp Lys Tyr Ser His Arg Arg His
                130                 135                 140

His Ser Asn Thr Gly Ser Leu Glu Arg Asp Glu Val Phe Val Pro Lys
145                 150                 155                 160

Ser Lys Ser Gln Leu Gly Trp Tyr Ser Lys Tyr Leu Asn Asn Pro Leu
                165                 170                 175

Gly Arg Val Ile Thr Leu Thr Val Thr Leu Thr Leu Gly Trp Pro Leu
                180                 185                 190

Tyr Leu Ala Phe Asn Val Ser Gly Arg Pro Tyr Asp Arg Phe Ala Cys
                195                 200                 205
```

```
His Tyr Asp Pro Tyr Gly Pro Ile Tyr Asn Asn Arg Glu Arg Leu Gln
    210                 215                 220
Ile Phe Leu Ser Asp Ala Gly Val Leu Gly Ala Cys Tyr Leu Leu Tyr
225                 230                 235                 240
Arg Val Ala Leu Val Lys Gly Leu Ala Trp Leu Val Cys Ile Tyr Gly
                245                 250                 255
Val Pro Leu Leu Val Val Asn Gly Phe Leu Val Leu Ile Thr Tyr Leu
                260                 265                 270
Gln His Thr His Pro Ser Leu Pro His Tyr Asp Ser Thr Glu Trp Asp
            275                 280                 285
Trp Leu Arg Gly Ala Leu Ala Thr Cys Asp Arg Asp Tyr Gly Val Leu
    290                 295                 300
Asn Lys Val Phe His Asn Ile Thr Asp Thr His Val Val His His Leu
305                 310                 315                 320
Phe Ser Ala Met Pro His Tyr Asn Ala Met Glu Ala Thr Lys Ala Val
                325                 330                 335
Lys Pro Leu Leu Gly Asp Tyr Tyr Gln Phe Asp Gly Thr Pro Ile Phe
                340                 345                 350
Lys Ala Met Trp Arg Glu Ala Lys Glu Cys Leu Tyr Val Glu Lys Asp
            355                 360                 365
Glu Ser Ser Gln Gly Lys Gly Val Phe Trp Tyr Lys Asn Lys Leu
    370                 375                 380
```

<210> SEQ ID NO 31
<211> LENGTH: 2613
<212> TYPE: DNA
<213> ORGANISM: Artificial Sequence
<220> FEATURE:
<223> OTHER INFORMATION: modified nucleic acid that can encode a
      modified FAE1 polypeptide

<400> SEQUENCE: 31

```
ttgtctaaat ttgataaaat atatgatgac gacaattccg gtggatcaca gtttgcttca      60
tttggctttt tttgtgtgtt tgtcaagttg ctattcaata agaatttgtg attttgattg     120
gtctcctcaa aattctgtga aattttagta acaaggaaga aattaacaaa tcacaacaag     180
aaagagatgt gagctgtcgt atcaaatctt attcgttttc tcaacgcaat cgttttagtt     240
ttttttaact taacgccact tctctgctcc atacactcct ttttgtccac gtactttcca     300
tttgtggtaa tccatttctt cactttggat cttcatctg aacaacaatt tcttgactca      360
atcaattacc acccgttctt gtgcttttgt atagattcat aatcttgtgt gtttcagctt     420
ctcattgctt tggttcttgt ttttttttct gcagaaacat gggtgcaggt ggaagaatga     480
cggttcctac ttcttccaag aagtctgaaa ccaatgcctt aaagcgtgtg ccgtgcgaga     540
aaccgccgtt cacgctcgga gaactgaaga agcaatcccc acagcattgt tcaatcgct      600
caatccctcg ctctttctcc taccttatct gggacatcat catagcctct tgcttctact     660
acgttgccac cacttacttc tctctcctcc ctcagcctct ctcttacttg gcttggcctc     720
tctattgggt ctgtcaaggc tgtgtcttaa ccggagtctg ggtcatagct cacgaatgcg     780
gccaccgc cttcagcgac taccaatggc ttgacgacac agtcggtctg atcttccatt       840
ctttcctcct cgtcccttac ttctcctgga aatacagcca ccgccgtcac cattccaaca     900
ccggatcact tgaaaaggac gaagtgtttg tccctaaaca gaaatccgcc atcaaatggt     960
acggcaagta cctcaacaac cctctgggac gcaccgtgat gttaaccgtc cagttcaccc    1020
```

```
ttggctggcc cttgtactta gccttcaacg tctcggggag accctacgac gggttcgctt    1080
gccacttcca ccatgacgtc cgttaacgtt aagctccttt accattacgt catcaccaac    1140
tttttcaacc tttgcttctt cccgttagcg gcgatcgttg ccggaaaagc ctctcggctt    1200
accacaaacg atcttcacca cttctactat tcctatctcc aacacaacct aataaccata    1260
tctctactct ttgccttcac cgttttcggt ttggctctct acatcgtaac ccggcccaaa    1320
ccggtttacc tcgttgacca ttcctgctac cttccaccat cgcatcttag aagcagtatc    1380
tctaaggtca tggatatctt ctatcaagta agattagccg atcctttacg gaacgcggca    1440
agcgatgatt cgtcctggct tgatttcttg aggaagattc aggagcggtc tggtctaggc    1500
gatgaaaccc acgccccga gggactgctt caggtccctc cacggaagac ttttgccgcg    1560
gcgcgtgaag aaacagagca agtgatcatc ggtgcgctcg aaaaactatt cgagaacacc    1620
aaagttaacc ctaaagagat tggtatactt gtggtgaact caagcatgtt taatccgact    1680
ccttcgctct cggcgatggt tgttaatact ttcaagctcc gaagcaacat cagaagcttt    1740
aatcttggag aatggggttg tagtgccggc gttatagcca ttgatctggc taaggacttg    1800
ttgcatgtcc ataaaaacac ttatgctctt gtggtgagca cagagaacat cacttacaac    1860
atttatgctg gtgataacag atccatgatg gtttcgaatt gcttgttccg tgttggtggg    1920
gccgcgattt tgctctccaa caagccgagg gaccggagac ggtccaagta ccagctactt    1980
cacacggttc ggacgcatac cggagctgac gacaagtctt tccgatgtgt gcaacaagaa    2040
gacgacgaga gcggtaaaac cggggtgtgt ttgtccaagg acataaccgg tgttgccggg    2100
agaactgttg agaaaaacat aacaacattg ggtccgttgg ttcttccttt tagcgagaaa    2160
tttcttttt tcgttacctt catcgccaag aaactcttta agacaagat caaacattac    2220
tacgtcccgg atttcaagct tgctatcgac cattttgta ttcatgccgg aggcagagcc    2280
gtgatcgatg tgctacagaa gaacttaggt ctattgccga tcgatgtgga ggcatctagg    2340
tcaacgttac atagatttgg gaacacttcg tctagctcaa tttggtatga attggcgtac    2400
atagaggcaa aaggaaggat gaagagaggg aacaaagttt ggcagattgc tttagggtca    2460
gggtttaagt gtaatagtgc ggtttgggtg gctctacgca atgtcaaggc ttcgacaaat    2520
agtccttggg aacattgcat tgatagatat ccagatgcaa ttgattctga ttcgggtaag    2580
tcagagactc gtgtccaaaa cggtcggtcc taa                                 2613
```

<210> SEQ ID NO 32
<211> LENGTH: 1521
<212> TYPE: DNA
<213> ORGANISM: Artificial Sequence
<220> FEATURE:
<223> OTHER INFORMATION: modified nucleic acid that can encode a
      modified FAE1 polypeptide

<400> SEQUENCE: 32

```
atgacgtccg ttaacgttaa gctcctttac cattacgtca tcaccaactt tttcaacctt      60
tgcttcttcc cgttagcggc gatcgttgcc ggaaaagcct ctcggcttac cacaaacgat     120
cttcaccact ctactattc ctatctccaa cacaacctaa taaccatatc tctactcttt      180
gccttcaccg ttttcggttt ggctctctac atcgtaaccc ggcccaaacc ggtttacctc     240
gttgaccatt cctgctacct tccaccatcg catcttagaa gcagtatctc taaggtcatg     300
gatatcttct atcaagtaag attagccgat cctttacgga acgcggcaag cgatgattcg     360
tcctggcttg atttcttgag gaagattcag gagcggtctg gtctaggcga tgaaacccac     420
```

```
ggccccgagg gactgcttca ggtccctcca cggaagactt ttgccgcggc gcgtgaagaa    480
acagagcaag tgatcatcgg tgcgctcgaa aaactattcg agaacaccaa agttaaccct    540
aaagagattg gtatacttgt ggtgaactca agcatgttta atccgactcc ttcgctctcg    600
gcgatggttg ttaatacttt caagctccga agcaacatca gaagctttaa tcttggagga    660
atgggttgta gtgccggcgt tatagccatt gatctggcta aggacttgtt gcatgtccat    720
aaaaacactt atgctcttgt ggtgagcaca gagaacatca cttacaacat ttatgctggt    780
gataacagat ccatgatggt ttcgaattgc ttgttccgtg ttggtggggc cgcgattttg    840
ctctccaaca agccgaggga ccggagacgg tccaagtacc agctacttca cacggttcgg    900
acgcataccg gagctgacga caagtctttc cgatgtgtgc aacaagaaga cgacgagagc    960
ggtaaaaccg gggtgtgttt gtccaaggac ataaccggtg ttgccgggag aactgtttag   1020
aaaaacataa caacattggg tccgttggtt cttccttta gcgagaaatt tcttttttc   1080 gttaccttca tcgccaagaa actctttaaa gacaagatca acattacta cgtcccggat   1140 ttcaagcttg ctatcgacca tttttgtatt catgccggag gcagagccgt gatcgatgtg   1200
ctacagaaga acttaggtct attgccgatc gatgtggagg catctaggtc aacgttacat   1260
agatttggga cacttcgtc tagctcaatt tggtatgaat tggcgtacat agaggcaaaa   1320
ggaaggatga agagagggaa caaagtttag cagattgctt tagggtcagg gtttaagtgt   1380
aatagtgcgg tttgggtggc tctacgcaat gtcaaggctc cgacaaatag tccttgggaa   1440
cattgcattg atagatatcc agatgcaatt gattctgatt cgggtaagtc agagactcgt   1500
gtccaaaacg gtcggtccta a                                             1521
```

<210> SEQ ID NO 33
<211> LENGTH: 446
<212> TYPE: PRT
<213> ORGANISM: Arabidopsis thaliana

<400> SEQUENCE: 33

Met Thr Ser Val Asn Val Lys Leu Leu Tyr Arg Tyr Val Leu Thr Asn
1               5                   10                  15

Phe Phe Asn Leu Cys Leu Phe Pro Leu Thr Ala Phe Leu Ala Gly Lys
            20                  25                  30

Ala Ser Arg Leu Thr Ile Asn Asp Leu His Asn Phe Leu Ser Tyr Leu
        35                  40                  45

Gln His Asn Leu Ile Thr Val Thr Leu Leu Phe Ala Phe Thr Val Phe
    50                  55                  60

Gly Leu Val Leu Tyr Ile Val Thr Arg Pro Asn Pro Val Tyr Leu Val
65                  70                  75                  80

Asp Tyr Ser Cys Tyr Leu Pro Pro Pro His Leu Lys Val Ser Val Ser
                85                  90                  95

Lys Val Met Asp Ile Phe Tyr Gln Ile Arg Lys Ala Asp Thr Ser Ser
            100                 105                 110

Arg Asn Val Ala Cys Asp Asp Pro Ser Ser Leu Asp Phe Leu Arg Lys
        115                 120                 125

Ile Gln Glu Arg Ser Gly Leu Gly Asp Glu Thr Tyr Ser Pro Glu Gly
    130                 135                 140

Leu Ile His Val Pro Pro Arg Lys Thr Phe Ala Ala Ser Arg Glu Glu
145                 150                 155                 160

Thr Glu Lys Val Ile Ile Gly Ala Leu Glu Asn Leu Phe Glu Asn Thr
                165                 170                 175

```
Lys Val Asn Pro Arg Glu Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Ile Lys Ser Phe Asn Leu Gly Gly Met Gly Cys Ser
    210                 215                 220

Ala Gly Val Ile Ala Ile Asp Leu Ala Lys Asp Leu His Val His
225                 230                 235                 240

Lys Asn Thr Tyr Ala Leu Val Val Ser Thr Glu Asn Ile Thr Gln Gly
                245                 250                 255

Ile Tyr Ala Gly Glu Asn Arg Ser Met Met Val Ser Asn Cys Leu Phe
            260                 265                 270

Arg Val Gly Gly Ala Ala Ile Leu Leu Ser Asn Lys Ser Gly Asp Arg
        275                 280                 285

Arg Arg Ser Lys Tyr Lys Leu Val His Thr Val Arg Thr His Thr Gly
    290                 295                 300

Ala Asp Asp Lys Ser Phe Arg Cys Val Gln Gln Glu Asp Asp Glu Ser
305                 310                 315                 320

Gly Lys Ile Gly Val Cys Leu Ser Lys Asp Ile Thr Asn Val Ala Gly
                325                 330                 335

Thr Thr Leu Thr Lys Asn Ile Ala Thr Leu Gly Pro Leu Ile Leu Pro
            340                 345                 350

Leu Ser Glu Lys Phe Leu Phe Phe Ala Thr Phe Val Ala Lys Lys Leu
        355                 360                 365

Leu Lys Asp Lys Ile Lys His Tyr Tyr Val Pro Asp Phe Arg Met Lys
    370                 375                 380

Lys Gly Asn Lys Ala Trp Gln Ile Ala Leu Gly Ser Gly Phe Lys Cys
385                 390                 395                 400

Asn Ser Ala Val Trp Val Ala Leu Arg Asn Val Lys Ala Ser Ala Asn
                405                 410                 415

Ser Pro Trp Gln His Cys Ile Asp Arg Tyr Pro Val Lys Ile Asp Ser
            420                 425                 430

Asp Leu Ser Lys Ser Lys Thr His Val Gln Asn Gly Arg Ser
        435                 440                 445

<210> SEQ ID NO 34
<211> LENGTH: 506
<212> TYPE: PRT
<213> ORGANISM: Thlaspi arvense

<400> SEQUENCE: 34

Met Thr Ser Val Asn Val Lys Leu Leu Tyr His Tyr Val Ile Thr Asn
1               5                   10                  15

Phe Phe Asn Leu Cys Phe Phe Pro Leu Ala Ala Ile Val Ala Gly Lys
            20                  25                  30

Ala Ser Arg Leu Thr Thr Asn Asp Leu His His Phe Tyr Tyr Ser Tyr
        35                  40                  45

Leu Gln His Asn Leu Ile Thr Ile Ser Leu Leu Phe Ala Phe Thr Val
    50                  55                  60

Phe Gly Leu Ala Leu Tyr Ile Val Thr Arg Pro Lys Pro Val Tyr Leu
65                  70                  75                  80

Val Asp His Ser Cys Tyr Leu Pro Pro Ser His Leu Arg Ser Ser Ile
                85                  90                  95

Ser Lys Val Met Asp Ile Phe Tyr Gln Val Arg Leu Ala Asp Pro Leu
            100                 105                 110
```

```
Arg Asn Ala Ala Ser Asp Asp Ser Trp Leu Asp Phe Leu Arg Lys
            115                 120                 125

Ile Gln Glu Arg Ser Gly Leu Gly Asp Glu Thr His Gly Pro Glu Gly
        130                 135                 140

Leu Leu Gln Val Pro Pro Arg Lys Thr Phe Ala Ala Arg Glu Glu
145                 150                 155                 160

Thr Glu Gln Val Ile Ile Gly Ala Leu Glu Lys Leu Phe Glu Asn Thr
                    165                 170                 175

Lys Val Asn Pro Lys Glu Ile Gly Ile Leu Val Val Asn Ser Ser Met
                180                 185                 190

Phe Asn Pro Thr Pro Ser Leu Ser Ala Met Val Val Asn Thr Phe Lys
                195                 200                 205

Leu Arg Ser Asn Ile Arg Ser Phe Asn Leu Gly Gly Met Gly Cys Ser
            210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                    245                 250                 255

Ile Tyr Ala Gly Asp Asn Arg Ser Met Met Val Ser Asn Cys Leu Phe
            260                 265                 270

Arg Val Gly Gly Ala Ala Ile Leu Leu Ser Asn Lys Pro Arg Asp Arg
        275                 280                 285

Arg Arg Ser Lys Tyr Gln Leu Leu His Thr Val Arg Thr His Thr Gly
        290                 295                 300

Ala Asp Asp Lys Ser Phe Arg Cys Val Gln Gln Glu Asp Asp Glu Ser
305                 310                 315                 320

Gly Lys Thr Gly Val Cys Leu Ser Lys Asp Ile Thr Gly Val Ala Gly
                    325                 330                 335

Arg Thr Val Gln Lys Asn Ile Thr Thr Leu Gly Pro Leu Val Leu Pro
                340                 345                 350

Phe Ser Glu Lys Phe Leu Phe Phe Val Thr Phe Ile Ala Lys Lys Leu
            355                 360                 365

Phe Lys Asp Lys Ile Lys His Tyr Tyr Val Pro Asp Phe Lys Leu Ala
        370                 375                 380

Ile Asp His Phe Cys Ile His Ala Gly Gly Arg Ala Val Ile Asp Val
385                 390                 395                 400

Leu Gln Lys Asn Leu Gly Leu Leu Pro Ile Asp Val Glu Ala Ser Arg
                    405                 410                 415

Ser Thr Leu His Arg Phe Gly Asn Thr Ser Ser Ser Ile Trp Tyr
                420                 425                 430

Glu Leu Ala Tyr Ile Glu Ala Lys Gly Arg Met Lys Arg Gly Asn Lys
            435                 440                 445

Val Trp Gln Ile Ala Leu Gly Ser Gly Phe Lys Cys Asn Ser Ala Val
        450                 455                 460

Trp Val Ala Leu Arg Asn Val Lys Ala Ser Thr Asn Ser Pro Trp Glu
465                 470                 475                 480

His Cys Ile Asp Arg Tyr Pro Asp Ala Ile Asp Ser Asp Ser Gly Lys
                    485                 490                 495

Ser Glu Thr Arg Val Gln Asn Gly Arg Ser
                500                 505

<210> SEQ ID NO 35
<211> LENGTH: 339
```

```
<212> TYPE: PRT
<213> ORGANISM: Artificial Sequence
<220> FEATURE:
<223> OTHER INFORMATION: modified FAE1 polypeptide

<400> SEQUENCE: 35
```

| | | | | | | | | | | | | | | | |
|---|---|---|---|---|---|---|---|---|---|---|---|---|---|---|---|
| Met | Thr | Ser | Val | Asn | Val | Lys | Leu | Leu | Tyr | His | Tyr | Val | Ile | Thr | Asn |
| 1 | | | | 5 | | | | | 10 | | | | | 15 | |
| Phe | Phe | Asn | Leu | Cys | Phe | Phe | Pro | Leu | Ala | Ala | Ile | Val | Ala | Gly | Lys |
| | | | 20 | | | | | 25 | | | | | 30 | | |
| Ala | Ser | Arg | Leu | Thr | Thr | Asn | Asp | Leu | His | His | Phe | Tyr | Tyr | Ser | Tyr |
| | | 35 | | | | | 40 | | | | | 45 | | | |
| Leu | Gln | His | Asn | Leu | Ile | Thr | Ile | Ser | Leu | Leu | Phe | Ala | Phe | Thr | Val |
| | 50 | | | | | 55 | | | | | 60 | | | | |
| Phe | Gly | Leu | Ala | Leu | Tyr | Ile | Val | Thr | Arg | Pro | Lys | Pro | Val | Tyr | Leu |
| 65 | | | | | 70 | | | | | 75 | | | | | 80 |
| Val | Asp | His | Ser | Cys | Tyr | Leu | Pro | Pro | Ser | His | Leu | Arg | Ser | Ser | Ile |
| | | | | 85 | | | | | 90 | | | | | 95 | |
| Ser | Lys | Val | Met | Asp | Ile | Phe | Tyr | Gln | Val | Arg | Leu | Ala | Asp | Pro | Leu |
| | | | 100 | | | | | 105 | | | | | 110 | | |
| Arg | Asn | Ala | Ala | Ser | Asp | Asp | Ser | Ser | Trp | Leu | Asp | Phe | Leu | Arg | Lys |
| | | | 115 | | | | | 120 | | | | | 125 | | |
| Ile | Gln | Glu | Arg | Ser | Gly | Leu | Gly | Asp | Glu | Thr | His | Gly | Pro | Glu | Gly |
| | 130 | | | | | 135 | | | | | 140 | | | | |
| Leu | Leu | Gln | Val | Pro | Pro | Arg | Lys | Thr | Phe | Ala | Ala | Ala | Arg | Glu | Glu |
| 145 | | | | | 150 | | | | | 155 | | | | | 160 |
| Thr | Glu | Gln | Val | Ile | Ile | Gly | Ala | Leu | Glu | Lys | Leu | Phe | Glu | Asn | Thr |
| | | | | 165 | | | | | 170 | | | | | 175 | |
| Lys | Val | Asn | Pro | Lys | Glu | Ile | Gly | Ile | Leu | Val | Val | Asn | Ser | Ser | Met |
| | | | 180 | | | | | 185 | | | | | 190 | | |
| Phe | Asn | Pro | Thr | Pro | Ser | Leu | Ser | Ala | Met | Val | Val | Asn | Thr | Phe | Lys |
| | | | 195 | | | | | 200 | | | | | 205 | | |
| Leu | Arg | Ser | Asn | Ile | Arg | Ser | Phe | Asn | Leu | Gly | Gly | Met | Gly | Cys | Ser |
| | 210 | | | | | 215 | | | | | 220 | | | | |
| Ala | Gly | Val | Ile | Ala | Ile | Asp | Leu | Ala | Lys | Asp | Leu | Leu | His | Val | His |
| 225 | | | | | 230 | | | | | 235 | | | | | 240 |
| Lys | Asn | Thr | Tyr | Ala | Leu | Val | Val | Ser | Thr | Glu | Asn | Ile | Thr | Tyr | Asn |
| | | | | 245 | | | | | 250 | | | | | 255 | |
| Ile | Tyr | Ala | Gly | Asp | Asn | Arg | Ser | Met | Met | Val | Ser | Asn | Cys | Leu | Phe |
| | | | 260 | | | | | 265 | | | | | 270 | | |
| Arg | Val | Gly | Gly | Ala | Ala | Ile | Leu | Leu | Ser | Asn | Lys | Pro | Arg | Asp | Arg |
| | | | 275 | | | | | 280 | | | | | 285 | | |
| Arg | Arg | Ser | Lys | Tyr | Gln | Leu | Leu | His | Thr | Val | Arg | Thr | His | Thr | Gly |
| | 290 | | | | | 295 | | | | | 300 | | | | |
| Ala | Asp | Asp | Lys | Ser | Phe | Arg | Cys | Val | Gln | Gln | Glu | Asp | Asp | Glu | Ser |
| 305 | | | | | 310 | | | | | 315 | | | | | 320 |
| Gly | Lys | Thr | Gly | Val | Cys | Leu | Ser | Lys | Asp | Ile | Thr | Gly | Val | Ala | Gly |
| | | | | 325 | | | | | 330 | | | | | 335 | |
| Arg | Thr | Val | | | | | | | | | | | | | |

```
<210> SEQ ID NO 36
<211> LENGTH: 449
<212> TYPE: PRT
<213> ORGANISM: Artificial Sequence
<220> FEATURE:
<223> OTHER INFORMATION: modified FAE1 polypeptide
```

<400> SEQUENCE: 36

```
Met Thr Ser Val Asn Val Lys Leu Leu Tyr His Tyr Val Ile Thr Asn
1               5                   10                  15

Phe Phe Asn Leu Cys Phe Phe Pro Leu Ala Ala Ile Val Ala Gly Lys
            20                  25                  30

Ala Ser Arg Leu Thr Thr Asn Asp Leu His His Phe Tyr Tyr Ser Tyr
        35                  40                  45

Leu Gln His Asn Leu Ile Thr Ile Ser Leu Leu Phe Ala Phe Thr Val
    50                  55                  60

Phe Gly Leu Ala Leu Tyr Ile Val Thr Arg Pro Lys Pro Val Tyr Leu
65                  70                  75                  80

Val Asp His Ser Cys Tyr Leu Pro Pro Ser His Leu Arg Ser Ser Ile
                85                  90                  95

Ser Lys Val Met Asp Ile Phe Tyr Gln Val Arg Leu Ala Asp Pro Leu
            100                 105                 110

Arg Asn Ala Ala Ser Asp Asp Ser Ser Trp Leu Asp Phe Leu Arg Lys
        115                 120                 125

Ile Gln Glu Arg Ser Gly Leu Gly Asp Glu Thr His Gly Pro Glu Gly
    130                 135                 140

Leu Leu Gln Val Pro Pro Arg Lys Thr Phe Ala Ala Arg Glu Glu
145                 150                 155                 160

Thr Glu Gln Val Ile Ile Gly Ala Leu Glu Lys Leu Phe Glu Asn Thr
                165                 170                 175

Lys Val Asn Pro Lys Glu Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Ile Arg Ser Phe Asn Leu Gly Gly Met Gly Cys Ser
    210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
            260                 265                 270

Arg Val Gly Gly Ala Ala Ile Leu Leu Ser Asn Lys Pro Arg Asp Arg
        275                 280                 285

Arg Arg Ser Lys Tyr Gln Leu Leu His Thr Val Arg Thr His Thr Gly
    290                 295                 300

Ala Asp Asp Lys Ser Phe Arg Cys Val Gln Gln Glu Asp Asp Glu Ser
305                 310                 315                 320

Gly Lys Thr Gly Val Cys Leu Ser Lys Asp Ile Thr Gly Val Ala Gly
                325                 330                 335

Arg Thr Val Gln Lys Asn Ile Thr Thr Leu Gly Pro Leu Val Leu Pro
            340                 345                 350

Phe Ser Glu Lys Phe Leu Phe Phe Val Thr Phe Ile Ala Lys Lys Leu
        355                 360                 365

Phe Lys Asp Lys Ile Lys His Tyr Tyr Val Pro Asp Phe Lys Leu Ala
    370                 375                 380

Ile Asp His Phe Cys Ile His Ala Gly Gly Arg Ala Val Ile Asp Val
385                 390                 395                 400
```

```
Leu Gln Lys Asn Leu Gly Leu Pro Ile Asp Val Glu Ala Ser Arg
            405                 410                 415

Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Arg Gly Asn Lys
            435                 440                 445

Val

<210> SEQ ID NO 37
<211> LENGTH: 513
<212> TYPE: PRT
<213> ORGANISM: Oryza sativa

<400> SEQUENCE: 37

Met Asn Gly Gly Asp Ala Ala Ala Ala Thr Pro Ser His Arg
1               5                   10                  15

Arg Leu Pro Asp Phe Leu Gln Ser Val Asn Leu Lys Tyr Val Lys Leu
                20                  25                  30

Gly Tyr His Tyr Leu Ile Thr His Leu Leu Thr Leu Leu Leu Leu Pro
            35                  40                  45

Leu Met Ala Val Ile Val Leu Glu Ala Gly Arg Thr Asp Pro Asp Asp
        50                  55                  60

Leu Arg Gln Leu Trp Leu His Leu Gln Tyr Asn Leu Val Ser Val Leu
65                  70                  75                  80

Val Leu Ser Ala Val Leu Val Phe Gly Ala Thr Val Tyr Val Leu Thr
                85                  90                  95

Arg Pro Arg Pro Val Tyr Leu Val Asp Phe Ala Cys Tyr Lys Pro Pro
            100                 105                 110

Asp Lys Leu Lys Val Arg Phe Asp Glu Phe Leu His His Ser Lys Leu
            115                 120                 125

Cys Gly Phe Asp Asp Cys Leu Glu Phe Gln Arg Lys Ile Leu Glu Arg
        130                 135                 140

Ser Gly Leu Ser Glu Glu Thr Tyr Val Pro Glu Ala Met His Leu Ile
145                 150                 155                 160

Pro Pro Glu Pro Thr Met Ala Asn Ala Arg Ala Glu Ala Glu Ser Val
                165                 170                 175

Met Phe Gly Ala Leu Asp Lys Leu Phe Lys Phe Thr Gly Val Lys Pro
            180                 185                 190

Lys Asp Val Gly Val Leu Val Val Asn Cys Ser Leu Phe Asn Pro Thr
        195                 200                 205

Pro Ser Leu Ser Ala Met Ile Val Asn Lys Tyr Lys Leu Arg Gly Asn
    210                 215                 220

Ile Lys Ser Phe Asn Leu Gly Gly Met Gly Cys Ser Ala Gly Val Ile
225                 230                 235                 240

Ala Val Asp Leu Ala Arg Asp Met Leu Gln Val His Arg Asn Thr Tyr
                245                 250                 255

Ala Val Val Val Ser Thr Glu Asn Ile Thr Gln Asn Trp Tyr Phe Gly
            260                 265                 270

Asn Arg Lys Ser Met Leu Ile Pro Asn Cys Leu Phe Arg Val Gly Gly
            275                 280                 285

Ala Ala Val Leu Leu Ser Asn Arg Gly Ala Asp Arg Arg Ala Lys
        290                 295                 300

Tyr Ala Leu Lys His Val Val Arg Thr His Lys Gly Ala Asp Asn Lys
305                 310                 315                 320
```

-continued

```
Ala Phe Asn Cys Val Tyr Gln Glu Gln Asp Asp Glu Gly Lys Thr Gly
            325                 330                 335

Val Ser Leu Ser Lys Asp Leu Met Ala Ile Ala Gly Gly Ala Leu Lys
        340                 345                 350

Thr Asn Ile Thr Thr Leu Gly Pro Leu Val Leu Pro Phe Ser Glu Gln
    355                 360                 365

Leu Leu Phe Phe Ala Thr Leu Val Ala Lys Lys Leu Phe Asn Ala Lys
370                 375                 380

Ile Lys Pro Tyr Ile Pro Asp Phe Lys Leu Ala Phe Glu His Phe Cys
385                 390                 395                 400

Ile His Ala Gly Gly Arg Ala Val Ile Asp Glu Leu Glu Lys Asn Leu
            405                 410                 415

Gln Leu Gln Pro Val His Val Glu Ala Ser Arg Met Thr Leu His Arg
        420                 425                 430

Phe Gly Asn Thr Ser Ser Ser Ile Trp Tyr Glu Leu Ala Tyr Met
    435                 440                 445

Glu Ala Lys Gly Arg Val Arg Arg Gly His Arg Ile Trp Gln Ile Ala
    450                 455                 460

Phe Gly Ser Gly Phe Lys Cys Asn Ser Ala Val Trp His Ala Leu Arg
465                 470                 475                 480

Asn Val Asn Pro Ser Pro Glu Ser Pro Trp Glu Asp Cys Ile Asp Arg
            485                 490                 495

Tyr Pro Val Glu Leu Val Asp Gly Phe Ala Thr His Asn Asn Thr Gln
        500                 505                 510

Gln

<210> SEQ ID NO 38
<211> LENGTH: 510
<212> TYPE: PRT
<213> ORGANISM: Glycine max

<400> SEQUENCE: 38

Met Thr Val Thr Met Ser Gly Glu Glu Ala Ala Val Gly Val Gln
1               5                   10                  15

Ile Gln Gln Lys Ser Arg Met Val Leu Pro Asp Phe Leu Gln Ser Val
            20                  25                  30

Asn Leu Lys Tyr Val Lys Leu Gly Tyr His Tyr Leu Ile Ser Asn Leu
        35                  40                  45

Val Thr Leu Phe Leu Val Pro Leu Ile Leu Val Thr Leu Ile Gln Val
    50                  55                  60

Ser Gln Thr Thr Asp Leu Arg His Leu Trp Leu His Leu Gln Tyr Asn
65                  70                  75                  80

Leu Leu Thr Ile Leu Thr Cys Ser Ala Val Leu Val Phe Gly Leu Thr
                85                  90                  95

Leu Tyr Ala Val Thr Cys Pro Arg Pro Val Tyr Leu Leu Asp Ser Ala
            100                 105                 110

Cys Phe Arg Pro Ala Asp His Leu Lys Ala Pro Phe Arg Ser Phe Met
        115                 120                 125

Asp His Ser Arg Leu Thr Gly Asp Phe Glu Ser Ser Leu Glu Phe
    130                 135                 140

Gln Arg Lys Ile Leu Glu Arg Ser Gly Leu Gly Glu Glu Thr Tyr Val
145                 150                 155                 160

Pro Asp Ala Met His Ser Ile Pro Pro Gln Pro Ser Met Ala Ala Ala
                165                 170                 175
```

Arg Ala Glu Ala Glu Gln Val Met Phe Gly Ala Leu Asp Asn Leu Phe
            180                 185                 190

Gln Ser Thr Asn Ile Lys Pro Lys Asp Ile Gly Ile Leu Ile Val Asn
        195                 200                 205

Cys Ser Leu Phe Asn Pro Thr Pro Ser Leu Ser Ser Met Ile Val Asn
    210                 215                 220

Lys Tyr Lys Leu Arg Gly Asn Ile Arg Ser Phe Asn Leu Gly Gly Met
225                 230                 235                 240

Gly Cys Ser Ala Gly Val Ile Ala Val Asp Leu Ala Lys Asp Leu Leu
                245                 250                 255

Gln Val His Arg Asn Thr Tyr Ala Val Val Ser Thr Glu Asn Ile
            260                 265                 270

Thr Gln Asn Trp Tyr Phe Gly Asn Lys Lys Ser Met Leu Ile Pro Asn
        275                 280                 285

Cys Leu Phe Arg Val Gly Cys Ser Val Leu Leu Ser Asn Lys Pro
    290                 295                 300

Ala Asp Arg Arg Arg Ala Lys Tyr Arg Leu Val His Val Val Arg Thr
305                 310                 315                 320

His Arg Gly Ala Asp Asp Lys Ala Phe Arg Cys Val Tyr Gln Glu Gln
                325                 330                 335

Asp Asp Ala Gly Lys Thr Gly Val Ser Leu Ser Lys Asp Leu Met Ala
            340                 345                 350

Ile Ala Gly Gly Ala Leu Lys Thr Asn Ile Thr Thr Leu Gly Pro Leu
        355                 360                 365

Val Leu Pro Ile Ser Glu Gln Leu Leu Phe Phe Val Thr Leu Leu Met
    370                 375                 380

Lys Lys Leu Phe Lys Ala Asp Val Lys Pro Tyr Ile Pro Asp Phe Lys
385                 390                 395                 400

Leu Ala Phe Asp His Phe Cys Ile His Ala Gly Gly Arg Ala Val Ile
                405                 410                 415

Asp Glu Leu Glu Lys Asn Leu Gln Leu Leu Pro Glu His Val Glu Ala
            420                 425                 430

Ser Arg Met Thr Leu His Arg Phe Gly Asn Thr Ser Ser Ser Ser Ile
        435                 440                 445

Trp Tyr Glu Leu Ala Tyr Ile Glu Ala Lys Gly Arg Ile Lys Lys Gly
    450                 455                 460

Asn Arg Ile Trp Gln Ile Ala Phe Gly Ser Gly Phe Lys Cys Asn Ser
465                 470                 475                 480

Ala Val Trp Gln Ala Leu Arg Asn Val Arg Pro Ser Pro Asn Gly Pro
                485                 490                 495

Trp Glu Asp Cys Ile Asp Lys Tyr Pro Val Glu Ile Val Ser
            500                 505                 510

<210> SEQ ID NO 39
<211> LENGTH: 517
<212> TYPE: PRT
<213> ORGANISM: Solanum lycopersicum

<400> SEQUENCE: 39

Met Asn Gly Ala Thr Gly Thr Gln Val Asn Thr Ala Asn Gly Gly
1               5                   10                  15

Gly Glu Pro Val Gly Val Gln Ile Gln Gln Ser Arg Arg Leu Pro Asp
            20                  25                  30

```
Phe Leu Gln Ser Val Asn Leu Lys Tyr Val Lys Leu Gly Tyr His Tyr
         35                  40                  45

Leu Ile Ser His Leu Leu Thr Leu Cys Leu Ile Pro Val Met Ala Val
 50                  55                  60

Ile Leu Ile Glu Ala Ser Gln Met Asn Pro Asp Asp Ile Arg Gln Leu
 65                  70                  75                  80

Trp Leu His Leu Gln Tyr Asn Leu Val Ser Val Ile Ile Cys Ser Ala
                 85                  90                  95

Val Leu Val Phe Gly Ser Thr Val Tyr Ile Met Thr Arg Pro Arg Pro
                100                 105                 110

Val Tyr Leu Ile Asp Tyr Ser Cys Tyr Lys Ala Pro Glu His Leu Lys
            115                 120                 125

Ala Pro Tyr Glu Arg Phe Met Gln His Ser Arg Leu Thr Gly Asp Phe
        130                 135                 140

Asp Glu Ser Ser Leu Glu Phe Gln Arg Lys Ile Leu Glu Arg Ser Gly
145                 150                 155                 160

Leu Gly Asp Glu Thr Tyr Val Pro Glu Ala Met His Gln Leu Pro Pro
                165                 170                 175

Gln Pro Ser Met Gln Ala Ala Arg Glu Glu Ala Glu Gln Val Met Phe
            180                 185                 190

Gly Ala Leu Asp Lys Leu Phe Ala Asn Thr Ser Val Lys Pro Lys Lys
        195                 200                 205

Ile Gly Val Leu Val Val Asn Cys Ser Leu Phe Asn Pro Thr Pro Ser
    210                 215                 220

Leu Ser Ala Met Ile Val Asn Lys Tyr Lys Leu Arg Gly Asn Ile Arg
225                 230                 235                 240

Ser Phe Asn Leu Gly Gly Met Gly Cys Ser Ala Gly Val Ile Ala Val
                245                 250                 255

Asp Leu Ala Lys Asp Met Leu Gln Val His Arg Asn Thr Tyr Ala Val
            260                 265                 270

Val Val Ser Thr Glu Asn Ile Thr Gln Asn Trp Tyr Phe Gly Asn Lys
        275                 280                 285

Lys Ser Met Leu Ile Pro Asn Cys Leu Phe Arg Val Gly Gly Ser Ala
    290                 295                 300

Val Leu Leu Ser Asn Lys Ser Val Asp Arg Arg Arg Ala Lys Tyr Lys
305                 310                 315                 320

Leu Val His Val Val Arg Thr His Arg Gly Ala Asp Asp Lys Ala Phe
                325                 330                 335

Arg Cys Val Tyr Gln Glu Gln Asp Ala Gly Lys Thr Gly Val Ser
            340                 345                 350

Leu Ser Lys Asp Leu Met Ala Ile Ala Gly Gly Ala Leu Lys Thr Asn
        355                 360                 365

Ile Thr Thr Leu Gly Pro Leu Val Leu Pro Ile Ser Glu Gln Leu Leu
    370                 375                 380

Phe Phe Gly Ser Leu Ile Ile Lys Lys Ile Phe Asn Lys His Ile Lys
385                 390                 395                 400

Pro Tyr Ile Pro Asp Phe Lys Leu Ala Phe Asp His Phe Cys Ile His
                405                 410                 415

Ala Gly Gly Arg Ala Val Ile Asp Glu Leu Glu Lys Asn Leu Gln Leu
            420                 425                 430

Thr Gln Val His Val Glu Ala Ser Arg Met Thr Leu His Arg Phe Gly
        435                 440                 445
```

```
Asn Thr Ser Ser Ser Ser Ile Trp Tyr Glu Leu Ala Tyr Ile Glu Ala
    450                 455                 460

Lys Gly Arg Met Lys Lys Gly Asn Lys Val Trp Gln Ile Ala Phe Gly
465                 470                 475                 480

Ser Gly Phe Lys Cys Asn Ser Ala Val Trp Gln Ala Leu Arg Asn Val
                485                 490                 495

Lys Pro Ser Pro Asp Gly Pro Trp Glu Asp Cys Ile Asp Arg Tyr Pro
            500                 505                 510

Val Lys Val Val Ser
        515

<210> SEQ ID NO 40
<211> LENGTH: 2146
<212> TYPE: DNA
<213> ORGANISM: Artificial Sequence
<220> FEATURE:
<223> OTHER INFORMATION: modified nucleic acid that can encode a
      modified ROD1 polypeptide

<400> SEQUENCE: 40
```

| | | | | | |
|---|---|---|---|---|---|
| atgtcaacta | aaaccgtcgt | ccctctccgt | cgcagatcta | agccccttaa | cggaaatcac | 60 |
| actaacggcg | tcgccattga | cggaagcctc | gacgacgacc | acaaccgtcg | catcggatca | 120 |
| gtaaatagcc | aaatggataa | cattgctaag | aaaacggacg | acggctacgc | aaacggcgga | 180 |
| ggaggaggag | gaggagggaa | agcaaggcg | tcgtttatga | cgtggacggc | gcgtgacgtt | 240 |
| gtgtacgtgg | cgaggtacca | ttggataccg | tgtttgttcg | cggtcggggt | tctgttcttc | 300 |
| acgggcgtga | agtacacgct | ccagatgatt | cccgcgaggt | ctgagccgtt | cgatattggg | 360 |
| tttgtggcca | cgcgctctct | gaatcgcgtc | ttggcaaatt | caccggatct | aacaccgtc | 420 |
| ttagccgctc | taaacacggt | aatttcgtac | taattaattt | agggtaaaaa | atatagtatt | 480 |
| taataatgac | tatcctcaat | tcctttcatg | cttcacctaa | tattttgttt | ttttttcgttg | 540 |
| tcattaaaat | cgtaataata | tattgagtta | gtcaaatgaa | aaaaacaagt | ggcggtagtg | 600 |
| attggaaaca | aatctcagat | cttttatctg | tttaataagg | tatttaatta | tccagctgga | 660 |
| attatgctgt | caagtgtcaa | cacagtagta | gtaacatgca | atggaatttc | tcaatagaaa | 720 |
| aaggtcttaa | ttagtataga | taattagtgg | acaaaaatgt | agttaatgta | atctctttgc | 780 |
| taagtagtta | tcataatcat | cttttttaaca | actgccattt | tgtctgtgtg | tttgttttac | 840 |
| aacgaagtag | tagtagaata | gatcgctttt | tagcttttga | aagtttcgaa | cccaaggaaa | 900 |
| agggacacat | gggttatgag | ttggagacac | gatcacatgc | aaacagagag | attggttaaa | 960 |
| ttatcgactt | tttgtagtac | tttttaaaaa | aaaactattt | atataaaaaa | catggtggat | 1020 |
| ggtggggaca | ggtgttcgta | gggatgcaaa | cgacgtatat | tgtatggaca | tggttaatgg | 1080 |
| aaggacgacc | acgagccacc | atctcggctt | gcttcatgtt | tacttgtcga | ggcattcttg | 1140 |
| gttactctac | tcagctccct | cttcctcagg | ttccaatcaa | cacttttctt | ctatctcttt | 1200 |
| tcttaattaa | aataattacc | aattaactaa | atgctaatca | gtcgatatat | catagttcca | 1260 |
| acgttttgga | cgtgtgattt | ccattggcca | ctaccatata | aaacaacaga | gtctctttat | 1320 |
| tcattattca | atatatattt | gagtattgat | attattcata | gggaggtttc | atttgtacta | 1380 |
| tcaataaaat | ttctacaact | cttggatttt | ttctgctaca | ttttgtagtt | atttttttaa | 1440 |
| ttacttttaa | aaacttgtga | ataggagaga | ctaatagtag | tacgtaatat | gattgtatca | 1500 |
| aatgctttaa | catgtggggt | ttgggttaac | tatcatcatt | tcatagatca | ctattttgtt | 1560 |
| ttcgtttgtt | acctaacttt | ttgttatctt | tgaaaaataa | tgttccacga | gttgattgac | 1620 |

| | | |
|---|---|---|
| tggacataaa aatcagattc tctcactcat ttacgttcta cggttctagc cactcgtttt | 1680 | |
| tttcttttc tttctgtggt gtaacacgta gataatggat tttctatgtg tgtcgtcttg | 1740 | |
| ctcaagaata ataaatgtgg ttaaaggtta aatatagctc tggaaattaa ttatctcctc | 1800 | |
| tttttttatt aaccaggatt ttctaggatc aggtgtcgat tttccggtgg gaaacgtctc | 1860 | |
| gttcttcctc ttctactcgg gtcacgtcgc cggttcgatg atcgcatctt tggacataag | 1920 | |
| gagaatgcag aggatgagac tagcgatgct ttttgacatc tcaatgtat tacaatcgat | 1980 | |
| caggctgctc gggacgagag gacactacac gattgatctc gctgtcggag ttggcgctgg | 2040 | |
| gattctcttt gattcattcg ccggcaagta cgaagagatg ataagcaaga gacacaattt | 2100 | |
| agtcaatggt tttggtttga tttcgaaaga ctcgctagtc aattaa | 2146 | |

<210> SEQ ID NO 41
<211> LENGTH: 906
<212> TYPE: DNA
<213> ORGANISM: Artificial Sequence
<220> FEATURE:
<223> OTHER INFORMATION: modified nucleic acid that can encode a
    modified ROD1 polypeptide

<400> SEQUENCE: 41

| | | |
|---|---|---|
| atgtcaacta aaccgtcgt ccctctccgt cgcagatcta agcccttaa cggaaatcac | 60 | |
| actaacggcg tcgccattga cggaagcctc gacgacgacc acaaccgtcg catcggatca | 120 | |
| gtaaatagcc aaatggataa cattgctaag aaaacggacg acggctacgc aaacggcgga | 180 | |
| ggaggaggag gaggagggaa aagcaaggcg tcgtttatga cgtggacggc gcgtgacgtt | 240 | |
| gtgtacgtgg cgaggtacca ttggataccg tgtttgttcg cggtcggggt tctgttcttc | 300 | |
| acgggcgtga agtacacgct ccagatgatt cccgcgaggt ctgagccgtt cgatattggg | 360 | |
| tttgtggcca cgcgctctct gaatcgcgtc ttggcaaatt caccggatct taacaccgtc | 420 | |
| ttagccgctc taaacacggt gttcgtaggg atgcaaacga cgtatattgt atggacatgg | 480 | |
| ttaatggaag gacgaccacg agccaccatc tcggcttgct tcatgtttac ttgtcgaggc | 540 | |
| attcttggtt actctactca gctccctctt cctcaggatt ttctaggatc aggtgtcgat | 600 | |
| tttccggtgg gaaacgtctc gttcttcctc ttctactcgg gtcacgtcgc cggttcgatg | 660 | |
| atcgcatctt tggacataag gagaatgcag aggatgagac tagcgatgct ttttgacatc | 720 | |
| ctcaatgtat tacaatcgat caggctgctc gggacgagag gacactacac gattgatctc | 780 | |
| gctgtcggag ttggcgctgg gattctcttt gattcattcg ccggcaagta cgaagagatg | 840 | |
| ataagcaaga gacacaattt agtcaatggt tttggtttga tttcgaaaga ctcgctagtc | 900 | |
| aattaa | 906 | |

<210> SEQ ID NO 42
<211> LENGTH: 2146
<212> TYPE: DNA
<213> ORGANISM: Artificial Sequence
<220> FEATURE:
<223> OTHER INFORMATION: modified nucleic acid that can encode a
    modified ROD1 polypeptide

<400> SEQUENCE: 42

| | | |
|---|---|---|
| atgtcaacta aaccgtcgt ccctctccgt cgcagatcta agcccttaa cggaaatcac | 60 | |
| actaacggcg tcgccattga cggaagcctc gacgacgacc acaaccgtcg catcggatca | 120 | |
| gtaaatagcc aaatggataa cattgctaag aaaacggacg acggctacgc aaacggcgga | 180 | |

```
ggaggaggag gaggagggaa aagcaaggcg tcgtttatga cgtggacggc gcgtgacgtt    240
gtgtacgtgg cgaggtacca ttggataccg tgtttgttcg cggtcggggt tctgttcttc    300
acgggcgtgg agtacacgct ccagatgatt cccgcgaggt ctgagccgtt cgatattggg    360
tttgtggcca cgcgctctct gaatcgcgtc ttggcaaatt caccggatct aacaccgtc     420 ttagccgctc taaacacggt aatttcgtac taattaattt agggtaaaaa atatagtatt    480
taataatgac tatcctcaat tcctttcatg cttcacctaa tattttgttt ttttcgttg     540 tcattaaaat cgtaataata tattgagtta gtcaaatgaa aaaacaagt ggcggtagtg     600 attggaaaca aatctcagat cttttatctg tttaataagg tatttaatta tccagctgga    660
attatgctgt caagtgtcaa cacagtagta gtaacatgca atggaatttc tcaatagaaa    720
aaggtcttaa ttagtataga taattagtgg acaaaaatgt agttaatgta atctctttgc    780
taagtagtta tcataatcat cttttttaaca actgccattt tgtctgtgtg tttgttttac   840
aacgaagtag tagtagaata gatcgctttt tagcttttga aagtttcgaa cccaaggaaa    900
agggacacat gggttatgag ttggagacac gatcacatgc aaacagagag attggttaaa    960
ttatcgactt tttgtagtac tttttaaaaa aaaactattt atataaaaaa catggtggat   1020
ggtggggaca ggtgttcgta gggatgcaaa cgacgtatat tgtatggaca tggttaatgg   1080
aaggacgacc acgagccacc atctcggctt gcttcatgtt tacttgtcga ggcattcttg   1140
gttactctac tcagctccct cttcctcagg ttccaatcaa cacttttctt ctatctcttt   1200
tcttaattaa aataattacc aattaactaa atgctaatca gtcgatatat catagttcca   1260
acgttttgga cgtgtgattt ccattggcca ctaccatata aaacaacaga gtctctttat   1320
tcattattca atatatattt gagtattgat attattcata gggaggtttc atttgtacta   1380
tcaataaaat ttctacaact cttggatttt ttctgctaca ttttgtagtt attttttaa    1440 ttacttttaa aaacttgtga ataggagaga ctaatagtag tacgtaatat gattgtatca   1500
aatgctttaa catgtggggt ttgggttaac tatcatcatt tcatagatca ctattttgtt   1560
ttcgtttgtt acctaacttt ttgttatctt tgaaaaataa tgttccacga gttgattgac   1620
tggacataaa aatcagattc tctcactcat ttacgttcta cggttctagc cactcgtttt   1680 tttcttttc tttctgtggt gtaacacgta gataatggat tttctatgtg tgtcgtcttg   1740
ctcaagaata ataaatgtgg ttaaaggtta aatatagctc tggaaattaa ttatctcctc   1800 ttttttatt aaccaggatt ttctaggatc aggtgtcgat tttccggtgg gaaacgtctc    1860
gttcttcctc ttctactcgg gtcacgtcgc cggttcgatg atcgcatctt tggacatgag   1920
gagaatgcag aggatgagac tagcgatgct ttttgacatc ctcaatgtat tacaatcgat   1980
caagctgctc gggacgagag gacactacac gattgatctc gctgtcggag ttggcgctgg   2040
gattctcttt gattcattcg ccggcaagta cgaagagatg ataagcaaga gacacaattt   2100
agtcaatggt tttggtttga tttcgaaaga ctcgctagtc aattaa                  2146
```

<210> SEQ ID NO 43
<211> LENGTH: 906
<212> TYPE: DNA
<213> ORGANISM: Artificial Sequence
<220> FEATURE:
<223> OTHER INFORMATION: modified nucleic acid that can encode a
      modified ROD1 polypeptide

<400> SEQUENCE: 43

```
atgtcaacta aaaccgtcgt ccctctccgt cgcagatcta agccccttaa cggaaatcac      60
actaacggcg tcgccattga cggaagcctc gacgacgacc acaaccgtcg catcggatca     120
gtaaatagcc aaatggataa cattgctaag aaaacgacg acggctacgc aaacggcgga     180
ggaggaggag gaggagggaa aagcaaggcg tcgtttatga cgtggacggc gcgtgacgtt     240
gtgtacgtgg cgaggtacca ttggataccg tgtttgttcg cggtcggggt tctgttcttc     300
acgggcgtgg agtacacgct ccagatgatt cccgcgaggt ctgagccgtt cgatattggg     360
tttgtggcca cgcgctctct gaatcgcgtc ttggcaaatt caccggatct taacaccgtc     420
ttagccgctc taaacacggg gttcgtaggg atgcaaacga cgtatattgt atggacatgg     480
ttaatggaag gacgaccacg agccaccatc tcggcttgct tcatgtttac ttgtcgaggc     540
attcttggtt actctactca gctccctctt cctcaggatt ttctaggatc aggtgtcgat     600
tttccggtgg aaacgtctc gttcttcctc ttctactcgg gtcacgtcgc cggttcgatg     660
atcgcatctt tggacatgag gagaatgcag aggatgagac tagcgatgct tttttgacatc     720
ctcaatgtat tacaatcgat caagctgctc gggacgagag gacactacac gattgatctc     780
gctgtcggag ttggcgctgg gattctcttt gattcattcg ccggcaagta cgaagagatg     840
ataagcaaga gacacaattt agtcaatggt tttggttttga tttcgaaaga ctcgctagtc     900
aattaa                                                                906
```

<210> SEQ ID NO 44
<211> LENGTH: 301
<212> TYPE: PRT
<213> ORGANISM: Arabidopsis thaliana

<400> SEQUENCE: 44

```
Met Ser Ala Ala Ala Glu Thr Asp Val Ser Leu Arg Arg Arg Ser
1               5                   10                  15

Asn Ser Leu Asn Gly Asn His Thr Asn Gly Val Ala Ile Asp Gly Thr
            20                  25                  30

Leu Asp Asn Asn Arg Arg Val Gly Asp Thr Asn Thr His Met Asp
        35                  40                  45

Ile Ser Ala Lys Lys Thr Asp Asn Gly Tyr Ala Asn Gly Val Gly Gly
    50                  55                  60

Gly Gly Trp Arg Ser Lys Ala Ser Phe Thr Thr Trp Thr Ala Arg Asp
65                  70                  75                  80

Ile Val Tyr Val Val Arg Tyr His Trp Ile Pro Cys Met Phe Ala Ala
                85                  90                  95

Gly Leu Leu Phe Phe Met Gly Val Glu Tyr Thr Leu Gln Met Ile Pro
            100                 105                 110

Ala Arg Ser Glu Pro Phe Asp Leu Gly Phe Val Val Thr Arg Ser Leu
        115                 120                 125

Asn Arg Val Leu Ala Ser Ser Pro Asp Leu Asn Thr Val Leu Ala Ala
    130                 135                 140

Leu Asn Thr Val Phe Val Gly Met Gln Thr Thr Tyr Ile Val Trp Thr
145                 150                 155                 160

Trp Leu Val Glu Gly Arg Ala Arg Ala Thr Ile Ala Ala Leu Phe Met
                165                 170                 175

Phe Thr Cys Arg Gly Ile Leu Gly Tyr Ser Thr Gln Leu Pro Leu Pro
            180                 185                 190
```

```
Gln Asp Phe Leu Gly Ser Gly Val Asp Phe Pro Val Gly Asn Val Ser
        195                 200                 205

Phe Phe Leu Phe Phe Ser Gly His Val Ala Gly Ser Met Ile Ala Ser
    210                 215                 220

Leu Asp Met Arg Arg Met Gln Arg Leu Arg Leu Ala Met Val Phe Asp
225                 230                 235                 240

Ile Leu Asn Val Leu Gln Ser Ile Arg Leu Leu Gly Thr Arg Gly His
                245                 250                 255

Tyr Thr Ile Asp Leu Ala Val Gly Val Gly Ala Gly Ile Leu Phe Asp
            260                 265                 270

Ser Leu Ala Gly Lys Tyr Glu Glu Met Met Ser Lys Arg His Leu Gly
        275                 280                 285

Thr Gly Phe Ser Leu Ile Ser Lys Asp Ser Leu Val Asn
    290                 295                 300

<210> SEQ ID NO 45
<211> LENGTH: 301
<212> TYPE: PRT
<213> ORGANISM: Thlaspi arvense

<400> SEQUENCE: 45

Met Ser Thr Lys Thr Val Val Pro Leu Arg Arg Ser Lys Pro Leu
1               5                   10                  15

Asn Gly Asn His Thr Asn Gly Val Ala Ile Asp Gly Ser Leu Asp Asp
            20                  25                  30

Asp His Asn Arg Arg Ile Gly Ser Val Asn Ser Gln Met Asp Asn Ile
        35                  40                  45

Ala Lys Lys Thr Asp Asp Gly Tyr Ala Asn Gly Gly Gly Gly Gly Gly
    50                  55                  60

Gly Gly Lys Ser Lys Ala Ser Phe Met Thr Trp Thr Ala Arg Asp Val
65                  70                  75                  80

Val Tyr Val Ala Arg Tyr His Trp Ile Pro Cys Leu Phe Ala Val Gly
                85                  90                  95

Val Leu Phe Phe Thr Gly Val Glu Tyr Thr Leu Gln Met Ile Pro Ala
            100                 105                 110

Arg Ser Glu Pro Phe Asp Ile Gly Phe Val Ala Thr Arg Ser Leu Asn
        115                 120                 125

Arg Val Leu Ala Asn Ser Pro Asp Leu Asn Thr Val Leu Ala Ala Leu
    130                 135                 140

Asn Thr Val Phe Val Gly Met Gln Thr Thr Tyr Ile Val Trp Thr Trp
145                 150                 155                 160

Leu Met Glu Gly Arg Pro Arg Ala Thr Ile Ser Ala Cys Phe Met Phe
                165                 170                 175

Thr Cys Arg Gly Ile Leu Gly Tyr Ser Thr Gln Leu Pro Leu Pro Gln
            180                 185                 190

Asp Phe Leu Gly Ser Gly Val Asp Phe Pro Val Gly Asn Val Ser Phe
        195                 200                 205

Phe Leu Phe Tyr Ser Gly His Val Ala Gly Ser Met Ile Ala Ser Leu
    210                 215                 220

Asp Met Arg Arg Met Gln Arg Met Arg Leu Ala Met Leu Phe Asp Ile
225                 230                 235                 240

Leu Asn Val Leu Gln Ser Ile Arg Leu Leu Gly Thr Arg Gly His Tyr
                245                 250                 255

Thr Ile Asp Leu Ala Val Gly Val Gly Ala Gly Ile Leu Phe Asp Ser
            260                 265                 270
```

-continued

```
Phe Ala Gly Lys Tyr Glu Glu Met Ile Ser Lys Arg His Asn Leu Val
        275                 280                 285

Asn Gly Phe Gly Leu Ile Ser Lys Asp Ser Leu Val Asn
290                 295                 300

<210> SEQ ID NO 46
<211> LENGTH: 301
<212> TYPE: PRT
<213> ORGANISM: Artificial Sequence
<220> FEATURE:
<223> OTHER INFORMATION: modified ROD1 polypeptide

<400> SEQUENCE: 46

Met Ser Thr Lys Thr Val Val Pro Leu Arg Arg Ser Lys Pro Leu
1               5                   10                  15

Asn Gly Asn His Thr Asn Gly Val Ala Ile Asp Gly Ser Leu Asp Asp
            20                  25                  30

Asp His Asn Arg Arg Ile Gly Ser Val Asn Ser Gln Met Asp Asn Ile
        35                  40                  45

Ala Lys Lys Thr Asp Asp Gly Tyr Ala Asn Gly Gly Gly Gly Gly
    50                  55                  60

Gly Gly Lys Ser Lys Ala Ser Phe Met Thr Trp Thr Ala Arg Asp Val
65                  70                  75                  80

Val Tyr Val Ala Arg Tyr His Trp Ile Pro Cys Leu Phe Ala Val Gly
                85                  90                  95

Val Leu Phe Phe Thr Gly Val Glu Tyr Thr Leu Gln Met Ile Pro Ala
            100                 105                 110

Arg Ser Glu Pro Phe Asp Ile Gly Phe Val Ala Thr Arg Ser Leu Asn
        115                 120                 125

Arg Val Leu Ala Asn Ser Pro Asp Leu Asn Thr Val Leu Ala Ala Leu
    130                 135                 140

Asn Thr Val Phe Val Gly Met Gln Thr Thr Tyr Ile Val Trp Thr Trp
145                 150                 155                 160

Leu Met Glu Gly Arg Pro Arg Ala Thr Ile Ser Ala Cys Phe Met Phe
                165                 170                 175

Thr Cys Arg Gly Ile Leu Gly Tyr Ser Thr Gln Leu Pro Leu Pro Gln
            180                 185                 190

Asp Phe Leu Gly Ser Gly Val Asp Phe Pro Val Gly Asn Val Ser Phe
        195                 200                 205

Phe Leu Phe Tyr Ser Gly His Val Ala Gly Ser Met Ile Ala Ser Leu
    210                 215                 220

Asp Ile Arg Arg Met Gln Arg Met Arg Leu Ala Met Leu Phe Asp Ile
225                 230                 235                 240

Leu Asn Val Leu Gln Ser Ile Arg Leu Leu Gly Thr Arg Gly His Tyr
                245                 250                 255

Thr Ile Asp Leu Ala Val Gly Val Gly Ala Gly Ile Leu Phe Asp Ser
            260                 265                 270

Phe Ala Gly Lys Tyr Glu Glu Met Ile Ser Lys Arg His Asn Leu Val
        275                 280                 285

Asn Gly Phe Gly Leu Ile Ser Lys Asp Ser Leu Val Asn
    290                 295                 300

<210> SEQ ID NO 47
<211> LENGTH: 301
<212> TYPE: PRT
<213> ORGANISM: Artificial Sequence
```

-continued

<220> FEATURE:
<223> OTHER INFORMATION: modified ROD1 polypeptide

<400> SEQUENCE: 47

Met Ser Thr Lys Thr Val Val Pro Leu Arg Arg Ser Lys Pro Leu
1               5                   10                  15

Asn Gly Asn His Thr Asn Gly Val Ala Ile Asp Gly Ser Leu Asp Asp
            20                  25                  30

Asp His Asn Arg Arg Ile Gly Ser Val Asn Ser Gln Met Asp Asn Ile
        35                  40                  45

Ala Lys Lys Thr Asp Asp Gly Tyr Ala Asn Gly Gly Gly Gly Gly
    50                  55                  60

Gly Gly Lys Ser Lys Ala Ser Phe Met Thr Trp Thr Ala Arg Asp Val
65                  70                  75                  80

Val Tyr Val Ala Arg Tyr His Trp Ile Pro Cys Leu Phe Ala Val Gly
                85                  90                  95

Val Leu Phe Phe Thr Gly Val Glu Tyr Thr Leu Gln Met Ile Pro Ala
            100                 105                 110

Arg Ser Glu Pro Phe Asp Ile Gly Phe Val Ala Thr Arg Ser Leu Asn
        115                 120                 125

Arg Val Leu Ala Asn Ser Pro Asp Leu Asn Thr Val Leu Ala Ala Leu
    130                 135                 140

Asn Thr Val Phe Val Gly Met Gln Thr Thr Tyr Ile Val Trp Thr Trp
145                 150                 155                 160

Leu Met Glu Gly Arg Pro Arg Ala Thr Ile Ser Ala Cys Phe Met Phe
                165                 170                 175

Thr Cys Arg Gly Ile Leu Gly Tyr Ser Thr Gln Leu Pro Leu Pro Gln
            180                 185                 190

Asp Phe Leu Gly Ser Gly Val Asp Phe Pro Val Gly Asn Val Ser Phe
        195                 200                 205

Phe Leu Phe Tyr Ser Gly His Val Ala Gly Ser Met Ile Ala Ser Leu
    210                 215                 220

Asp Met Arg Arg Met Gln Arg Met Arg Leu Ala Met Leu Phe Asp Ile
225                 230                 235                 240

Leu Asn Val Leu Gln Ser Ile Lys Leu Leu Gly Thr Arg Gly His Tyr
                245                 250                 255

Thr Ile Asp Leu Ala Val Gly Val Gly Ala Gly Ile Leu Phe Asp Ser
            260                 265                 270

Phe Ala Gly Lys Tyr Glu Glu Met Ile Ser Lys Arg His Asn Leu Val
        275                 280                 285

Asn Gly Phe Gly Leu Ile Ser Lys Asp Ser Leu Val Asn
    290                 295                 300

<210> SEQ ID NO 48
<211> LENGTH: 307
<212> TYPE: PRT
<213> ORGANISM: Oryza sativa

<400> SEQUENCE: 48

Met Pro Pro Pro Pro Pro Ser Leu Thr Ala Asn Thr Ala Ser Ser
1               5                   10                  15

Met Gly Asn Ala Glu Ala Val Val Leu Pro Ala Asn Gly Gly Ala
            20                  25                  30

Arg Arg Arg Ala Asp Lys Val Val His Pro Ala Pro Met Pro Asp Arg
        35                  40                  45

```
Ala Ala Gly Gly Ala Met Glu Arg Glu Gly Gly Val Gly Gly Gly
     50                  55                  60

Gly Glu Val Gly Gly Trp Arg Arg Pro Glu Trp Cys Ser Ala Ala Gly
 65                  70                  75                  80

Val Ala Gly Val Leu Arg Arg His Pro Ala Ala Ala Phe Gly Cys
                 85                  90                  95

Gly Leu Leu Leu Phe Met Ala Val Glu Tyr Thr Ile Pro Met Val Pro
                100                 105                 110

Pro Ala Ala Pro Pro Val Asp Leu Gly Phe Ala Ala Thr Ala Ala Leu
                115                 120                 125

His Ala Gly Ile Ala Ala Arg Pro Trp Leu Asn Ser Leu Leu Ala Ala
            130                 135                 140

Leu Asn Thr Val Phe Val Ala Met Gln Ala Ala Tyr Ile Leu Trp Ala
145                 150                 155                 160

Ile Leu Gly Glu Gly Arg Pro Arg Ala Ala Val Ala Ala Met Met Met
                165                 170                 175

Phe Thr Cys Arg Gly Ala Leu Gly Cys Ala Thr Gln Leu Pro Leu Pro
                180                 185                 190

Ala Glu Phe Leu Gly Ser Gly Met Asp Phe Pro Val Gly Asn Val Ser
            195                 200                 205

Phe Phe Leu Phe Phe Ser Gly His Val Ala Gly Ala Val Ile Ala Ala
210                 215                 220

Glu Asp Met Arg Arg Ala Gly Arg Arg Gly Met Ala Arg Leu Tyr Asp
225                 230                 235                 240

Ala Leu Asn Leu Leu Gln Gly Val Arg Leu Leu Ala Cys Arg Gly His
                245                 250                 255

Tyr Thr Ile Asp Leu Ala Val Gly Val Gly Ala Gly Leu Leu Phe Asp
                260                 265                 270

Met Leu Ala Gly Arg Tyr Leu Asp Gly Lys Asn Thr Val Asp Gly Gly
            275                 280                 285

Ala Ala Val Ala Pro Gly Ser Arg Cys Cys Ser Cys His Lys Ala Leu
            290                 295                 300

Leu Ser Gln
305

<210> SEQ ID NO 49
<211> LENGTH: 279
<212> TYPE: PRT
<213> ORGANISM: Glycine max

<400> SEQUENCE: 49

Met Asn Gly Gly Ala Glu Ala Ser Val Asn His Arg Arg His Gln
  1               5                  10                  15

Ala Ala Ser Ala Asn Gly Val Lys Ile Ala Asn Gly Ala Met Ala Lys
                 20                  25                  30

Pro Ser Ser Thr Leu Cys Tyr Asp Ala Ser Phe Met Lys Trp Thr Val
             35                  40                  45

Ala Asp Ala Val His Val Ala Thr His His Trp Met Pro Cys Leu Phe
 50                  55                  60

Ala Leu Gly Leu Leu Phe Phe Met Ala Val Glu Tyr Thr Leu Leu Met
 65                  70                  75                  80

Val Pro Pro Ser Ser Pro Pro Phe Asp Leu Gly Phe Ile Ala Thr Arg
                 85                  90                  95

Ser Leu His Ala Leu Leu Glu Ser Pro Asn Leu Asn Thr Leu Phe
                100                 105                 110
```

```
Ala Gly Leu Asn Thr Val Phe Val Gly Met Gln Thr Ser Tyr Ile Leu
            115                 120                 125

Trp Thr Trp Leu Ile Glu Gly Arg Pro Arg Ala Thr Ile Ser Ala Leu
        130                 135                 140

Phe Met Phe Thr Cys Arg Gly Ile Leu Gly Tyr Ser Thr Gln Leu Pro
145                 150                 155                 160

Leu Pro Gln Gly Phe Leu Gly Ser Gly Val Asp Phe Pro Val Gly Asn
                165                 170                 175

Val Ser Phe Phe Leu Phe Phe Ser Gly His Val Ala Gly Ser Val Ile
            180                 185                 190

Ala Ser Leu Asp Met Arg Arg Met Gln Arg Trp Glu Leu Ala Trp Thr
        195                 200                 205

Phe Asp Val Leu Asn Val Leu Gln Ala Val Arg Leu Leu Gly Thr Arg
210                 215                 220

Gly His Tyr Thr Ile Asp Leu Ala Val Gly Val Gly Ala Gly Ile Leu
225                 230                 235                 240

Phe Asp Ser Leu Ala Gly Lys Tyr Glu Asp Ser Lys Arg Asn Ala Ala
                245                 250                 255

Leu Ser Thr Thr His Arg Ala Gln Phe Asp Cys Val Asn Asn Val Asp
            260                 265                 270

Ile Ala Lys Lys Ile Asn Lys
            275

<210> SEQ ID NO 50
<211> LENGTH: 293
<212> TYPE: PRT
<213> ORGANISM: Solanum lycopersicum

<400> SEQUENCE: 50

Met Asn Gly Asp Thr Phe His Ser Arg Asn Ser Ser Ser Thr Leu
1               5                   10                  15

Ser Lys Arg Asn Thr Thr Glu Arg Lys Val Asp Val Thr Glu Met Lys
            20                  25                  30

Lys Lys Ser Ala Ser Ala Thr Gly Thr Glu Val Gly Gly Tyr Gly Trp
        35                  40                  45

Trp Leu Gly Asn Ala Tyr Phe Met Lys Trp Arg Met Glu Asp Val Phe
    50                  55                  60

Gly Val Val Lys Tyr His Pro Ile Pro Cys Ile Phe Ala Ala Ser Leu
65                  70                  75                  80

Leu Phe Phe Met Gly Val Glu Tyr Thr Leu His Met Ile Pro Ala Ser
                85                  90                  95

Ala Pro Pro Phe Asp Leu Gly Phe Ile Val Thr Val Pro Leu Asn Arg
            100                 105                 110

Leu Leu Ala Ala Lys Pro Ala Leu Asn Thr Leu Phe Ala Gly Leu Asn
        115                 120                 125

Thr Val Phe Val Ala Met Gln Thr Ala Tyr Ile Leu Gly Thr Phe Leu
130                 135                 140

Ile Glu Gly Arg Pro Arg Ala Thr Ile Ser Ala Leu Phe Met Phe Thr
145                 150                 155                 160

Phe Arg Gly Ile Leu Gly Tyr Ala Thr Gln Leu Pro Leu Pro Glu Asp
                165                 170                 175

Phe Leu Gly Ser Gly Val Asp Phe Pro Val Gly Asn Val Ser Phe Phe
            180                 185                 190
```

-continued

```
Leu Phe Tyr Ser Gly His Val Ala Ala Ser Val Ile Ala Ser Leu Asp
        195                 200                 205

Met Lys Arg Met Gln Arg Trp Glu Met Ala Arg Val Phe Asp Ala Leu
    210                 215                 220

Asn Val Leu Gln Val Val Arg Leu Leu Ser Thr Arg Gly His Tyr Thr
225                 230                 235                 240

Ile Asp Leu Ala Val Gly Ile Gly Ala Gly Ile Leu Phe Asp Ser Met
            245                 250                 255

Ala Gly Asn Tyr Val Glu Thr Arg Thr Lys Leu Ser Ala Thr Asn Gly
            260                 265                 270

Ile Gly Val Glu Tyr Ser Pro Lys His Glu Asn Gly Val Lys Tyr Gln
        275                 280                 285

Ser Val Ser Ser Asp
    290
```

PLANTS HAVING INCREASED OIL QUALITY

CROSS-REFERENCE TO RELATED APPLICATIONS

This application claims the benefit of U.S. Patent Application Ser. No. 62/825,283, filed on Mar. 28, 2019. The disclosure of the prior application is considered part of (and is incorporated by reference in) the disclosure of this application.

STATEMENT REGARDING FEDERAL FUNDING

This invention was made with government support under 2014-67009-22305 and 2018-67009-27374 awarded by the United States Department of Agriculture. The government has certain rights in the invention.

BACKGROUND

1. Technical Field

This document relates to oilseed plants (e.g., pennycress plants) having increased levels of one or more saturated fatty acids, increased levels of one or more polyunsaturated fatty acids (PUFAs), altered (e.g., increased or decreased) levels of oleic acid, and/or altered (e.g., increased or decreased) levels of erucic acid. For example, oilseed plants having reduced polypeptide levels and/or reduced polypeptide activity of one or more polypeptides involved in triglyceride synthesis (e.g., diacylglycerol O-acyltransferase 1 (TAG1) can have increased levels of one or more saturated fatty acids, increased levels of one or more PUFAs, altered levels of oleic acid, and/or altered levels of erucic acid. Also provided herein are methods and materials for making and using oilseed plants having increased levels of one or more saturated fatty acids, increased levels of one or more PUFAs, altered levels of oleic acid, and/or altered levels of erucic acid.

2. Background Information

Oilseed crops are sources of oils and seed meal having a multitude of uses. Winter annual varieties of pennycress (*Thlaspi arvense* L.) have been developed into a crop species that can be grown on the fallow land available between the harvest of corn and the sowing of soybeans the following year (Phippen et al., 2012 *Crop Science,* 52:2767-2773). There are over eighty million acres of land undergoing the corn/soybean rotation (e.g., in the United States, Argentina, and elsewhere) that could be used for double cropping pennycress. In addition, both winter and spring varieties of pennycress can be grown on land in the spring and harvested as an early stand-alone summer crop. Pennycress can yield over 2000 pounds per acre of oilseeds that naturally contain up to 35% oil (Boateng et al., 2010 *Energy & Fuels,* 24:6624-6632; and Warwick et al., 2002 *Canadian Journal of Plant Science,* 82:803-823). The extracted oil can be easily converted into a variety of biofuels including biodiesel and jet fuel (Moser et al., 2009 *Energy & Fuels,* 23:4149-4155). However, natural fatty acid profiles of wild pennycress strains make pennycress oil inedible for humans (Bell, 1993 *Canadian Journal of Animal Science,* 73:679-697), and render pennycress oil of suboptimal quality for both biofuel and food production.

SUMMARY

This document provides oilseed plants (e.g., pennycress plants) having increased levels of one or more saturated fatty acids, increased levels of one or more PUFAs, altered (e.g., increased or decreased) levels of oleic acid, and/or altered (e.g., increased or decreased) levels of erucic acid (e.g., as compared to corresponding wild type plants). For example, oilseed plants having reduced polypeptide levels and/or reduced polypeptide activity of one or more polypeptides involved in triglyceride synthesis (e.g., TAG1) can have increased levels of one or more saturated fatty acids, increased levels of one or more PUFAs, altered (e.g., increased or decreased) levels of oleic acid, and/or altered (e.g., increased or decreased) levels of erucic acid (e.g., as compared to corresponding wild type plants). Also provided herein are methods and materials for making and using oilseed plants having increased levels of one or more saturated fatty acids, increased levels of one or more PUFAs, and/or altered (e.g., increased or decreased) levels of oleic acid, and/or altered (e.g., increased or decreased) levels of erucic acid.

As demonstrated herein, pennycress plants having one or more modifications in a nucleic acid encoding a TAG1 polypeptide (e.g., such that the encoded TAG1 polypeptide having reduced TAG1 polypeptide activity) produce seeds having seed oils with increased levels of one or more saturated fatty acids, increased levels of PUFAs, altered (e.g., increased or decreased) levels of oleic acid, and/or altered (e.g., increased or decreased) levels of erucic acid.

Stearic acid and palmitic acid can be used in the formation of many products including cosmetics, foods, medical lotions, and other bio-products. Currently the main source for stearic acid is palm oil. The demand for palm oil is one factor driving the destruction of rain forests in Southeast Asia. Having the ability to design oilseed plants (e.g., pennycress plants) having increased levels of one or more saturated fatty acids such as stearic acid, increased levels of PUFAs, altered (e.g., increased or decreased) levels of oleic acid, and/or altered (e.g., increased or decreased) levels of erucic acid provides a unique and unrealized opportunity to grow plants having improved oil quality. For example, the oilseed plants provided herein can be grown in the interval between the harvest of summer crops (e.g., corn) and the establishment of the following spring crops (e.g., soybean) or as a stand-alone crops (e.g., stand-alone crops grown in the early spring and harvested in the early summer) in the Midwestern United States, thereby maximizing potential production from land already in use and reducing the cost of producing the oilseed plants provided herein. The oilseed plants described herein can provide a new source of oilseeds and/or oils that can be used to produce (e.g., can be used as an ingredient in) a variety of products including both food products and non-food products. For example, oils with increased levels of one or more saturated fatty acids can be used in (e.g., used in the production of) food products (e.g., for human consumption and/or as a feedstock), cosmetics, lotions (e.g., medical lotions), and/or bio-based products (e.g., biofuels such as biodiesel and bio jet fuel, bioproducts such as biopolymers used for the production of, for example, bioplastics). For example, oils with increased levels PUFAs can be used as a drying agent (e.g., a drying agent in paints), as a food additive (e.g., a heart healthy food additive such as a high omega-3 food supplement), and/or as food for farmed fish. Oil with increased erucic acid can be used as an industrial feedstock, while oil with reduced erucic acid is suitable as a food source for humans and animals. Further, oilseed plants described herein can be used as a model system to analyze fatty-acid flux in oilseeds.

In general, one aspect of this document features oilseed plants having an increased level of a saturated fatty acid, as compared to a corresponding wild type oilseed plant, where the oilseed plant includes a modified nucleic acid encoding a TAG1 polypeptide, and where the modified nucleic acid can encode a modified TAG1 polypeptide. The saturated fatty acid can include stearic acid or palmitic acid. The saturated fatty acid can include stearic acid and palmitic acid. The modified TAG1 polypeptide can have a reduced expression level and/or reduced polypeptide activity. The modified nucleic acid encoding a TAG1 polypeptide can include a single base-pair substitution. In some cases, the modified nucleic acid encoding a TAG1 polypeptide can have a nucleic acid sequence set forth in SEQ ID NO:11 or SEQ ID NO:12. The modified nucleic acid encoding a TAG1 polypeptide can encode a modified TAG1 polypeptide having an amino acid sequence set forth in SEQ ID NO:3. In some cases, the modified nucleic acid encoding a TAG1 polypeptide can have a nucleic acid sequence set forth in SEQ ID NO:13 or SEQ ID NO:14. The modified nucleic acid encoding a TAG1 polypeptide can encode a modified TAG1 polypeptide having an amino acid sequence set forth in SEQ ID NO:4. In some cases, the modified nucleic acid encoding a TAG1 polypeptide can have a nucleic acid sequence set forth in SEQ ID NO:15 or SEQ ID NO:16. The modified nucleic acid encoding a TAG1 polypeptide can encode a modified TAG1 polypeptide having an amino acid sequence set forth in SEQ ID NO:5. The oilseed plant also can include a modified nucleic acid encoding a polypeptide involved in fatty acid biosynthesis, where the modified nucleic acid can encode a modified polypeptide involved in fatty acid biosynthesis having a reduced expression levels and/or reduced polypeptide activity. The polypeptide involved in fatty acid biosynthesis can be a fatty acid dehydrogenase 2 (FAD2) polypeptide, a fatty acid elongase 1 (FAE1) polypeptide, or a reduced oleate desaturation 1 (ROD1) polypeptide. In some cases, the polypeptide involved in fatty acid biosynthesis can be a FAD2 polypeptide, and the modified nucleic acid encoding the FAD2 polypeptide can encode a modified FAD2 polypeptide having an amino acid sequence set forth in SEQ ID NO:25. The modified nucleic acid encoding the modified FAD2 polypeptide can include a nucleic acid sequence set forth in SEQ ID NO:17 or SEQ ID NO:18. In some cases, polypeptide involved in fatty acid biosynthesis can be a FAD2 polypeptide, and the modified nucleic acid encoding said FAD2 polypeptide can encode a modified FAD2 polypeptide having an amino acid sequence set forth in SEQ ID NO:26. The modified nucleic acid encoding the modified FAD2 polypeptide can include a nucleic acid sequence set forth in SEQ ID NO:19 or SEQ ID NO:20. In some cases, the polypeptide involved in fatty acid biosynthesis can be a FAD2 polypeptide, and the modified nucleic acid encoding said FAD2 polypeptide can encode a modified FAD2 polypeptide having an amino acid sequence set forth in SEQ ID NO:27. The modified nucleic acid encoding the modified FAD2 polypeptide can include a nucleic acid sequence set forth in SEQ ID NO:21 or SEQ ID NO:22. In some cases, the polypeptide involved in fatty acid biosynthesis can be a FAE1 polypeptide, and the modified nucleic acid encoding said FAE1 polypeptide can encode a modified FAE1 polypeptide comprising an amino acid sequence set forth in SEQ ID NO:35.

The modified nucleic acid encoding the modified FAE1 polypeptide can include a nucleic acid sequence set forth in SEQ ID NO:31. In some cases, the polypeptide involved in fatty acid biosynthesis can be a FAE1 polypeptide, and the modified nucleic acid encoding the FAE1 polypeptide can encode a modified FAE1 polypeptide having an amino acid sequence set forth in SEQ ID NO:36. The modified nucleic acid encoding the modified FAE1 polypeptide can include a nucleic acid sequence set forth in SEQ ID NO:32. In some cases, the polypeptide involved in fatty acid biosynthesis can be a ROD1 polypeptide, and the modified nucleic acid encoding the ROD1 polypeptide can encode a modified ROD1 polypeptide having an amino acid sequence set forth in SEQ ID NO:46. The modified nucleic acid encoding said modified ROD1 polypeptide can include a nucleic acid sequence set forth in SEQ ID NO:40 or SEQ ID NO:41. In some cases, the polypeptide involved in fatty acid biosynthesis can be a ROD1 polypeptide, and the modified nucleic acid encoding the ROD1 polypeptide can encode a modified ROD1 polypeptide having an amino acid sequence set forth in SEQ ID NO:47. The modified nucleic acid encoding the modified ROD1 polypeptide can include a nucleic acid sequence set forth in SEQ ID NO:42 or SEQ ID NO:43. The oilseed plant can be a pennycress, rapeseed, soybean, sunflower, peanut, canola, flax, camelina, carinata, crambe, or lepidium plant.

In another aspect, this document features oilseed plants having an increased level of a PUFA, as compared to a corresponding wild type oilseed plant, where the oilseed plant includes a modified nucleic acid encoding a TAG1 polypeptide, and where the modified nucleic acid can encode a modified TAG1 polypeptide. The PUFA can include linoleic acid or linolenic acid. The PUFA can include linoleic acid and linolenic acid. The modified TAG1 polypeptide can have a reduced expression level and/or reduced polypeptide activity. The modified nucleic acid encoding a TAG1 polypeptide can include a single base-pair substitution. In some cases, the modified nucleic acid encoding a TAG1 polypeptide can have a nucleic acid sequence set forth in SEQ ID NO:11 or SEQ ID NO:12. The modified nucleic acid encoding a TAG1 polypeptide can encode a modified TAG1 polypeptide having an amino acid sequence set forth in SEQ ID NO:3. In some cases, the modified nucleic acid encoding a TAG1 polypeptide can have a nucleic acid sequence set forth in SEQ ID NO:13 or SEQ ID NO:14. The modified nucleic acid encoding a TAG1 polypeptide can encode a modified TAG1 polypeptide having an amino acid sequence set forth in SEQ ID NO:4. In some cases, the modified nucleic acid encoding a TAG1 polypeptide can have a nucleic acid sequence set forth in SEQ ID NO:15 or SEQ ID NO:16. The modified nucleic acid encoding a TAG1 polypeptide can encode a modified TAG1 polypeptide having an amino acid sequence set forth in SEQ ID NO:5. The oilseed plant also can include a modified nucleic acid encoding a polypeptide involved in fatty acid biosynthesis, where the modified nucleic acid can encode a modified polypeptide involved in fatty acid biosynthesis having a reduced expression levels and/or reduced polypeptide activity. The polypeptide involved in fatty acid biosynthesis can be a fatty acid dehydrogenase 2 (FAD2) polypeptide, a fatty acid elongase 1 (FAE1) polypeptide, or a reduced oleate desaturation 1 (ROD1) polypeptide. In some cases, the polypeptide involved in fatty acid biosynthesis can be a FAD2 polypeptide, and the modified nucleic acid encoding the FAD2 polypeptide can encode a modified FAD2 polypeptide having an amino acid sequence set forth in SEQ ID NO:25. The modified nucleic acid encoding the modified FAD2 polypeptide can include a nucleic acid sequence set forth in SEQ ID NO:17 or SEQ ID NO:18. In some cases, polypeptide involved in fatty acid biosynthesis can be a FAD2 polypeptide, and the modified nucleic acid encoding said FAD2 polypeptide can encode a modified FAD2 polypeptide having an amino acid sequence set forth in SEQ ID NO:26. The modified nucleic acid encoding the modified FAD2 polypeptide can include a nucleic acid sequence set forth in SEQ ID NO:19 or SEQ ID NO:20. In some cases, the polypeptide involved in fatty acid biosynthesis can be a FAD2 polypeptide, and the modified nucleic acid encoding said FAD2 polypeptide can encode a modified FAD2 polypeptide having an amino acid sequence set forth in SEQ ID NO:27. The modified nucleic acid encoding the modified FAD2 polypeptide can include a nucleic acid sequence set forth in SEQ ID NO:21 or SEQ ID NO:22. In some cases, the polypeptide involved in fatty acid biosynthesis can be a FAE1 polypeptide, and the modified nucleic acid encoding said FAE1 polypeptide can encode a modified FAE1 polypeptide comprising an amino acid sequence set forth in SEQ ID NO:35. The modified nucleic acid encoding the modified FAE1 polypeptide can include a nucleic acid sequence set forth in SEQ ID NO:31. In some cases, the polypeptide involved in fatty acid biosynthesis can be a FAE1 polypeptide, and the modified nucleic acid encoding the FAE1 polypeptide can encode a modified FAE1 polypeptide having an amino acid sequence set forth in SEQ ID NO:36. The modified nucleic acid encoding the modified FAE1 polypeptide can include a nucleic acid sequence set forth in SEQ ID NO:32. In some cases, the polypeptide involved in fatty acid biosynthesis can be a ROD1 polypeptide, and the modified nucleic acid encoding the ROD1 polypeptide can encode a modified ROD1 polypeptide having an amino acid sequence set forth in SEQ ID NO:46. The modified nucleic acid encoding said modified ROD1 polypeptide can include a nucleic acid sequence set forth in SEQ ID NO:40 or SEQ ID NO:41. In some cases, the polypeptide involved in fatty acid biosynthesis can be a ROD1 polypeptide, and the modified nucleic acid encoding the ROD1 polypeptide can encode a modified ROD1 polypeptide having an amino acid sequence set forth in SEQ ID NO:47. The modified nucleic acid encoding the modified ROD1 polypeptide can include a nucleic acid sequence set forth in SEQ ID NO:42 or SEQ ID NO:43. The oilseed plant can be a pennycress, rapeseed, soybean, sunflower, peanut, canola, flax, camelina, carinata, crambe, or lepidium plant.

In another aspect, this document features oilseed plants having a decreased levels of oleic acid, as compared to a corresponding wild type oilseed plant, where the oilseed plant comprises a modified nucleic acid encoding a TAG1 polypeptide, and where the modified nucleic acid can encode a modified TAG1 polypeptide. The modified TAG1 polypeptide can have a reduced expression level and/or reduced polypeptide activity. The modified nucleic acid encoding a TAG1 polypeptide can include a single base-pair substitution. In some cases, the modified nucleic acid encoding a TAG1 polypeptide can have a nucleic acid sequence set forth in SEQ ID NO:11 or SEQ ID NO:12. The modified nucleic acid encoding a TAG1 polypeptide can encode a modified TAG1 polypeptide having an amino acid sequence set forth in SEQ ID NO:3. In some cases, the modified nucleic acid encoding a TAG1 polypeptide can have a nucleic acid sequence set forth in SEQ ID NO:13 or SEQ ID NO:14. The modified nucleic acid encoding a TAG1 polypeptide can encode a modified TAG1 polypeptide having an amino acid sequence set forth in SEQ ID NO:4. In some cases, the modified nucleic acid encoding a TAG1 polypeptide can have a nucleic acid sequence set forth in SEQ ID NO:15 or SEQ ID NO:16. The modified nucleic acid encoding a TAG1 polypeptide can encode a modified TAG1 polypeptide having an amino acid sequence set forth in SEQ ID NO:5. The oilseed plant also can include a modified nucleic acid encoding a polypeptide involved in fatty acid biosynthesis, where the modified nucleic acid can encode a modified polypeptide involved in fatty acid biosynthesis having a reduced expression levels and/or reduced polypeptide activity. The polypeptide involved in fatty acid biosynthesis can be a fatty acid dehydrogenase 2 (FAD2) polypeptide, a fatty acid elongase 1 (FAE1) polypeptide, or a reduced oleate desaturation 1 (ROD1) polypeptide. In some cases, the polypeptide involved in fatty acid biosynthesis can be a FAD2 polypeptide, and the modified nucleic acid encoding the FAD2 polypeptide can encode a modified FAD2 polypeptide having an amino acid sequence set forth in SEQ ID NO:25. The modified nucleic acid encoding the modified FAD2 polypeptide can include a nucleic acid sequence set forth in SEQ ID NO:17 or SEQ ID NO:18. In some cases, polypeptide involved in fatty acid biosynthesis can be a FAD2 polypeptide, and the modified nucleic acid encoding said FAD2 polypeptide can encode a modified FAD2 polypeptide having an amino acid sequence set forth in SEQ ID NO:26. The modified nucleic acid encoding the modified FAD2 polypeptide can include a nucleic acid sequence set forth in SEQ ID NO:19 or SEQ ID NO:20. In some cases, the polypeptide involved in fatty acid biosynthesis can be a FAD2 polypeptide, and the modified nucleic acid encoding said FAD2 polypeptide can encode a modified FAD2 polypeptide having an amino acid sequence set forth in SEQ ID NO:27. The modified nucleic acid encoding the modified FAD2 polypeptide can include a nucleic acid sequence set forth in SEQ ID NO:21 or SEQ ID NO:22. In some cases, the polypeptide involved in fatty acid biosynthesis can be a FAE1 polypeptide, and the modified nucleic acid encoding said FAE1 polypeptide can encode a modified FAE1 polypeptide comprising an amino acid sequence set forth in SEQ ID NO:35. The modified nucleic acid encoding the modified FAE1 polypeptide can include a nucleic acid sequence set forth in SEQ ID NO:31. In some cases, the polypeptide involved in fatty acid biosynthesis can be a FAE1 polypeptide, and the modified nucleic acid encoding the FAE1 polypeptide can encode a modified FAE1 polypeptide having an amino acid sequence set forth in SEQ ID NO:36. The modified nucleic acid encoding the modified FAE1 polypeptide can include a nucleic acid sequence set forth in SEQ ID NO:32. In some cases, the polypeptide involved in fatty acid biosynthesis can be a ROD1 polypeptide, and the modified nucleic acid encoding the ROD1 polypeptide can encode a modified ROD1 polypeptide having an amino acid sequence set forth in SEQ ID NO:46. The modified nucleic acid encoding said modified ROD1 polypeptide can include a nucleic acid sequence set forth in SEQ ID NO:40 or SEQ ID NO:41. In some cases, the polypeptide involved in fatty acid biosynthesis can be a ROD1 polypeptide, and the modified nucleic acid encoding the ROD1 polypeptide can encode a modified ROD1 polypeptide having an amino acid sequence set forth in SEQ ID NO:47. The modified nucleic acid encoding the modified ROD1 polypeptide can include a nucleic acid sequence set forth in SEQ ID NO:42 or SEQ ID NO:43. The oilseed plant can be a pennycress, rapeseed, soybean, sunflower, peanut, canola, flax, camelina, carinata, crambe, or lepidium plant.

In another aspect, this document features oilseed plants having a decreased level of erucic acid, as compared to a corresponding wild type oilseed plant, where the oilseed plant comprises a modified nucleic acid encoding a TAG1 polypeptide, and where the modified nucleic acid can encode a modified TAG1 polypeptide. The modified TAG1 polypeptide can have a reduced expression level and/or reduced polypeptide activity. The modified nucleic acid encoding a TAG1 polypeptide can include a single base-pair substitution. In some cases, the modified nucleic acid encoding a TAG1 polypeptide can have a nucleic acid sequence set forth in SEQ ID NO:11 or SEQ ID NO:12. The modified nucleic acid encoding a TAG1 polypeptide can encode a modified TAG1 polypeptide having an amino acid sequence set forth in SEQ ID NO:3. In some cases, the modified nucleic acid encoding a TAG1 polypeptide can have a nucleic acid sequence set forth in SEQ ID NO:13 or SEQ ID NO:14. The modified nucleic acid encoding a TAG1 polypeptide can encode a modified TAG1 polypeptide having an amino acid sequence set forth in SEQ ID NO:4. In some cases, the modified nucleic acid encoding a TAG1 polypeptide can have a nucleic acid sequence set forth in SEQ ID NO:15 or SEQ ID NO:16. The modified nucleic acid encoding a TAG1 polypeptide can encode a modified TAG1 polypeptide having an amino acid sequence set forth in SEQ ID NO:5. The oilseed plant also can include a modified nucleic acid encoding a polypeptide involved in fatty acid biosynthesis, where the modified nucleic acid can encode a modified polypeptide involved in fatty acid biosynthesis having a reduced expression levels and/or reduced polypeptide activity. The polypeptide involved in fatty acid biosynthesis can be a fatty acid dehydrogenase 2 (FAD2) polypeptide, a fatty acid elongase 1 (FAE1) polypeptide, or a reduced oleate desaturation 1 (ROD1) polypeptide. In some cases, the polypeptide involved in fatty acid biosynthesis can be a FAD2 polypeptide, and the modified nucleic acid encoding the FAD2 polypeptide can encode a modified FAD2 polypeptide having an amino acid sequence set forth in SEQ ID NO:25. The modified nucleic acid encoding the modified FAD2 polypeptide can include a nucleic acid sequence set forth in SEQ ID NO:17 or SEQ ID NO:18. In some cases, polypeptide involved in fatty acid biosynthesis can be a FAD2 polypeptide, and the modified nucleic acid encoding said FAD2 polypeptide can encode a modified FAD2 polypeptide having an amino acid sequence set forth in SEQ ID NO:26. The modified nucleic acid encoding the modified FAD2 polypeptide can include a nucleic acid sequence set forth in SEQ ID NO:19 or SEQ ID NO:20. In some cases, the polypeptide involved in fatty acid biosynthesis can be a FAD2 polypeptide, and the modified nucleic acid encoding said FAD2 polypeptide can encode a modified FAD2 polypeptide having an amino acid sequence set forth in SEQ ID NO:27. The modified nucleic acid encoding the modified FAD2 polypeptide can include a nucleic acid sequence set forth in SEQ ID NO:21 or SEQ ID NO:22. In some cases, the polypeptide involved in fatty acid biosynthesis can be a FAE1 polypeptide, and the modified nucleic acid encoding said FAE1 polypeptide can encode a modified FAE1 polypeptide comprising an amino acid sequence set forth in SEQ ID NO:35. The modified nucleic acid encoding the modified FAE1 polypeptide can include a nucleic acid sequence set forth in SEQ ID NO:31. In some cases, the polypeptide involved in fatty acid biosynthesis can be a FAE1 polypeptide, and the modified nucleic acid encoding the FAE1 polypeptide can encode a modified FAE1 polypeptide having an amino acid sequence set forth in SEQ ID NO:36. The modified nucleic acid encoding the modified FAE1 polypeptide can include a nucleic acid sequence set forth in SEQ ID NO:32. In some cases, the polypeptide involved in fatty acid biosynthesis can be a ROD1 polypeptide, and the modified nucleic acid encoding the ROD1 polypeptide can encode a modified ROD1 polypeptide having an amino acid sequence set forth in SEQ ID NO:46. The modified nucleic acid encoding said modified ROD1 polypeptide can include a nucleic acid sequence set forth in SEQ ID NO:40 or SEQ ID NO:41. In some cases, the polypeptide involved in fatty acid biosynthesis can be a ROD1 polypeptide, and the modified nucleic acid encoding the ROD1 polypeptide can encode a modified ROD1 polypeptide having an amino acid sequence set forth in SEQ ID NO:47. The modified nucleic acid encoding the modified ROD1 polypeptide can include a nucleic acid sequence set forth in SEQ ID NO:42 or SEQ ID NO:43. The oilseed plant can be a pennycress, rapeseed, soybean, sunflower, peanut, canola, flax, camelina, carinata, crambe, or lepidium plant.

In another aspect, this document features a seed produced by any oilseed plant provided herein as well as seed oil obtained from any oilseed plant provided herein.

In another aspect, this document features pennycress plants having an increased level of stearic acid, as compared to a corresponding wild type oilseed plant, wherein said pennycress plant comprises a) a modified nucleic acid encoding a TAG1 polypeptide, wherein said modified nucleic acid encoding a TAG1 polypeptide can encode a modified TAG1 polypeptide, wherein said modified TAG1 polypeptide has a reduced expression level and/or reduced polypeptide activity; and b) a modified nucleic acid encoding a FAD2 polypeptide, wherein said modified nucleic acid encoding a FAD2 polypeptide can encode a modified FAD2 polypeptide. The pennycress plant can produce oil having from 5 mole % to 55 mole % stearic acid in the total fatty acid content of the oil. The modified nucleic acid encoding a TAG1 polypeptide can include a nucleic acid sequence set forth in SEQ ID NO:11 or SEQ ID NO:12, and the modified nucleic acid encoding a TAG1 polypeptide can encode a modified TAG1 polypeptide having an amino acid sequence set forth in SEQ ID NO:3. The modified nucleic acid encoding a TAG1 polypeptide can include a nucleic acid sequence set forth in SEQ ID NO:13 or SEQ ID NO:14, and the modified nucleic acid encoding a TAG1 polypeptide can encode a modified TAG1 polypeptide having an amino acid sequence set forth in SEQ ID NO:4. The modified nucleic acid encoding a TAG1 polypeptide can include a nucleic acid sequence set forth in SEQ ID NO:15 or SEQ ID NO:16, and the modified nucleic acid encoding a TAG1 polypeptide can encode a modified TAG1 polypeptide having an amino acid sequence set forth in SEQ ID NO:5. The modified nucleic acid encoding a FAD2 polypeptide can include a nucleic acid sequence set forth in SEQ ID NO:17 or SEQ ID NO:18, and the modified nucleic acid encoding said FAD2 polypeptide can encode a modified FAD2 polypeptide having an amino acid sequence set forth in SEQ ID NO:25. The modified nucleic acid encoding a FAD2 polypeptide can include a nucleic acid sequence set forth in SEQ ID NO:19 or SEQ ID NO:20, and the modified nucleic acid encoding said FAD2 polypeptide can encode a modified FAD2 polypeptide having an amino acid sequence set forth in SEQ ID NO:26. The modified nucleic acid encoding a FAD2 polypeptide can include a nucleic acid sequence set forth in SEQ ID NO:21 or SEQ ID NO:22, and the modified nucleic acid encoding said FAD2 polypeptide can encode a modified FAD2 polypeptide having an amino acid sequence set forth in SEQ ID NO:27.

In another aspect, this document features pennycress plants having a decreased level of erucic acid, as compared to a corresponding wild type oilseed plant, wherein said pennycress plant comprises a) a modified nucleic acid encoding a TAG1 polypeptide, wherein said modified nucleic acid encoding a TAG1 polypeptide can encode a modified TAG1 polypeptide, wherein said modified TAG1 polypeptide has a reduced expression level and/or reduced polypeptide activity; and b) a modified nucleic acid encoding a FAD2 polypeptide, wherein said modified nucleic acid encoding a FAD2 polypeptide can encode a modified FAD2 polypeptide. The pennycress plant can produce oil having from 0 mole % to 35 mole % erucic acid in the total fatty acid content of the oil. The modified nucleic acid encoding a TAG1 polypeptide can include a nucleic acid sequence set forth in SEQ ID NO:11 or SEQ ID NO:12, and the modified nucleic acid encoding a TAG1 polypeptide can encode a modified TAG1 polypeptide having an amino acid sequence set forth in SEQ ID NO:3. The modified nucleic acid encoding a TAG1 polypeptide can include a nucleic acid sequence set forth in SEQ ID NO:13 or SEQ ID NO:14, and the modified nucleic acid encoding a TAG1 polypeptide can encode a modified TAG1 polypeptide having an amino acid sequence set forth in SEQ ID NO:4. The modified nucleic acid encoding a TAG1 polypeptide can include a nucleic acid sequence set forth in SEQ ID NO:15 or SEQ ID NO:16, and the modified nucleic acid encoding a TAG1 polypeptide can encode a modified TAG1 polypeptide having an amino acid sequence set forth in SEQ ID NO:5. The modified nucleic acid encoding a FAD2 polypeptide can include a nucleic acid sequence set forth in SEQ ID NO:17 or SEQ ID NO:18, and the modified nucleic acid encoding said FAD2 polypeptide can encode a modified FAD2 polypeptide having an amino acid sequence set forth in SEQ ID NO:25. The modified nucleic acid encoding a FAD2 polypeptide can include a nucleic acid sequence set forth in SEQ ID NO:19 or SEQ ID NO:20, and the modified nucleic acid encoding said FAD2 polypeptide can encode a modified FAD2 polypeptide having an amino acid sequence set forth in SEQ ID NO:26. The modified nucleic acid encoding a FAD2 polypeptide can include a nucleic acid sequence set forth in SEQ ID NO:21 or SEQ ID NO:22, and the modified nucleic acid encoding said FAD2 polypeptide can encode a modified FAD2 polypeptide having an amino acid sequence set forth in SEQ ID NO:27.

In another aspect, this document features pennycress plants having a decreased level of oleic acid, as compared to a corresponding wild type oilseed plant, wherein said pennycress plant comprises a) a modified nucleic acid encoding a TAG1 polypeptide, wherein said modified nucleic acid encoding a TAG1 polypeptide can encode a modified TAG1 polypeptide, wherein said modified TAG1 polypeptide has a reduced expression level and/or reduced polypeptide activity; and b) a modified nucleic acid encoding a FAD2 polypeptide, wherein said modified nucleic acid encoding a FAD2 polypeptide can encode a modified FAD2 polypeptide. The pennycress plant can produce oil having from 0 mole % to 10 mole %. The modified nucleic acid encoding a TAG1 polypeptide can include a nucleic acid sequence set forth in SEQ ID NO:11 or SEQ ID NO:12, and the modified nucleic acid encoding a TAG1 polypeptide can encode a modified TAG1 polypeptide having an amino acid sequence set forth in SEQ ID NO:3. The modified nucleic acid encoding a TAG1 polypeptide can include a nucleic acid sequence set forth in SEQ ID NO:13 or SEQ ID NO:14, and the modified nucleic acid encoding a TAG1 polypeptide can encode a modified TAG1 polypeptide having an amino acid sequence set forth in SEQ ID NO:4. The modified nucleic acid encoding a TAG1 polypeptide can include a nucleic acid sequence set forth in SEQ ID NO:15 or SEQ ID NO:16, and the modified nucleic acid encoding a TAG1 polypeptide can encode a modified TAG1 polypeptide having an amino acid sequence set forth in SEQ ID NO:5. The modified nucleic acid encoding a FAD2 polypeptide can include a nucleic acid sequence set forth in SEQ ID NO:17 or SEQ ID NO:18, and the modified nucleic acid encoding said FAD2 polypeptide can encode a modified FAD2 polypeptide having an amino acid sequence set forth in SEQ ID NO:25. The modified nucleic acid encoding a FAD2 polypeptide can include a nucleic acid sequence set forth in SEQ ID NO:19 or SEQ ID NO:20, and the modified nucleic acid encoding said FAD2 polypeptide can encode a modified FAD2 polypeptide having an amino acid sequence set forth in SEQ ID NO:26. The modified nucleic acid encoding a FAD2 polypeptide can include a nucleic acid sequence set forth in SEQ ID NO:21 or SEQ ID NO:22, and the modified nucleic acid encoding said FAD2 polypeptide can encode a modified FAD2 polypeptide having an amino acid sequence set forth in SEQ ID NO:27.

In another aspect, this document features oilseed plants having a decreased level of erucic acid, as compared to a corresponding wild type oilseed plant, where the oilseed plants comprises a modified nucleic acid encoding a TAG1 polypeptide, and where the modified TAG1 polypeptide has a reduced expression level or reduced polypeptide activity. The oilseed plant can produce oil having from 0 mole % to about 35 mole % erucic acid in the total fatty acid content of the oil. The modified TAG1 polypeptide can be a modified TAG1 polypeptide comprising an amino acid sequence set forth in SEQ ID NO:3, a modified TAG1 polypeptide comprising an amino acid sequence set forth in SEQ ID NO:4, or a modified TAG1 polypeptide comprising an amino acid sequence set forth in SEQ ID NO:5. When the modified TAG1 polypeptide includes an amino acid sequence set forth in SEQ ID NO:3, the modified TAG1 polypeptide can be encoded by a nucleic acid sequence set forth in SEQ ID NO:11 or SEQ ID NO:12. When the modified TAG1 polypeptide includes an amino acid sequence set forth in SEQ ID NO:4, the modified TAG1 polypeptide can be encoded by a nucleic acid sequence set forth in SEQ ID NO:13 or SEQ ID NO:14. When the modified TAG1 polypeptide includes an amino acid sequence set forth in SEQ ID NO:5, the modified TAG1 polypeptide can be encoded by a nucleic acid sequence set forth in SEQ ID NO:15 or SEQ ID NO:16. The oilseed plant can be a pennycress, a rapeseed, a soybean, a sunflower, a peanut, a canola, a flax, a camelina, a carinata, a crambe, or a lepidium plant. This document also features seed produced by oilseed plants having a decreased level of erucic acid, as compared to a corresponding wild type oilseed plant, where the oilseed plants comprises a modified nucleic acid encoding a TAG1 polypeptide, and where the modified TAG1 polypeptide has a reduced expression level or reduced polypeptide activity as well as seed oil obtained from oilseed plants having a decreased level of erucic acid, as compared to a corresponding wild type oilseed plant, where the oilseed plants comprises a modified nucleic acid encoding a TAG1 polypeptide, and where the modified TAG1 polypeptide has a reduced expression level or reduced polypeptide activity.

In another aspect, this document features oilseed plants having an increased level of a saturated fatty acid, as compared to a corresponding wild type oilseed plant, wherein said oilseed plants comprises: a) a modified nucleic acid encoding a TAG1 polypeptide, where the modified nucleic acid encoding a TAG1 polypeptide can encode a modified TAG1 polypeptide, and where the modified TAG1 polypeptide has a reduced expression level or reduced polypeptide activity; and b) a modified nucleic acid encoding a FAD2 polypeptide, where the modified nucleic acid encoding a FAD2 polypeptide can encode a modified FAD2 polypeptide, and where the modified FAD2 polypeptide has a reduced expression levels or reduced polypeptide activity. The oilseed plant can produce oil having from 5 mole % to 55 mole % of the saturated fatty acid in the total fatty acid content of the oil. The saturated fatty acid can be stearic acid and/or palmitic acid. The modified TAG1 polypeptide can be a modified TAG1 polypeptide comprising an amino acid sequence set forth in SEQ ID NO:3, a modified TAG1 polypeptide comprising an amino acid sequence set forth in SEQ ID NO:4, or a modified TAG1 polypeptide comprising an amino acid sequence set forth in SEQ ID NO:5. When the modified TAG1 polypeptide includes an amino acid sequence set forth in SEQ ID NO:3, the modified TAG1 polypeptide can be encoded by a nucleic acid sequence set forth in SEQ ID NO:11 or SEQ ID NO:12. When the modified TAG1 polypeptide includes an amino acid sequence set forth in SEQ ID NO:4, the modified TAG1 polypeptide can be encoded by a nucleic acid sequence set forth in SEQ ID NO:13 or SEQ ID NO:14. When the modified TAG1 polypeptide includes an amino acid sequence set forth in SEQ ID NO:5, the modified TAG1 polypeptide can be encoded by a nucleic acid sequence set forth in SEQ ID NO:15 or SEQ ID NO:16. The oilseed plant can be a pennycress, a rapeseed, a soybean, a sunflower, a peanut, a canola, a flax, a camelina, a carinata, a crambe, or a lepidium plant. This document also features seed produced by oilseed plants comprises: a) a modified nucleic acid encoding a TAG1 polypeptide, where the modified nucleic acid encoding a TAG1 polypeptide can encode a modified TAG1 polypeptide, and where the modified TAG1 polypeptide has a reduced expression level or reduced polypeptide activity; and b) a modified nucleic acid encoding a FAD2 polypeptide, where the modified nucleic acid encoding a FAD2 polypeptide can encode a modified FAD2 polypeptide, and where the modified FAD2 polypeptide has a reduced expression levels or reduced polypeptide activity, as well as seed oil obtained from oilseed plants comprises: a) a modified nucleic acid encoding a TAG1 polypeptide, where the modified nucleic acid encoding a TAG1 polypeptide can encode a modified TAG1 polypeptide, and where the modified TAG1 polypeptide has a reduced expression level or reduced polypeptide activity; and b) a modified nucleic acid encoding a FAD2 polypeptide, where the modified nucleic acid encoding a FAD2 polypeptide can encode a modified FAD2 polypeptide, and where the modified FAD2 polypeptide has a reduced expression levels or reduced polypeptide activity.

In another aspect, this document features oilseed plants having an increased level of a polyunsaturated fatty acid, as compared to a corresponding wild type oilseed plant, where the oilseed plants comprises: a) a modified nucleic acid encoding a TAG1 polypeptide, where the modified nucleic acid encoding a TAG1 polypeptide can encode a modified TAG1 polypeptide, and where the modified TAG1 polypeptide has a reduced expression level or reduced polypeptide activity; and where the oilseed plants comprises: i) a modified nucleic acid encoding a FAE1 polypeptide, where the modified nucleic acid encoding a FAE1 polypeptide can encode a modified FAE1 polypeptide, and where the modified FAE1 polypeptide has a reduced expression levels or reduced polypeptide activity; or ii) a modified nucleic acid encoding a ROD1 polypeptide, where the modified nucleic acid encoding a ROD1 polypeptide can encode a modified ROD1 polypeptide, and where the modified ROD1 polypeptide has a reduced expression levels or reduced polypeptide activity. The polyunsaturated fatty acid can be linolenic acid, and the oilseed plant can produce oil having from 22 mole % to 35 mole % linolenic acid. The polyunsaturated fatty acid can be linoleic acid, and the oilseed plant can produce oil having from 30 mole % to 45 mole % linoleic acid. The modified TAG1 polypeptide can be a modified TAG1 polypeptide comprising an amino acid sequence set forth in SEQ ID NO:3, a modified TAG1 polypeptide comprising an amino acid sequence set forth in SEQ ID NO:4, or a modified TAG1 polypeptide comprising an amino acid sequence set forth in SEQ ID NO:5. When the modified TAG1 polypeptide includes an amino acid sequence set forth in SEQ ID NO:3, the modified TAG1 polypeptide can be encoded by a nucleic acid sequence set forth in SEQ ID NO:11 or SEQ ID NO:12. When the modified TAG1 polypeptide includes an amino acid sequence set forth in SEQ ID NO:4, the modified TAG1 polypeptide can be encoded by a nucleic acid sequence set forth in SEQ ID NO:13 or SEQ ID NO:14. When the modified TAG1 polypeptide includes an amino acid sequence set forth in SEQ ID NO:5, the modified TAG1 polypeptide can be encoded by a nucleic acid sequence set forth in SEQ ID NO:15 or SEQ ID NO:16. The oilseed plant can be a pennycress, a rapeseed, a soybean, a sunflower, a peanut, a canola, a flax, a camelina, a carinata, a crambe, or a lepidium plant. This document also provides seed produced by oilseed plants comprises: a) a modified nucleic acid encoding a TAG1 polypeptide, where the modified nucleic acid encoding a TAG1 polypeptide can encode a modified TAG1 polypeptide, and where the modified TAG1 polypeptide has a reduced expression level or reduced polypeptide activity; and where the oilseed plants comprises: i) a modified nucleic acid encoding a FAE1 polypeptide, where the modified nucleic acid encoding a FAE1 polypeptide can encode a modified FAE1 polypeptide, and where the modified FAE1 polypeptide has a reduced expression levels or reduced polypeptide activity; or ii) a modified nucleic acid encoding a ROD1 polypeptide, where the modified nucleic acid encoding a ROD1 polypeptide can encode a modified ROD1 polypeptide, and where the modified ROD1 polypeptide has a reduced expression levels or reduced polypeptide activity, as well as seed oil obtained from oilseed plants comprises: a) a modified nucleic acid encoding a TAG1 polypeptide, where the modified nucleic acid encoding a TAG1 polypeptide can encode a modified TAG1 polypeptide, and where the modified TAG1 polypeptide has a reduced expression level or reduced polypeptide activity; and where the oilseed plants comprises: i) a modified nucleic acid encoding a FAE1 polypeptide, where the modified nucleic acid encoding a FAE1 polypeptide can encode a modified FAE1 polypeptide, and where the modified FAE1 polypeptide has a reduced expression levels or reduced polypeptide activity; or ii) a modified nucleic acid encoding a ROD1 polypeptide, where the modified nucleic acid encoding a ROD1 polypeptide can encode a modified ROD1 polypeptide, and where the modified ROD1 polypeptide has a reduced expression levels or reduced polypeptide activity.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 contains an amino acid alignment including a wild type *Arabidopsis thaliana* TAG1 amino acid sequence (At_TAG1; SEQ ID NO:1), a wild type pennycress TAG1 amino acid sequence (Ta_TAG1; SEQ ID NO:2), a modified pennycress TAG1 amino acid sequence (Ta_tag1-1; SEQ ID NO:3), a modified pennycress TAG1 amino acid sequence (Ta_tag1-2; SEQ ID NO:4), a modified pennycress TAG1 amino acid sequence (Ta_tag1-3; SEQ ID NO:5), a wild type *Glycine max* TAG1 amino acid sequence (Gm_TAG1; SEQ ID NO:6), a wild type *Oryza sativa* TAG1 amino acid sequence (Os_TAG1; SEQ ID NO:7), and a wild type *Solanum lycopersicum* TAG1 amino acid sequence (Sl_TAG1; SEQ ID NO:8). Changes in pennycress mutant sequences relative to wild type pennycress TAG1 are shown in bold font. In *Arabidopsis* and in other plant species TAG1 is also known as acyl-CoA-diacylglycerol acyltransferase 1 (DGAT1). TAG1 catalyzes the final step in the triacylglycerol biosynthesis pathway.

FIG. 2A shows a table of the molecular percent of various fatty acids in oil isolated from various single and double mutant combinations. FIG. 2B contains a graph showing fatty acid profiles for various single and double mutant combinations.

FIGS. 3A-3C shown exemplary nucleic acid sequences of modified pennycress nucleic acids that can encode a modified FAD2 polypeptide. FIG. 3A shows modified nucleic acid sequences that can encode a Ta-fad2-1 polypeptide (SEQ ID NO:17 and SEQ ID NO:18). FIG. 3B shows modified nucleic acid sequences that can encode a Ta-fad2-2 polypeptide (SEQ ID NO:19 and SEQ ID NO:20). FIG. 3C shows modified nucleic acid sequences that can encode a Ta-fad2-3 polypeptide (SEQ ID NO:21 and SEQ ID NO:22). Modified nucleic acids relative to wild type pennycress FAE1 are shown in bold font.

FIG. 4 contains an amino acid alignment of FAD2 polypeptides. Sequences shown include a wild type *Arabidopsis thaliana* (At) FAD2 (SEQ ID NO:23), a wild type pennycress (Ta) FAD2 (SEQ ID NO:24), a modified pennycress FAD2 sequence (Ta-fad2-1; SEQ ID NO:25), a modified pennycress FAD2 sequence (Ta-fad2-2; SEQ ID NO:26), a modified pennycress FAD2 sequence (Ta-fad2-3; SEQ ID NO:27), a wild type *Oryza sativa* (Os) FAD2 (SEQ ID NO:28, a wild type *Glycine max* (Gm) FAD2 (SEQ ID NO:29), and a wild type *Solanum lycopersicum* (Sl) FAD2 (SEQ ID NO:30). Changes in pennycress mutant sequences relative to wild type pennycress FAD2 are shown in bold font.

FIGS. 5A-5B shown exemplary nucleic acid sequences of modified pennycress nucleic acids that can encode a modified FAE1 polypeptide. FIG. 5A shows a modified nucleic acid sequence that can encode a Ta-fae1-1 polypeptide (SEQ ID NO:31). FIG. 5B shows a modified nucleic acid sequence that can encode a Ta-fae1-2 polypeptide (SEQ ID NO:32). Modified nucleic acids relative to wild type pennycress FAE1 are shown in bold font.

FIG. 6 contains an amino acid alignment of FAE1 polypeptides. Sequences shown include a wild type *Arabidopsis thaliana* (At) FAE1 (SEQ ID NO:33), a wild type pennycress (Ta) FAE1 (SEQ ID NO:34), a mutant pennycress FAE1 sequence (Ta-fae1-1; SEQ ID NO:35), a mutant pennycress FAE1 sequence (Ta-fae1-2; SEQ ID NO:36), a wild type *Oryza sativa* (Os) FAE1 (SEQ ID NO:37), a wild type *Glycine max* (Gm) FAE1 (SEQ ID NO:38), and a wild type *Solanum lycopersicum* (Sl) FAE1 (SEQ ID NO:39). Changes in pennycress mutant sequences relative to wild type pennycress FAE1 are shown in bold font.

FIGS. 7A-7B shown exemplary nucleic acid sequences of modified pennycress nucleic acids that can encode a modified ROD1 polypeptide. FIG. 7A shows modified nucleic acid sequences that can encode a Ta-rod1-1 polypeptide (SEQ ID NO:40 and SEQ ID NO:41). FIG. 7B shows modified nucleic acid sequences that can encode a Ta-rod1-2 polypeptide (SEQ ID NO:42 and SEQ ID NO:43). Modified nucleic acids relative to wild type pennycress FAE1 are shown in bold font.

FIG. 8 contains an amino acid alignment including ROD1 polypeptides. Sequences shown include a wild type *Arabidopsis thaliana* (At) ROD1 (SEQ ID NO:44), a wild type pennycress (Ta) ROD1 (SEQ ID NO:45), a mutant pennycress ROD1 sequence (Ta-rod1-1; SEQ ID NO:46), a mutant pennycress ROD1 sequence (Ta-rod1-2; SEQ ID NO:47), a wild type *Oryza sativa* (Os) ROD1 (SEQ ID NO:48), a wild type *Glycine max* (Gm) ROD1 (SEQ ID NO:49), and a wild type *Solanum lycopersicum* (Sl) ROD1 (SEQ ID NO:50). Changes in pennycress mutant sequences relative to wild type pennycress ROD1 are shown in bold font.

FIG. 11 is a table of the molecular percent of fatty acids in oil isolated from wild type pennycress plants (MN106), from pennycress plants having a modification in a single gene that encodes a polypeptide involved in triglyceride synthesis, or from pennycress plants having a modification in two genes that each encode a polypeptide involved in triglyceride synthesis is shown.

DETAILED DESCRIPTION

This document provides oilseed plants (e.g., pennycress plants) having increased levels of one or more saturated fatty acids, increased levels of one or more PUFAs, altered (e.g., increased or decreased) levels of oleic acid, and/or altered (e.g., increased or decreased) levels of erucic acid (e.g., as compared to corresponding wild type plants). In some cases, this document provides oilseed plants having reduced polypeptide levels and/or reduced polypeptide activity of one or more polypeptides involved in triglyceride synthesis (e.g., TAG1), as compared to corresponding wild type plants. For example, oilseed plants having reduced polypeptide levels and/or reduced polypeptide activity of one or more polypeptides involved in triglyceride synthesis of one or more polypeptides involved in triglyceride synthesis (e.g., TAG1) can have increased levels of stearic acid, increased levels of one or more PUFAs, altered (e.g., increased or decreased) levels of oleic acid, and/or altered (e.g., increased or decreased) levels of erucic acid (e.g., as compared to corresponding wild type plants).

This document also provides methods and materials for making and using oilseed plants (e.g., pennycress plants) described herein (e.g., oilseed plants having increased levels of one or more saturated fatty acids, increased levels of one or more PUFAs, altered levels of oleic acid, and/or altered levels of erucic acid). In some cases, site-specific gene editing can be used to modify a nucleic acid encoding a TAG1 polypeptide (e.g., a TAG1 gene), and, optionally, to modify a nucleic acid encoding a FAD2 polypeptide (e.g., a FAD2 gene), a nucleic acid encoding a FAE1 polypeptide (e.g., a FAE1 gene), and/or a nucleic acid encoding a ROD1 polypeptide (e.g., a ROD1 gene). For example, site-specific editing can be used to modify the TAG1 gene in an oilseed plant genome to reduce the level of TAG1 polypeptides and/or to reduce TAG1 polypeptide activity. For example, site-specific editing can be used to modify the FAD2 gene in an oilseed plant genome to reduce the level of FAD2 polypeptides and/or to reduce FAD2 polypeptide activity. For example, site-specific editing can be used to modify the FAE1 gene in an oilseed plant genome to reduce the level of FAE1 polypeptides and/or to reduce FAE1 polypeptide activity.

Figures 2A, 2B:
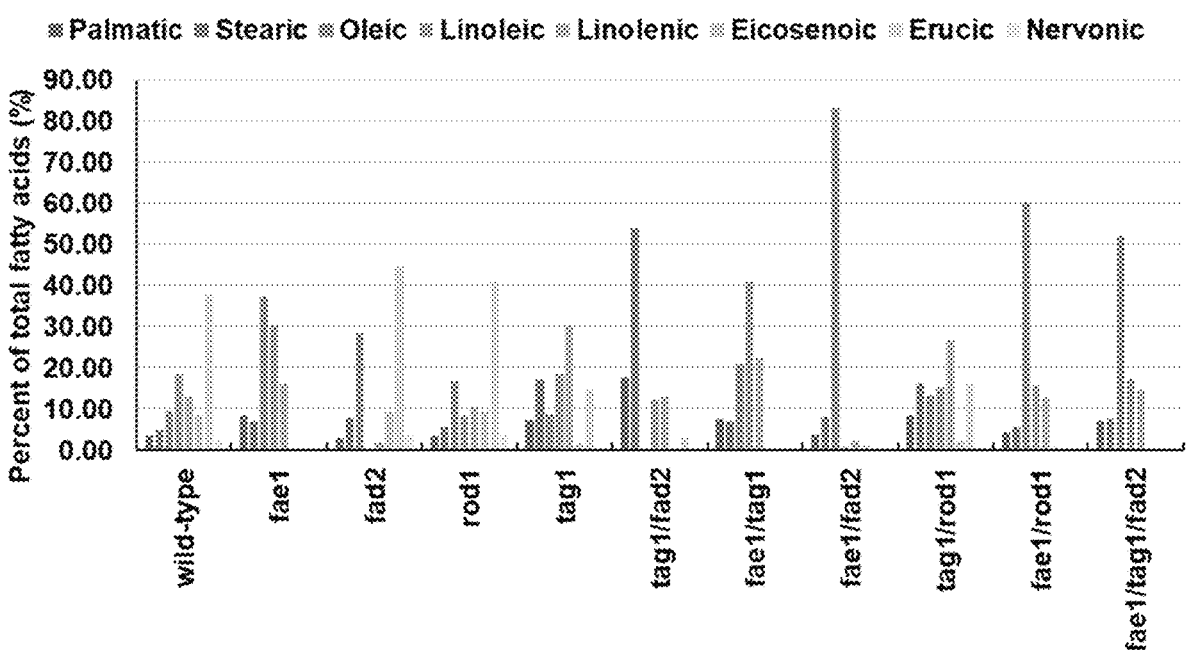
FIGS. 2A-2B show that pennycress plants having a modified nucleic acid encoding a TAG1 polypeptide, and, optionally, a modified nucleic acid encoding a FAD2 polypeptide, a modified nucleic acid encoding a FAE1 polypeptide, or a modified nucleic acid encoding a ROD1 polypeptide can produce seeds having increased levels of one or more saturated fatty acids, altered levels of one or more PUFAs, altered levels of oleic acid, and/or altered levels of erucic acid as compared to corresponding wild type plants.

In some cases, oilseed plants (e.g., pennycress plants) described herein (e.g., oilseed plants having increased levels of one or more saturated fatty acids, increased levels of one or more PUFAs, altered levels of oleic acid, and/or altered levels of erucic acid) can have (e.g., can produce seeds whose oil can have) a fatty acid composition that is unique. For example, oilseed plants described herein can have a fatty acid profile that is not observed in other plant species (see, e.g., FIGS. 2A and 2B).

Figure 9:
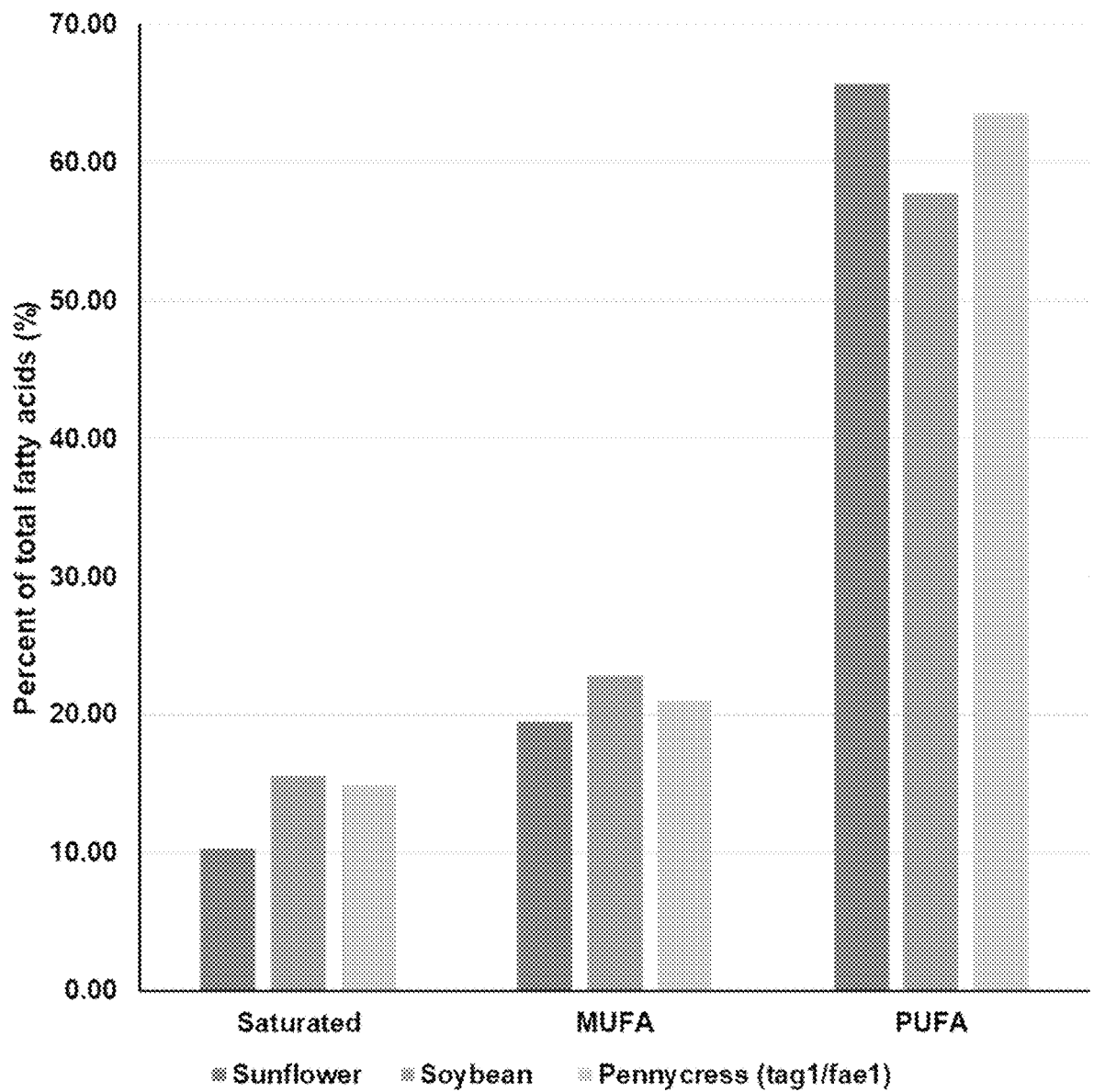
FIG. 9 contains a graph showing representative fatty acid profiles for pennycress plants having a modified nucleic acid encoding a TAG1 polypeptide, and pennycress plants having a modified nucleic acid encoding a FAE1 polypeptide. Fatty acid profiles for the modified pennycress plants are compared with representative fatty acid profiles of sunflower oil and Soybean oil.

In some cases, oilseed plants (e.g., pennycress plants) described herein (e.g., oilseed plants having increased levels of one or more saturated fatty acids, increased levels of one or more PUFAs, altered levels of oleic acid, and/or altered levels of erucic acid) can have (e.g., can produce seeds whose oil can have) a fatty acid composition including increased levels of PUFAs. For example, oilseed plants described herein can have a fatty acid profile that that is similar to the fatty acid composition of soybean oil (see, e.g., FIGS. 2A and 2B). The fatty acid profile of soybean oil can be as shown in FIG. 9. For example, oilseed plants described herein can have a fatty acid profile that that is similar to the fatty acid composition of sunflower oil (see, e.g., FIGS. 2A and 2B). The fatty acid profile of soybean oil can be as shown in FIG. 9.

Figure 10:
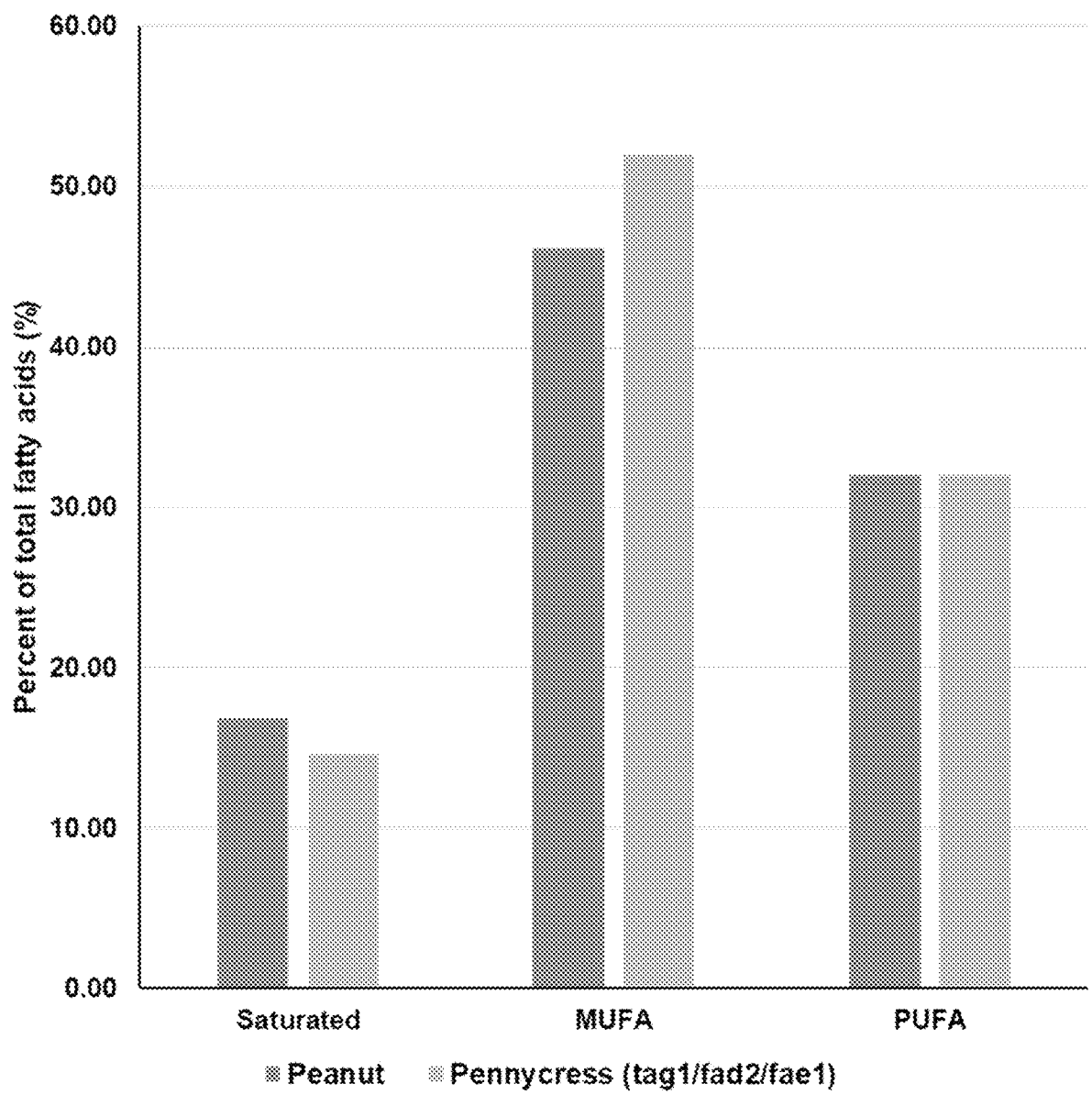
FIG. 10 contains a graph showing representative fatty acid profiles for pennycress plants having a modified nucleic acid encoding a TAG1 polypeptide, and pennycress plants having a modified nucleic acid encoding a FAE1 polypeptide and a modified nucleic acid encoding a FAD2 polypeptide. Fatty acid profiles for pennycress plants are compared with a representative fatty acid profile of peanut oil.

In some cases, oilseed plants (e.g., pennycress plants) described herein (e.g., oilseed plants having increased levels of one or more saturated fatty acids, increased levels of one or more PUFAs, altered levels of oleic acid, and/or altered levels of erucic acid) can have (e.g., can produce seeds whose oil can have) a fatty acid composition including increased levels of oleic acid. For example, oilseed plants described herein can have a fatty acid profile that that is similar to the fatty acid composition of peanut oil (see, e.g., FIGS. 2A and 2B). The fatty acid profile of peanut oil can be as shown in FIG. 10.

Oilseed plants (e.g., pennycress plants) described herein (e.g., oilseed plants having increased levels of one or more saturated fatty acids, increased levels of one or more PUFAs, altered levels of oleic acid, and/or altered levels of erucic acid) can be derived from any appropriate species of oilseed plant. An oilseed plant can be a monocotyledonous oilseed plant. An oilseed plant can be a dicotyledonous oilseed plant. An oilseed plant can be a member of the family Brassicaceae (e.g., the mustard family). For example, an oilseed plant can be a member of the genus *Brassica*. Examples of oilseed plants include, without limitation, pennycress, rapeseed, soybean, sunflower, peanut, canola, flax, camelina, carinata, crambe, and lepidium plants. In some cases, an oilseed plant that produces seeds whose oil can have increased levels of one or more saturated fatty acids, increased levels of one or more PUFAs, altered (e.g., increased or decreased) levels of oleic acid, and/or altered (e.g., increased or decreased) levels of erucic acid as described herein can be a pennycress plant.

Oilseed plants (e.g., pennycress plants) described herein (e.g., oilseed plants having increased levels of one or more saturated fatty acids, increased levels of one or more PUFAs, altered levels of oleic acid, and/or altered levels of erucic acid) can have increased levels of one or more saturated fatty acids, increased levels of one or more PUFAs, altered (e.g., increased or decreased) levels of oleic acid, and/or altered (e.g., increased or decreased) levels of erucic acid in any appropriate plant tissues. In some cases, oilseed plants described herein can have increased levels of one or more saturated fatty acids, increased levels of one or more PUFAs, altered (e.g., increased or decreased) levels of oleic acid, and/or altered (e.g., increased or decreased) levels of erucic acid in one or more (e.g., 1, 2, 3, 4, 5, or more) plant tissues. In some cases, an oilseed plant described herein can have increased levels of one or more saturated fatty acids, increased levels of one or more PUFAs, altered (e.g., increased or decreased) levels of oleic acid, and/or altered (e.g., increased or decreased) levels of erucic acid in the seeds. For example, an oilseed plant described herein can produce seeds whose oil can have increased levels of one or more saturated fatty acids, increased levels of one or more PUFAs, altered (e.g., increased or decreased) levels of oleic acid, and/or altered (e.g., increased or decreased) levels of erucic acid. In other cases, an oilseed plant described herein can have increased levels of one or more saturated fatty acids, increased levels of one or more PUFAs, altered (e.g., increased or decreased) levels of oleic acid, and/or altered (e.g., increased or decreased) levels of erucic acid in vegetative and storage tissues (e.g., natural and/or man-made) including stems, leaves, roots, and tubers.

When oilseed plants (e.g., pennycress plants) described herein (e.g., oilseed plants having increased levels of one or more saturated fatty acids, increased levels of one or more PUFAs, altered levels of oleic acid, and/or altered levels of erucic acid) can have increased levels of one or more (e.g., one, two, three, four, or more) saturated fatty acids, a saturated fatty acid can be any appropriate saturated fatty acid. In some cases, an oilseed plant having increased levels of one or more saturated fatty acids as described herein can have increased levels of one, two, three, four, or more saturated fatty acids. In some cases, a saturated fatty acid can be a long-chain fatty acid (LCFA; e.g., a fatty acid having an aliphatic tail including from about 13 to about 22 carbons). In some cases, a saturated fatty acid can be a very long chain fatty acid (VLCFA; e.g., a fatty acid having an aliphatic tail including about 22 or more carbons). Examples of saturated fatty acids can include, without limitation, stearic acid (18:0), palmitic acid (16:0), myristic acid (14:0), lauric acid (12:0), and capric acid (10:0). For example, a pennycress plant having increased levels of one or more saturated fatty acids can have increased levels of stearic acid and/or increased levels of palmitic acid.

When oilseed plants (e.g., pennycress plants) described herein (e.g., oilseed plants having increased levels of one or more saturated fatty acids, increased levels of one or more PUFAs, altered levels of oleic acid, and/or altered levels of erucic acid) have increased levels of one or more saturated fatty acids, the level of a saturated fatty acid can be any level that is greater than the median level of the same saturated fatty acid typically observed in a corresponding wild type plant. The term "increased level" as used herein with respect to a level of a saturated fatty acid in an oilseed plant described herein (e.g., in the oil obtained from an oilseed plant described herein) refers to any level that is higher than a reference level of a saturated fatty acid. The term "reference level" as used herein with respect to a saturated fatty acid refers to the level of the saturated fatty acid typically observed in oil obtained from a wild type oilseed plant. It will be appreciated that levels of a saturated fatty acid in oil obtained from comparable oilseed plants are used when determining whether or not the level of a saturated fatty acid in oil obtained from a particular oilseed plant is an increased level. In some cases, the level of a saturated fatty acid in an oilseed plant described herein can be from about 2 fold to about 10 fold (e.g., from about 3 fold to about 10 fold, from about 5 fold to about 10 fold, from about 8 fold to about 10 fold, from about 2 fold to about 8 fold, from about 2 fold to about 5 fold, from about 2 fold to about 3 fold, from about 3 fold to about 9 fold, from about 5 fold to about 8 fold, or from about 2 fold to about 5 fold) more than the level of that saturated fatty acid in a corresponding wild type oilseed plant. A wild type pennycress plant typically produces oil having about 4 mole % to about 5 mole % stearic acid and having about 4 mole % to about 5 mole % palmitic acid in the total fatty acid content of the oil (see, e.g., FIGS. 2A and 2B). For example, a pennycress plant having increased levels of one or more saturated fatty acids can have from about 5 mole % to about 55 mole % (e.g., from about 5 mole % to about 50 mole %, from about 5 mole % to about 40 mole %, from about 5 mole % to about 30 mole %, from about 5 mole % to about 25 mole %, from about 5 mole % to about 20 mole %, from about 5 mole % to about 15 mole %, from about 5 mole % to about 10 mole %, from about 10 mole % to about 55 mole %, from about 25 mole % to about 55 mole %, from about 40 mole % to about 55 mole %, from about 6 mole % to about 53 mole %, from about 10 mole % to about 50 mole %, from about 20 mole % to about 40 mole %, from about 10 mole % to about 20 mole %, from about 20 mole % to about 30 mole %, from about 30 mole % to about 40 mole %, or from about 40 mole % to about 50 mole %) of stearic acid (e.g., in the total fatty acid content of the oil). For example, a pennycress plant having increased levels of one or more saturated fatty acids can have from about 5 mole % to about 20 mole % (e.g., from about 7 mole % to about 20 mole %, from about 10 mole % to about 20 mole %, from about 15 mole % to about 20 mole %, from about 5 mole % to about 18 mole %, from about 5 mole % to about 15 mole %, from about 5 mole % to about 12 mole %, from about 5 mole % to about 10 mole %, from about 7 mole % to about 17 mole %, from about 10 mole % to about 15 mole %, from about 8 mole % to about 12 mole %, or from about 12 mole % to about 18 mole %) of palmitic acid (e.g., in the total fatty acid content of the oil).

When oilseed plants (e.g., pennycress plants) described herein (e.g., oilseed plants having increased levels of one or more saturated fatty acids, increased levels of one or more PUFAs, altered levels of oleic acid, and/or altered levels of erucic acid) have increased levels of one or more (e.g., one, two, three, four, or more) PUFAs, a PUFA can be any appropriate PUFA. In some cases, an oilseed plant having increased levels of PUFAs as described herein can have increased levels of one, two, three, four, or more PUFAs. In some cases, a PUFA can be a long-chain fatty acid (LCFA; e.g., a fatty acid having an aliphatic tail including from about 13 to about 21 carbons). In some cases, a PUFA can be a very long chain fatty acid (VLCFA; e.g., a fatty acid having an aliphatic tail including about 22 or more carbons). In some cases, a PUFA can be an Omega 3 fatty acid. In some cases, a PUFA can be an Omega 6 fatty acid. In some cases, a PUFA can be an Omega 9 fatty acid. Examples of PUFAs can include, without limitation, linoleic acid (18:2), linolenic acid (18:3), eicosadienoic acid (20:2), dihomo-gamma-linolenic acid (20:3), and arachidonic acid (20:4). For example, a pennycress plant having increased levels of one or more PUFAs can have increased levels of linoleic acid and/or increased levels of linolenic acid. For example, a pennycress plant having increased levels of one or more PUFAs can have increased levels of linoleic acid and increased levels of linolenic acid.

When oilseed plants (e.g., pennycress plants) described herein (e.g., oilseed plants having increased levels of one or more saturated fatty acids, increased levels of one or more PUFAs, altered levels of oleic acid, and/or altered levels of erucic acid) have increased levels of one or more PUFAs, the level of a PUFA can be any level that is greater than the median level of the same PUFA typically observed in a corresponding wild type plant. The term "increased level" as used herein with respect to a level of a PUFA in an oilseed plant described herein (e.g., in the oil obtained from an oilseed plant described herein) refers to any level that is higher than a reference level of a PUFA. The term "reference level" as used herein with respect to a PUFA refers to the level of the PUFA typically observed in oil obtained from a wild type oilseed plant. It will be appreciated that levels of a PUFA in oil obtained from comparable oilseed plants are used when determining whether or not the level of a PUFA in oil obtained from a particular oilseed plant is an increased level. In some cases, the level of a PUFA in an oilseed plant in an oilseed plant described herein can be from about 1.5 fold to about 3 fold more (e.g., about 2.5 fold) than the level of that PUFA in a corresponding wild type oilseed plant. A wild type pennycress plant typically produces oil having about 32 mole % PUFAs (e.g., combined PUFAs) in the total fatty acid content of the oil, with about 19 mole % linoleic acid and about 13 mole % linolenic acid (see, e.g., FIGS. 2A and 2B). For example, a pennycress plant having increased levels of one or more PUFAs can have from about 30 mole % to about 45 mole % (e.g., from about 30 mole % to about 42 mole %, from about 30 mole % to about 40 mole %, from about 30 mole % to about 35 mole %, from about 31 mole % to about 45 mole %, from about 32 mole % to about 45 mole %, from about 35 mole % to about 45 mole %, from about 38 mole % to about 45 mole %, from about 40 mole % to about 45 mole %, from about 32 mole % to about 42 mole %, from about 35 mole % to about 40 mole %, from about 32 mole % to about 35 mole %, or from about 35 mole % to about 40 mole %) of linoleic acid (e.g., in the total fatty acid content of the oil). For example, a pennycress plant having increased levels of one or more PUFAs can have from about 22 mole % to about 35 mole % (e.g., from about 22 mole % to about 32 mole %, from about 22 mole % to about 30 mole %, from about 22 mole % to about 28 mole %, from about 22 mole % to about 25 mole %, from about 23 mole % to about 35 mole %, from about 25 mole % to about 35 mole %, from about 28 mole % to about 35 mole %, from about 30 mole % to about 35 mole %, from about 32 mole % to about 35 mole %, from about 23 mole % to about 32 mole %, or from about 25 mole % to about 30 mole %) of linolenic acid (e.g., in the total fatty acid content of the oil).

When oilseed plants (e.g., pennycress plants) described herein (e.g., oilseed plants having increased levels of one or more saturated fatty acids, increased levels of one or more PUFAs, altered levels of oleic acid, and/or altered levels of erucic acid) have altered levels of oleic acid, the level of a oleic acid can an increased level (e.g., any level that is higher than the median level of oleic acid typically observed in a corresponding wild type plant) or a decreased level (e.g., any level that is lower than the median level of oleic acid typically observed in a corresponding wild type plant). The term "increased level" as used herein with respect to a level of oleic acid in the oil obtained from an oilseed (e.g., pennycress) plant refers to any level that is higher than a reference level of oleic acid. The term "decreased level" as used herein with respect to a level of oleic acid in the oil obtained from an oilseed (e.g., pennycress) plant refers to any level that is lower than a reference level of oleic acid. The term "reference level" as used herein with respect to oleic acid refers to the level of oleic acid typically observed in the oil obtained from a wild type oilseed plant. It will be appreciated that levels of oleic acid in the oil obtained from comparable oilseed plants are used when determining whether or not the level of oleic acid in the oil obtained from a particular oilseed plant is an increased level or a decreased level. A wild type pennycress plant typically produces oil having about 10 mole % to about 13 mole % oleic acid in the total fatty acid content of the oil (see, e.g., Moser et al., 2009 *Energy and Fuels*, 23:4149-4155). In some cases, an oilseed plant having increased levels of oleic acid as described herein can have from about 20 mole % to about 95 mole % (e.g., from about 20 mole % to about 92 mole %, from about 20 mole % to about 90 mole %, from about 20 mole % to about 85 mole %, from about 20 mole % to about 80 mole %, from about 20 mole % to about 75 mole %, from about 20 mole % to about 60 mole %, from about 20 mole % to about 50 mole %, from about 20 mole % to about 40 mole %, from about 20 mole % to about 30 mole %, from about 22 mole % to about 95 mole %, from about 25 mole % to about 95 mole %, from about 30 mole % to about 95 mole %, from about 40 mole % to about 95 mole %, from about 50 mole % to about 95 mole %, from about 60 mole % to about 95 mole %, from about 70 mole % to about 95 mole %, from about 80 mole % to about 95 mole %, from about 21 mole % to about 92 mole %, from about 25 mole % to about 90 mole %, from about 30 mole % to about 75 mole %, from about 40 mole % to about 60 mole %, from about 30 mole % to about 50 mole %, or from about 50 mole % to about 75 mole %) of oleic acid (e.g., in the total fatty acid content of the oil). In some cases, an oilseed plant having decreased levels of oleic acid as described herein can have from about 0 mole % to about 10 mole % (e.g., from about 0 mole % to about 8 mole %, from about 0 mole % to about 5 mole %, from about 1 mole % to about 10 mole %, from about 2 mole % to about 10 mole %, from about 3 mole % to about 10 mole %, from about 5 mole % to about 10 mole %, from about 1 mole % to about 8 mole %, from about 2 mole % to about 5 mole %, or from about 5 mole % to about 8 mole %) of oleic acid (e.g., in the total fatty acid content of the oil).

When oilseed plants (e.g., pennycress plants) described herein (e.g., oilseed plants having increased levels of one or more saturated fatty acids, increased levels of one or more PUFAs, altered levels of oleic acid, and/or altered levels of erucic acid) have altered levels of erucic acid, the level of a erucic acid can a decreased level (e.g., any level that is lower than the median level of erucic acid typically observed in a corresponding wild type plant). The term "decreased level" as used herein with respect to a level of erucic acid in the oil obtained from an oilseed (e.g., pennycress) plant refers to any level that is lower than a reference level of erucic acid. The term "reference level" as used herein with respect to erucic acid refers to the level of erucic acid typically observed in the oil obtained from a wild type oilseed plant. It will be appreciated that levels of erucic acid in the oil obtained from comparable oilseed plants are used when determining whether or not the level of erucic acid in the oil obtained from a particular oilseed plant is a decreased level. A wild type pennycress plant typically produces oil having about 35 mole % to about 40 mole % erucic acid in the total fatty acid content of the oil (see, e.g., FIGS. 2A and 2B). In some cases, an oilseed plant having decreased levels of erucic acid as described herein can have from about 0 mole % to about 35 mole % (e.g., from about 0 mole % to about 30 mole %, from about 0 mole % to about 25 mole %, from about 0 mole % to about 20 mole %, from about 0 mole % to about 15 mole %, from about 0 mole % to about 10 mole %, from about 0 mole % to about 5 mole %, from about 5 mole % to about 35 mole %, from about 10 mole % to about 35 mole %, from about 15 mole % to about 35 mole %, from about 20 mole % to about 35 mole %, from about 25 mole % to about 35 mole %, from about 5 mole % to about 30 mole %, from about 10 mole % to about 25 mole %, from about 5 mole % to about 15 mole %, from about 10 mole % to about 20 mole %, or from about 20 mole % to about 30 mole %) erucic acid (e.g., in the total fatty acid content of the oil).

Figure 18:
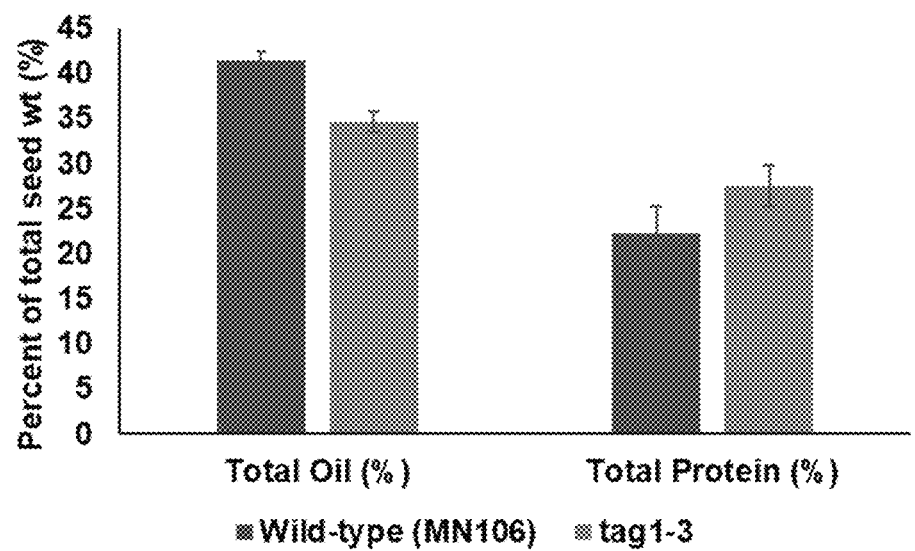
FIG. 18 contains a graph showing a percent of total oil and total protein from wild type pennycress plants (MN106) and from pennycress plants having a modified nucleic acid encoding a TAG1 polypeptide (tag1-3).

In some cases, one or more tissues from oilseed plants (e.g., pennycress plants) described herein (e.g., oilseed plants having increased levels of one or more saturated fatty acids, increased levels of one or more PUFAs, altered levels of oleic acid, and/or altered levels of erucic acid) can have a decreased level of total oil content (e.g., as compared to corresponding wild type plants). When oilseed plants (e.g., pennycress plants) described herein have a decreased level of total oil content, the decreased level of total oil content can be in any appropriate plant tissue. For example, an oilseed plant described herein can have a decreased level of total oil content in vegetative and storage tissues (e.g., natural and/or man-made) including stems, leaves, roots, and/or tubers of the plant. In some cases, an oilseed plant described herein can have a decreased level of total oil content in seeds obtained from the plant. The term "decreased level" as used herein with respect to a level of total oil content obtained from a tissue of an oilseed (e.g., pennycress) plant refers to any level that is lower than a reference level of total oil content. The term "reference level" as used herein with respect to total oil content obtained from a tissue of an oilseed plant refers to the level of total oil content typically obtained from that tissue in a wild type oilseed plant. It will be appreciated that levels of total oil content in a tissue obtained from comparable oilseed plants are used when determining whether or not the level of total oil content obtained from a particular tissue of an oilseed plant is a decreased level. A wild type pennycress plant typically produces seeds containing about 32% to about 42% oil content (see, e.g., FIG. 18; and Chopra et al., 2019 *Industrial Crops and Products*, 128:55-61). In some cases, a tissue from an oilseed plant described herein can have less than about 32% (e.g., about 30%, about 27%, about 25%, about 22%, about 20%, about 18%, about 16%, or less) oil content. It will be appreciated that total oil content can vary based on, for example, the growth conditions of the plants and/or the availability of fertilizer.

In some cases, one or more tissues from oilseed plants (e.g., pennycress plants) described herein (e.g., oilseed plants having increased levels of one or more saturated fatty acids, increased levels of one or more PUFAs, altered levels of oleic acid, and/or altered levels of erucic acid) can have an increased level of total protein content (e.g., as compared to corresponding wild type plants). When oilseed plants (e.g., pennycress plants) described herein have an increased level of total protein content, the increased level of total protein content can be in any appropriate plant tissue. For example, an oilseed plant described herein can have an increased level of total protein content in vegetative and storage tissues (e.g., natural and/or man-made) including stems, leaves, roots, and/or tubers of the plant. In some cases, an oilseed plant described herein can have an increased level of total protein content in seeds obtained from the plant. The term "increased level" as used herein with respect to a level of total protein content obtained from a tissue of an oilseed (e.g., pennycress) plant refers to any level that is higher than a reference level of total protein content. The term "reference level" as used herein with respect to total protein content obtained from a tissue of an oilseed plant refers to the level of total protein content typically obtained from that tissue in a wild type oilseed plant. It will be appreciated that levels of total protein content in a tissue obtained from comparable oilseed plants are used when determining whether or not the level of total protein content obtained from a particular tissue of an oilseed plant is an increased level. A wild type pennycress plant typically produces seeds containing about 19% to about 25% protein content (see, e.g., FIG. 18; and Chopra et al., 2019 *Industrial Crops and Products*, 128:55-61). In some cases, a tissue from an oilseed plant described herein can have greater than about 22% (e.g., about 25%, about 26%, about 27%, about 28%, about 29%, about 30%, or more) protein content. It will be appreciated that total protein content can vary based on, for example, the growth conditions of the plants and/or the availability of fertilizer.

In some cases, oilseed plants (e.g., pennycress plants) described herein (e.g., oilseed plants having increased levels of one or more saturated fatty acids, increased levels of one or more PUFAs, altered levels of oleic acid, and/or altered levels of erucic acid) can be as described in the Examples. For example, oilseed plants described herein can include Ta-tag1-1 (line E5-547), Ta-tag1-2 (line E5-519), and Ta-tag1-3 (line E5-289), or can be progeny from those lines.

Oilseed plants (e.g., pennycress plants) described herein (e.g., oilseed plants having increased levels of one or more saturated fatty acids, increased levels of one or more PUFAs, altered levels of oleic acid, and/or altered levels of erucic acid) can include one or more modifications in a nucleic acid (e.g., a gene) that can encode a polypeptide involved in triglyceride synthesis. In some cases, the one or more modifications in a gene that can encode a polypeptide involved in triglyceride synthesis can be in the coding sequence. Polypeptides involved in triglyceride synthesis can include, without limitation, TAG1 polypeptides, FAE1 polypeptides, FAD2 polypeptides, and ROD1 polypeptides. For example, oilseed plants described herein can include one or more modifications in a nucleic acid that can encode a TAG1 polypeptide.

In some cases, oilseed plants (e.g., pennycress plants) described herein (e.g., oilseed plants having increased levels of one or more saturated fatty acids, increased levels of one or more PUFAs, altered levels of oleic acid, and/or altered levels of erucic acid) can include one or more modifications in a nucleic acid (e.g., a TAG1 gene) that can encode a TAG1 polypeptide (e.g., one or more modifications as compared to a wild type nucleic acid that can encode a TAG1 polypeptide). A representative wild type nucleic acid that can encode a TAG1 polypeptide can include the following nucleic acid sequence (SEQ ID NO:9), with upper case letters representing the TAG1 coding sequence and the lower case letters representing introns:

ATGGCGATTTTGGATTCTGGAGGCGTCACTATGCCGACGGAGAACGGTGG

CGGAGAGTTTGCGGATCTCGATACTCTTCGTCGACGGAAATCACGATCGG

ATTCCAACGAACCTCTTTCCGATTCCGCACCCGGTACCGATGCTTTCCCA

TCAGATGATGTTGGAGCTCCGTCCGACGCGAGGGATCGGATTGATTCAGC

TGTCGACGACGCTCAGGGAACAGCGAATTTGGCAGGAGATAACGGCGGAG

ATACCGAAATTAGGGAAACTGGTGGAGGAGGAGGCGGCGGTGAAGCAAGA

GGAGACGCCGATACAAGGTATACGTATCGTCCGTCGGTTCCAGCTCATCG

GAGGGCTAGGGAAAGTCCACTCAGCTCCGACGCAATCTTCAAACAGgtaa atctcagattctacgctggacaatctccgaatttggtgcttgatactgtc taatgttagaggagaatttcaaactgagtttcatgttaactttagagag gacaatttcttcatttcatttgactcgagtttgtgttgtcttccatggca gAGCCATGCCGGATTATTCAACCTGTGTGTAGTAGTTCTTATTGCTGTAA ACAGTAGACTCATCATCGAGAACTTGATGAAGgttagttacttttttct cctatggcttgaaaattgaattaggtttgttcttgagctgagaactttat caagaccttaccttttgttgttgccttcattcctgtagTACGGTTGGTTGA

TCAGAACAGATTTCTGGTTTAGTTCAACATCGCTGCGAGATTGGCCGCTT

TTCATgtgttggtaatatataatttttttttctttcgtaatgttacattc ttattcatataatgatgtgtttagagattcagatattctataaattctt ctgttgcagTATCTCTCTTTCGATCTTTCCTCTGGCTGCCTTTACCGTCG AGAAACTGGTACTTCAGAAATGCATATCTGAACCTGTGAgtaaactactg actatatagctattactggattgtttactgaagACAAGTTTGTTGTATCC

TGGAGAACTTATAAGTTTCTTTCTGATAATATTAAAGGTTGTCATCATTC

TTCATATTATAATCACAATGACAGAGGTCTTGTATCCAGTTTACGTCACC

CTAAGgtgtgaattaagctaaggtgtttctgatctcagcttgtgatactc tcttttttaattctagTTGACTAACTCGATGATCTTGAAAATGGACAGGT

GTGATTCCGCCTTCTTGTCAGGTGTCACATTGATGCTCCTCACTTGCATT

GTGTGGCTAAAGTTGGTTTCTTATGCTCATACTAGCTACGACATAAGAAC

CCTAGCCAATTCAGCTGATAAGgtaaaagaatcaaaagaaatatatacta gtcactagccttgtgttactatttaaccagatactgttatgaactaaag

GCCAATCCTGAAGTCTCCTACTATGTTAGCTTGAAGAGCTTGGCATATTT

CATGGTTGCTCCCACATTGTGTTATCAGgtaatgagatgcgtctttttt aatagcatcaaacattcttaaacttacaaaagcttcttgtctaaaccttg cgtctttgcttttttcccagCTGAGCTATCCACGTTCTCCTTGTATCCGGA

AGGGTTGGGTGGCTCGTCAATTTGCAAAACTGGTCATATTCACTGGATTC

ATGGGATTTATAATAGAGCAAgtgcgttctcaacatcttgcttttttattt ttccttgtgaaaatcatcatctctgcatcgtcaatcgcttgacttctgtt ttttttttgttactttttttggcagTATATAAATCCTATTGTTAGGAACT

CAAAGCATCCTTTGAAAGGGGATCTTCTATACGCTATTGAAAGAGTCTTG

AAGCTTTCAGTTCCAAATTTATACGTGTGGCTCTGCATGTTCTACTGCTT

CTTCCACCTTTGgtatgtcgtgatcccttctctttcgatgtagtttccag agacgaacaacagaaataagctgtctcgtcaagaaattgataaatttatag ccagggatgtaatttcagttactgaacacaaatctcttttgcgttgttctt gtccccagGTTAAACATATTGGCAGAGCTCCTCTGCTTCGGGGATCGTGA ATTCTACAAAGATTGGTGGAATGCAAAAAGTGTGGGAGACgtgagttgtt attacatacgtcttactcaaaaagcatatgatttttatatgctatcgttg ttttgaggtcacttaactaaccaaaattcatgtttccatcacttgtcttc ctttatcagTATTGGAGAATGTGGAATATGgtaaggttcttttcctaaaa catcgccttcttttctatacaaaacataagaagagaggtaatacagatct tgttttctctaacagCCTGTTCATAAATGGATGGTTCGACATATATACTT

TCCGTGTCTGCGCAGCAAGATACCAAAAGTGAGTAATATGTATGATAGTG

ATTTGCGATGGCCGAGATTATATTCCgttttttttttctaaaactacaatc atccactcattttcttgttctcagGTACCTGCCATTATCATTGCTTTCTT AGTCTCTGCAGTCTTTCATGAGgtatatatatcctctgcattgcactgtc tctaatattcaaagcattgttgttacgcacattctcatgtttacaaattt ccttgcagTTATGCATCGCTGTTCCTTGCCGTCTCTTCAACCTATGGGCT TTCATGGGGATTATGTTTCAGgtataaaaaaattgacaaaacaatctgga agttttgtcatttctaatctcattttcttaccaccaccaaatgtgttttg agtagGTGCCTTTGGTCTTTATCACAAACTATCTACAAGAAAGGTTTGGC TCCATGgtatgctctctaaaggccgaataacactttctgatcatagcca -continued
cttaaatatttaattttttttgatggaaactaaaaagattgactgttttgg aatgtgatcatttagGTGGGCAACATGGTTTTCTGGTTCATCTTCTGCAT

TTTCGGTCAACCCATGTGTGTGCTTCTTTATTACCACGATCTGATGAACC

GCAAAGGATCCATGGCC

Another wild type nucleic acid that can encode a TAG1 polypeptide can include the following nucleic acid sequence (SEQ ID NO:10).

ATGGCGATTTTGGATTCTGGAGGCGTCACTATGCCGACGGAGAACGGTGG

CGGAGAGTTTGCGGATCTCGATACTCTTCGTCGACGGAAATCACGATCGG

ATTCCAACGAACCTCTTTCCGATTCCGCACCCGGTACCGATGCTTTCCCA

TCAGATGATGTTGGAGCTCCGTCCGACGCGAGGGATCGGATTGATTCAGC

TGTCGACGACGCTCAGGGAACAGCGAATTTGGCAGGAGATAACGGCGGAG

ATACCGAATTAGGGAAACTGGTGGAGGAGGAGGCGGCGGTGAAGCAAGA

GGAGACGCCGATACAAGGTATACGTATCGTCCGTCGGTTCCAGCTCATCG

GAGGGCTAGGGAAAGTCCACTCAGCTCCGACGCAATCTTCAAACAGAGCC

ATGCCGGATTATTCAACCTGTGTGTAGTAGTTCTTATTGCTGTAAACAGT

AGACTCATCATCGAGAACTTGATGAAGTACGGTTGGTTGATCAGAACAGA

TTTCTGGTTTAGTTCAACATCGCTGCGAGATTGGCCGCTTTTCATTATCT

CTCTTTCGATCTTTCCTCTGGCTGCCTTTACCGTCGAGAAACTGGTACTT

CAGAAATGCATATCTGAACCTGTGAACAAGTTTGTTGTATCCTGGAGAAC

TTATAAGTTTCTTTCTGATAATATTAAAGGTTGTCATCATTCTTCATATT

ATAATCACAATGACAGAGGTCTTGTATCCAGTTTACGTCACCCTAAGTTG

ACTAACTCGATGATCTTGAAAATGGACAGGTGTGATTCCGCCTTCTTGTC

AGGTGTCACATTGATGCTCCTCACTTGCATTGTGTGGCTAAAGTTGGTTT

CTTATGCTCATACTAGCTACGACATAAGAACCCTAGCCAATTCAGCTGAT

AAGGCCAATCCTGAAGTCTCCTACTATGTTAGCTTGAAGAGCTTGGCATA

TTTCATGGTTGCTCCCACATTGTGTTATCAGCTGAGCTATCCACGTTCTC

CTTGTATCCGGAAGGGTTGGGTGGCTCGTCAATTTGCAAAACTGGTCATA

TTCACTGGATTCATGGGATTTATAATAGAGCAATATATAAATCCTATTGT

TAGGAACTCAAAGCATCCTTTGAAAGGGGATCTTCTATACGCTATTGAAA

GAGTCTTGAAGCTTTCAGTTCCAAATTTATACGTGTGGCTCTGCATGTTC

TACTGCTTCTTCCACCTTTGGTTAAACATATTGGCAGAGCTCCTCTGCTT

CGGGGATCGTGAATTCTACAAAGATTGGTGGAATGCAAAAGTGTGGGAG

ACTATTGGAGAATGTGGAATATGCCTGTTCATAAATGGATGGTTCGACAT

ATATACTTTCCGTGTCTGCGCAGCAAGATACCAAAAGTGAGTAATATGTA

TGATAGTGATTTGCGATGGCCGAGATTATATTCCGTACCTGCCATTATCA

TTGCTTTCTTAGTCTCTGCAGTCTTTCATGAGTTATGCATCGCTGTTCCT

TGCCGTCTCTTCAACCTATGGGCTTTCATGGGATTATGTTTCAGGTGCC

TTTGGTCTTTATCACAAACTATCTACAAGAAAGGTTTGGCTCCATGGTGG

GCAACATGGTTTTCTGGTTCATCTTCTGCATTTTCGGTCAACCCATGTGT

GTGCTTCTTTATTACCACGATCTGATGAACCGCAAAGGATCCATGGCC

In some cases, a wild type nucleic acid that can encode a TAG1 polypeptide can have a sequence that deviates from a representative nucleic acid sequences set forth above (SEQ ID NO:9 or SEQ ID NO:10), sometimes referred to as a variant sequence, provided that the variant sequence encodes a wild type TAG1 polypeptide. A representative polypeptide sequence for a wild type TAG1 polypeptide can include an amino acid sequence as set forth in SEQ ID NO:2 (see, e.g., FIG. 1). In some cases, a wild type TAG1 polypeptide can have a sequence that deviates from SEQ ID NO:2, sometimes referred to as a variant sequence, provided that the polypeptide maintains its wild type activity (e.g., its level of wild type activity). For example, a TAG1 polypeptide can have at least 80 (e.g., at least 85, at least 90, at least 95, at least 98, or at least 99) percent sequence identity to SEQ ID NO:2. For example, a TAG1 polypeptide can have one or more (e.g., 2, 3, 4, 5, 6, 7, 8, 9, or 10) amino acid modifications (e.g., substitutions) relative to SEQ ID NO:2.

In some cases, oilseed plants (e.g., pennycress plants) described herein (e.g., oilseed plants having increased levels of one or more saturated fatty acids, increased levels of one or more PUFAs, altered levels of oleic acid, and/or altered levels of erucic acid) can include a loss-of-function modification in a nucleic acid (e.g., a TAG1 gene) that can encode a TAG1 polypeptide (e.g., can include a modified nucleic acid that can encode a TAG1 polypeptide). As used herein, a loss-of-function modification in a nucleic acid that can encode a TAG1 polypeptide can be any modification that is effective to reduce TAG1 polypeptide expression or TAG1 polypeptide function. In some cases, reduced TAG1 polypeptide expression or reduced TAG1 polypeptide function can be eliminated TAG1 polypeptide expression or eliminated TAG1 polypeptide function. A loss-of-function modification can be any appropriate type of genetic modification. Examples of genetic modifications can include, without limitation, deletions, insertions, substitutions, frameshifts, duplications, and rearrangements.

In some cases, oilseed plants (e.g., pennycress plants) described herein (e.g., oilseed plants having increased levels of one or more saturated fatty acids, increased levels of one or more PUFAs, altered levels of oleic acid, and/or altered levels of erucic acid) can include a substitution (e.g., a single base-pair insertion) in a nucleic acid (e.g., a TAG1 gene) that can encode a TAG1 polypeptide relative to a wild type nucleic acid that can encode a TAG1 polypeptide (e.g., SEQ ID NO:9 or SEQ ID NO:10). A single base-pair substitution can be a substitution of any appropriate nucleotide (e.g., substitution of an adenine (A), a cytosine (C), a guanine (G), or a thymine (T)). A single base-pair substitution can be a substitution of one or more nucleotides at any location within a nucleic acid (e.g., a TAG1 gene) that can encode a TAG1 polypeptide.

In some cases, a modified nucleic acid that can encode a TAG1 polypeptide can include a G to A substitution at nucleotide residue 754 (e.g., nucleotide residue 754 as corresponding to the numbering of a wild type nucleic acid that can encode a TAG1 polypeptide such as SEQ ID NO:9). A representative modified nucleic acid that can encode a TAG1 polypeptide having a loss-of-function G to A substitution at nucleotide residue 754 (e.g., nucleotide residue 754 as corresponding to the numbering of SEQ ID NO:9) can include the following nucleic acid sequence (SEQ ID NO:11), with upper case letters representing the TAG1 coding sequence and the lower case letters representing introns:

```
ATGGCGATTTTGGATTCTGGAGGCGTCACTATGCCGACGGAGAACGGTG
GCGGAGAGTTTGCGGATCTCGATACTCTTCGTCGACGGAAATCACGATC
GGATTCCAACGAACCTCTTTCCGATTCCGCACCCGGTACCGATGCTTTC
CCATCAGATGATGTTGGAGCTCCGTCCGACGCGAGGGATCGGATTGATT
CAGCTGTCGACGACGCTCAGGGAACAGCGAATTTGGCAGGAGATAACGG
CGGAGATACCGAAATTAGGGAAACTGGTGGAGGAGGAGGCGGCGGTGAA
GCAAGAGGAGACGCCGATACAAGGTATACGTATCGTCCGTCGGTTCCAG
CTCATCGGAGGGCTAGGGAAAGTCCACTCAGCTCCGACGCAATCTTCAA
ACAGgtaaatctcagattctacgctggacaatctccgaatttggtgctt
gatactgtctaatgttagaggagaatttcaaactgagtttcatgttaac
ttttagagaggacaatttcttcatttcatttgactcgagtttgtgttgt
cttccatggcagAGCCATGCCGGATTATTCAACCTGTGTGTAGTAGTTC
TTATTGCTGTAAACAGTAGACTCATCATCGAGAACTTGATGAAGgttag
ttactttttttctcctatggcttgaaaattgaattaggtttgttcttga
gctgagaactttatcaagaccttacctttgttgttgccttcattcctgt
agTACGGTTGGTTGATCA※AACAGATTTCTGGTTTAGTTCAACATCGCT
GCGAGATTGGCCGCTTTTCATgtgttggtaatatataattttttttct
ttcgtaatgttacattcttattcatataatgatgtgtttagagattcag
atatttctataaattcttctgttgcagTATCTCTCTTTCGATCTTTCCT
CTGGCTGCCTTTACCGTCGAGAAACTGGTACTTCAGAAATGCATATCTG
AACCTGTGAgtaaactactgactatatagctattactggattgtttact
gaagACAAGTTTGTTGTATCCTGGAGAACTTATAAGTTTCTTTCTGATA
ATATTAAAGGTTGTCATCATTCTTCATATTATAATCACAATGACAGAGG
TCTTGTATCCAGTTTACGTCACCCTAAGgtgtgaattaagctaaggtgt
ttctgatctcagcttgtgatactctcttttttaattctagTTGACTAAC
TCGATGATCTTGAAAATGGACAGGTGTGATTCCGCCTTCTTGTCAGGTG
TCACATTGATGCTCCTCACTTGCATTGTGTGGCTAAAGTTGGTTTCTTA
TGCTCATACTAGCTACGACATAAGAACCCTAGCCAATTCAGCTGATAAG
gtaaagaatcaaaagaaatatatactagtcactagccttgtgttacta
ttttaaccagatactgttatgaactaaagGCCAATCCTGAAGTCTCCTA
CTATGTTAGCTTGAAGAGCTTGGCATATTTCATGGTTGCTCCCACATTG
TGTTATCAGgtaatgagatgcgtctttttttaatagcatcaaacattct
taaacttacaaaagcttcttgtctaaaccttgcgtctttgcttttttccc
agCTGAGCTATCCACGTTCTCCTTGTATCCGAAGGGTTGGGTGGCTCG
TCAATTTGCAAAACTGGTCATATTCACTGGATTCATGGGATTTATAATA
GAGCAAgtgcgttctcaacatcttgcttttttattttttccttgtgaaaat
catcatctctgcatcgtcaatcgcttgacttctgtttttttttttgttac
ttttttttggcagTATATAAATCCTATTGTTAGGAACTCAAAGCATCCTT
TGAAAGGGGATCTTCTATACGTATTGAAAGAGTCTTGAAGCTTTCAGT
TCCAAATTTATACGTGTGGCTCTGCATGTTCTACTGCTTCTTCCACCTT
TGgtatgtcgtgatcccttctctttcgatgtagtttccagagacgaaca
```

```
acagaaataagctgtctcgtcaagaaattgataatttatagccagggat
gtaatttcagttactgaacacaaatctctttgcgttgttcttgtcccca
gGTTAAACATATTGGCAGAGCTCCTCTGCTTCGGGGATCGTGAATTCTA
CAAAGATTGGTGGAATGCAAAAAGTGTGGGAGACgtgagttgttattac
atacgtcttactcaaaaagcatatgattttatatgctatcgttgtttt
gaggtcacttaactaaccaaaattcatgtttccatcacttgtcttcctt
tatcagTATTGGAGAATGTGGAATATGgtaaggttctttcctaaaaca
tcgcttctttctatacaaaacataagaagagaggtaatacagatctt
gttttctctaacagCCTGTTCATAAATGGATGGTTCGACATATATACTT
TCCGTGTCTGCGCAGCAAGATACCAAAAGTGAGTAATATGTATGATAGT
GATTTGCGATGGCCGAGATTATATTCCgtttttttttctaaaactacaa
tcatccactcatttcttgttctcagGTACCTGCCATTATCATTGCTTT
CTTAGTCTCTGCAGTCTTTCATGAGgtatatatatcctctgcattgcac
tgtctctaatattcaaagcattgttgttacgcacattctcatgtttaca
aatttccttgcagTTATGCATCGCTGTTCCTTGCCGTCTCTTCAACCTA
TGGGCTTTCATGGGATTATGTTTCAGgtataaaaaaattgacaaaaca
atctggaagttttgtcatttctaatctcatttcttaccaccaccaaat
gtgttttgagtagGTGCCTTTGGTCTTTATCACAAACTATCTACAAGAA
AGGTTTGGCTCCATGgtatgctctctaaaggccgaataacactttctg
atcatagccacttaaatatttaatttttttgatggaaactaaaaagatt
gactgtttggaatgtgatcatttagGTGGGCAACATGGTTTTCTGGTT
CATCTTCTGCATTTTCGGTCAACCCATGTGTGTGCTTCTTTATTACCAC
GATCTGATGAACCGCAAAGGATCCATGGCC
```

Another representative modified nucleic acid that can encode a TAG1 polypeptide having a loss-of-function G to A substitution at nucleotide residue 754 (e.g., nucleotide residue 754 as corresponding to the numbering of SEQ ID NO:9) can include the following nucleic acid sequence

```
CAGAAATGCATATCTGAACCTGTGAACAAGTTTGTTGTATCCTGGAGAAC
TTATAAGTTTCTTTCTGATAATATTAAAGGTTGTCATCATTCTTCATATT
ATAATCACAATGACAGAGGTCTTGTATCCAGTTTACGTCACCCTAAGTTG
ACTAACTCGATGATCTTGAAAATGGACAGGTGTGATTCCGCCTTCTTGTC
AGGTGTCACATTGATGCTCCTCACTTGCATTGTGTGGCTAAAGTTGGTTT
CTTATGCTCATACTAGCTACGACATAAGAACCCTAGCCAATTCAGCTGAT
AAGGCCAATCCTGAAGTCTCCTACTATGTTAGCTTGAAGAGCTTGGCATA
TTTCATGGTTGCTCCCACATTGTGTTATCAGCTGAGCTATCCACGTTCTC
CTTGTATCCGGAAGGGTTGGGTGGCTCGTCAATTTGCAAAACTGGTCATA
TTCACTGGATTCATGGGATTTATAATAGAGCAATATATAAATCCTATTGT
TAGGAACTCAAAGCATCCTTTGAAAGGGGATCTTCTATACGCTATTGAAA
GAGTCTTGAAGCTTTCAGTTCCAAATTTATACGTGTGGCTCTGCATGTTC
TACTGCTTCTTCCACCTTTGGTTAAACATATTGGCAGAGCTCCTCTGCTT
CGGGGATCGTGAATTCTACAAAGATTGGTGGAATGCAAAAAGTGTGGGAG
ACTATTGGAGAATGTGGAATATGCCTGTTCATAAATGGATGGTTCGACAT
ATATACTTTCCGTGTCTGCGCAGCAAGATACCAAAAGTGAGTAATATGTA
TGATAGTGATTTGCGATGGCCGAGATTATATTCCGTACCTGCCATTATCA
TTGCTTTCTTAGTCTCTGCAGTCTTTCATGAGTTATGCATCGCTGTTCCT
TGCCGTCTCTTCAACCTATGGGCTTTCATGGGGATTATGTTTCAGGTGCC
TTTGGTCTTTATCACAAACTATCTACAAGAAAGGTTTGGCTCCATGGTGG
GCAACATGGTTTTCTGGTTCATCTTCTGCATTTTCGGTCAACCCATGTGT
GTGCTTCTTTATTACCACGATCTGATGAACCGCAAAGGATCCATGGCC
```

A modified nucleic acid that can encode a TAG1 polypeptide having a loss-of-function G to A substitution at nucleotide residue 754 (e.g., nucleotide residue 754 as corresponding to the numbering of SEQ ID NO:9) can encode a modified TAG1 polypeptide (e.g., a TAG1 polypeptide having an amino acid substitution). For example, a modified nucleic acid that can encode a TAG1 polypeptide having a loss-of-function G to A substitution at nucleotide residue 754 (e.g., a modified nucleic acid that can include a nucleic acid set forth in SEQ ID NO:11 or SEQ ID NO:12) can encode a TAG1 polypeptide having an arginine (R or Arg) to lysine (K or Lys) amino acid substitution at amino acid residue 165 (e.g., amino acid residue 165 as corresponding to the numbering of SEQ ID NO:2). A representative modified TAG1 polypeptide having a R to K amino acid substitution at amino acid residue 165 can include an amino acid sequence as set forth in SEQ ID NO:3 (see, e.g., FIG. 1).

In some cases, a modified nucleic acid that can encode a TAG1 polypeptide can include a G to A substitution at nucleotide residue 1296 (e.g., nucleotide residue 1296 as corresponding to the numbering of a wild type nucleic acid that can encode a TAG1 polypeptide such as SEQ ID NO:9). A representative modified nucleic acid that can encode a TAG1 polypeptide having a loss-of-function G to A substitution at nucleotide residue 1296 (e.g., nucleotide residue 1296 as corresponding to the numbering of SEQ ID NO:9) can include the following nucleic acid sequence (SEQ ID NO:13), with upper case letters representing the TAG1 coding sequence and the lower case letters representing introns:

```
ATGGCGATTTTGGATTCTGGAGGCGTCACTATGCCGACGGAGAACGGTGG
CGGAGAGTTTGCGGATCTCGATACTCTTCGTCGACGGAAATCACGATCGG
ATTCCAACGAACCTCTTTCCGATTCCGCACCCGGTACCGATGCTTTCCCA
TCAGATGATGTTGGAGCTCCGTCCGACGCGAGGGATCGGATTGATTCAGC
TGTCGACGACGCTCAGGGAACAGCGAATTTGGCAGGAGATAACGGCGGAG
ATACCGAAATTAGGGAAACTGGTGGAGGAGGAGGCGGCGGTGAAGCAAGA
GGAGACGCCGATACAAGGTATACGTATCGTCCGTCGGTTCCAGCTCATCG
GAGGGCTAGGGAAAGTCCACTCAGCTCCGACGCAATCTTCAAACAGgtaa
atctcagattctacgctggacaatctccgaatttggtgcttgatactgtc
taatgttagaggagaatttcaaactgagtttcatgttaacttttagagag
gacaatttcttcatttcatttgactcgagtttgtgttgtcttccatggca
gAGCCATGCCGGATTATTCAACCTGTGTGTAGTAGTTCTTATTGCTGTAA
ACAGTAGACTCATCATCGAGAACTTGATGAAGgttagttactttttttct
cctatggcttgaaaattgaattaggtttgttcttgagctgagaactttat
caagaccttacctttgttgttgccttcattcctgtagTACGGTTGGTTGA
TCAGAACAGATTTCTGGTTTAGTTCAACATCGCTGCGAGATTGGCCGCTT
TTCATgtgttggtaatatataatttttttttctttcgtaatgttacattc
ttattcatataatgatgtgtttagagattcagatatttctataaattctt
ctgttgcagTATCTCTCTTTCGATCTTTCCTCTGGCTGCCTTTACCGTCG
AGAAACTGGTACTTCAGAAATGCATATCTGAACCTGTGAgtaaactactg
actatatagctattactggattgtttactgaagACAAGTTTGTTGTATCC
TGGAGAACTTATAAGTTTCTTTCTGATAATATTAAAGGTTGTCATCATTC
TTCATATTATAATCACAATGACAGAGGTCTTGTATCCAGTTTACGTCACC
CTAAGgtgtgaattaagctaaggtgtttctgatctcagcttgtgatactc
tctttttaattctagTTGACTAACTCGATGATCTTGAAAATGGACAGGT
GTGATTCCGCCTTCTTGTCAGGTGTCACATTGATGCTCCTCACTTACATT
GTGTGGCTAAAGTTGGTTTCTTATGCTCATACTAGCTACGACATAAGAAC
CCTAGCCAATTCAGCTGATAAGgtaaaagaatcaaaagaaatatatacta
gtcactagccttgtgttactattttaaccagatactgttatgaactaaag
GCCAATCCTGAAGTCTCCTACTATGTTAGCTTGAAGAGCTTGGCATATTT
CATGGTTGCTCCCACATTGTGTTATCAGgtaatgagatgcgtcttttttt
aatagcatcaaacattcttaaacttacaaaagcttcttgtctaaaccttg
cgtctttgctttttcccagCTGAGCTATCCACGTTCTCCTTGTATCCGGA
AGGGTTGGGTGGCTCGTCAATTTGCAAAACTGGTCATATTCACTGGATTC
ATGGGATTTATAATAGAGCAAgtgcgttctcaacatcttgctttttattt
ttccttgtgaaaatcatcatctctgcatcgtcaatcgcttgacttctgtt
ttttttttgttactttttttggcagTATATAAATCCTATTGTTAGGAACT
CAAAGCATCCTTTGAAAGGGGATCTTCTATACGCTATTGAAAGAGTCTTG
AAGCTTTCAGTTCCAAATTTATACGTGTGGCTCTGCATGTTCTACTGCTT
CTTCCACCTTTGgtatgtcgtgatcccttctctttcgatgtagtttccag
agacgaacaacagaaataagctgtctcgtcaagaaattgataatttatag
```

```
ccagggatgtaatttcagttactgaacacaaatctctttgcgttgttctt
gtccccagGTTAAACATATTGGCAGAGCTCCTCTGCTTCGGGGATCGTGA
ATTCTACAAAGATTGGTGGAATGCAAAAAGTGTGGGAGACgtgagttgtt
attacatacgtcttactcaaaaagcatatgattttttatatgctatcgttg
ttttgaggtcacttaactaaccaaaattcatgtttccatcacttgtcttc
ctttatcagTATTGGAGAATGTGGAATATGgtaaggttcttttcctaaaa
catcgccttcttttctatacaaaacataagaagagaggtaatacagatct
tgttttctctaacagCCTGTTCATAAATGGATGGTTCGACATATATACTT
TCCGTGTCTGCGCAGCAAGATACCAAAAGTGAGTAATATGTATGATAGTG
ATTTGCGATGGCCGAGATTATATTCCgtttttttttctaaaactacaatc
atccactcattttcttgttctcagGTACCTGCCATTATCATTGCTTTCTT
AGTCTCTGCAGTCTTTCATGAGgtatatatatcctctgcattgcactgtc
tctaatattcaaagcattgttgttacgcacattctcatgtttacaaattt
ccttgcagTTATGCATCGCTGTTCCTTGCCGTCTCTTCAACCTATGGGCT
TTCATGGGATTATGTTTCAGgtataaaaaaattgacaaaacaatctgga
agttttgtcatttctaatctcattttcttaccaccaccaaatgtgttttg
agtagGTGCCTTTGGTCTTTATCACAAACTATCTACAAGAAAGGTTTGGC
TCCATGgtatgctctctaaaggccgaataacacttttctgatcatagcca
cttaaatatttaattttttgatggaaactaaaaagattgactgttttgg
aatgtgatcatttagGTGGGCAACATGGTTTTCTGGTTCATCTTCTGCAT
TTTCGGTCAACCCATGTGTGTGCTTCTTTATTACCACGATCTGATGAACC
GCAAAGGATCCATGGCC
```

Another representative modified nucleic acid that can encode a TAG1 polypeptide having a loss-of-function G to A substitution at nucleotide residue 1296 (e.g., nucleotide residue 1296 as corresponding to the numbering of SEQ ID NO:9) can include the following nucleic acid sequence (SEQ ID NO:14):

```
ATGGCGATTTTGGATTCTGGAGGCGTCACTATGCCGACGGAGAACGGTGG
CGGAGAGTTTGCGGATCTCGATACTCTTCGTCGACGGAAATCACGATCGG
ATTCCAACGAACCTCTTTCCGATTCCGCACCCGGTACCGATGCTTTCCCA
TCAGATGATGTTGGAGCTCCGTCCGACGCGAGGGATCGGATTGATTCAGC
TGTCGACGACGCTCAGGGAACAGCGAATTTGGCAGGAGATAACGGCGGAG
ATACCGAAATTAGGGAAACTGGTGGAGGAGGAGGCGGCGGTGAAGCAAGA
GGAGACGCCGATACAAGGTATACGTATCGTCCGTCGGTTCCAGCTCATCG
GAGGGCTAGGGAAAGTCCACTCAGCTCCGACGCAATCTTCAAACAGAGCC
ATGCCGGATTATTCAACCTGTGTGTAGTAGTTCTTATTGCTGTAAACAGT
AGACTCATCATCGAAACTTGATGAAGTACGGTTGGTTGATCAGAACAGA
TTTCTGGTTTAGTTCAACATCGCTGCGAGATTGGCCGCTTTTCATTATCT
CTCTTTCGATCTTTCCTCTGGCTGCCTTTACCGTCGAGAAACTGGTACTT
CAGAAATGCATATCTGAACCTGTGAACAAGTTTGTTGTATCCTGGAGAAC
TTATAAGTTTCTTTCTGATAATATTAAAGGTTGTCATCATTCTTCATATT
ATAATCACAATGACAGAGGTCTTGTATCCAGTTTACGTCACCCTAAGTTG
ACTAACTCGATGATCTTGAAAATGGACAGGTGTGATTCCGCCTTCTTGTC
AGGTGTCACATTGATGCTCCTCACTT[X]CATTGTGTGGCTAAAGTTGGTTT
CTTATGCTCATACTAGCTACGACATAAGAACCCTAGCCAATTCAGCTGAT
AAGGCCAATCCTGAAGTCTCCTACTATGTTAGCTTGAAGAGCTTGGCATA
TTTCATGGTTGCTCCCACATTGTGTTATCAGCTGAGCTATCCACGTTCTC
CTTGTATCCGGAAGGGTTGGGTGGCTCGTCAATTTGCAAAACTGGTCATA
TTCACTGGATTCATGGGATTTATAATAGAGCAATATATAAATCCTATTGT
TAGGAACTCAAAGCATCCTTTGAAAGGGGATCTTCTATACGCTATTGAAA
GAGTCTTGAAGCTTTCAGTTCCAAATTTATACGTGTGGCTCTGCATGTTC
TACTGCTTCTTCCACCTTTGGTTAAACATATTGGCAGAGCTCCTCTGCTT
CGGGGATCGTGAATTCTACAAAGATTGGTGGAATGCAAAAAGTGTGGGAG
ACTATTGGAGAATGTGGAATATGCCTGTTCATAAATGGATGGTTCGACAT
ATATACTTTCCGTGTCTGCGCAGCAAGATACCAAAAGTGAGTAATATGTA
TGATAGTGATTTGCGATGGCCGAGATTATATTCCGTACCTGCCATTATCA
TTGCTTTCTTAGTCTCTGCAGTCTTTCATGAGTTATGCATCGCTGTTCCT
TGCCGTCTCTTCAACCTATGGGCTTTCATGGGATTATGTTTCAGGTGCC
TTTGGTCTTTATCACAAACTATCTACAAGAAAGGTTTGGCTCCATGGTGG
GCAACATGGTTTTCTGGTTCATCTTCTGCATTTTCGGTCAACCCATGTGT
GTGCTTCTTTATTACCACGATCTGATGAACCGCAAAGGATCCATGGCC
```

A modified nucleic acid that can encode a TAG1 polypeptide having a loss-of-function G to A substitution at nucleotide residue 1296 (e.g., nucleotide residue 1296 as corresponding to the numbering of SEQ ID NO:9 such as SEQ ID NO:13 or SEQ ID NO:14) can encode a modified TAG1 polypeptide (e.g., a TAG1 polypeptide having an amino acid substitution). For example, a modified nucleic acid that can encode a TAG1 polypeptide having a loss-of-function G to A substitution at nucleotide residue 1296 (e.g., a modified nucleic acid that can include a nucleic acid set forth in SEQ ID NO:13 or SEQ ID NO:14) can encode a TAG1 polypeptide having a cystine (C or Cys) to tyrosine (Y or Tyr) amino acid substitution at amino acid residue 165 (e.g., amino acid residue 276 as corresponding to the numbering of SEQ ID NO:2). A representative modified TAG1 polypeptide having a C to Y amino acid substitution at amino acid residue 276 can include an amino acid sequence as set forth in SEQ ID NO:4 (see, e.g., FIG. 1).

In some cases, a modified nucleic acid that can encode a TAG1 polypeptide can include a G to A substitution at nucleotide residue 2166 (e.g., nucleotide residue 2166 as corresponding to the numbering of a wild type nucleic acid that can encode a TAG1 polypeptide such as SEQ ID NO:9). A representative modified nucleic acid that can encode a TAG1 polypeptide having a loss-of-function G to A substitution at nucleotide residue 2166 (e.g., nucleotide residue 2166 as corresponding to the numbering of SEQ ID NO:9) can include the following nucleic acid sequence (SEQ ID NO:15), with upper case letters representing the TAG1 coding sequence and the lower case letters representing introns:

ATGGCGATTTTGGATTCTGGAGGCGTCACTATGCCGACGGAGAACGGTGG
CGGAGAGTTTGCGGATCTCGATACTCTTCGTCGACGGAAATCACGATCGG
ATTCCAACGAACCTCTTTCCGATTCCGCACCCGGTACCGATGCTTTCCCA
TCAGATGATGTTGGAGCTCCGTCCGACGCGAGGGATCGGATTGATTCAGC
TGTCGACGACGCTCAGGGAACAGCGAATTTGGCAGGAGATAACGGCGGAG
ATACCGAAATTAGGGAAACTGGTGGAGGAGGAGGCGGCGGTGAAGCAAGA
GGAGACGCCGATACAAGGTATACGTATCGTCCGTCGGTTCCAGCTCATCG
GAGGGCTAGGGAAAGTCCACTCAGCTCCGACGCAATCTTCAAACAGgtaa
atctcagattctacgctggacaatctccgaatttggtgcttgatactgtc
taatgttagaggagaatttcaaactgagtttcatgttaacttttagagag
gacaatttcttcatttcatttgactcgagtttgtgttgtcttccatggca
gAGCCATGCCGGATTATTCAACCTGTGTGTAGTAGTTCTTATTGCTGTAA
ACAGTAGACTCATCATCGAGAACTTGATGAAGgttagttactttttttct
cctatggcttgaaaattgaattaggtttgttcttgagctgagaactttat
caagaccttacctttgttgttgccttcattcctgtagTACGGTTGGTTGA
TCAGAACAGATTTCTGGTTTAGTTCAACATCGCTGCGAGATTGGCCGCTT
TTCATgtgttggtaatatataatttttttttctttcgtaatgttacattc
ttattcatataatgatgtgtttagagattcagatatttctataaattctt
ctgttgcagTATCTCTCTTTCGATCTTTCCTCTGGCTGCCTTTACCGTCG
AGAAACTGGTACTTCAGAAATGCATATCTGAACCTGTGAgtaaactactg
actatatagctattactggattgtttactgaagACAAGTTTGTTGTATCC
TGGAGAACTTATAAGTTTCTTTCTGATAATATTAAAGGTTGTCATCATTC
TTCATATTATAATCACAATGACAGAGGTCTTGTATCCAGTTTACGTCACC
CTAAGgtgtgaattaagctaaggtgtttctgatctcagcttgtgatactc
tctttttaattctagTTGACTAACTCGATGATCTTGAAAATGGACAGGT
GTGATTCCGCCTTCTTGTCAGGTGTCACATTGATGCTCCTCACTTGCATT
GTGTGGCTAAAGTTGGTTTCTTATGCTCATACTAGCTACGACATAAGAAC
CCTAGCCAATTCAGCTGATAAGgtaaaagaatcaaaagaaatatatacta
gtcactagccttgtgttactattttaaccagatactgttatgaactaaag
GCCAATCCTGAAGTCTCCTACTATGTTAGCTTGAAGAGCTTGGCATATTT
CATGGTTGCTCCCACATTGTGTTATCAGgtaatgagatgcgtctttttt
aatagcatcaaacattcttaaacttacaaaagcttcttgtctaaaccttg
cgtctttgctttttcccagCTGAGCTATCCACGTTCTCCTTGTATCCGGA
AGGGTTGGGTGGCTCGTCAATTTGCAAAACTGGTCATATTCACTGGATTC
ATGGGATTTATAATAGAGCAAgtgcgttctcaacatcttgctttttattt
ttccttgtgaaaatcatcatctctgcatcgtcaatcgcttgacttctgtt
ttttttttgttactttttttggcagTATATAAATCCTATTGTTAGGAACT
CAAAGCATCCTTTGAAAGGGGATCTTCTATACGCTATTGAAAGAGTCTTG
AAGCTTTCAGTTCCAAATTTATACGTGTGGCTCTGCATGTTCTACTGCTT
CTTCCACCTTTGgtatgtcgtgatcccttctctttcgatgtagtttccag
agacgaacaacagaaataagctgtctcgtcaagaaattgataatttatag -continued ccagggatgtaatttcagttactgaacacaaatctctttgcgttgttctt
gtccccagGTTAAACATATTGGCAGAGCTCCTCTGCTTCGGGGATCGTGA
ATTCTACAAAGATTGATGGAATGCAAAAAGTGTGGGAGACgtgagttgtt
attacatacgtottactcaaaaagcatatgatttttatatgctatcgttg
ttttgaggtcacttaactaaccaaaattcatgtttccatcacttgtcttc
ctttatcagTATTGGAGAATGTGGAATATGgtaaggttcttttcctaaaa
catcgccttcttttctatacaaaacataagaagagaggtaatacagatct
tgttttctctaacagCCTGTTCATAAATGGATGGTTCGACATATATACTT
TCCGTGTCTGCGCAGCAAGATACCAAAAGTGAGTAATATGTATGATAGTG
ATTTGCGATGGCCGAGATTATATTCCgtttttttttctaaaactacaatc
atccactcatttcttgttctcagGTACCTGCCATTATCATTGCTTTCTT
AGTCTCTGCAGTCTTTCATGAGgtatatatatcctctgcattgcactgtc
tctaatattcaaagcattgttgttacgcacattctcatgtttacaaattt
ccttgcagTTATGCATCGCTGTTCCTTGCCGTCTCTTCAACCTATGGGCT
TTCATGGGGATTATGTTTCAGgtataaaaaaattgacaaaacaatctgga
agttttgtcatttctaatctcatttcttaccaccaccaaatgtgttttg
agtagGTGCCTTTGGTCTTTATCACAAACTATCTACAAGAAAGGTTTGGC
TCCATGgtatgctctctaaaggccgaataacacttttctgatcatagcca
cttaaatatttaatttttttgatggaaactaaaaagattgactgttttgg
aatgtgatcatttagGTGGGCAACATGGTTTTCTGGTTCATCTTCTGCAT
TTTCGGTCAACCCATGTGTGTGCTTCTTTATTACCACGATCTGATGAACC
GCAAAGGATCCATGGCC Another representative modified nucleic acid that can encode a TAG1 polypeptide having a loss-of-function G to A substitution at nucleotide residue 2166 (e.g., nucleotide residue 2166 as corresponding to the numbering of SEQ ID NO:9) can include the following nucleic acid sequence (SEQ ID NO:16):

ATGGCGATTTTGGATTCTGGAGGCGTCACTATGCCGACGGAGAACGGTGG
CGGAGAGTTTGCGGATCTCGATACTCTTCGTCGACGGAAATCACGATCGG
ATTCCAACGAACCTCTTTCCGATTCCGCACCCGGTACCGATGCTTTCCCA
TCAGATGATGTTGGAGCTCCGTCCGACGCGAGGGATCGGATTGATTCAGC
TGTCGACGACGCTCAGGGAACAGCGAATTTGGCAGGAGATAACGGCGGAG
ATACCGAAATTAGGGAAACTGGTGGAGGAGGAGGCGGCGGTGAAGCAAGA
GGAGACGCCGATACAAGGTATACGTATCGTCCGTCGGTTCCAGCTCATCG
GAGGGCTAGGGAAAGTCCACTCAGCTCCGACGCAATCTTCAAACAGAGCC
ATGCCGGATTATTCAACCTGTGTGTAGTAGTTCTTATTGCTGTAAACAGT
AGACTCATCATCGAGAACTTGATGAAGTACGGTTGGTTGATCAGAACAGA
TTTCTGGTTTAGTTCAACATCGCTGCGAGATTGGCCGCTTTTCATTATCT
CTCTTTCGATCTTTCCTCTGGCTGCCTTTACCGTCGAGAAACTGGTACTT
CAGAAATGCATATCTGAACCTGTGAACAAGTTTGTTGTATCCTGGAGAAC

-continued
```
TTATAAGTTTCTTTCTGATAATATTAAAGGTTGTCATCATTCTTCATATT

ATAATCACAATGACAGAGGTCTTGTATCCAGTTTACGTCACCCTAAGTTG

ACTAACTCGATGATCTTGAAAATGGACAGGTGTGATTCCGCCTTCTTGTC

AGGTGTCACATTGATGCTCCTCACTTGCATTGTGTGGCTAAAGTTGGTTT

CTTATGCTCATACTAGCTACGACATAAGAACCCTAGCCAATTCAGCTGAT

AAGGCCAATCCTGAAGTCTCCTACTATGTTAGCTTGAAGAGCTTGGCATA

TTTCATGGTTGCTCCCACATTGTGTTATCAGCTGAGCTATCCACGTTCTC

CTTGTATCCGGAAGGGTTGGGTGGCTCGTCAATTTGCAAAACTGGTCATA

TTCACTGGATTCATGGGATTTATAATAGAGCAATATATAAATCCTATTGT

TAGGAACTCAAAGCATCCTTTGAAAGGGGATCTTCTATACGCTATTGAAA

GAGTCTTGAAGCTTTCAGTTCCAAATTTATACGTGTGGCTCTGCATGTTC

TACTGCTTCTTCCACCTTTGGTTAAACATATTGGCAGAGCTCCTCTGCTT

CGGGGATCGTGAATTCTACAAAGATTCATGGAATGCAAAAGTGTGGGAG

ACTATTGGAGAATGTGGAATATGCCTGTTCATAAATGGATGGTTCGACAT

ATATACTTTCCGTGTCTGCGCAGCAAGATACCAAAAGTGAGTAATATGTA

TGATAGTGATTTGCGATGGCCGAGATTATATTCCGTACCTGCCATTATCA

TTGCTTTCTTAGTCTCTGCAGTCTTTCATGAGTTATGCATCGCTGTTCCT

TGCCGTCTCTTCAACCTATGGGCTTTCATGGGGATTATGTTTCAGGTGCC

TTTGGTCTTTATCACAAACTATCTACAAGAAAGGTTTGGCTCCATGGTGG

GCAACATGGTTTTCTGGTTCATCTTCTGCATTTTCGGTCAACCCATGTGT

GTGCTTCTTTATTACCACGATCTGATGAACCGCAAAGGATCCATGGCC
```

A modified nucleic acid that can encode a TAG1 polypeptide having a loss-of-function G to A substitution at nucleotide residue 2166 (e.g., nucleotide residue 2166 as corresponding to the numbering of SEQ ID NO:9 such as SEQ ID NO:15 or SEQ ID NO:16) can encode a modified TAG1 polypeptide (e.g., a TAG1 polypeptide having an amino acid substitution). For example, a modified nucleic acid that can encode a TAG1 polypeptide having a loss-of-function G to A substitution at nucleotide residue 2166 (e.g., a modified nucleic acid that can include a nucleic acid set forth in SEQ ID NO:15 or SEQ ID NO:16) can encode a TAG1 polypeptide having a tryptophan (W or Trp) to stop codon amino acid substitution (e.g., can cause a truncation) at amino acid residue 426 (e.g., amino acid residue 426 as corresponding to the numbering of SEQ ID NO:2). A representative modified TAG1 polypeptide having a R to K amino acid substitution at amino acid residue 426 can include an amino acid sequence as set forth in SEQ ID NO:5 (see, e.g., FIG. 1).

In some cases, oilseed plants (e.g., pennycress plants) described herein (e.g., oilseed plants having increased levels of one or more saturated fatty acids, increased levels of one or more PUFAs, altered levels of oleic acid, and/or altered levels of erucic acid) also can include one or more loss-of-function modifications in one or more nucleic acid that can encode a polypeptide involved in fatty acid biosynthesis. Examples of polypeptides involved in fatty acid biosynthesis can include, without limitation, FAD2 polypeptides, FAE1 polypeptides, and ROD1 polypeptides.

A modified nucleic acid that can encode a polypeptide involved in fatty acid biosynthesis, can encode a modified polypeptide involved in fatty acid biosynthesis (e.g., a modified FAD2 polypeptide, a modified FAE1 polypeptide, and a modified ROD1 polypeptide).

In some cases, a modified nucleic acid that can encode a FAD2 polypeptide, can encode a modified FAD2 polypeptide. Exemplary modified nucleic acids that can encode a modified FAD2 polypeptide can include the nucleic acid sequences set forth in SEQ ID NO:17, SEQ ID NO:18, SEQ ID NO:19, SEQ ID NO:20, SEQ ID NO:21, and SEQ ID NO:22 (see, e.g., FIG. 3). Exemplary modified FAD2 polypeptides can include the amino acid sequences as set forth in SEQ ID NO:25, SEQ ID NO:26, and SEQ ID NO:27 (see, e.g., FIG. 4). For example, a modified nucleic acid that includes a nucleic acid sequence set forth in SEQ ID NO:17 or SEQ ID NO:18 can encode a modified FAD2 polypeptide that includes the amino acid sequence set forth in SEQ ID NO:25. For example, a modified nucleic acid that includes a nucleic acid sequence set forth in SEQ ID NO:19 or SEQ ID NO:20 can encode a modified FAD2 polypeptide that includes the amino acid sequence set forth in SEQ ID NO:26. For example, a modified nucleic acid that includes a nucleic acid sequence set forth in SEQ ID NO:21 or SEQ ID NO:22 can encode a modified FAD2 polypeptide that includes the amino acid sequence set forth in SEQ ID NO:27.

In some cases, modified nucleic acid that can encode a FAE1 polypeptide, can encode a modified FAE1 polypeptide. Exemplary modified nucleic acids that can encode a modified FAE1 polypeptide can include the nucleic acid sequences set forth in SEQ ID NO:31 and SEQ ID NO:32 (see, e.g., FIG. 5). Exemplary modified FAE1 polypeptides can include the amino acid sequences as set forth in SEQ ID NO:35 and SEQ ID NO:36 (see, e.g., FIG. 6). For example, a modified nucleic acid that can encode a FAE1 polypeptide, can encode a modified FAE1 polypeptide. For example, a modified nucleic acid that includes a nucleic acid sequence set forth in SEQ ID NO:31 can encode a modified FAE1 polypeptide that includes the amino acid sequence set forth in SEQ ID NO:35. For example, a modified nucleic acid that includes a nucleic acid sequence set forth in SEQ ID NO:32 can encode a modified FAE1 polypeptide that includes the amino acid sequence set forth in SEQ ID NO:36.

In some cases, a modified nucleic acid that can encode a ROD1 polypeptide, can encode a modified ROD1 polypeptide. Exemplary modified nucleic acids that can encode a modified ROD1 polypeptide can include the nucleic acid sequences set forth in SEQ ID NO:40, SEQ ID NO:41, SEQ ID NO:42, and SEQ ID NO:43 (see, e.g., FIG. 7). Exemplary modified ROD1 polypeptides can include the amino acid sequences as set forth in SEQ ID NO:46 and SEQ ID NO:47 (see, e.g., FIG. 8). For example, a modified nucleic acid that includes a nucleic acid sequence set forth in SEQ ID NO:40 or SEQ ID NO:41 can encode a modified ROD1 polypeptide that includes the amino acid sequence set forth in SEQ ID NO:46. For example, a modified nucleic acid that includes a nucleic acid sequence set forth in SEQ ID NO:42 or SEQ ID NO:43 can encode a modified ROD1 polypeptide that includes the amino acid sequence set forth in SEQ ID NO:47.

In some cases, a modified nucleic acid that can encode a modified polypeptide involved in fatty acid biosynthesis can be as described elsewhere. For example, modified nucleic acids that can encode modified polypeptides involved in fatty acid biosynthesis, and modified polypeptides involved in fatty acid biosynthesis, can be as described in WO 2018/140782, and International Application No.: PCT/US2018/015536, filed Jan. 26, 2018.

Any appropriate method can be used to introduce one or more modifications into a nucleic acid encoding a TAG1 polypeptide (e.g., a TAG1 gene), and, optionally, to modify a nucleic acid encoding a FAD2 polypeptide (e.g., a FAD2 gene), a nucleic acid encoding a FAE1 polypeptide (e.g., a FAE1 gene), and/or a nucleic acid encoding a ROD1 polypeptide (e.g., a ROD1 gene) to produce oilseed plants (e.g., pennycress plants) described herein (e.g., oilseed plants having increased levels of one or more saturated fatty acids, increased levels of one or more PUFAs, altered levels of oleic acid, and/or altered levels of erucic acid). Examples of methods for modifying a nucleic acid include, without limitation, genome editing (e.g., genome editing with engineered nucleases (GEEN)) and introduction of a transgene (e.g., gene transfer). For example, genome editing can be used to produce oilseed plants described herein. Genome editing can insert, replace, or remove DNA from a genome using one or more site-specific nucleases (SSN) and, in some cases, a repair template (RT). Nucleases can be targeted to a specific position in the genome, where their action can introduce a particular modification to the endogenous sequences. For example, a SSN can introduce a targeted double-strand break (DSB) in the genome, such that cellular DSB repair mechanisms incorporate a RT into the genome in a configuration that produces heritable genome edits (e.g., a loss-of-function modification in a nuclide acid such as a coding sequence) in the cell, in a plant regenerated from the cell, and in any progeny of the regenerated plant. Nucleases useful for genome editing include, without limitation, CRISPR-associated (Cas) nucleases, zinc finger nucleases (ZFNs), transcription activator-like effector (TALE) nucleases, and homing endonucleases (HE; also referred to as meganucleases).

In some cases, a CRISPR/Cas system can be used to introduce one or more loss-of-function modifications described herein into a nucleic acid encoding a TAG1 polypeptide (e.g., a TAG1 gene), and, optionally, to into a nucleic acid encoding a FAD2 polypeptide (e.g., a FAD2 gene), a nucleic acid encoding a FAE1 polypeptide (e.g., a FAE1 gene), and/or a nucleic acid encoding a ROD1 polypeptide (e.g., a ROD1 gene). For example, a CRISPR/Cas vector can include at least one guide sequence (e.g., a protospacer sequence) specific to a nucleic acid encoding a TAG1 polypeptide (and, optionally, specific to a nucleic acid encoding a FAD2 polypeptide, a nucleic acid encoding a FAE1 polypeptide, and/or a nucleic acid encoding a ROD1 polypeptide) upstream of a protospacer adjacent motif (PAM). A Cas enzyme will bind to and cleave within a target sequence (e.g., a nucleic acid sequence specific to a coding sequence of a gene involved in fatty acid biosynthesis) only if the target site is followed by a PAM sequence. For example, the canonical PAM includes the sequence 5'-NGG-3', where N is any nucleotide followed by two guanine (G) nucleotides. In some cases, a PAM sequence can be a 5'-TTGGGT-3' sequence. In some cases, a PAM can be a 5'-CGG-3' sequence. The Cas component of a CRISP/Cas system described herein can be any appropriate Cas nuclease. Examples of Cas nucleases include, without limitation, Cas1, Cas2, Cas3, Cas9, Cas10, and Cpf1. In some cases, the Cas component of a CRISPR/Cas system designed to introduce one or more loss-of-function modifications described herein into an FAD2 coding sequence can be a Cas9 nuclease. In some cases, the Cas component of a CRISPR/Cas system can be a Cas9 nuclease. For example, the Cas9 nuclease of a CRISPR/Cas9 system described herein can be a *Staphylococcus aureus* Cas9 (SaCas9). One example of a SaCas9 is described in, for example, Steinert et al., 2015, *Plant J.*, 84:1295-305. For example, the Cas9 nuclease of a CRISPR/Cas9 system described herein can be a *Streptococcus pyogenes* Cas9 (spCas9). One example of a spCas9 is described in, for example, Fauser et al., 2014 *The Plant Journal* 79:348-359.

The genome editing reagents described herein can be introduced into an oilseed plant by any appropriate method. In some cases, nucleic acids encoding the genome editing reagents can be introduced into a plant cell using *Agrobacterium* or *Ensifer* mediated transformation, particle bombardment, liposome delivery, nanoparticle delivery, electroporation, polyethylene glycol (PEG) transformation, or any other method suitable for introducing a nucleic acid into a plant cell. In some cases, the SSN or other expressed gene editing reagents can be delivered as RNAs or as proteins to a plant cell and the RT, if one is used, can be delivered as DNA.

The oilseed plants (e.g., pennycress plants) described herein (e.g., oilseed plants having increased levels of one or more saturated fatty acids, increased levels of one or more PUFAs, altered levels of oleic acid, and/or altered levels of erucic acid) can be identified by, for example, an NIR analyzer (e.g., as described in the Examples).

The invention will be further described in the following examples, which do not limit the scope of the invention described in the claims.

EXAMPLES

Example 1: Generation of Pennycress Plants Having Increased Levels of One or More Saturated Fatty Acids, Increased Levels of One or More PUFAs, and Decreased Levels of Oleic Acid The plant oil pathways have been well studied in plants leading to a good understanding of most of the steps needed to produce triglycerides in the seeds for the storage of energy (see, e.g., Baud et al., 2010 *Prog Lipid Res.* 49:235-49). This study used a mutagenesis approach to create changes in *Thlaspi arvense* (pennycress) genes required for seed oil biosynthesis, and to identify modifications resulting in improvements in the oil produced in the pennycress seeds.

Materials and Methods

Mutagenesis of Pennycress

Seeds of wild type pennycress seeds were treated with 0.2% ethyl methane sulfonate (EMS) for 18 hours. After extensive washing the seeds were planted into outdoor fields during the late summer or early fall to produce an M1 generation of mutagenized plants. In the spring the plants produced stems and flowers on which the M2 seed generation was harvested. Within the M1 plants, some plants were observed to have whole yellow sectors. These are sectors are an indication that the mutagenesis was successful.

M2 seeds were collected from the M1 plants harvested in the late spring and stored in coin envelopes. During the late summer and fall, the M2 seeds were sowed into rows in outdoor fields. M3 generation seeds were collected from individual mature M2 plants.

Near Infrared (NIR) Analysis

Individual lots of M3 were subjected to NIR analysis using a DA 7250 NIR analyzer obtained from Perten Instruments (A PerkinElmer Company). During the scan the M3 seeds were illuminated with a source emitting electron magnetic irradiation at wavelengths between 900 nm and 1800 nm. The intensity of the reflectance at wavelengths in the interval was captured and graphed. Calibration data from Perten was used to estimate the chemical composition of the seeds. Oleic acid, linoleic acid, linolenic acid, and erucic acid contents were among the various chemicals whose values were estimated.

NIR scans from individual M2 plants can be used to predict the fatty acid composition of M3 seeds.

Identification of Modifications

NIR data were scanned for lines containing increased levels of saturated fatty acids, increased levels of PUFAs, and/or decreased levels of oleic acid, and DNA sequence analyses were used to identify mutations contained in these lines.

Results

Pennycress TAG1 mutants were identified in an NIR screen of over 15,000 individual seed lots with the goal of identifying mutant with altered seed oil fatty acid composition. During this screen three mutant lines were identified with an increase in linoleic (18:2) and linolenic (18:3) fatty acids.

Pennycress TAG1 mutants were found to contain a mutation in the TAG1/DGAT1 gene (FIG. 1). Pennycress plants with reduced TAG1 activity, Ta_tag1-3, produce oils with increased levels of PUFAs (18:2 and 18:3 fatty acids) and higher than wild type levels stearic and linolenic acids (FIG. 2). At the same time the levels of oleic and acid decreased (FIG. 2). Ta_tag1-3 showed a ~2.5-fold increase in linolenic acid over the starting wild type material. The high levels of linolenic (18:3—also known as ALA, an omega3 fatty acid) allow the oil to be used in several new types of applications for example t as a drying agent in paints to a use as a high omega3 fish food supplement and in general—a heart healthy food additive.

Example 2: Creation of Double and Triple Mutant Pennycress Plants Having Increased Levels of One or More Saturated Fatty Acids, Increased Levels of One or More PUFAs, and Decreased Levels of Oleic Acid To explore the ability to improve and widen the utility of the Tatag1 oils, the Tatag1-3 line was crossed with a Tafad2-2 mutant containing elevated levels of erucic acid, a Tafae1-1 mutant, or a Tarod1-1 mutant as described elsewhere (see, e.g., WO 2018/140782, and International Application No.: PCT/US2018/015536, filed Jan. 26, 2018). Double and triple homozygous mutants showed wild type or increased levels of one or more saturated fatty acids, wild type or increased levels of one or more PUFAs, and/or increased or levels of oleic acid, and/or increased or decreased erucic acid (FIG. 2).

The double Tafae1-1 Tatag1-3 line produced an increased level of linoleic acid and an increased level of linolenic acid. This oil has similar features as high PUFA soybean or sunflower oil.

The double Tatag1-3 Tafad2-2 line produced an increased level of palmitic acid, an increased level of stearic acid, and a decreased level of erucic acid. The reduction in erucic make this oil fit for human consumption and for use as an animal feed supplement.

The double Tatag1-3 Tarod1-1 line produced an increased level of stearic acid and an increased level of linolenic acid.

The triple Tatag1-3 Tafad2-2 Tafae1-1 line produced an increased level of oleic acid and a decreased level of erucic acid.

Example 3: Fatty Acid Profiles of Pennycress Plants Having Modified Triglyceride Synthesis The fatty acid profiles of oil from pennycress plants having modified triglyceride synthesis as compared to wild type pennycress plants were determined.

Materials and Methods

Seed Source and Segregating Populations

Mutants characterized were derived from an EMS population. One allele from three genes—TAG1 (tag1-3) (Trp426Stop), FAD2 (fad2-2) (Gly141Asp), FAE1 (fae1-1) (Gln340Stop), and ROD1 (rod1-1) (Met226Ile) were selected. Crosses were performed between EMS lines having a tag1-3 allele with a rod1-1 allele, fae1-1, and fad2-2 allele. F1 plants were tested for the heterozygous mutations in the respective crosses and plants were grown to complete maturity to produce F2 seeds for further analysis. Homozygous F2 plants were isolated using allele-specific markers tag1-3/fae1-1 and tag1-3/rod1-1. To isolate homozygous F2 seeds of tag1-3/fad2-2 combination a single seed method was used as described in FIG. 19.

Methylation of Fatty Acids and Gas Chromatography

Oil from single seeds or bulk seeds was extracted using hexane. FAME analysis was performed as described herein. Briefly, one or pool of seeds was crushed with 500 µL of hexane containing (C17:0) internal standard and methylation was performed by adding 0.5 mL of methanolic-sodium hydroxide and incubating at 95° C. for 10 minutes, followed by addition of 0.5 mL of boron trifluoride methanol (Sigma—CAS Number 373-57-9) and incubating for another 10 minutes at 95° C. Methylated oil was separated by the addition of 1 mL each of saturated sodium chloride and GC-grade hexane (Sigma CAS 110-54-3). Anhydrous sodium thiosulphate was added to the extracted methylated oil to remove any remaining water molecules. Samples were then transferred to GC vials for analysis of fatty-acid methyl esters (FAMEs). External standards were prepared using RM-3 and RM-5 from Sigma (O7256-1AMP, CRMO7506) to estimate and identify the peaks from the GC analyses. Flame ionization detection (FID) was performed using an Agilent Hewlet Packard 5890 Gas Chromatograph with a 7673A autosampler. FAMEs were separated using a Supelco Omegawax® 250 FUSED SILICA Capillary Column 30 m×0.25 mm×0.25 µm film thickness.

DNA Extraction and Allele-Specific Genotyping

DNA was extracted using the Sigma Extract-N-Amp Plant Extraction and Dilution Solution (Sigma-Aldrich, D5688 and E7526) from single defatted seeds, and pools of defatted seeds. The samples of interest were incubated with 50 µL of extraction buffer at 95° C. for 10 minutes, followed by the addition of a 50 µL dilution buffer and mixing.

Allele-specific genotyping was performed on PCR mixes consisting of a final volume of 10 µL containing 5 µL of 2×KASP (LGC Bioresearch Technologies, Hoddesdon, UK) Reaction Mix, 0.15 µL allele specific primer mix, and 1 µL of diluted PCR product generated with the pre-amplification primers above. Thermal cycling was performed on a Light-Cycler 480 (Roche, Branford, Conn.) using the following parameters: 15 minutes at 94° C.; 10 touchdown cycles of 20 seconds at 94° C., 60 seconds at 65-57° C. (dropping 0.8° C. per cycle); and 26 cycles of 20 seconds at 94° C., 60 seconds at 57° C. A final read at 37° C. for 5 seconds was taken using the built-in plate reader. PCR products were scanned at two different wavelength regions 523-558 nm and 483-533 nm, respectively, to differentiate wild-type and mutant alleles.
Results A table containing the molecular percent of fatty acids in oil isolated from pennycress plants having a modification in a single gene that encodes a polypeptide involved in triglyceride synthesis and in oil isolated from pennycress plants having a modification in two genes that each encode a polypeptide involved in triglyceride synthesis is shown in FIG. 11.

Figure 12:
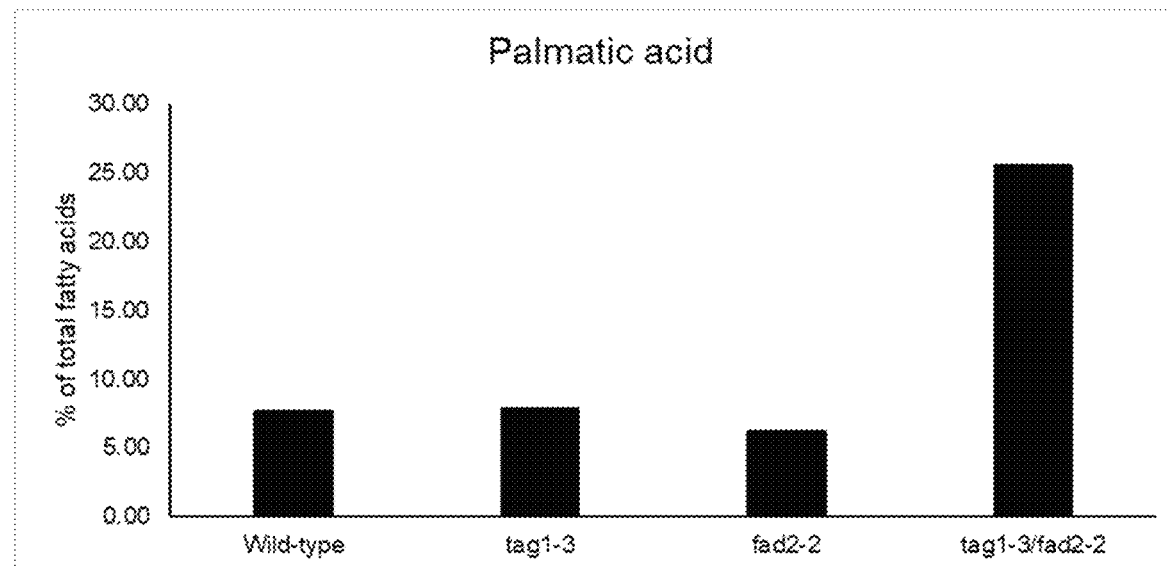
FIG. 12 contains a graph showing a percent of palmitic acid (16:0) in oil from wild type pennycress plants (MN106) and from pennycress plants having a modified nucleic acid encoding a TAG1 polypeptide (tag1-3), having a modified nucleic acid encoding a FAD2 polypeptide (fad2-2), or having both a modified nucleic acid encoding a TAG1 polypeptide and a modified nucleic acid encoding a FAD2 polypeptide (tag1-3/fad2-2).
Figure 13:
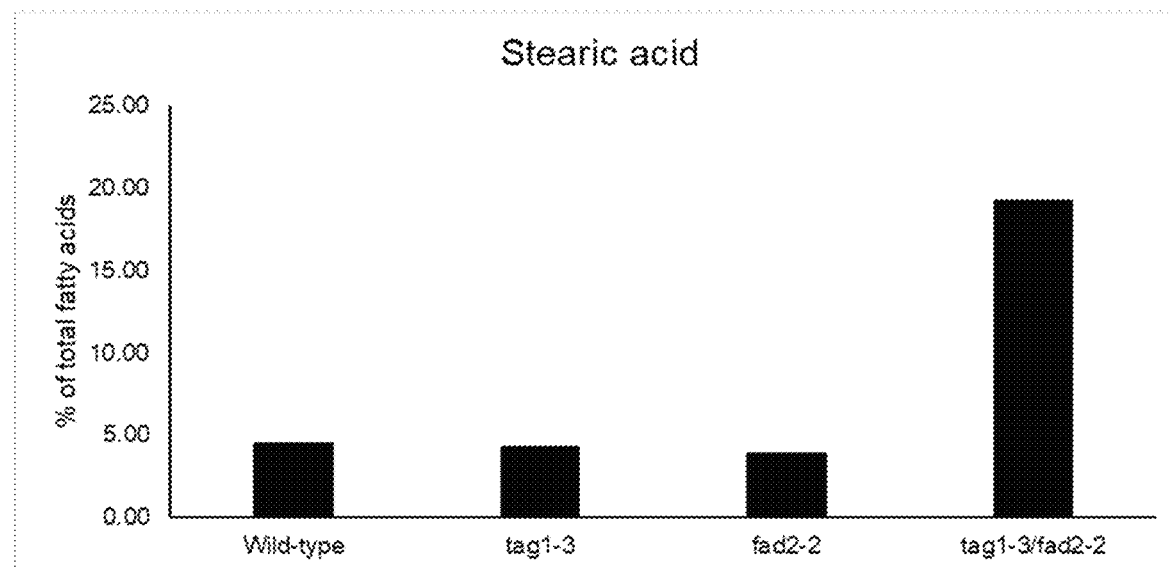
FIG. 13 contains a graph showing a percent of stearic acid (18:0) in oil from wild type pennycress plants (MN106) and from pennycress plants having a modified nucleic acid encoding a TAG1 polypeptide (tag1-3), having a modified nucleic acid encoding a FAD2 polypeptide (fad2-2), or having both a modified nucleic acid encoding a TAG1 polypeptide and a modified nucleic acid encoding a FAD2 polypeptide (tag1-3/fad2-2).

A pennycress line having a modification in nucleic acid that encodes a TAG1 polypeptide and a modification in nucleic acid that encodes a FAD2 polypeptide produced oil having an increased level of palmitic acid (FIG. 12) and an increased level of stearic acid (FIG. 13).

Figure 14:
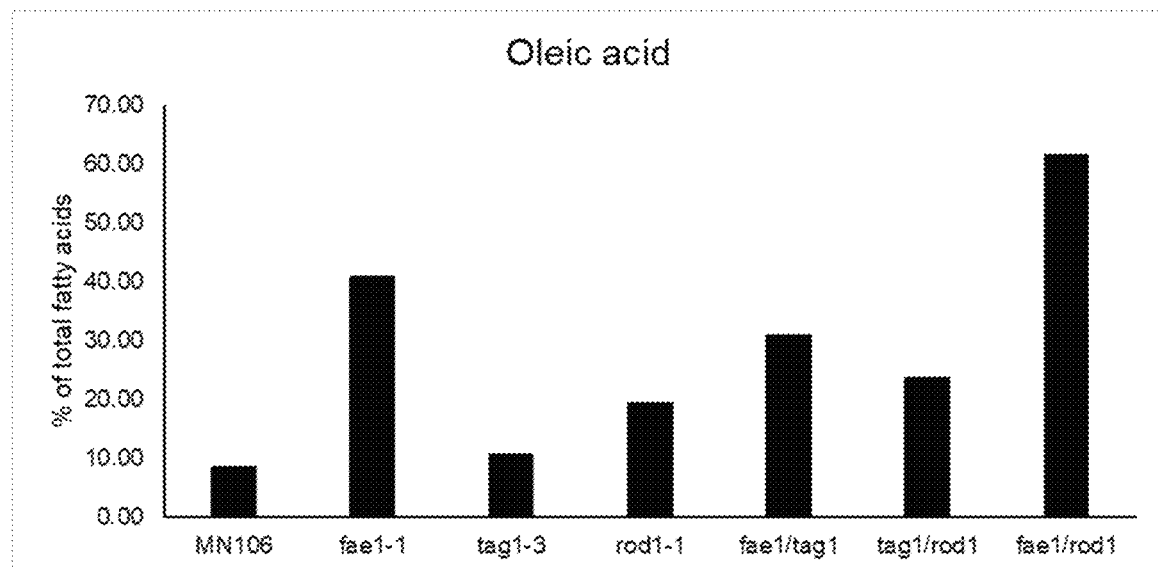
FIG. 14 contains a graph showing a percent of oleic acid (18:1) in oil from wild type pennycress plants (MN106) and from pennycress plants having a modified nucleic acid encoding a FAE1 polypeptide (fae1-1), having a modified nucleic acid encoding a TAG1 polypeptide (tag1-3), having a modified nucleic acid encoding a ROD1 polypeptide (rod1-1), having both a modified nucleic acid encoding a FAE1 polypeptide and a modified nucleic acid encoding a TAG1 polypeptide (fae1/tag1), having both a modified nucleic acid encoding a TAG1 polypeptide and a modified nucleic acid encoding a ROD1 polypeptide (tag1/rod1), or having both a modified nucleic acid encoding a FAE1 polypeptide and a modified nucleic acid encoding a ROD1 polypeptide (fae1/rod1).

Pennycress lines having a modification in nucleic acid that encodes a TAG1 polypeptide did not appear to alter the level of oleic acid in oil produced by the plants (FIG. 14).

Figure 15:
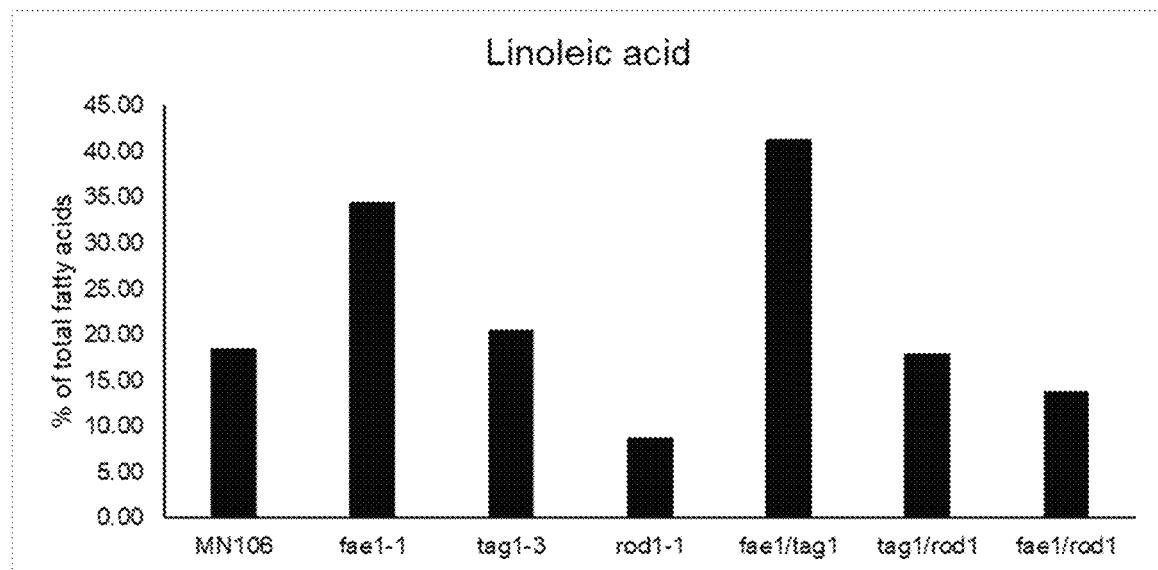
FIG. 15 contains a graph showing a percent of linoleic acid (18:2) in oil from wild type pennycress plants (MN106) and from pennycress plants having a modified nucleic acid encoding a FAE1 polypeptide (fae1-1), having a modified nucleic acid encoding a TAG1 polypeptide (tag1-3), having a modified nucleic acid encoding a ROD1 polypeptide (rod1-1), having both a modified nucleic acid encoding a FAE1 polypeptide and a modified nucleic acid encoding a TAG1 polypeptide (fae1/tag1), having both a modified nucleic acid encoding a TAG1 polypeptide and a modified nucleic acid encoding a ROD1 polypeptide (tag1/rod1), or having both a modified nucleic acid encoding a FAE1 polypeptide and a modified nucleic acid encoding a ROD1 polypeptide (fae1/rod1).
Figure 16:
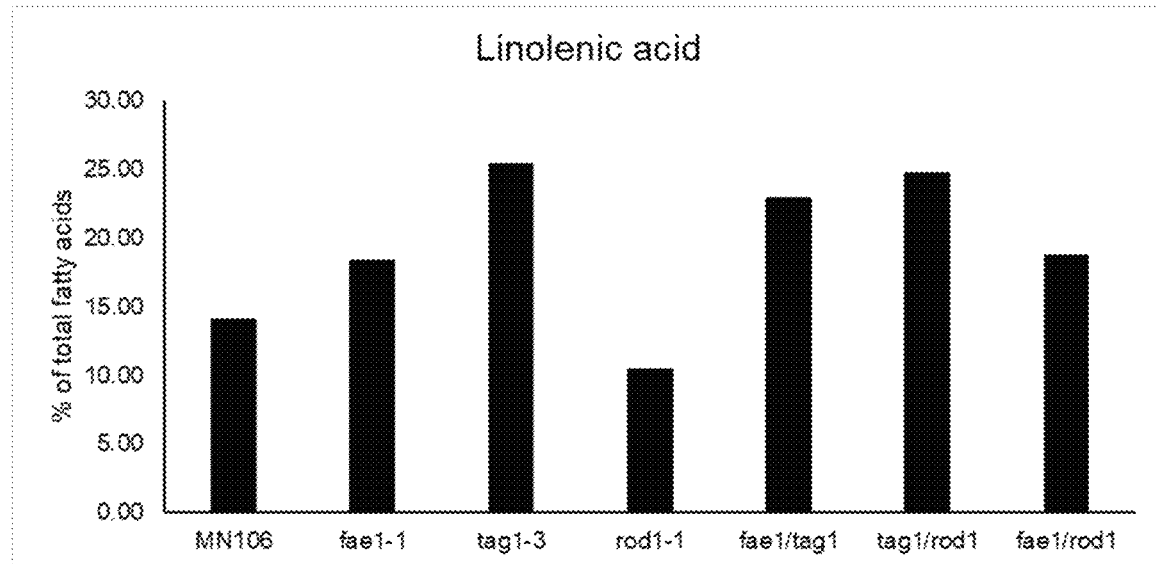
FIG. 16 contains a graph showing a percent of linolenic acid (18:3) in oil from wild type pennycress plants (MN106) and from pennycress plants having a modified nucleic acid encoding a FAE1 polypeptide (fae1-1), having a modified nucleic acid encoding a TAG1 polypeptide (tag1-3), having a modified nucleic acid encoding a ROD1 polypeptide (rod1-1), having both a modified nucleic acid encoding a FAE1 polypeptide and a modified nucleic acid encoding a TAG1 polypeptide (fae1/tag1), having both a modified nucleic acid encoding a TAG1 polypeptide and a modified nucleic acid encoding a ROD1 polypeptide (tag1/rod1), or having both a modified nucleic acid encoding a FAE1 polypeptide and a modified nucleic acid encoding a ROD1 polypeptide (fae1/rod1).

A pennycress line having a modification in nucleic acid that encodes a TAG1 polypeptide, and a pennycress line having a modification in nucleic acid that encodes a TAG1 polypeptide and a modification in nucleic acid that encodes a FAE1 polypeptide produced oil having an increased level of linoleic acid (FIG. 15) and an increased level of linolenic acid (FIG. 16).

Figure 17:
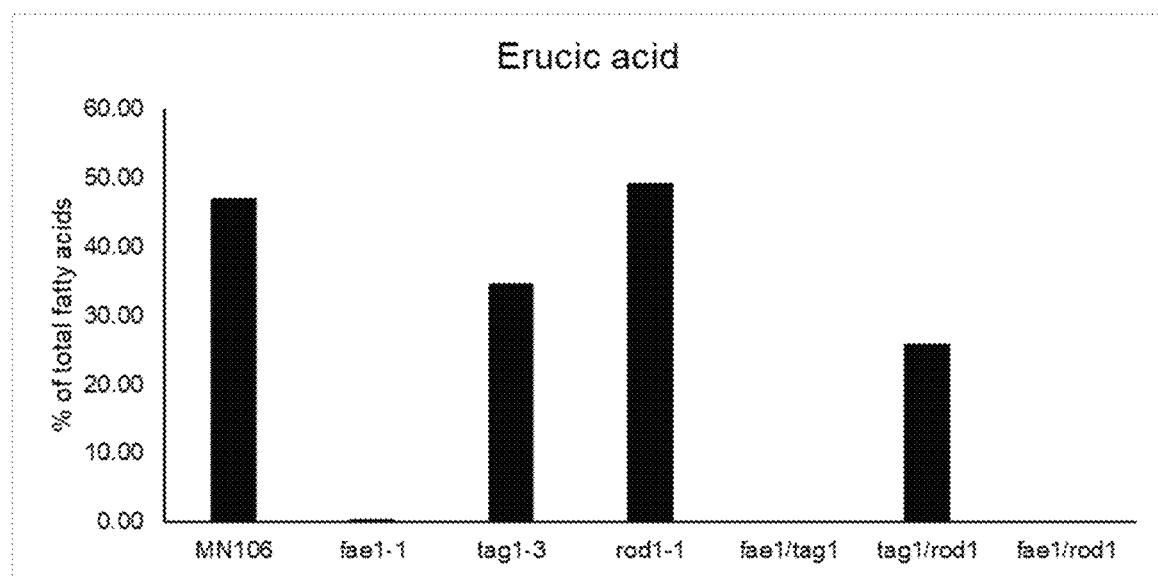
FIG. 17 contains a graph showing a percent of erucic acid (22:1) in oil from wild type pennycress plants (MN106) and from pennycress plants having a modified nucleic acid encoding a FAE1 polypeptide (fae1-1), having a modified nucleic acid encoding a TAG1 polypeptide (tag1-3), having a modified nucleic acid encoding a ROD1 polypeptide (rod1-1), having both a modified nucleic acid encoding a FAE1 polypeptide and a modified nucleic acid encoding a TAG1 polypeptide (fae1/tag1), having both a modified nucleic acid encoding a TAG1 polypeptide and a modified nucleic acid encoding a ROD1 polypeptide (tag1/rod1), or having both a modified nucleic acid encoding a FAE1 polypeptide and a modified nucleic acid encoding a ROD1 polypeptide (fae1/rod1).

A pennycress line having a modification in nucleic acid that encodes a TAG1 polypeptide, and a pennycress line having a modification in nucleic acid that encodes a TAG1 polypeptide and a modification in nucleic acid that encodes a ROD1 polypeptide produced oil having a decreased level of erucic acid (FIG. 17). A pennycress line having a modification in nucleic acid that encodes a TAG1 polypeptide and a modification in nucleic acid that encodes a FAE1 polypeptide produced oil in which erucic acid could not be detected (FIG. 17).

Example 4: Oil and Protein Content of Pennycress Plants

Materials and Methods
Near Infrared (NIR) Analysis

Individual F2 plants of tag1-3 and wild-type pennycress plants were subjected to NIR analysis using a DA 7250 NIR analyzer obtained from Perten Instruments (A PerkinElmer Company). During the scan the F2 seeds and MN106 seeds were illuminated with a source emitting electron magnetic irradiation at wavelengths between 900 nm and 1800 nm. The intensity of the reflectance at wavelengths in the interval was captured and graphed. Calibration data from Perten was used to estimate the chemical composition of the seeds. Oleic acid, linoleic acid, linolenic acid, and erucic acid contents were among the various chemicals whose values were estimated.

Identification of Modifications

Figure 19:
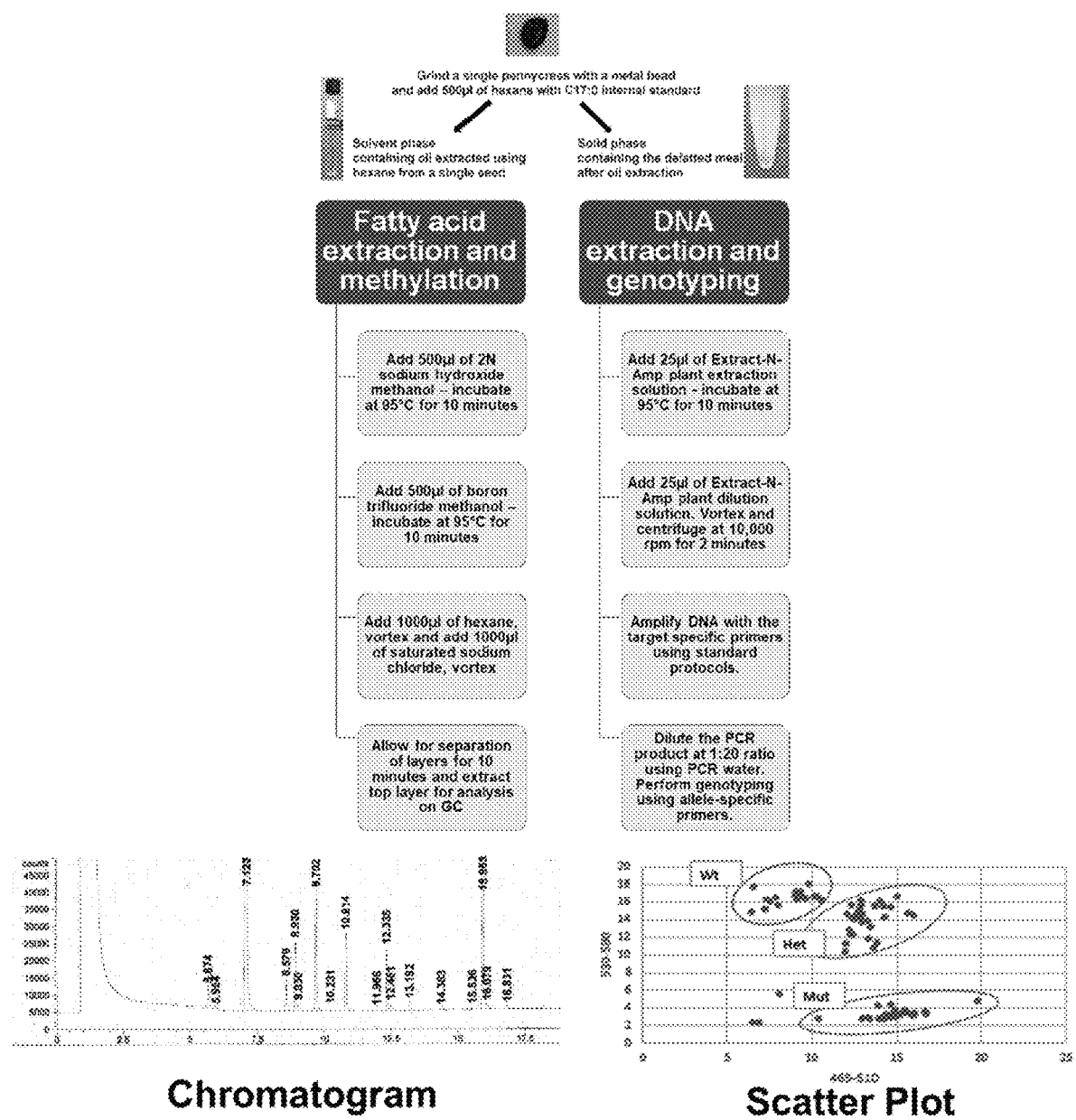
FIG. 19 contains a flow chart that can be used for genotyping and phenotyping single seeds of segregating populations.

NIR data were scanned for lines containing increased or decreased levels of oil and protein content.
Results A table containing the percent of total oil and protein from pennycress plants having a modification in a single gene that encodes a polypeptide involved in triglyceride synthesis is shown in FIG. 19.

A pennycress line having a modification in nucleic acid that encodes a TAG1 polypeptide produced seeds with reduced oil content and increased protein content.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A non-naturally occurring pennycress mutant plant having an increased level of a polyunsaturated fatty acid, as compared to a corresponding wild type pennycress plant, wherein said non-naturally occurring pennycress mutant plant comprises:
   a) a modified nucleic acid encoding a modified TAG1 polypeptide, wherein said modified TAG1 polypeptide has a reduced expression level or reduced polypeptide activity, wherein the non-modified TAG1 polypeptide comprises the amino acid sequence set forth in SEQ ID NO:2, and wherein said reduced expression level or reduced polypeptide activity of said modified TAG1 polypeptide is due to mutations within endogenous genomic nucleic acid sequence encoding wild type SEQ ID NO: 2; and
   b) a modified nucleic acid encoding a modified FAE1 polypeptide, wherein said modified FAE1 polypeptide has a reduced expression levels or reduced polypeptide activity, wherein the non-modified FAE1 polypeptide comprises the amino acid sequence set forth in SEQ ID NO:34, and wherein said reduced expression level or reduced polypeptide activity of said modified FAE1 polypeptide is due to mutations within endogenous genomic nucleic acid sequence encoding wild type SEQ ID NO: 34.

2. The non-naturally occurring pennycress mutant plant of claim 1, wherein said polyunsaturated fatty acid is linolenic acid, and wherein said non-naturally occurring pennycress mutant plant produces oil having from 22 mole % to 35 mole % of said linolenic acid.

3. The non-naturally occurring pennycress mutant plant of claim 1, wherein said polyunsaturated fatty acid is linoleic acid, and wherein said non-naturally occurring pennycress mutant plant produces oil having from 30 mole % to 45 mole % of said linoleic acid.

4. The non-naturally occurring pennycress mutant plant of claim 1, wherein said modified TAG1 polypeptide is selected from the group consisting of a modified TAG1 polypeptide comprising the amino acid sequence set forth in SEQ ID NO:3, a modified TAG1 polypeptide comprising the amino acid sequence set forth in SEQ ID NO:4, and a modified TAG1 polypeptide comprising the amino acid sequence set forth in SEQ ID NO:5.

5. A non-naturally occurring mutant seed produced by the non-naturally occurring pennycress mutant plant of claim 1, wherein said seed comprises a) the modified nucleic acid encoding the modified TAG1 polypeptide and b) the modified nucleic acid encoding the modified FAE1 polypeptide.

* * * * *